(12) United States Patent
Faure

(10) Patent No.: US 10,718,029 B2
(45) Date of Patent: Jul. 21, 2020

(54) TREATMENT TARGETING ONCOLOGY AND NEURODEGENERATION

(71) Applicant: Laurence Faure, Paris (FR)

(72) Inventor: Laurence Faure, Paris (FR)

(*) Notice: Subject to any disclaimer, the term of this patent is extended or adjusted under 35 U.S.C. 154(b) by 0 days.

(21) Appl. No.: 15/814,100

(22) Filed: Nov. 15, 2017

(65) Prior Publication Data
US 2018/0291462 A1 Oct. 11, 2018

Related U.S. Application Data

(63) Continuation of application No. 13/681,164, filed on Nov. 19, 2012, now abandoned, which is a continuation-in-part of application No. 12/282,117, filed on Sep. 8, 2008, now Pat. No. 8,314,221, which is a continuation-in-part of application No. PCT/FR2011/000155, filed on Mar. 18, 2011.

(51) Int. Cl.
| | |
|---|---|
| C12N 15/11 | (2006.01) |
| C12Q 1/6886 | (2018.01) |
| C07K 14/47 | (2006.01) |
| C12Q 1/6883 | (2018.01) |
| C12N 15/113 | (2010.01) |
| A61K 31/7105 | (2006.01) |
| A61K 31/7088 | (2006.01) |

(52) U.S. Cl.
CPC .......... *C12Q 1/6886* (2013.01); *C07K 14/47* (2013.01); *C12Q 1/6883* (2013.01); *A61K 31/7088* (2013.01); *A61K 31/7105* (2013.01); *C12N 15/11* (2013.01); *C12N 15/113* (2013.01); *C12N 2310/14* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 5,474,796 A | 12/1995 | Brennan | |
| 7,635,561 B2* | 12/2009 | Giordano | C12Q 1/6886 435/6.14 |
| 7,871,769 B2* | 1/2011 | Baker | C12Q 1/6886 435/6.14 |
| 8,039,439 B2 | 10/2011 | Faure | |
| 8,314,221 B2 | 11/2012 | Faure | |
| 2004/0152212 A1 | 8/2004 | Huang et al. | |
| 2005/0019828 A1 | 1/2005 | Qiao et al. | |
| 2005/0019944 A1 | 1/2005 | Qiao et al. | |
| 2005/0157445 A1 | 7/2005 | Bradley et al. | |
| 2006/0170925 A1 | 8/2006 | Lin et al. | |
| 2007/0218077 A1 | 9/2007 | Felgner et al. | |
| 2008/0045418 A1 | 2/2008 | Kia | |
| 2008/0213130 A1 | 9/2008 | Pison et al. | |
| 2009/0275020 A1 | 11/2009 | Faure | |
| 2010/0285971 A1 | 11/2010 | Faure | |
| 2013/0059792 A1 | 3/2013 | Faure | |

FOREIGN PATENT DOCUMENTS

| | | |
|---|---|---|
| EP | D465529 B1 | 4/1998 |
| EP | 1869209 A2 | 12/2007 |
| EP | 2066806 A2 | 6/2009 |
| FR | M82753 A1 | 9/2006 |
| FR | M82754 A1 | 9/2006 |
| FR | 2950075 A1 | 3/2011 |
| FR | M50076 A1 | 3/2011 |
| WO | 01/64736 A2 | 9/2001 |
| WO | 2005/016515 A3 | 6/2005 |
| WO | 2006/095086 A2 | 9/2006 |
| WO | 2008/029031 A2 | 3/2008 |
| WO | 2012/127124 A1 | 9/2012 |

OTHER PUBLICATIONS

Wu et al., "FJ Five novel genes from 17q23 amplicon have different amplification and overexpression frequency in breast cancers", Apr. 2008. cited in U.S. Appl. No. 13/681,164.
Yamashiro et al., "Expression of TrkC in favorable human neuroblastomas", Oncogene, 1996, pp. 37-41, vol. 12, No. 1. cited in U.S. Appl. No. 13/681,164.
Yonish-Rouach, "The p53 tumour suppressor gene: a mediator of a G1 growth arrest and of apoptosis", Experientia, 1996, pp. 1001-1007, vol. 52, No. 10-11. cited in U.S. Appl. No. 13/681,164.
Lecanda et al., "TGR3 prevents proteasomal degradation of the cyclin-dependent kinase inhibitor p27kip1 for cell aycle arrest", Cell Cycle, 2009, pp. 742-756, vol. 8, No. 5. cited in U.S. Appl. No. 13/681,164.
Ahnen, "Tissue markers of colon cancer risk", Gastrointestinal Endoscopy, 1999, pp. S50-S59, vol. 49, No. 3, Part 2. cited in U.S. Appl. No. 13/681,164.
Database Geneseq, "Human BEC/LEC-related protein sequence Seq ID 129", (Jul. 2004). cited in U.S. Appl. No. 13/681,164.
Ahmed et al., "Microarrays and breast cancer clinical studies: forgetting what we have not yet learnt", Breast Cancer Research, 2005, pp. 96-99, vol. 7, No. 3. cited in U.S. Appl. No. 13/681,164.
Radu et al., "Expression of Follicle-Stimulating Hormone Receptor in Tumor Blood Vessels", The New England Journal of Medicine, 2010, pp. 1621-1680, vol. 363, No. 17. cited in U.S. Appl. No. 13/681,164.
Balique et al., "Tobacco Mosaic Virus in the Lungs of Mice following Intra-Tracheal Inoculation", Plos One, 2013, vol. 8, No. 1, article No. e54993. cited in U.S. Appl. No. 13/681,164.

(Continued)

*Primary Examiner* — Patrick T Lewis
(74) *Attorney, Agent, or Firm* — Young & Thompson

(57) ABSTRACT

The present invention relates to the field of medicine and biology. It concerns a new test for screening and therapeutic follow-up in oncology. More particularly, it relates to diagnostic and/or therapeutic tests in oncology and on neurodegenerative diseases. Molecular targeting by peptide vectors and antibodies or by small interfering RNAs (siRNAs) opens a new concept of interdependence for diagnostic and therapeutic tools.

2 Claims, 34 Drawing Sheets

Figure 1A:
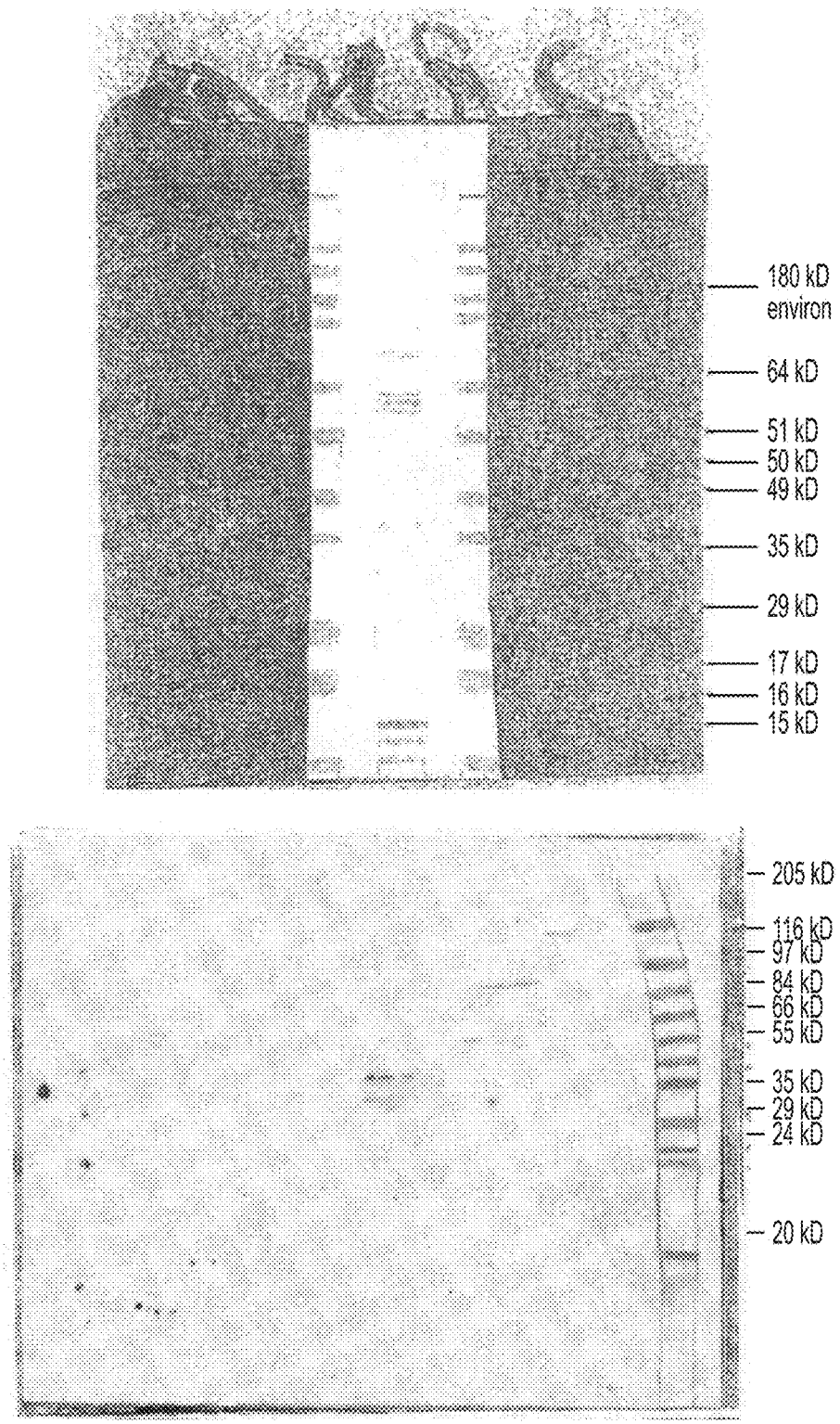

Specification includes a Sequence Listing.

(56) References Cited

OTHER PUBLICATIONS

Bar et al., "The evolution of cortical development: An hypothesis based on the role of the Reelin signaling pathway", Jan. 2000. cited in U.S. Appl. No. 13/681,164.

Barnes et al., "P53, apoptosis, and breast cancer", Journal of Mammary Gland Biology and Neoplasia, 1996, pp. 163-175, vol. 1, No. 2. cited in U.S. Appl. No. 13/681,164.

Barthlen et al., "Impact of experimental peritonitis on bone marrow cell function", Surgery, 1999, pp. 41-47, vol. 126, No. 1. cited in U.S. Appl. No. 13/681,164.

Berthold et al., "The role of chemotherapy in the treatment of children with neuroblastoma stage IV: The GPO (German Pediatric Oncology Society) experience", Klinische Padiatrie, 1990, pp. 262-269, vol. 202, No. 4. cited in U.S. Appl. No. 13/681,164.

Bian et al., "Chemotherapy-induced Apoptosis of S-type Neuroblastoma Cells Requires Caspase-9 and Is Augmented py CD95/Fas Stimulation", The Journal of Biological Chemistry, 2004, pp. 46634669, vol. 279, No. 6. cited in U.S. Appl. No. 13/681,164.

Borrello et al., "trk and ret proto-oncogene expression in human neuroblastoma specimens: High frequency of trk expression in non-advanced stages", International Journal of Cancer, 1993, pp. 540-545, vol. 54, No. 4. cited in U.S. Appl. No. 13/681,164.

Caroll et al., "A Pure Estrogen Antagonist Inhibits Cyclin E-Cdk2 Activity in MCF-7 Breast Cancer Cells and Induces Accumulation of p130-E2F4 Complexes Characteristic of Quiescence", The Journal of Biological Chemistry, 2000, pp. 38221-38229, vol. 275, No. 49. cited in U.S. Appl. No. 13/681,164.

Caruana et al., "Les pararétrovirus endogènes (EPRV), voie nouvelle de transmission des virus de plantes", Virologie, 2003, vol. 7, No. 4. cited in U.S. Appl. No. 13/681,164.

Chang et al., "Genomic approaches in the management and treatment of breast cancer", British Journal of Cancer, 2005, pp. 618-624, vol. 92, No. 4. cited in U.S. Appl. No. 13/681,164.

Database Geneseq, "cDNA sequence #460 encoding novel human secreted protein", May 2002. cited in U.S. Appl. No. 13/681,164.

Database Geneseq, "Novel human polypeptide SeqID8519", May 2004. cited in U.S. Appl. No. 13/681,164.

Eggert et al., "Molecular dissection of TrkA signal transduction pathways mediating differentiation in human neuroblastoma cells", Oncogene, 2000, pp. 2043-2051, vol. 19. cited in U.S. Appl. No. 13/681,164.

Regazzi et al., "The 27,000 daltons stress proteins are phosphorylated by protein kinase C during the tumor promoter-mediated growth inhibition of human mammary carcinoma cells", 1988, pp. 62-68, vol. 152, No. 1. cited in U.S. Appl. No. 13/681,164.

Fry et al., "Position-Dependent Transcriptional Regulation of the Murine Dihydrofolate Reductase Promoter by the E2F Transactivation Domain", Molecular and Cellular Biology, 1997, pp. 1966-1976, vol. 17, No. 4. ;Red in U.S. Parent Application No. 13/681,164.

Fraering et al., "Purification and Characterization of the Human y-Secretase Complex", Biochemistry, 2004, pp. 9774-9789, vol. 43, No. 30. cited in U.S. Appl. No. 13/681,164.

Gao et al., "Diagnostic and prognostic markers for human prostate cancer", the Prostate, 1997, pp. 264-281, vol. 31, No. 4. cited in U.S. Appl. No. 13/681,164.

Gross et al., "Expression of Fas (Apo-1/CD95) and Fas ligand (FasL) in human neuroblastoma", Medical and pediatric oncology, 2001, pp. 111-114, vol. 36, No. 1. cited in U.S. Appl. No. 13/681,164.

Harlow et al., "Antibodies: a laboratory Manual", CSH Press, Jan. 1988. cited in U.S. Appl. No. 13/681,164.

Horman et al., "Changes in the phosphorylation status of the 27 kDa heat shock protein (HSP27) associated with the modulation of growth and/or differentiation in MCF-7 cells", Cell Proliferation, 1997, pp. 21-35, vol. 30. cited in U.S. Appl. No. 13/681,164.

Hughes et al., "Adaptor plasmids simplify the insertion of foreign DNA into helper-independent retroviral vectors", Journal of Virology, 1987, pp. 3004-3012, Vol. 61, No. 10. cited in U.S. Appl. No. 13/681,164.

Human Genome U95 Set, Announcement Affymetrix, Apr. 2000, pp. 1-2. cited in U.S. Appl. No. 13/681,164.

International Preliminary Report on Patentability for PCT/FR2007/001449, dated Sep. 7, 2007. cited in U.S. Appl. No. 13/681,164.

International Search Report from PCT/FR2006/000510, dated Oct. 20, 2006. cited in U.S. Appl. No. 13/681,164.

International Search Report from PCT/FR2011/000155, dated Jul. 16, 2012. cited in U.S. Appl. No. 13/681,164.

Kastner et al., "Transient Accumulation of Retinoblastoma/E2F-1 Protein Complexes Correlates with the Onset of Neuronal Differentiation in the Developing Quail Neural Retina", 1998, pp. 857-867, vol. 9. cited in U.S. Appl. No. 13/681,164.

Katalin et al., "Characterization of Protein N-Glycosylation", Methods in Molecular Biology, vol. 446, Jan. 2008, pp. 293-316. cited in U.S. Appl. No. 13/681,164.

Kisenge et al., "Expression of short-form caspase 8 correlates with decreased sensitivity to Fas-mediated apoptosis in neuroblastoma cells", Cancer Science, 2003, pp. 598-605, vol. 94, No. 7. cited in U.S. Appl. No. 13/681,164.

Knauf et al., "Involvement of Protein Kinase Ce (PKCe) in Thyroid Cell Death", The Journal of Biological Chemistry, 1999, pp. 23414-23425, vol. 274, No. 33. cited in U.S. Appl. No. 13/681,164.

Medzihradszky et al., "Characterization of Protein N-Glycosylation", Methods in Enzymology, 2005, pp. 116-138, vol. 405. cited in U.S. Appl. No. 13/681,164.

Shah, M. A., and G. K. Schwartz. "Cyclin-dependent kinases as targets for cancer therapy." Cancer chemotherapy and biological response modifiers 22 (2005): 135-162. cited in U.S. Appl. No. 13/681,164.

Arya et al., "Muscle ring finger protein-1 inhibits PKCe activation and prevents cardiomyocyte hypertrophy", The Journal of Cell Biology, 2004, pp. 1147-1159, vol. 167, No. 6. cited in U.S. Appl. No. 13/681,164.

Carroll et al., "A Pure Estrogen Antagonist Inhibits Cyclin E-Cdk2 Activity in MCF-7 Breast Cancer Cells and Induces Accumulation of p130-E2F4 Complexes Characteristic of Quiescence", The Journal of Biological Chemistry, 2000, pp. 38221-38229, vol. 275, No. 49. cited in U.S. Appl. No. 13/681,164.

Chau et al., "Coordinated Regulation of Life and Death by RB", Nature Reviews Cancer, 2003, pp. 130-138, vol. 3, No. 2. cited in U.S. Appl. No. 13/681,164.

Cheng et al., "Cell Cycle Entry of Hematopoietic Stem and Progenitor Cells Controlled by Distinct Cyclin-Dependent Kinase Inhibitors", International Journal of Hematology, 2002, pp. 460-465, vol. 75, No. 5. cited in U.S. Appl. No. 13/681,164.

Classon et al., "The retinoblastoma tumour suppressor in development and cancer", Nature Reviews Cancer, 2002, pages 910-917, vol. 2, No. 12. cited in U.S. Appl. No. 13/681,164.

Coqueret, "Linking cyclins to transcriptional control", Gene, 2002, pp. 35-55, vol. 299, No. 12. cited in U.S. Appl. No. 13/681,164.

Crisanti et al., "Cloning and characterization of a novel transcription factor involved in cellular proliferation arrest: PATF", Oncogene, 2001, pp. 5475-5483, vol. 20. cited in U.S. Appl. No. 13/681,164.

Durocher et al., "The Molecular Basis of Fha Domain:Phosphopeptide Binding Specificity and Implications for Jhospho-Dependent Signaling Mechanisms", Molecular Cell, 2000, pp. 1169-1182, vol. 6. cited in U.S. Parent 4pplication No. 13/681,164.

Durocher et al., "The Fha domain", Febs Letters, 2002, pp. 58-66, vol. 513. cited in U.S. Parent Application 'lo. 13/681,164.

Espanel et al., "Regulation of E2F-1 gene expression in avian cells", Oncogene, 1998, pp. 585-594, vol. 17. cited in U.S. Appl. No. 13/681,164.

Regazzi et al., "Effects of tumor promoters on growth and on cellular redistribution of phospholipid/CA2+-dependent Protein kinase in human breast cancer cells", International Journal of Cancer, 1986, pp. 731-737, vol. 37, No. 5. cited in U.S. Appl. No. 13/681,164.

Han et al., "Increased expression of cyclin D1 in a murine mammary epithelial cell line induces p27kip1, inhibits growth, and enhances apoptosis", Cell Growth Differ, 1996 pp. 699-710, vol. 7, No. 6. cited in U.S. Appl. No. 13/681,164.

(56) References Cited

OTHER PUBLICATIONS

He et al., "In vivo analysis of the molecular pathogenesis of acute promyelocytic leukemia in the mouse and its therapeutic implications", Oncogene, 1999, pp. 5278-5292, vol. 18. cited in U.S. Appl. No. 13/681,164.
Helin, "Regulation of cell proliferation by the E2F transcription factors", Current Opinion in Genetics & Development, 1998, pp. 28-35, vol. 8, No. 1 cited in U.S. Appl. No. 13/681,164.
Köhler et al., "Continuous cultures of fused cells secreting antibody of predefined specificity", Nature, 1975, pp. 195-497, vol. 256. cited in U.S. Appl. No. 13/681,164.
Mundle et al., "Evolving intricacies and implications of E2F1 regulation", The FASEB Journal, 2003, pp. 569-574, vol. 17, No. 6. cited in U.S. Appl. No. 13/681,164.
Opalka et al., "Apoptotic Genes in Cancer Therapy", Cells Tissues Organs, 2002, pp. 126-132, vol. 172, No. 2. cited in U.S. Appl. No. 13/681,164.
Schneider et al., "Involvement of nuclear steroid/thyroid/retinoid receptors and of protein kinases in the regulation of growth and of c-erbB and retinoic acid receptor expression in MCF-7 breast cancer cells", Breast Cancer Research and Treatment, 1999, pp. 171-181, vol. 58, No. 2. cited in U.S. Appl. No. 13/681,164.
Senderowicz, "Cyclin-dependent kinases as targets for cancer therapy", Cancer chemotherapy and biological response modifiers, 2002, pp. 169-196, vol. 20. cited in U.S. Appl. No. 13/681,164.
Stiegler et al., "The Family of Retinoblastoma Proteins", Critical Reviews in Eukaryotic Gene Expression, 2001, pp. 59-76, vol. 11, No. 1-3. cited in U.S. Appl. No. 13/681,164.
Stevaux et al., "A revised picture of the E2F transcriptional network and Rb function", Current Opinion in Cell Biology, 2002, pp. 684-691, vol. 14, Issue 6. cited in U.S. Appl. No. 13/681,164.
Toma et al., "Desflurane Preconditioning Induces Time-dependent Activation of Protein Kinase C Epsilon and Extracellular Signal-regulated Kinase 1 and 2 in the Rat Heart in Vivo", Anesthesiology, 2004, pp. 1372-1380, vol. 101, No. 6. cited in U.S. Appl. No. 13/681,164.
Ward et al., "Binding activities of a repertoire of single immuno-globulin variable domains secreted from Escherichia ecoli", Nature, 1989, pp. 544-546, Vol. 341. cited in U.S. Appl. No. 13/681,164.
Wu et al., "In Vivo Association of E2F and DP Family Proteins", Molecular and Cellular Biology, 1995, pp. 2536-2546, vol. 15, No. 5. cited in U.S. Appl. No. 13/681,164.
Yaffe, "Phosphotyrosine-Binding Domains in Signal Transduction", Nature Reviews - Molecular Cell Biology, 2002, pp. 177-186, vol. 3. cited in U.S. Appl. No. 13/681,164.
Yamasaki, "Growth Regulation by the E2F and Dp Transcription Factor Families", Results and Problems in Cell Differentiation, 1998, pp. 199-227, vol. 22. cited in U.S. Appl. No. 13/681,164.
Park et al., "Identification of Individual Proteins in Complex Protein Mixtures by High-Resolution, High-Mass-Accuracy Maldi TOF-Mass Spectrometry Analysis of In-Solution Thermal Denaturation/Enzymatic Digestion", Analytical chemistry, 2001, pp. 2558-2564, vol. 73, No. 11. cited in U.S. Appl. No. 13/681,164.
Lee et al., "Amyloid beta peptide directly inhibits PKC activation", Molecular and Cellular Neuroscience, 2004, pp. 222-231, vol. 26. cited in U.S. Appl. No. 13/681,164.
Lemke, "Glial Control of Neuronal Development", Annual Review of Neuroscience, Molecular Neurobiology Laboratory, The Salk Institute, 2001, pp. 87-105, vol. 24. cited in U.S. Appl. No. 13/681,164.
Mairesse et al., "Antisense Inhibition of the 27 kDa Heat Shock Protein Production Affects 3ROWTH Rate and Cytoskeletal Organization in MCF-7 Cells", Cell Biology International, 1996, pp. 205-212, vol. 20, No. 3. cited in U.S. Appl. No. 13/681,164.

Matunis, "On the Road to Repair: Pcna Encounters Sumo and Ubiquitin Modifications", Molecular Cell, 2002, pp. 441-442, vol. 10, No. 3. cited in U.S. Appl. No. 13/681,164.
Melchior et al., "Sumo-1 and p53", Cell Cycle, 2002, pp. 245-249, vol. 1, No. 4. cited in U.S. Parent Application Vo. 13/681,164.
Vakagawara et al., "Expression and function of Trk-B and Bdnf in human neuroblastomas", Molecular and cellular Biology, 1994, pp. 759-767_ cited in U.S. Parent Application No. 13/681,164.
Oren, "Relationship of p53 to the control of apoptotic cell death", Seminars in Cancer Biology, 1994, pp. 221-227, vol. 3. cited in U.S. Appl. No. 13/681,164.
Pardo et al., "Cyclin D1 induced apoptosis maintains the integrity of the G1/S checkpoint following ionizing radiation rradiation", Somatic Cell and Molecular Genetics, 1996, pp. 135-144, vol. 22, No. 2. cited in U.S. Appl. No. 13/681,164.
Pawson, "SH2 domains, interaction modules and cellular wiring", Trends in Cell Biology, 2001, pp. 504-511, vol. 11, No. 12. cited in U.S. Appl. No. 13/681,164.
Platet et al., "Breast Cancer Cell Invasiveness: Correlation With Protein Kinase C Activity And Differential Regulation by Phorbol Ester in Estrogen Receptor-Positive and - Vegative Cells", International Journal of Cancer, 1998, pp. 750-756, vol. 75, No. 5. cited in U.S. Appl. No. 13/681,164.
Ree et al., "Regulation of tissue-degrading factors and in vitro invasiveness in progression of breast cancer cells", :::linical & Experimental Metastasis, 1998, pp. 205-215, vol. 16, No. 3. cited in U.S. Parent Application No. 13/681,164.
Regazzi et al., "Effects of tumor promoters on growth and on cellular redistribution of phospholipid/CA2+-dependent Protein kinase in human breast cancer cells", International Journal of Cancer, 1986, pp. 731-737, vol. 37, No. 5. sited in U.S. Appl. No. 13/681,164.
Santa Cruz Technology, sc-214, ogy sc-860. cited in U.S. Appl. No. 13/681,164.
Slansky et al., "Introduction to the E2F family: protein structure and gene regulation", Curr Top Microbiol Immunol, 1996, pp. 347-360, vol. 53. cited in U.S. Parent Application No. 13/681,164.
Songyang et al., "SH2 domains recognize specific phosphopeptide sequences", Cell, 1993, pp. 767-778, vol. 72, No. 5. cited in U.S. Parent Application No_ 131681,164.
Starzec et al., "Proliferative responses of epithelial cells to 8-bromo-cyclic Amp and to a phorbol ester change luring breast Pathogenesis", 1994, Journal of Cellular Physiology, pp. 31-38, vol. 161, No. t cited in U.S. Parent Application No. 13/681,164.
Sun et al., "Improved breast cancer prognosis through the combination of clinical and genetic markers", 310INFORMATICS, 2007, pp. 30-37, Vol_ 23, No. 1. cited in U.S. Parent Application No_ 13/681,164.
Matsumura, Itaru, Hirokazu Tanaka, and Yuzuru Kanakura, "E2F1 and c-Myc in Cell Growth and Death", Cell cycle, 2003, Vol_ 2, No. 4_ cited in U.S. Parent Application No. 13/681,164.
Toma, "Activation of PKcs by Dag, Agpi: oleic acid, linoleic acid, arachidonic acid", 2004. cited in U.S. Parent Application No. 13/681,164.
Vaitukaitis et al., "A method for producing specific antisera with small doses of immunogen", the Journal of Clinical Endocrinology & Metabolism, 1971, pp. 988-991, vol. 33, No_ 6_ cited in U.S. Parent Application No. 13/681,164.
Written Opinion, dated Jul. 3, 2006, from PCT application No. PCT/EP2006/00510. cited in U.S. Appl. No. 13/681,164.
Written Opinion of the International Searching Authority for PCT/FR2007/001449, dated Sep. 14, 2016. cited in U.S. Appl. No. 13/681,164.
Written Opinion of the International Search Authority for PCT/FR2011/000155, dated Mar. 18, 2011 cited in U.S. Appl. No. 13/681,164.

* cited by examiner

| Band 1 | Band 2 | | | | | | |
|---|---|---|---|---|---|---|---|
| m/z | m/z | SN | P.es. | intens | m/z | SN | Res. | intens |
| 726.3739 | 525.380 | 75.6 | 1903 | 3408.00 | 1748.844 | 4.9 | 16483 | 221.00 |
| 768.5312 | 545.322 | 133.8 | 1436 | 6029.00 | 1783.031 | 5.0 | 12143 | 223.00 |
| 842.5103 | 550.330 | 142.9 | 1612 | 8438.00 | 1794.832 | 17.1 | 15898 | 446.26 |
| 870.5261 | 568.541 | 790.6 | 2123 | 35626.00 | 1836.904 | 3.6 | 15701 | 162.00 |
| 882.5552 | 580.777 | 26.4 | 2516 | 1190.00 | 1866.950 | 4.6 | 12370 | 214.00 |
| 949.5031 | 587.667 | 33.3 | 2795 | 1501.00 | 1873.917 | 15.9 | 17904 | 420.12 |
| 963.5154 | 631.470 | 66.4 | 6569 | 2991.00 | 1878.979 | 15.8 | 16250 | 407.25 |
| 1017.5794 | 659.447 | 30.9 | 6811 | 1394.00 | 1880.935 | 20.1 | 11590 | 515.13 |
| 1051.6872 | 662.431 | 67.2 | 9193 | 3027.00 | 1927.967 | 6.2 | 11723 | 281.00 |
| 1135.5636 | 667.159 | 41.0 | 10087 | 1846.00 | 1928.974 | 6.2 | 14954 | 152.02 |
| 1151.5455 | 711.153 | 34.5 | 10289 | 1553.00 | 1942.020 | 4.7 | 19798 | 211.00 |
| 1167.6043 | 713.175 | 42.7 | 11689 | 1922.00 | 1944.019 | 20.0 | 15714 | 478.21 |
| 1206.5889 | 739.151 | 20.4 | 12971 | 918.00 | 2021.003 | 137.1 | 14814 | 3500.82 |
| 1233.6074 | 757.168 | 13.8 | 13762 | 797.82 | 2037.013 | 8.2 | 10928 | 212.04 |
| 1240.6366 | 790.491 | 14.4 | 12895 | 649.00 | 2045.020 | 7.3 | 15747 | 330.00 |
| 1251.7080 | 842.510 | 19.8 | 11687 | 767.71 | 2059.030 | 4.2 | 14227 | 191.00 |
| 1267.6791 | 870.537 | 8.8 | 11748 | 897.00 | 2125.002 | 5.9 | 14783 | 264.00 |
| 1295.6359 | 881.256 | 23.3 | 13598 | 829.82 | 2211.105 | 151.9 | 13211 | 3373.88 |
| 1324.6345 | 921.541 | 17.0 | 12241 | 600.49 | 2225.106 | 17.2 | 14637 | 773.00 |
| 1336.6586 | 1330.770 | 6.3 | 15012 | 284.00 | 2283.181 | 48.1 | 12236 | 2167.00 |
| 1354.6603 | 1341.706 | 3.3 | 7921 | 149.00 | 2311.205 | 10.0 | 15157 | 207.42 |
| 1369.6215 | 1373.739 | 21.3 | 15547 | 533.87 | 2383.261 | 73.2 | 10466 | 1204.30 |
| 1399.6775 | 1439.840 | 20.1 | 14012 | 522.60 | 2461.196 | 11.1 | 11453 | 196.62 |
| 1410.7223 | 1451.764 | 15.2 | 13759 | 401.95 | 2477.117 | 1.9 | 15432 | 85.00 |
| 1442.6973 | 1467.871 | 4.6 | 16096 | 201.00 | 2511.375 | 9.1 | 9656 | 154.80 |
| 1507.7352 | 1479.823 | 10.1 | 13230 | 266.63 | 2539.329 | 11.0 | 9640 | 180.05 |
| 1586.7312 | 1486.853 | 7.0 | 21505 | 316.00 | 2549.262 | 3.4 | 13928 | 155.00 |
| 1599.8580 | 1534.956 | 17.1 | 14704 | 481.02 | 2587.249 | 3.4 | 11702 | 153.00 |
| 1604.7104 | 1537.826 | 23.5 | 14898 | 675.26 | 2591.295 | 25.7 | 10330 | 388.23 |
| 1687.8247 | 1567.775 | 37.8 | 15022 | 1065.43 | 2650.220 | 8.7 | 10510 | 132.78 |
| 1728.8549 | 1570.816 | 14.6 | 16144 | 408.22 | 2750.500 | 42.2 | 10212 | 533.12 |
| 1746.8813 | 1593.926 | 155.9 | 15098 | 4349.81 | 2766.494 | 9.3 | 8850 | 133.86 |
| 1794.7933 | 1607.944 | 3.5 | 10703 | 157.00 | 2780.508 | 8.7 | 10597 | 391.00 |
| 1800.9407 | 1639.938 | 9.4 | 11769 | 238.84 | 2823.368 | 40.4 | 9128 | 513.24 |
| 1830.9074 | 1684.943 | 21.2 | 6015 | 538.84 | 2837.393 | 13.1 | 6755 | 161.25 |
| 1871.9277 | 1694.843 | 15.6 | 8084 | 407.76 | 3265.643 | 9.2 | 6905 | 58.89 |
| 1937.0540 | 1698.906 | 16.6 | 15134 | 431.33 | 3324.905 | 1.5 | 31230 | 68.00 |
| 1951.0366 | 1721.377 | 4.6 | 17947 | 207.00 | 3338.673 | 2.1 | 6212 | 94.00 |
| 1986.9046 | | | | | | | | |
| 2074.1188 | | | | | | | | |
| 2087.0345 | | | | | | | | |
| 2197.0986 | | | | | | | | |
| 2691.2664 | | | | | | | | |
| 2748.3890 | | | | | | | | |

Figure 3A 66.08; 101.08; 112.08; 175.11; 197.12; 232.13; 240.20; 259.20;284.10; 311.27; 331.20; 343.26; 370.20; 397.22; 411.23; 428.25; 470.24; 493.24; 515.28; 517.29; 550.45; 568.28; 575.36; 581.36; 614.31; 623.34; 626.38; 669.26; 727.41; 735.96; 741.99; 745.25; 751.92; 753.92; 757.93; 761.17; 774.47; 791.4l ;828.37; 876.84; 887.4; 902.28; 927.6; 929.55; 930.76;934.58; 942.60
944.58; 946.93;997.0

LAHYNKR SEQ ID NO: 343
YYGRILHYLK SEQ ID NO: 344
TLPSSSCLVAYK SEQ ID NO: 20

TFKNLC SEQ ID NO: 16
MEEALGRVK SEQ ID NO: 345
EEALGRVK' SEQ ID NO: 346
ETPASDKK SEQ ID NO: 347

List of masses corresponding with a chromatogram detailling a monoisotopic peak of spectrogram of the sample
(Analysis ESI MS MS)

6 FC

LIST OF MONOISOTOPIC PEAK OF THE 6 FC BAND.

788.452
857.475
901.489
915.512
929.537
943.553
944.523
953.576
953.551
958.529
970.526
971.543
985.561
986.563
989.582
1032.584 → Item T0 Fc: 180 to 190Kd
1046.564
1111.554
1135.541
1137.506
1151.560 → Item T0 Fc
1183.555
1168.592
1173.622
1180.618
1250.707
1325.739
1333.780   = T0 Fc
1335.687
1335.700 → Item T0 Fc
1349.717
1433.700
1461.846
1475.874
1481.834
1489.865                    1812.85
1503.893                    2041.1
1506.897       →            2032.97
1508.792    FOLLOWING        2163.051
1522.775                    2189.041
1546.872                    2273.146
1603.82                     2289.148
1642.755
1692.942    11/08/0'

Figure 4B

Figure 5

Taxonomy       : Eukaryota (eucaryotes) (150050 sequences)
Timestamp      : 4 Mar 2006 at 20:47:45 GMT
Top Score      : 81 for P15516-00-01-00, (HIS3_HUMAN)

Splice isoform Displayed

Probability Based Mowse Score

Protein score is -10*Log(P), where P is the probability that the observed match
Protein scores greater than 64 are significant (p<0.05).

is a random event

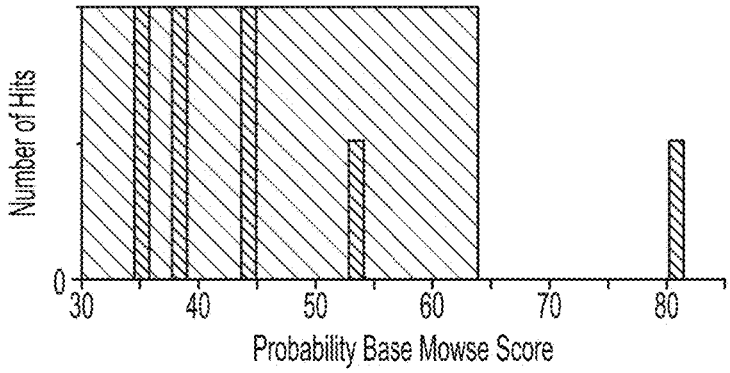

P15516-00-01-00   Mass: 5449   Score: 81   Expect: 0.0012   Queries matc
(HIS3_HUMAN) Splice isoform Displayed: Variant histatin-3-2; Conflict Displ
P15516-00-01-00   Mass: 6145   Score: 80   Expect: 0.0017   Queries matc
(HIS3_HUMAN) Splice isoform Displayed: VariantDisplayed; Conflict Display Match to: P15516-00-01-00 Score: 81 expert: 0.0012
(HIS3_HUMAN) Splice isoform Displayed: Variant histatin-3-2; Conflict Displayed:

Nominal mass ($M_r$): 5449; Calculated pI value: 10.38
NCBI BLAST search of P15516-00-01-00 against nr
Unformatted sequence string for pasting into other applications Taxonomy: Homo sapiens
Cleavage by Trypsin: cure C-term side of KR unless next residue is P
Sequence Coerage: 52%
Matched peptides shown in Bold Red

1 MKFFFALIL ALMLSMTGAD SHAKRHHGYK RKFHEKHHSH QGYRSN   SEQ ID NO: 348

[ Show predicted peptides also ]

[ Sort Peptides By ]   ● Residue Number   ○ Increasing Mass   ○ Decreasing Mass

| Start - End | Observed | Mr(expt) | Mr(calc) | Delta | Miss | Sequence |
|---|---|---|---|---|---|---|
| 2 - 24 | 2511.3740 | 2510.3667 | 2510.3428 | 0.0239 | 1 | M.KFFVFALILAIML |
| 3 - 24 | 2383.2600 | 2382.2527 | 2382.2479 | 0.0048 | 0 | K.FFVFALILAIMLS |
| 3 - 25 | 2539.3280 | 2538.3207 | 2538.3490 | -0.0283 | 1 | K.FFVFALILAIMLS |

Figure 6

A1S1 M13 rev   SEQ ID N" 217
NNNNNNNNNNTNTANGNGANNATAGANACTCAAGCTATGCATCCAACGCGTTGGGAGCTCTCCCATATGG
TCGACCTGCAGGCGGCCGCGAATTCACTAGTGATTTCCTATGCTTGACTATTAGCCTTTCAGTGAGAGCA
GTTGCTCAGAGTTGAGGACACTCGGAACAACCATCAACTGTCAATTAAGAAACATGGCAAATTATTTCAG
TGGTTTTCCCTGGCTCTTGCTGAGTTTATTACCACAATGCTCAGTTGTTGTTTACTTAGGGAATCAATGC
CAAGTTTGAAGTGACTGAAGAACCAGCCTGTATGAACAGTCCATGTGGAAGAGCTACGTGTGAGAGTATT
TTCAGAGAAGCTGAGAAAACGCTAAATGAGTACAGCCTAAACTGGAATATGCTAGGCAGTGTTACAACTG
ATGGTGGTAAAAATGCGCCGAACAGAAAGGGGGTCAAACATGCAAAACCTGTGTAAGGGTTACTCACTGC
ATTACTCATGAGCATGTACCTTGTGGGAAACACATGAATCTATTGTGCTCATGAACGAGTAATGTCAGTG
ATGAATTTAACACGCTCCTGTGAACCTGACCATCAGCAGGTCATGAGTTTCTGTCAGAAACAAAAAGTGA
AAATTCTGACACACTTCGATGTCTTAGCAGCGCTAAAGTTTTACTGACTTTTTTCTGAGCACAGGGATGG
AACTGATTTCTTTTCCTGAACAAGAACTACCCTTAACCACTATTGTTGAACGCTGAATGGNTTCGGAAAT
TAGCCTTNGGGCAGACTTGATTTGATTTCTGAATGAATTCAACCTAAAATTACAAGGCAAACGNACTNNN
NNAAACTTACACTCTGGNAAAGTCATTTCGACAGCTAGCATANTTTTTAANCAAAANNATGTCNNACNGN
NTTTNANNNNANN >AGENCOURT_15165417
GGCAGCTGGGTTGCATGGAGAGGTCCAGGAGGGACCGGAGGTGTGACAGATACTGTGAGC
GGCAGCTGGGTTGCATGGAGAGGTCCAGGAGGGACCGGAGGTGTGACAGATACTGTGAGC
CCGGCGGGCCGCGCCTGGCTGGGTGCCTCGGTACTTGAATTCTGTCTTGTTTTCCGCATT
GTGTCTGTCCACCCGAGTTCTCTGTCGTCACTTAACTTTGCATTGGATTTGGTTGTTGTA
CTTTGCCCCTGAATGTGGACAAAGCTGTGGGCAAGAGGTCAGCAGGACCCGCCTGGGGGT
GCCGGCGTTGGTGACTGCGGGTCGGGCTCCTAGAACATAGGAGCCGGCTGCCTGGCCTC
CTTTCTCCTCCAGGAAGAGTCATTCTTTGGCATTTGTGTTTAGAGCCAGGAGGAAGGCGG
AAGGTAGGGAGGGAGGGCTGGTCCCCCTCTGAGGGGGCTCTAGTGCCTGACCCTGACCTG
TCCTCATTCGACAGCTGAAACTGTTAAGCGCTGGCCCAGTCCCCCCACCCCACCCAGCCG
TGTACTGCCTGGGCTCCCCTCAAAGGGAAATTTTTACGGAAACATCTTGGCAGCAAGTGG
AAAAAGATCTATGGCCCATGAACCAACTGAAAACTCCAAGAACCCTCTGTCTGCCTCTGC
CAGCAGCGAGTCCTAAGCGCAGAATCCAGAGCTCGTAGCTGTCCTCAGCTGTAACTACTG
TTTCAGAATGTTGCTGCTGCATACATTTGTCATGTCAGCCAGCCAGCTCCGTGGGTGAAA
GTGTGCGTGTGCGCGTGTCTGTGTGTGTGCGTGTCTGTGTGTGCACGTCTGTGCGT
GCGCGTCCGTGCATGTGTGTGTCTGTGCGTGTGTGCGTCCGTGTGTGTGCGTCTGTGTGC
GCGTGTGTGTCCCCCTTCTGTATGTGTGCACGCCGCGTC

Figure 7B

Quality control of the RNA extractions performed on three cell pellets of the SH-SY5Y cell line.

| Sample ID | PCR T° | Sense/ Antisense |
|---|---|---|
| 4* | | BV1/hA2 |
| 8* | | avsplic/GDBR1 |
| 7'8* | | avsplic/GDBR1 |
| 9* | 55°C | Hsplic (A1)/GDBR1 |
| 22* | | hA2/GDBR1 |
| 23* | | A2/GDBR1 |
| 24* | | hA2/Splic |
| 25* | | A2/splic |
| 26* | | BV3/hA2 |
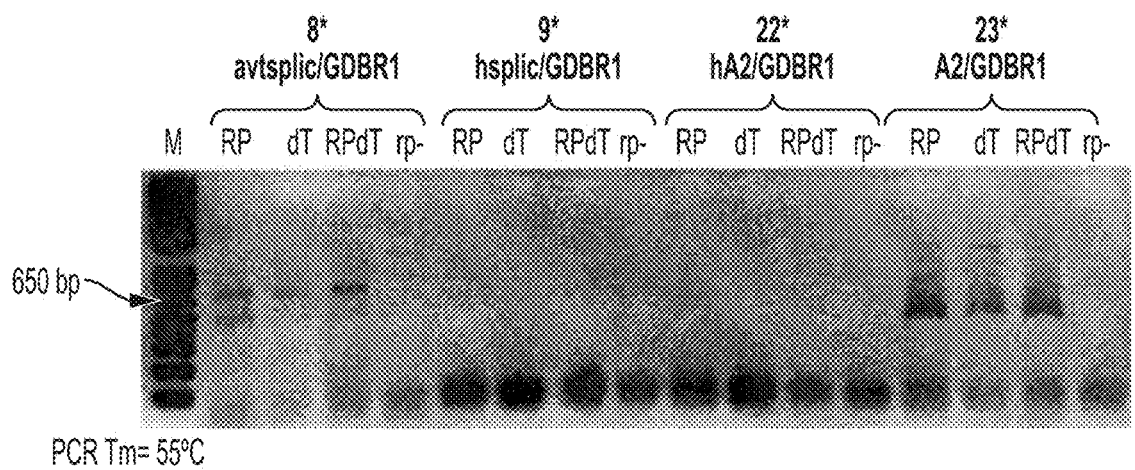
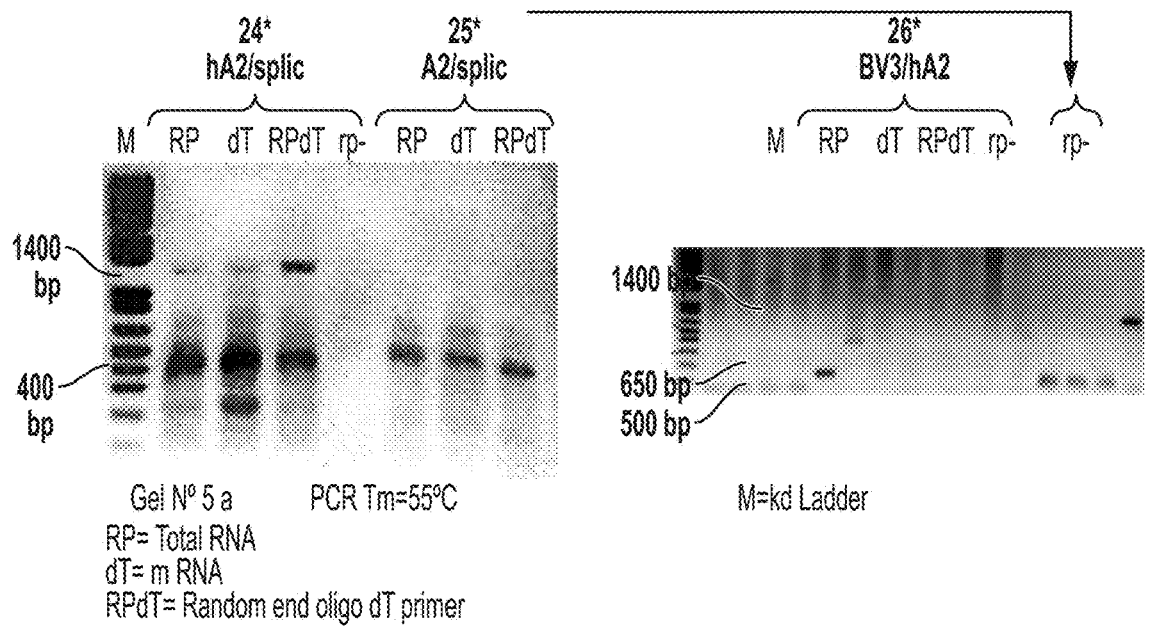
Gel N° 5 a   PCR Tm=55°C
RP= Total RNA
dT= m RNA
RPdT= Random end oligo dT primer
M=kd Ladder
Figure 10

| N° | Primers pairs Sense/Antisense | Tm PCR | Fragments | | | | |
|---|---|---|---|---|---|---|---|
| 4* | BV1/hA2 | 55°C | 850 bp 400 bp 850 bp 400 bp | 4* | BV1/hA2 | 55°C | 650 bp 650 bp |
| 8* | avsplic/GDRB1 | 55°C | 850 bp | 25* | A2/splic | 55°C | / |
| 23* | A2/GDBR1 | 55°C | 650 bp | 26* | BV3/hA2 | 55°C | 1400 bp |
| 24* | hA2/Splic | 55°C | 1400 bp 400 bp 200 bp | 9* | hsplic/GDBR1 | 55°C | / |
| 25 | A2/splic | 55°C | 400 bp | 22* | hA2/GDBR1 | 55°C | / |
| 26* | BV3/hA2 | 55°C | 1400 bp 650 bp 500 bp 300 bp | 23* | A2/GDBR1 | 55°C | / |
| 4* | BV1/hA2 | 55°C | 650 bp 650 bp | 24* | hA2/Splic | 55°C | 500 bp |

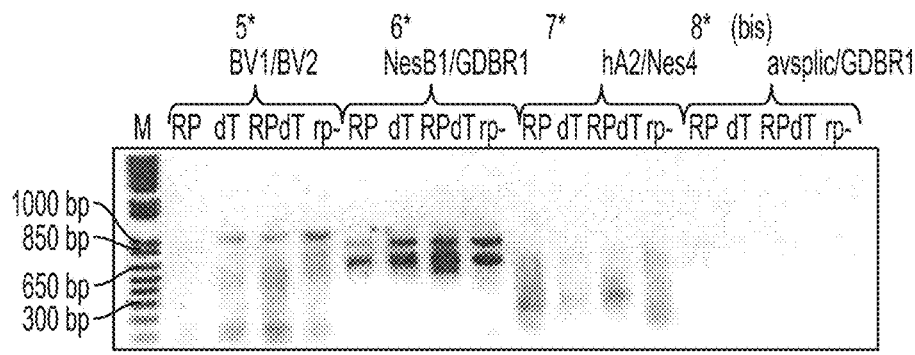

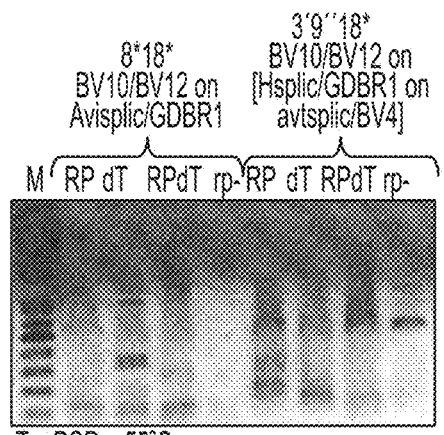

Tm PCR = 55°C

| Primer pairs for PCR | | | Results |
|---|---|---|---|
| N° | Sense/Antisense | Tm PCR | Fragments |
| 8*18* | BV10/BV12 on Avtsplic/GDBR1 | 55°C | 1500 bp 1000 bp 400 bp 300 bp |
| 3'9"18* | BV10/BV12 on [Hsplic/GDBR1 on avtsplic/BV4] | | 650 bp 200 bp |

Figure 11A

| Cell compartment/marker | cytoplasm | nuclei |
|---|---|---|
| LIV21 | | ae |
| RB2 | - | ae |
| PKCa | a | |
| HDAC1 | - | ae |
| E2F4 | a | ae |
| BCAS4 | - | a |
| UV21P | a | ae |
| control | | |

Cell culture or pathological fluid

| Cell compartment/marker | cytoplasm | nuclei |
|---|---|---|
| LIV 21 | ae | a |
| RB2 | - | a |
| PKCa | ae | |
| HDAC1 | - | a |
| E2F4 | ae | a |
| BCAS4 | - | ae |
| UV21P | ae | a |
| control | | |

Cell culture or fluid of the safe subject

Legend:

| a = + = overexpression | - = TRIVIAL AMOUNT |
|---|---|
| ae = under-expression | OR NOT SIGNIFICANT |

Figure 12

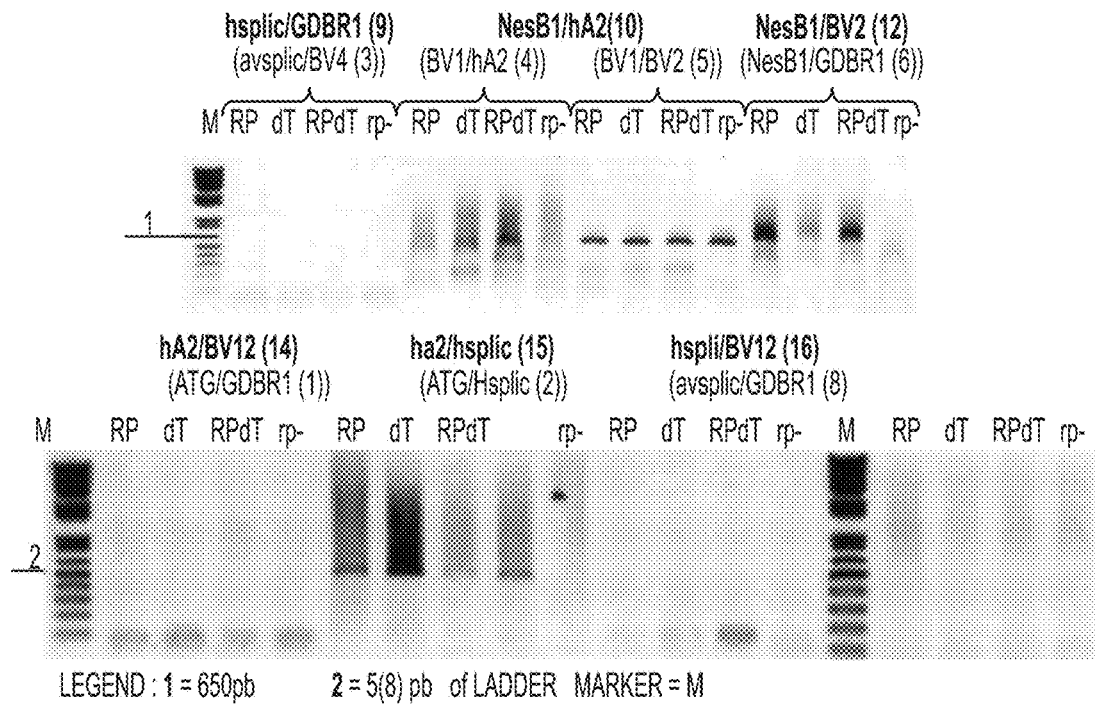
| Sample ID | PCR T° | Primer pairs for Nested PCR Sense/antisense | | cDNA obtained with primer pairs below Sense/antisense on Sense/antisense | N° |
|---|---|---|---|---|---|
| 7'9 | 55°C | Hsplic/GDBR1 | 9 | hA2/Nes4 | 7 |
| 1'17 | 55°C | Avtsplic/BV12 | 17 | (BV3=ATG) ATG/GDBR1 | 1 |
| 7'13"19 | 55°C | Hsplic/BV9 | 19 | hA2/BV12 on BV3=ATG/GDBR1 | 1'14 |
| 8'16"20 | 55°C | Hsplic/BV2 | 20 | Avsplic/BV10 on hA2/Nes4 | 7'13 |
| | | | | Hsplic/BV12 on Avsplic/GDNR1 | 8'16 |
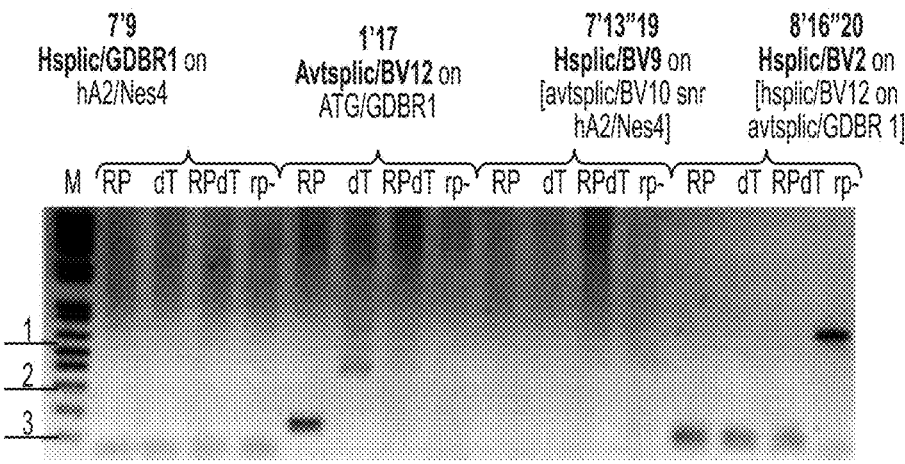
Figure 13

| Primers for PCR | | | Primers for PCR | | |
|---|---|---|---|---|---|
| SEQ ID N° | Sens | Antisens | Sens | Antisens | SEQ ID N° |
| 128 | A1 = BV1 |  | NesB1 |  | 136 |
| 129 |  | BV2 AS |  | SPLIC AS | 137 |
| 130 | ATG = BV3 |  | AVANTSPLIC |  | 138 |
| 131 |  | BV4 AS | HUMANSPLIC |  | 139 |
| 132 | A2 S |  |  | HUMANSPLIC | 140 |
| 133 |  | A2 AS | HUM A2 S |  | 141 |
| 134 | GDBR1 S |  |  | HUM A2 AS | 142 |
| 135 |  | NES 4 AS |  | GDBR1 AS | 154 |
| 151 | BV12 S |  | AVANTBV1 S |  | 155 |
| 152 |  | BV12 AS | BV8S |  | 210 |
| 153 | BV10 S |  | BV7S |  | 211 |
| 209 | BV9 S |  | BV6 S |  | 212 |

S55T and S55M recombinant clones
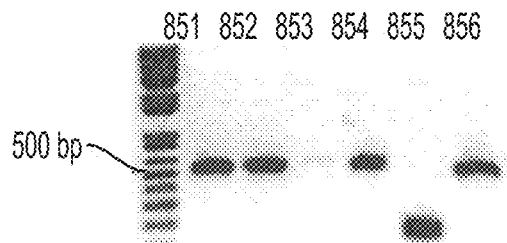
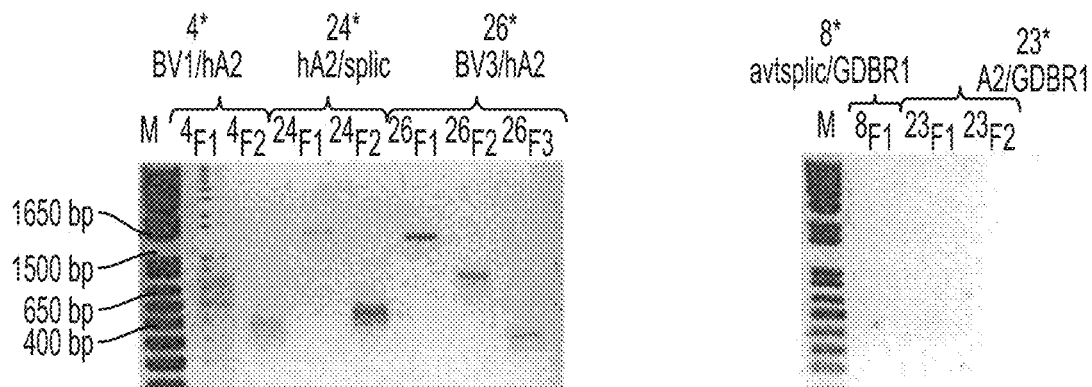
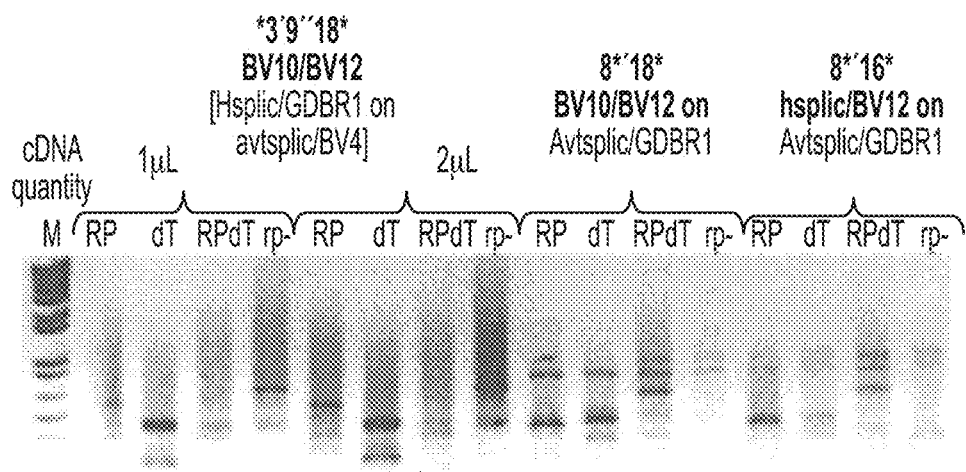
Tm PCR = 55°C
FIGURE 17

A1S6 M13 rev
NNNNNNNNNNTNTANGNGANNATAGANACTCAAGCTATGCATCCAACGCGTTGGGAGCTCTCCCATAT
GGTCGACCTGCAGGCGGCCGCGAATTCACTAGTGATTTCCTATGCTTGACTATTAGCCTTTCAGTGAG
AGCAGTTGCTCAGAGTTGAGGACACTCGGAACAACCATCAACTGTCAATTAAGAAACATGGCAAATTA
TTTCAGTGGTTTTCCCTGGCTCTTGCTGAGTTTATTACCACAATGCTCAGTTGTTGTTTACTTAGGGA
ATCAATGCCAAGTTTGAAGTGACTGAAGAACCAGCCTGTATGAACAGTCCATGTGGAAGAGCTACGTG
TGAGAGTATTTTCAGAGAAGCTGAGAAAACGCTAAATGAGTACAGCCTAAACTGGAATATGCTAGGCA
GTGTTACAACTGATGGTGGTAAAAATGCGCGGAACAGAAAGGGGGTCAAACATGCAAAACCTGTGTAA
GGGTTACTCACTGCATTACTCATGAGCATGTACCTTGTGGGAAACACATGAATCTATTGTGCTCATGA
ACGAGTAATGTCAGTGATGAATTTAACACGCTCCTGTGAACCTGACCATCAGCAGGTCATGAGTTTCT
GTCAGAAACAAAAAGTGAAAATTCTGACACAGTTCGATGTCTTAGCAGCGCTAAAGTTTTACTGACTT
TTTTCTGAGCACAGGGATGGAACTGATTTCTTTTCCTGAACAAGAACTACCCTTAACCACTATTGTTG
AACGCTGAATGGNTTCGGAAATTAGCCTTNGGGCAGACTTGATTTGATTTCTGAATGAATTCAACCTA
AAATTACAAGGCAAACGNACTNNNNNAAAACTTACACTCTGGNAAAGTCATTTCGACAGCTAGCATANT
TTTTAANCAAAANNATGTCNAACNGNNTTTNANNNNANN Blast A1 S6 T7
>gi|22213386|gb|AC037487.12|     Homo sapiens chromosome 17, clone RP11-583F2
complete sequence
Length = 176807
Score = 1572 bits (793), Expect = 0.0
Identities = 813/820 (99%), Gaps = 0/820 (0%)
Strand = Plus/Plus Query  63     TTAGCATGTCATTACATTGCAGATTAACCACTTGAAGGTTAGGTAGAAGCTCTTCACTTG    122
              |||||||||||||||||||||||||||||||||||||||||||||||||||||||| |||
Sbjct  37052  TTAGCATGTCATTACATTGCAGATTAACCACTTGAAGGTTAGGTAGAAGCTCTTCATTTG   37111

Query  123    CGTAGTTAAAAGGATTTTGAAATATGGAAATTTCCTTTGCACTTACATAGGGGTCTGAAA    182
              ||||||||||  ||||||||||||||||||||||||||||||||||||||||||||||||
Sbjct  37112  CGTAGTTAAATGGATTTTGAAATATGGAAATTTCCTTTGCACTTACATAGGGGTCTGAAA   37171

Query  163    GATGCTGTTGGAACTGTAGTTAGAGTTTAGAAATATTATGTCCACTGGGAATTTGTATGG    242
              ||||||||||||||||||||||||||||||||||||||||||||||||| ||||||||||
Sbjct  37172  GATGCTGTTGGAACTGTAGTTAGAGTTTAGAAATATTATGTCCACTGGAAATTTGTATGG   37233

Query  243    GAATGGAAGTCTCACTTTTTGTTTTAACTTTTGACAGCAAAGAAAGTATATAAAGCAGTT    302
              ||| ||||||||||||||||||||||||||||||||||||||||||||||||||||||||
Sbjct  37233  GAATGAAAGTCTCACTTTTTGTTTTAACTTTTGACAGCAAAGAAAGTATATAAAGCAGTT   37291

Query  303    TGACATTGTTTTGATTAAAACTATGCTAGCTGTCGAAATGACTTTACCAGAGTGTAAGTT    362
              ||||||||||||||||||||||||||||||||||||||||||||||||||||||||||||
Sbjct  37292  TGACATTGTTTTGATTAAAACTATGCTAGCTGTCGAAATGACTTTACCAGAGTGTAAGTT   37581

Query  363    TCACCAACAGTGCCGTTTTGCCTTGTAATTTTAGGTTGAATTCATTCAGAAATCAAATCA    422
              ||||||||||||||||||||||||||||||||||||||||||||||||||||||||||||
Sbjct  37362  TCACCAACAGTGCCGTTTTGCCTTGTAATTTTAGGTTGAATTCATTCAGAAATCAAATCA   37411

Query  423    AGTCTGCCCTAAGGCTAATTTCCGAAACCATTCAGCGTTCAACAATAGTGGTTAAGGGTA    482
              ||||||||||||||||||||||||||||||||||||||||||||||||||||||||||||
Sbjct  37412  AGTCTGCCCTAAGGCTAATTTCCGAAACCATTCAGCGTTCAACAATAGTGGTTAAGGGTA   37471

Query  463    GTTCTTGTTCAGGAAAGAAATCAGTTCCATCCCTGTGCTCAGAAAAAGTCAGTAAAAC     542
              ||||||||||||||||||||||||||||||||||||||||||||||||||||||||||
Sbjct  37472  GTTCTTGTTCAGGAAAGAAATCAGTTCCATCCCTGTGCTCAGAAAAAGTCAGTAAAAC    37531

Query  543    TTTAGCGCTGCTAAGACATCGAACTGTGTCAGAATTTTCACTTTTTGTTTCTGACAGAAA    662
              ||||||||||||||||||||||||||||||||||||||||||||||||||||||||||||
Sbjct  37532  TTTAGCGCTGCTAAGACATCGAACTGTGTCAGAATTTTCACTTTTTGTTTCTGACAGAAA   37591

Query  603    CTCATGACCTGCTGATGGTCAGGTTCACAGGAGCGTGTTAAATTCATCACTGACATTACT    662
              ||||||||||||||||||||||||||||||||||||||||||||||||||||||||||||

Figure 18

| | | | |
|---|---|---|---|
| GGGAGUAGCCCAAGAAUCAUUC_{AA} | SEQ ID NO: 348 | GCUACCUUACCUUUGGCAUUC_{AA} | SEQ ID NO: 365 |
| UUCCCUCAUCGGGUUCUAGUAG^{AG} | SEQ ID NO: 69 | UUCGAUGGAAUGGAAACGUAG^{AG} | SEQ ID NO: 86 |
| GUUGGAGCUCUCCCAUAUUC_{AA} | SEQ ID NO: 349 | GCCGCGAAUUCACUAGUGAUUC_{AA} | SEQ ID NO: 357 |
| UUCAACCCUCGAGAGGGUAUAAG^{AG} | SEQ ID NO: 70 | UUCGGCGCUUAAGUGAUCACUAG^{AG} | SEQ ID NO: 78 |
| GGGCAAGACUCUGUCUCAAUUC_{AA} | SEQ ID NO: 350 | GGGAGCUCUCCCAUAUGGUUUC_{AA} | SEQ ID NO: 358 |
| UUCCCGUUCUGAGACAGAGUUAG^{AG} | SEQ ID NO: 71 | UUCCCUCGAGAGGGUAUACCAAG^{AG} | SEQ ID NO: 79 |
| GGUUAAGCUGAGAUCUGAAUUC_{AA} | SEQ ID NO: 351 | GCCUGGCCAACAUGGCAAAUUC_{AA} | SEQ ID NO: 359 |
| UUCCAAUUCGACUCUAGACUUAG^{AG} | SEQ ID NO: 72 | UUCGGACCGGUUGUACCGUUUAG^{AG} | SEQ ID NO: 80 |
| GAGUAGCCCAAGAAUCACUUUC_{AA} | SEQ ID NO: 352 | GGUAACAGGGCAAGACUCUUUC_{AA} | SEQ ID NO: 360 |
| UUCUCAUCGGGUUCUUAGUGAAG^{AG-} | SEQ ID NO: 73 | UUCCAUUGUCCCGUUCUGAGAAG^{AG} | SEQ ID NO: 81 |
| GUGAGCCAAGACCACAUGAUUC_{AA} | SEQ ID NO: 353 | GCCCGUAAUCCCAGCUACUUUC_{AA} | SEQ ID NO: 361 |
| UUCACUCGGUUCUGGUGUAGUAG^{AG} | SEQ ID NO: 74 | UUCGGGCAUUAGGGUCGAUGAAG^{AG} | SEQ ID NO: 82 |
| GAUGGUUAAGCUGAGAUCUUUC_{AA} | SEQ ID NO: 354 | GGCCAGGAGUUCAAGACCAUUC_{AA} | SEQ ID NO: 362 |
| UUCUACCAAUUCGACUCUAGAAG^{AG} | SEQ ID NO: 75 | UUCCGGUCCUCAAGUUCUGGUAG_{AG} | SEQ ID NO: 83 |
| GUGAUGGUUAAGCUGAGAUUUC_{AA} | SEQ ID NO: 355 | GAAGUGAUGGUUAAGCUGAUUC_{AA} | SEQ ID NO: 363 |
| UUCACUACCAAUUCGACUCUAAG^{AG} | SEQ ID NO: 76 | UUCUUCACUACCAAUUCGACUAG^{AG} | SEQ ID NO: 84 |
| GGCGGCCGCUAAUUCACUAUUC_{AA} | SEQ ID NO: 356 | GCACACGCCCGUAAUCCCAUUC_{AA} | SEQ ID NO: 364 |
| UUCCGCCGGCGCUUAAGUGAUAG^{AG} | SEQ ID NO: 77 | UUCGUGUGCGGGCAUUAGGGUAG^{AG} | SEQ ID NO: 85 |

Figure 19A

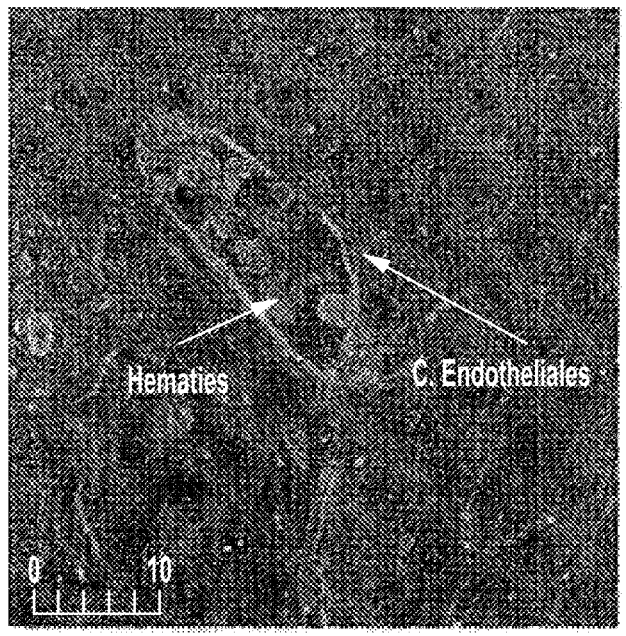
LEGEND:
Hèmaties = Erythrocytes
Canaux galactophores = Ducts
C. Endothéliales =
        Endothelial cells
L1-a5     green = alexa
              Red = propidium
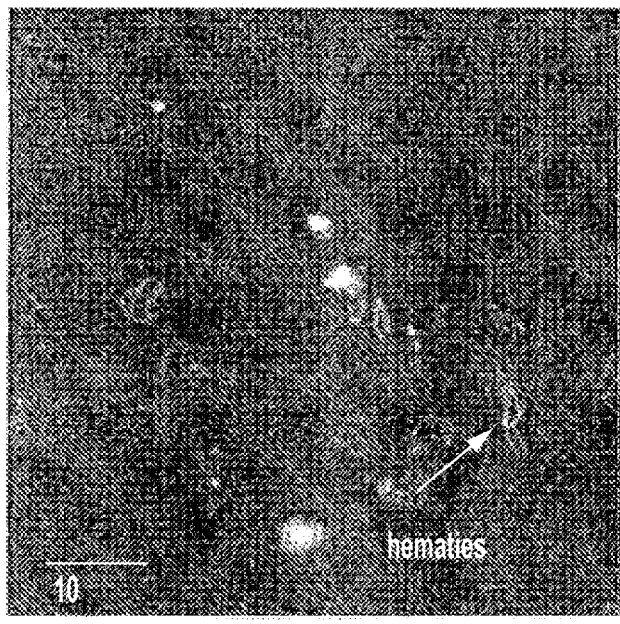 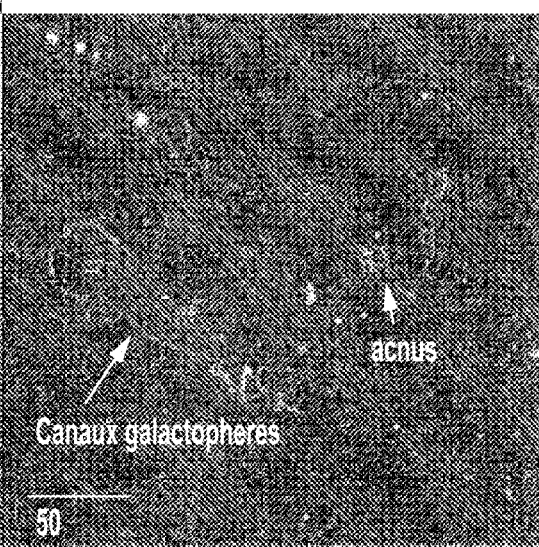
LAMET-A1   ALEXA   L1A6 ALEXA
CONFOCAL MICROSCOPY REVEALED A MARKER OF LIV21 (LIV21H)
IN BREAST TISSUE CELLS IN WOMEN
Figure 19B Aurora A, Survlvine, BCAS4, BCAS3, Receptor FSH hCG1814693 [Homo sapiens] 350 350 100% 5e-95 BAC85767.1

EAW88192.1 hCG1814693 [Homo sapiens] Length = 175 Score = 350 bits (897),
Expect = 5e-95, Method: Compositional matrix adjust Identities 175/175 (100%),
Positives = 175/175 (100%), Gaps = 0/175 (0%) Query 1
MCVSVRVCVCVCASVCACVCASVCMCARASVCTCVSLHACLCMCARVCLC
VCTRVHVTTG  60

PHARMACO DIAGNOSIS BIOCHIP

EXAMPLE OF 16 BIOMARKERS ON BIOCHIP (PAGE 41)

SiRNA SEQ NO 150 and SEQ NO 173 (SEQ NO 91 to 118)
SiRNA SEQ NO 150 and SEQ NO 173 (SEQ NO 91 to 118)
SiRNA SEQ NO 150 and SEQ NO 173 (SEQ NO 91 to 118)

| BIOCHIP | 20 SPOTS | EXAMPLE 5.2 |
|---|---|---|
| DKK1 |  | |
| CRABPII |  | |
| MYCN |  | |
| ALK |  | 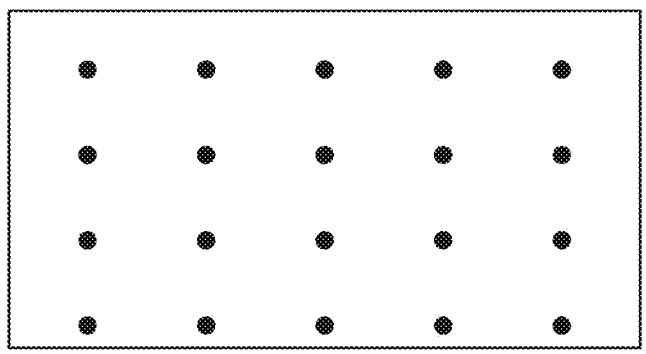 |
| NLRR1 |  | |
| DDX1 |  | |
| Liv21K |  | |
| P21 |  | |
| ID2 |  | ⬈ OVER EXPRESSION OF BIOMARKER |
| SKP2 |  | ⬊ UNDER EXPRESSION OF BIOMARKER |

Figure 20A

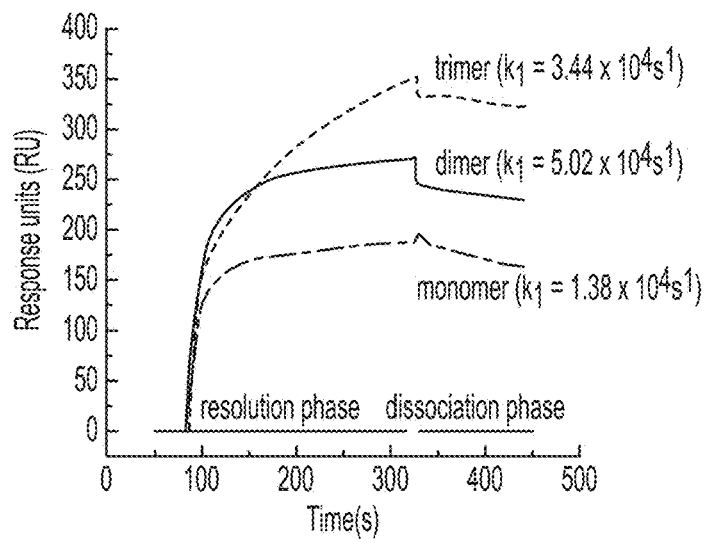
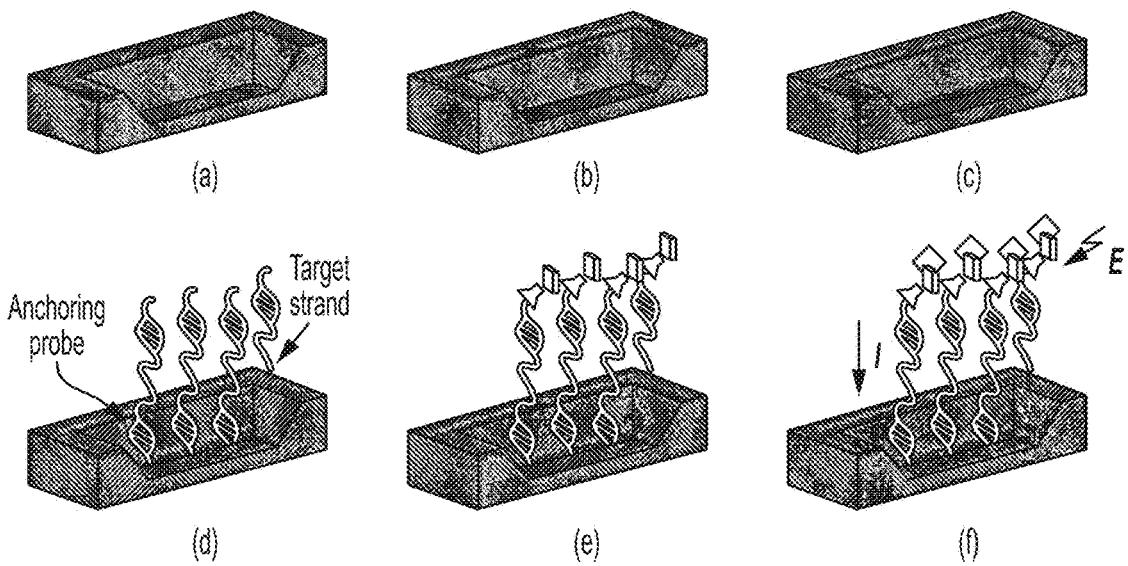
SENSOR BIOCHIP
PROBE N° 1 = Control
PROBE N° 2 = CRABPII (overexpressed = OE)
PROBE N° 3 = INP1 underexpressed (UE)
PROBE N° 4 = DDX1 (OE)
SECOND SENSORBIOCHIP:
PROBE N° 1 = MYC N (OE)
PROBE N° 2 = HUD (UE)
PROBE N° 3 = P21 (UE)
PROBE N° 4 = TP 53 (UE)
Figure 21

SPR BIOCHIP MICROFLUIDIC CHANNELS

20 SPOTS: BIOMARKERS:
Underexpression DKK 1, SKP2, DKK3., 1D2, p21, SKP2, TP531NP1, ID2, P73 is observed whereas an on-expression of MYC N, ALK, NLRR1(the leucine rich neuronal repeat is transactivated), CRABPII DDX1, .LIV21K, AURORA. kinase A.

Biochip with RNA and MicroRNA

| | |
|---|---|
| GGAAUCUCCUACAUUGCCUUUCAA | SEQ ID NO: 366 |
| UUCCUUAGAGGAUGUAACGGAAGAG | SEQ ID NO: 367 |
| GACUCUCAGCUUUAGGUGUUUCAA | SEQ ID NO: 368 |
| UUCUGAGAGUCGAAAUCCACAAGAG | SEQ ID NO: 369 |
| GCUCAUGCCCGUAAUCCCAUUCAA | SEQ ID NO: 370 |
| UUCGAGUACGGGCAUUAGGGUAGAG | SEQ ID NO: 371 |
| GGAAUUGAAUUAAUGGAGUUUCAA | SEQ ID NO: 372 |
| UUCCUUAACUUAAUUACCUCAAGAG | SEQ ID NO: 373 |
| GGCAGGCAGAUCAUGAGGUUUCAA | SEQ ID NO: 374 |
| UUCCGUCCGUCUAGUACUCCAAGAG | SEQ ID NO: 375 |
| GAAUCUCCUACAUUGCCUAUUCAA | SEQ ID NO: 376 |
| UUCUUAGAGGAUGUAACGGAUAGAG | SEQ ID NO: 377 |

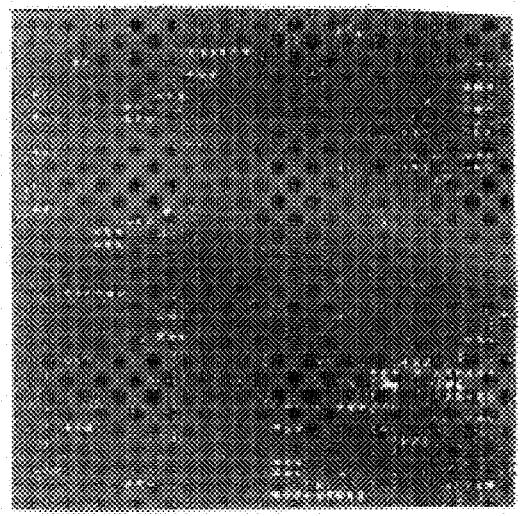

>age-mir-21 MI0002626    SEQ ID N° 214 (SIMILARITY)
UGUCGGGUAGCUUAUCAGACUGAUGUUGACUGUUGAAUCUCAUGGCAACACCAGUCGAUGGGCUGUCUGACA

Figure 23A

>dre-miR-21 MIMAT0001787    SEQ ID No. 281
UAGCUUAUCAGACUGGUGUUGGC
Scaffoid99
>fru-miR-21 MI0003325    SEQ ID No. 282
UGUCAAAUAGCUUAUCAGACUGGUGUUGGCUGUUAAGAUUGCAAGGCCACAAACAGUCUGUAGGCUGUCUGACA
>fru-miR-21 MIMAT0002999    SEQ ID No. 283
UAGCUUAUCAGACUGGUGUUGGC
>gga-miR-21 MI0004994    SEQ ID No. 284
UGUACCAUUCCUGUCCGGAUAGCUUAUCAGACUGAGGUUGUCGGGAUCUCAUGGCAACAACAGUCGGUAGGCUG
UCUGACAUUUUGGUAUCDCUCA
>gga-miR-21 MIMAT0003774    SEQ ID No. 285
UAGCUUAUCAGACUGAUGUUGA
>ggo-mir-21 MI0002623    SEQ ID No. 286
UGUCGGGUAGCUUAUCAGACUGAUGUUGACUGUUGAAUCUCAUGGCAACACCAGUCGAUGGGCUGUCUGACA
>ggo-miR-21 MIMAT0002322    SEQ ID No. 287
UAGCUUAUCAGACUGAUGUUGA
>mdo-mir-21 MI0005275    SEQ ID No. 288
UGUCGGAUAGCUUAUCAGACUGAUGUUGACUGUUGAAUCUCAUGGCAACAGGAGUCGAUGAGCUGUCUGACAUU
>mdo-miR-21 MIMAT0004091
UAGCUUAUCAGACUGAUGUUGA
>mml-mir-21 MI0002621
UGUACGGGUAGCUUAUCAGACUGAUGUUGACUGUUGAAUCUCAUGGCAACACCAGUCGAUGGGCUGUCUGACA
>mml-miR-21 MIMAT0002820
UAGCUUAUCAGACUGAUGUUGA
>mml-mir-21 MI0000569
UGUACCACCUGUCCGGAUAGCUUAUCAGACUGAUGUUGACUGUUGAAUCUCAUGGCAACAGCAGUCGAUGGCUG
UCUGACAUUUUGGUAUC
>mml-miR-21 MIMAT0000530
UAGCUUAUCAGACUGAUGUUGA
>mmm-miR-21 MIMAT0004628
CAACAGCAGUCGAUGGGCUGUC
>mna-mir-21 MI0002625
UGUCGGGUAGCUUAUCAGACUGAUGUUGACUGUUGAAUCUCAUGGCAACACCAGUCGAUGGGCUGUCUGACA Figure 23B
Example No. 8

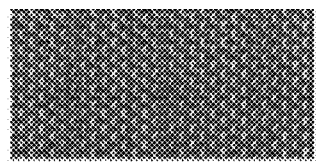 PROBES: SEQ ID N° 128 to 144 and 151 to 155 and SEq ID N° 209 to 212
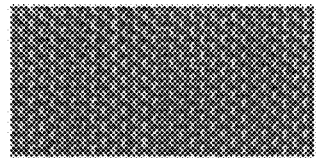 PROBES: SEQ ID N° 119 to 122 and 173 to 177
Each DNA spot contains picomoles ($10^{-12}$ moles) of a specific DNA sequence, known as probes
Figure 24

TREATMENT TARGETING ONCOLOGY AND NEURODEGENERATION

CROSS REFERENCE TO RELATED APPLICATION

This application is a continuation of U.S. patent application Ser. No. 13/681,164 filed on Nov. 19, 2012, which is a continuation in part application of U.S. patent application Ser. No. 12/282,117 filed on Sep. 8, 2008 and which is also a continuation in part application of International Patent Application Serial No. PCT/FR2011/000155 filed on Mar. 18, 2011.

The Sequence Listing in ASCII text file format of 149,705 bytes in size, created on Jun. 28, 2018, with the file name "2018-06-28SequenceListing-FAURE3B," filed in the U.S. Patent and Trademark Office on Jun. 28, 2018, is hereby incorporated herein by reference.

FIELD OF THE INVENTION

The present invention relates to the field of medicine and biology. It concerns a new test for screening and therapeutic follow-up in oncology. More particularly, it relates to diagnostic and/or therapeutic tests in oncology and on neurodegenerative diseases. Molecular targeting by peptide vectors and antibodies or by small interfering RNAs (siRNAs) opens a new concept of interdependence for diagnostic and therapeutic tools.

The inventor highlights the mechanisms of molecular interactions and the interest of biochips dedicated according to cancers with a multi-therapy added with therapeutic additives to slow down the formation of these lesions.

The comprehension of the plays of balance between under-expression and over-expression of genes according to their localization in a cellular compartment allows to open a field of finer differential analysis and to adapt a multi-therapy with siRNA and peptides by molecular targeting.

DESCRIPTION OF THE STATE OF THE ART

Age-related neurodegenerative diseases and cancers both involve a modification of the physiological process of programmed cell death or apoptosis. Neuronal death is abnormally accelerated during neurodegenerative diseases such as Alzheimer's disease, Huntington's disease, Parkinson's disease etc. . . . On the other hand, the cancerization process corresponds to a blocking of apoptosis, which results in an uncontrolled multiplication of cells. The link between these two processes has currently become a major field of investigation in research on aging. The control of the balance between cell division (mitosis), differentiation and programmed cell death (apoptosis), is fundamental during normal physiological processes, including embryonic development, tissue regeneration and aging. An impairment of this balance can lead to major pathological situations such as the formation of tumors or some neurodegenerative diseases.

Cancer is one of the principal causes of mortality throughout the world. While, over the course of the last generation, the percentages of deaths related to cardiac and cardiovascular diseases and a large number of other diseases has decreased, the number of deaths related to the various forms of cancer has increased.

Despite the rapid advance in our understanding of the various forms of cancer, the low survival rates can generally be attributed to inadequate diagnosis and inadequate treatment. Most tumors can only be detected when they reach a size of approximately 1 cm. Since a continuously developing tumor takes a relatively short period of time to evolve to a stage which is incompatible with survival, this leaves little time for a therapeutic intervention. Early diagnosis therefore becomes the key to success for the treatment of cancer. Skin cancer for example, is the most widespread cancer in Canada. In 1992 alone, 50 300 new cases of skin cancer were reported, compared with 19 300 cases of lung cancer, 16 200 cases of colorectal cancer and 15 700 cases of breast cancer. In other words, skin cancer is as common as the three main types of cancer combined. Its incidence continues to increase, with 64 200 new cases thereof in 1997, corresponding to an increase of 14 000 cases in 5 years. In particular, the incidence of malignant melanoma is increasing at a rate of 2% per year. Early diagnosis remains the key to an effective treatment. A malignant tumor is readily accessible and can be removed with minor surgery. In fact, recovery is 100% if skin cancer is detected early enough. Early diagnosis of skin cancer remains however difficult . . . . . It thus becomes important to be able to distinguish these two types of skin cancers. A final diagnosis of skin cancer requires a biopsy and a histological analysis. However, the decision to send a biopsy for analysis (or even if a patient must be referred with a dermatologist) becomes very subjective. There are several biopsies which are not taken whereas they would have being.

Colon cancer is the third most common cause of cancer-related mortality in men and women in North America (16 200 cases per year). Early detection, leading to an early intervention, has demonstrated that treatment success and survival rate can be improved. For example, the 5-year survival rate is 92% for a patient whose disease was detected at an early stage, whereas the rate drops to approximately 60% in patients with a localized cancer, and to approximately 6% in those with metastases. However, only a third of colon cancers are detected at an early stage. One of the reasons for this delay in diagnosis is the absence of a sensitive, relatively inexpensive and non-invasive screening test. Breast cancer is one of the most common cancers in women, together with colon cancer. The mortality rate is the highest among cancers affecting women. There are very few diagnostic markers allowing the detection of breast cancer and they only have a predictive value of 20%, There are no markers, either, which can detect or determine the invasiveness or the aggressiveness of metastatic cancer cells or which permit therapeutic monitoring.

For a multitude of reasons, early diagnosis remains illusory for most forms of cancer. For certain forms of cancer, disease-specific markers are not available or are only available at an advanced stage of the disease, making diagnosis difficult. In other forms of cancer, the markers are available but are not always specific for the disease or they may be associated with its benign form.

A hope this year with the marker who is the receiver with the FSH is possible. As one of our markers of the LIV21 complex (cf. figure) it is common to several cancers and allows an early diagnosis, it also appears in the vessels as ours which one can see in Alexa revealed on the level of the endothelial cells, but in more we observe a marking of the erythrocytes and also collagen. During the last years, considerable progresses were made in the comprehension of the means implemented by the oncogenes and tumor suppressor genes to control cell proliferation and the apoptosis. One of the main targets of these regulators is the family of E2F-type transcription factors in the E2F and RB protein signaling pathway.

In other cases still, the techniques exist but the prohibitory cost to in general implement them to the population makes them inappropriate.

These cancers may find it beneficial to be studied and diagnosed by biochip including the bio-markers of the major pathways of regulation to allow an adjustment of the multi-therapy according to the results of under expression and over-expression of genes of the complex Liv21.

Thus the processing by standard molecular targeting siRNA or monoclonal antibodies combined or not with chemical therapeutic assets is of a greater effectiveness.

The neuroblastes are neuronal precursors resulting from the splitting of the neuro-epithelial cells. There are immature embryonic neurons which can still divide contrary to the mature neurons which cannot enter in mitosis.

The neuroblastoma, also called sympathoblastome, is a malignant tumor developed at the expense of the cells of the neural crest, which give rise to the sympathetic nervous system. It is of the solid tumor most frequent in the child (8 to 10% of cancers before 15 years) and in particular about the very young child (average age 4 years with 90% which have less than 5 years). Its incidence is from 1 to 3 cases for 100 000 older children from 0 to 14 years. There are no causes nor of recognized mailmen which support occurred of a neuroblastoma.

The neuroblastoma is discovered starting from symptoms due to the primary neoplasm (mass tumoral, in particular abdominal, or compression of a nearby part, such spinal-cord), to metastases or an endocrine secretion (deterioration of the general state, diarrhea, arterial hypertension . . . ). The neuroblastoma can develop starting from an unspecified component of the system highly-strung person sympathetic nerve, generally at the abdominal level. At the time of the diagnosis, the tumor can be localized on the level of one only part, the local or regional level, or be from the disseminated start. The metastatic sites most frequent are the bone, bone marrow, the liver and the skin. Thus, the majority of the localized tumors have an excellent forecast. It is the same for those of the children of less than one year, independently of the stage of the tumor. Some of these tumors regress even spontaneously. On the contrary, approximately 60% of the children of more than one year forward a metastatic neuroblastoma from the start of poor prognosis.

The variety of the clinical presentation is in relation to the expression of certain biochemical markers and molecular (DNA ploidy, amplification of the oncogene n-myc, Trk receptor expression, loss of the chromosome 1p, excess of the 17q . . . ). Thus, diffuse tumors occurring in the child of more than 1 year and on-expressing the oncogene myc are often chemo-resistant and have a poor prognosis (Berthold and A1, 1990; Schweigerer and A1, 1990). In the same way, the TrkB receptor expression and of BDNF allows a system of survival autocrine neuroblastic cells and induces the neuritic growth. It is also associated with the amplification of N-Myc and thus with a poor prognosis (Nakagawara and A1, 1994). On the contrary, the TrkA receptor expression, which induces the differentiation of the neuroblastoma (Borrello and A1, 1993; Eggert and A1, 2000), and TrkC (Yamashiro and A1, 1996) are rather associated with a good forecast. Thus, it is common to say that the TrkA receptor expression is conversely correlated with the amplification of the oncogene n-myc.

During the development, the gliaux precursors give rise to the astrocytes, oligodendrocytes, microglial cells, choroidal cells and ependymaires cells in the SNC, and with the Schwann cells in the peripheral nervous system. Thus, the cells gliales play a crucial role in differentiation (Lemke, 2001) and the survival of the neurons (Bar, 2000). These cells ensure the nutrition of the neurons, manage connected them inter-neuronal, control the neurotransmitters.

The glioblastomas are the malignant tumors astrocytaires (grade IV according to the classification of the World Health Organization) most undifferentiated of SNC and they are generally found on the level of the cerebral hemispheres. In the adult, they are the most frequent brain tumors (20% of all the intracranial tumors) with an angle of attack of about 3 new cases a year and for 100.000 inhabitants, that is to say approximately 2400 new cases a year in France. They occur at any age but in 70% of the cases between 45 and 70 years.

The glioblastomas form soft masses, rich in blood-vessels, from 3 to 10 cm in diameter, of vinous color, heterogeneous with active compact areas and areas of necroses wide, strewn with vessels thromboses and which infiltrate brain tissue. However, these tumors are not practically ever associated with the appearance of metastases. There are surrounded by a edema which increases the suffering of the brain. Typically, they are expressed by signs of intracranial hypertension which often joins changes of the behavior, with crises comitiales, focal neurologic deficits.

This tumor evolves quickly, in 2-3 month, and even after surgery, radiotherapy then chemotherapy, its forecast remains dark except if the glioblastoma comes from the tumor can be localized on the level of one only part, the local or regional level, or be from the disseminated start. The metastatic sites most frequent are the bone, bone marrow, the liver and the skin. Thus, the majority of the localized tumors have an excellent forecast. It is the same for those of the children of less than one year, independently of the stage of the tumor. Some of these tumors regress even spontaneously. On the contrary, approximately 60% of the children of more than one year forward a metastatic neuroblastoma from the start of poor prognosis.

The variety of the clinical presentation is in relation to the expression of certain biochemical markers and molecular (DNA ploidy, amplification of the oncogene n-myc, Trk receptor expression, loss of the chromosome 1p, excess of the 17q . . . ). Thus, diffuse tumors occurring in the child of more than 1 year and on-expressing the oncogene myc are often chemo-resistant and have a poor prognosis (Berthold and A1, 1990; Schweigerer and A1, 1990). In the same way, the TrkB receptor expression and of BDNF allows a system of survival autocrine neuroblastic cells and induces the neuritic growth. It is also associated with the amplification of N-Myc and thus with a poor prognosis (Nakagawara and A1, 1994). On the contrary, the TrkA receptor expression, which induces the differentiation of the neuroblastomata (Borrello and A1, 1993; Eggert and A1, 2000), and TrkC (Yamashiro and A1, 1996) are rather associated with a good forecast. Thus, it is common to say that the TrkA receptor expression is conversely correlated with the amplification of the oncogene n-myc.

The receivers of the superfamily of TNF-R were studied in the neuroblastic cells. Thus, the Fas receiver could be highlighted at the level of certain neuroblastic cells (Gross et al., 2001), cells which can be (Barthlen et al., 1999; Riffkin et al., 2001) or not (Bian et al., 2004) resistant to the apoptosis induced by Fas. The sensitivity of the neuroblastic cells does not depend only on the Fas receptor expression but on the presence or not of the caspase-8 in cells (Kisenge et al., 2003). The receptors of TRAIL are also expressed in the neuroblastic cells.

The neuroblastoma is one of most common in the child. Death rate is the highest of all cancers assigning the children.

There are very few diagnostic markers able to detect the neuroblastoma. There are no either markers which can detect or determine the invasivity and the aggressiveness of the metastatic cancerous cells or which allows a therapeutic follow-up.

During the last years, considerable progresses were made in the comprehension of the means implemented by the oncogenes and tumor suppressor genes to control cell proliferation and the apoptosis. One of the main targets of these regulators is the family of the mailmen of transcription of the type E2Fs (E2F1, E2F2, E2F3, E2F4 etc. . . . ) in the channel of indication of the proteins E2Fs and RB. These proteins play a central role in the control of cell division by coupling the regulation of genes necessary to the cell cycle progression with the extracellular signals (mitogens, inhibitors of the proliferation). It behaves as an oncogene by stimulating tumor cell proliferation. Myc N and Aurora kinase are also oncogenes implied in the proliferation of the neuroblastoma. E2F3 modulates the form of the RNA m of Aurora during the cell cycle. In addition, certain data suggest that the mailmen of transcription E2F are critical for total activation and the repression of Myc N in the neuroblastoma. The combination of the dosages of genes of Myc N and the Survivin by RTPCR is correlated at the stage of the clinical change of the neuroblastoma.

Among the expressed genes are found:
over-expression of the E2F4 transcription factor and the c-myc oncogene which induce apoptosis of post-mitotic cells by accumulation of oxygenated reactants (Tanaka, 2002) and the N Myc which is amplified in 35% of the cases of neuroblastoma, gene ALK, DDX1 and CRABP II too. HGMA1 and the Survivin also. The repression of HGMA1 by RNA interference reduces the cell proliferation of the neuroblastoma. N Myc induces the expression of FAK. N Myc down reguls the expression mRNA of many genes having a role in cellular architecture.

the gene p53, which belongs to the tumor suppressor gene family, blocks the cell cycle in the case of DNA lesion. It has now been demonstrated that this gene is also involved in the progression of apoptosis (Oren, 1994; Yonish-Rouach, 1996);

the cyclin D1, one of the proteins constituting the regulatory subunits of cell cycle kinases, which is essential for cell cycle progression. This protein is also expressed during apoptosis in various cell types (Han et al, 1996; Pardo et al, 1996).

A transcription factor Zinc finger can stop the activity of the D1 cyclin and lock the cycle. Data suggest that the mailmen of transcription E2F are critical for total activation and the repression of MYCN in the neuroblastomas.

chk1 and 2, crb2, p21 and other oncogenes and cytokines such as TNF alpha etc. . . .

It would be of great interest to have novel diagnostic methods detecting the Presence of cancer with greater specificity and making it possible to distinguish between aggressive cancer cells with the tendency to metastasize and those which are more localized and have a lower probability of metastasizing. A marker capable of revealing cell proliferation would therefore be of great use. The works of the professor Jean Louis Mendel about the glial markers and in particular on the GFAP and the NF70 advanced the diagnosis, the expression of the synemine in the glial tumors is an important way of research like the study of the mutations of the Ras/MAPK channel. The deletion of chromosome 1 in the area 1p36 and the amplification of gene MYC N sign the state of proliferation, a forecast of neuroblastoma and an unfavourable histology. In 35% of the cases, MYC N is amplified, in 58% of the cases it is chromosome 17 in q23 and in 35% of the cases chromosome 1 in p36 is deleted.

Complex LIV21 will be studied by RT PCR and biochip and its cytoplasmic markers of interest and the membrane protein of the complex Liv 21 too.

21 additional markers and new sequences of complex LIV21 compared to the first and with the second patent deposited will allow a notable improvement and an improvement of the pharmaco diagnostic tests which we propose.

It is thanks to this improvement that the therapeutic adjustment in multi-therapy will be able to allow a greater effectiveness of processing and as it is thanks to this improvement as the diagnosis of the glial tumors will be done more precisely with a thorough knowledge on the forecast, the grade and the development of these tumors. Another improvement made it possible to have a larger precision in the study of the expression levels of various important genes for the diagnosis of glial tumor, it is the troubleshoot of a standardization of the tissue samples like punctures of the cerebrospinal fluid. Thus the comparisons of profiles of expression are more reliable and undergo less fluctuations due to skews of observation. All these new parameters which do not increase the number of variables but which decrease the background noise largely improve the diagnosis and the processing of the gliales tumors. ki 67 and CafI are nuclear markers indicating the proliferation state of many cancers (Almouzny; Curie Institut). Liv21 complex genes will be the cytoplasmic markers at least equal and complementary to the previously identified nuclear ones.

SUMMARY OF THE INVENTION

The present invention concerns new polypeptide, ribonuclotidic and nucleotidic sequences to integrate into a novel test for screening for reinduction of the cell cycle targeting oncology and the use of some of these same functionalized sequences, like auxiliary processing by molecular targeting. It is about a major improvement without which the diagnosis and the test pharmaco diagnostic could be only partial. The consequence would be a less effective processing and of less broad implementation according to the heterogeneity of cancers. It is thus about a diagnostic test and a prognostic test for various cancers. More particularly, the invention concerns the use of the genes or proteins of the Liv21 complex and of their derivatives as therapeutic tools or as diagnostic and prognostic markers for cancers. The invention therefore concerns the detection of the LIV21 gene or LIV21 protein with a kit comprising LIV21-specific antibodies or LIV21 specific probes. The present invention also consist in using all the proliferation markers and transcription factors which play a role in the cancerization and in some cases, neurodegeneration process. The invention lies in the use of quantitative RT PCR and the PCR (QPCR) twinned at the manufacture of diagnostic DNA biochips, proteins biochips and antibody arrays including known antibodies directed against various proteins of the LIV21-associated complex according to the phases of the cell cycle, that is, without restriction thereto: peptides and antibodies specific for RBP2, E2F4, E2F1, SUMO, HDACl, crb2, Int2, cmd2, cycE/cdk2, cdkl, CREB1 and p300, Rb, p107 and p130 of the pocket protein family. In addition, antibodies specific for NFkB, cdc2A, mdm2, p21, p53, p65, BRCA1, TNFalpha, TGF beta. The new sequences are the polynucleotidic and polypeptide sequences of Liv21F, Liv21H, etc. . . . (list additional of the sequences: SEQ ID NO 171 to 185) and the sequences of genes, proteins, and corresponding antibodies lately integrated in the pharmaco-diagnostic biochips are: Myc N, ALK, HMGA1, DDX1, GFAP, NF70, AD7cNTP, FAB3, Serin C2, Synemine, PDX1, HDAC6, TPX2, DKK1, DKK3, HUD, ID2, SKP2, TP53INP1, VEGF, NLRR1, PAX3-FKHR, NDP kinase A, Bora ?, Aurora A, Survivin The protein arrays will make it possible to study the proteinic interactions and the post traductional modifications, more particularly the phosphorylations and methylations of certain proteins which sign a state characteristic of the sick cell different from the proteinic interactions and metabolism of the healthy cell. The state of expression and silencing of certain genes being different. The rate of expression of each biomolecule in front of being observed distinctly in each cellular compartment to be able in the second time controlled being (under expressed or on expressed by a standard auxiliary processing biomolecule or siRNA or vectorized peptides).

The biochips with nucleotidic sequences will make it possible to study in nuclear cellular extracts and in addition cytoplasmic or membrane, under expressions or on gene expressions and the ratios between genes as between proteins of complex Liv21 and its associated partners, the analysis of the interactions within the metabolic complexes is a key of the diagnosis and also passes by the study of the functional fields.

A first objective of the present invention is to demonstrate a method for the detection and prognosis of cancer and of its metastatic potential which makes it possible to adjust a multitherapy targeted. Preferably, the cancer is selected from breast cancer on cerebral cancers and more particularly the glioblastoma, the neuroblastoma, without being limited thereto.

One aspect of the present invention consists of the use of LIV21 complex new sequences as prognostic indicator for cancer and his therapeutic monitoring.

Indeed, when Liv21 is localized in the cytoplasm, the cancer cells in tissues are aggressive. Conversely, when the product of gene expression Liv21F is preferentially localized in the cellular core, this is a prognostic indicator that the tissue cells are differentiated and quiescent and thus noninvasive. We define the Liv21 complex by the protein extract and peptides studied by mass spectrometry such as Maldi and ESIMSMS or Maldi Tof Tof. The said extract has been obtained by binding of the Liv21 complex to one of its polyclonal antibodies described in the patent (PCT/FR2006/000510).

Figure 14:
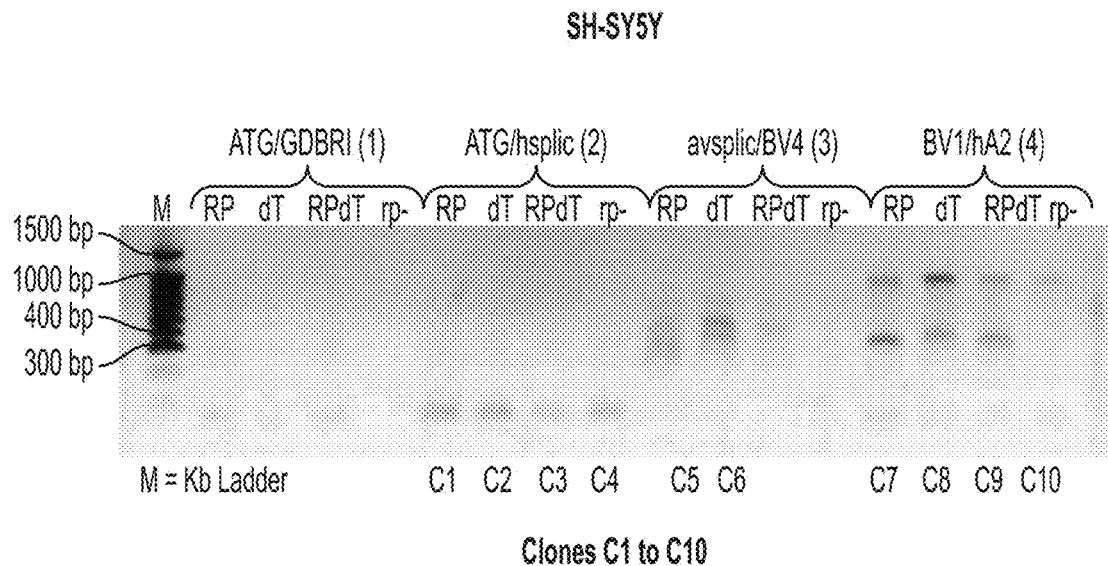

The Liv21 complex is defined by its mass spectrometry global profile (FIG. 5) and the number and the molecular weight of protein extracts bands obtained on the acrylamide gels of FIGS. 1A and IB as a function of temperature at which the sample is submitted and of described migration conditions. In fact, when for example Liv21F peptide is located in the cytoplasm and we reveal directly for example by in situ hybridization or by biochip analysis its higher expression in the cytoplasm, the cancer cells in the tissues are aggressive. Conversely, when the LIV21 gene expression product or the expression of Liv21F peptide is preferentially located in the cell nucleus, this is a prognostic indicator that the cells of the tissue are differentiated and quiescent and therefore noninvasive. This observation is associated under investigation with expression, phosphorylation and localization of the other factors of complex Liv21 and with these partners of interaction. The effectiveness of a cancer treatment can also be monitored by the traceability of new sequences and of these proteins Liv21F and Liv21K of this Liv21 protein complex, and of its derivatives and ratios with the associated proteins but also by Diagmicroarray and sensorchip including among others this protein and its Liv21 associated complex (FIG. 12 and FIG. 14).

Moreover, detection of protein kinase C epsilon (PKcs) is also advantageous since it has been determined that PKcs phosphorylates the LIV21 protein in order to maintain it in the cytoplasm. Thus, a significant increase in PKcs is indicative of the presence of cancer cells. Moreover, the LIV21/PKCS ratio increases in the cytoplasmic fraction of cancer cells. The same is true of the detection of HDAC1, which has been shown to be involved in PML/SUMO/Rb/HDAC-1. More generally, the HDACs family plays a key role in the regulation of gene expression, when the HDACs are overexpressed, they induce tumor suppressor gene silencing, hence the advantage of using HDAC inhibitors in therapy, combined with other inhibitors which regulate the metabolic pathway involving the protein complex which contains Liv21.

In addition, the detection of the E2F1, E2F2, E2F3 and/or E2F4 proteins is advantageous. In fact, the LIV21 protein forms a complex with E2F4, which is capable of inhibiting the expression of the E2F1 gene in the nucleus, E2F1 gene expression being a sign of cell proliferation. Thus, a decrease in the association of LIV21 with the E2F4 protein is indicative of the presence of cancer cells. Similarly, the presence of the E2F1 protein in the nucleus is indicative of the presence of cancer cells.

Consequently, the present invention concerns a method for the detection of cancer cells in a biological tissue sample (for example, breast, ovary, endometrium, bladder, melanoma, prostate, glioblastoma, etc.) from patients, this method comprising the detection of the products of expression of the LIV21 complex genes in the nucleus comparatively to the same products in the cytoplasm and the membranes of the cells in the biological tissue sample from said patient, this method comprising detection of the product of expression of liv21F gene in the core and/or the cells cytoplasm in the biological tissue sample from said patient, a localization of said products of expression of the LIV21F gene in the cytoplasm is indicative of the presence of cancer cells and a localization of said products of expression of the LIV21 complex genes in the nucleus is indicative of the presence of noncancer cells. Preferably, a localization of said products of expression of the LIV21 gene in the cytoplasm is indicative of the presence of invasive and/or metastatic cancer cells, the localizations of the products of expression of the LIV21 complex genes and its associated partners described in the examples of biochips shows or not the cancer cells presence. Optionally, the method according to the present invention also comprises the detection of the product of expression of at least one gene selected from the group consisting of the protein kinase C epsilon (PKcs) gene, the E2F1 gene and the E2F4 gene. The method can in particular comprise the detection of the product of expression of two of these genes or of the three genes. Moreover, at least one of the ratios LIV21/PKCS, LIV21/E2F4 and LIV21/E2F1 can be determined in the present method. This ratio can be determined in the cytoplasm and/or in the nucleus preferably separated. Preferably, these ratios are determined in the nucleus. Preferably, these ratios are compared with those obtained in a normal cell. The level of expression of each enzyme or polypeptide of the SUMO/Rb/HDAC complex or, for certain cell types, of the PML/SUMO/Rb/HDAC complex is an additional indicator of the proliferative state of the cell.

These ratios of expression or silencing can be detected via the protein expression or inhibition level themselves in the protein arrays (biochips) fabricated according to conventional methods described (Lubman David M, QIAO TIECH-ENG Alex, Mathew A B Y J etc.) or novel tools for the automation of hybridization and of reading, US2004152212 and Yu Xinglong US 2005019828 and novel supports which attach polypeptides (patents US 2008 213130 and US 2005/0157445 or US 2006170925 or WO 2005 016515, Klages Claus Peter and example figure).

Before describing the principle of these biochips, which are well known by man skilled in the art, we will give the following definitions: The biological sample can be in particular sample of blood, serum, saliva, tissue, tumor, bone marrow, circling cells from the patient. The biological sample can be recovered by any type of sampling know by those skilled in the art. According to the present invention, we consider a biological sample any material allowing the detection of expression of a target gene. The biological material can include in particular proteins, or nucleic acids such as desoxyribonucleoic acid (DNA) and rybonucleic acid (RNA). The nucleic acid can in particular be an RNA (rybonucleic acid). According to a preferred embodiment of the invention, the biological material comprises nucleic acids, in particular RNAs and even more specifically total RNAs. Total RNAs include transfer RNAs, messenger RNAs (mRNAs), such as mRNAs transcribed from the target gene, but also transcribed from any other gene, and ribosomal RNAs. This biological material includes specific material of the target gene, such as in particular mRNAs transcribed from the target gene or proteins issued from these RNAs, but it can also include material unspecific to the target gene, such as in particular mRNAs transcribed from a gene different from the target gene, tRNAs, rRNAs issued from other genes than the target gene. When the extracts to be studied consist of cell cultures, they will preferably be analyzed on fresh cultures (with or without previous treatment) that underwent an extraction protocol separating cellular compartments. This type of kit known by those skilled in the art allows the specific extraction of membranes or solely the cytoplasmic or nuclear or cytoskeletal content in a differential fashion by using different solutions. For instance, the kit Proteo extract (ref 539790) from Calbiochem can be used.

The other aspect of the present invention is the use of the genes and the proteins mentioned above as markers for the invasiveness and the metastatic aggressiveness of cancer cells of the prostate,—colon, bladder, melanoma, ovary, endometrium and cervix, and cancers in neurobiology or in ORL etc. . . . In fact, sequential pharmacodiagnostic tests during treatment monitoring will permit to observe, by comparing at different time points, variations of the expression level or of their silencing and therefore to better evaluate the treatment efficiency, to readjust these treatments in the case of a suitable multitherapy in such a way that the physiological equilibrium of the different products of genes involved in metabolic complexes are maintained. The plasticity of these equilibriums justifies the use of diagnostic biochips and for the therapeutic monitoring with the most pertinent genes of metabolic complexes involved in the physiology of anarchic proliferation in the case of breast cancer, which is highly heterogeneous. Therefore each individual or each phenotypic subgroup of individuals will show an under or over expression profile of genes of the metabolic complexes which is specific to him.

In one embodiment, the expression product of the genes is detected at the mRNA level. mRNA can be detected by RT-PCR analysis (i.e. following examples). It can also be detected by Northern blotting analysis or by SPR if the RNAm and DNA are functionalized at the surface of electroapplied on a support of biochip (techniques described therefore in the patents US 2008 213130 and US 2005 0157445 or US 2006 170925 or WO 2005 016515). The MICAM technique which uses the electric piezo effect in its biochips can be also used for the above mentioned invention of pharmaco diagnostic biochip dedicated to the cerebral neuroblastoma and other cerebral cancers, of biochips diagnostic dedicated to the epidermoid cancers and more specifically dedicated to the breast, ovarian and prostate cancers.

In an alternative mode of realization, the product of gene expression is detected on the level of protein or peptides characterizing complex Liv21 and its partners of interaction. Preferably, the protein and/or proteinic complex Liv21 associated, are detected using an specific antibody. For example, the protein can be detected by analysis Western Blot and SPR, a system of biochip using a wave of transverse propagation (evanescent wave) of surface plasmonic resonance (SPR). The interaction can be done with an electronic surface, conducting semi surface creates an exiton by luminescence or fluorescence. In a mode of preferred embodiment, it is detected by immuno histochimy, immuno cytochemistry, microfluidic, radiography or peroxidase labeling or any other means of optical, sonic imagery or of spectroscopy.

In one specific embodiment of the method comprising the detection of the expression product of the PKCε gene, a significant increase in PKCε is indicative of the presence of cancer cells. Moreover, the method can also comprise the determination of the LIV21/PKCε ratio in 5 the nucleus, the membranes and the cytoplasm. This ratio can be compared with the one observed in a normal cell. An increase in the LIV21/PKCε ratio in the cytoplasmic fraction is indicative of cancer cells.

In another specific embodiment of the method comprising the detection of the expression product of the E2F4 gene, the method comprises the detection of the association of LIV21 with the E2F4 protein, a decrease in this association in the cell nucleus being indicative of the presence of cancer cells. Moreover, the method can also comprise the determination of the LIV21/E2F4 ratio in the nucleus and/or the cytoplasm. This ratio can be compared with the one observed in a normal cell.

In an additional embodiment of the method comprising the detection of the expression product of the E2F1 gene, the presence of the E2F1 protein in the nucleus is indicative of the presence of cancer cells. Moreover, the method can also comprise the determination of the LIV21/E2F1 ratio in the nucleus and/or the cytoplasm. This ratio can be compared with that observed in a normal cell.

In a specific embodiment, the method comprises the detection of a labelled small interfering RNA (siRNA) in order to target its specific sequence and therefore signal the locus of messenger RNA expression of the gene of interest. In this way, the specific small interfering RNA can be used as a diagnosis marker similarly to an antibody. The specific siRNA would allow to locate in a specific case such as in extemporaneous tissues or any kind of sample from a patient, such as cancer tissues sample, the fluorescence signal or any other marker used on the siRNA is found in a cellular compartment on the sample. An siRNA targeting the E2F1, E2F4 and PKC epsilon would allow a complementary diagnosis.

The method according to the present invention allows in particular the detection of metastasized cancer, therapeutic monitoring and/or recurrences following treatment.

A second aspect of the invention concerns the human LIV21 protein and also the fragments thereof. More particularly, the present invention concerns a purified or recombinant isolated human LIV21 protein. It concerns in particular an isolated polypeptide comprising a peptide sequence selected among SEQ ID Nos 1 to 5 and more broadly selected among the peptide sequences characterizing it and obtained by MALDI (FIGS. 3, 4 and 5) and NanoLC-ESI-MS. In a preferred embodiment, the polypeptide comprises the three peptide sequences SEQ ID Nos 1 and 2 and 3. Preferably, the LIV21F protein and certain proteins of the Liv21 complex comprises a leucine zipper motif, a basic domain characteristic of DNA binding domains (FIG. 2), and a nuclearization sequence.

Figure 5:
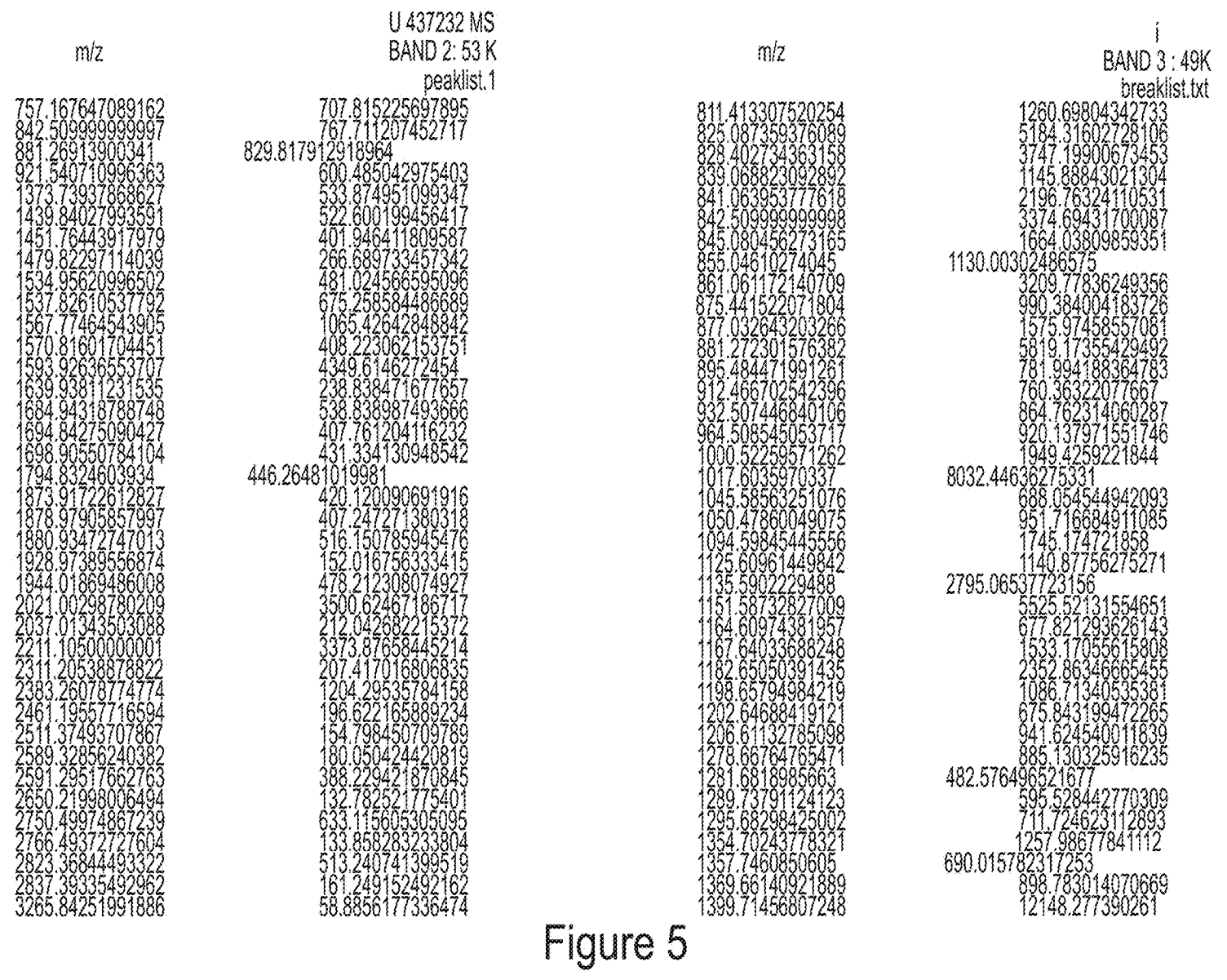

In an even more preferred embodiment, the present invention concerns the polypeptides with peptide sequences characterized by spectrograms of FIGS. 3, 4, 5 of gel bands 1, 2 and 3, selected among SEQ ID Nos 1 and 2 and 3 and 4 and 5 and a hundred additional non ordered sequences supplement (i.e. listing sequences in annex), the other sequences of the proteins must being checked compared with their homologies with contaminants and order during spectrometries of mass MSMS on the unmatched fragments identified in the Maldi Tof analysis (i.e. FIGS. 3, 4, 5), these unmatched fragments corresponding to the masses M (H+) untagged characterized in part the Liv21 protein and some elements of the Liv21 protein complex.

A third aspect of the invention concerns an antibody, which the present invention. More particularly, the antibody can bind specifically to a polypeptide comprising a peptide sequence selected from SEQ ID NO s 1-180, preferably from SEQ ID NO s 1 and 2 or 3 and/or 5 or 51, or a sequence having more than 80% identity to said sequences. The present invention concerns in particular an anti-LIV21 serum produced by immunizing an animal or a human with a polypeptide according to the present invention, in particular a polypeptide comprising a peptide sequence selected from SEQ ID NO s 1-180, preferably from SEQ ID NO s 1-5 and 51, or a sequence having 70%, 80% or 90% identity to said sequences.

A fourth aspect of the invention concerns a kit for the detection of cancer cells in a biological sample from a patient, this kit comprising one or more elements selected from the group consisting of an antibody which binds specifically to human LIV21F according to the present invention and an anti-LIV21F serum according to the present invention, a specific oligonucleotide mRNA probe of Liv21F and a pair of primers specific of mRNA. In a specific embodiment of the invention, the kit also comprises means for detecting the product of expression of a gene or a specific oligonucleotide mRNA probe of factors selected from the group consisting of the protein kinase C epsilon (PKCε) gene, the E2F1 gene and the E2F4 gene. But also the antibodies in a specific antibodies microarray from the antibodies group consisting of RBP2, SUMO, HDAC, TNFalpha, crb2, cycE/cdk2, cdkl, CREB1, p300, Rb, p107, p130, NFkB, cdc2A, mdm2, p21, p53, p65. It also comprises Microarray with said proteins above and specific peptides known by a person skilled in the art, their antigens being referenced. The combination of these different peptides corresponding to the specific interactions of protein complexes acting in metabolic deregulation, induces anarchical proliferation, which is a specific feature of cancer or neurodegeneration. The invention concerns the use of an antibody specific for human LIV21 for the diagnosis of cancer, and antibodies specific for its protein complex, but also specific antibodies for RBP2, SUMO, HDAC, TNFalpha, crb2, cycE/cdk2, cdkl, CREB1 and p300, Rb, p107, p130, NFKB, cdc2A, mdm2, p21, p53, p65, p73. Also, the invention concerns the used of primers pair or LIV21 specific probe for the cancer diagnosis. Preferably, the diagnosis is performed ex vivo on samples from a patient (puncture of the cerebral spinal fluid, blood test, biopsy, ground cellular material, bronchial aspirations, DNA/protein/antibodies arrays, plasmionics (SPR), hydrophobic or ion metal supports, etc). Method according to claim 15, characterized in that in addition, it implements at least any of the specific probes of the sequences of known as said complex Liv21 and these associated partners. The method is characterized in that the aforementioned biochip is: a biochip with protein, or a biochip with nucleotidic antibodies or a biochip with acids, or a biochip with mRNA, or a biochip with SiRNA.

Method is characterized in that the aforementioned biochip with protein, or the aforementioned biochip with antibody, consists of a biochip of fluidic microcomputer and for which the aforementioned stage of detection consists of a detection by SPR.

Method is characterized in that it understands a stage of amplification/retro-transcription by RT-PCR of at least a nucleotidic sequence of the known as human Liv21 complex according to claim 1 or 2 or of the known as Liv21 complex and its associated partners.

Method is characterized in that it understands a pharmaco-diagnostic test for diagnosis of the cancer or the follow-up of the development of a cellular proliferation, the aforementioned cancer being preferentially choose in the group consisted the neuroblastome, the glioblastomas and other cancers touching tissues of the nervous system.

BRIEF DESCRIPTION OF THE DRAWING FIGURES

Figure 1B:
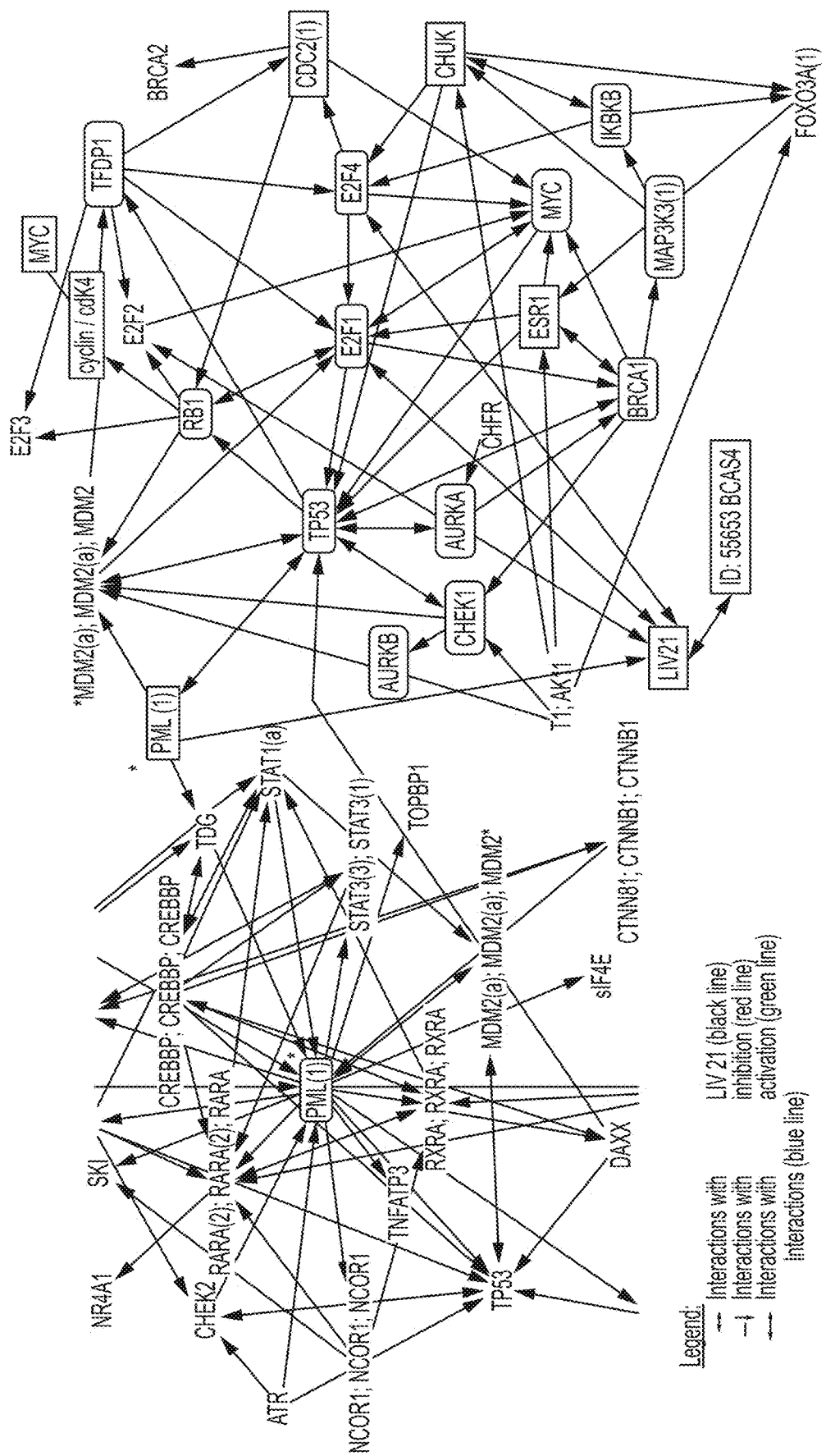
Figure 2:
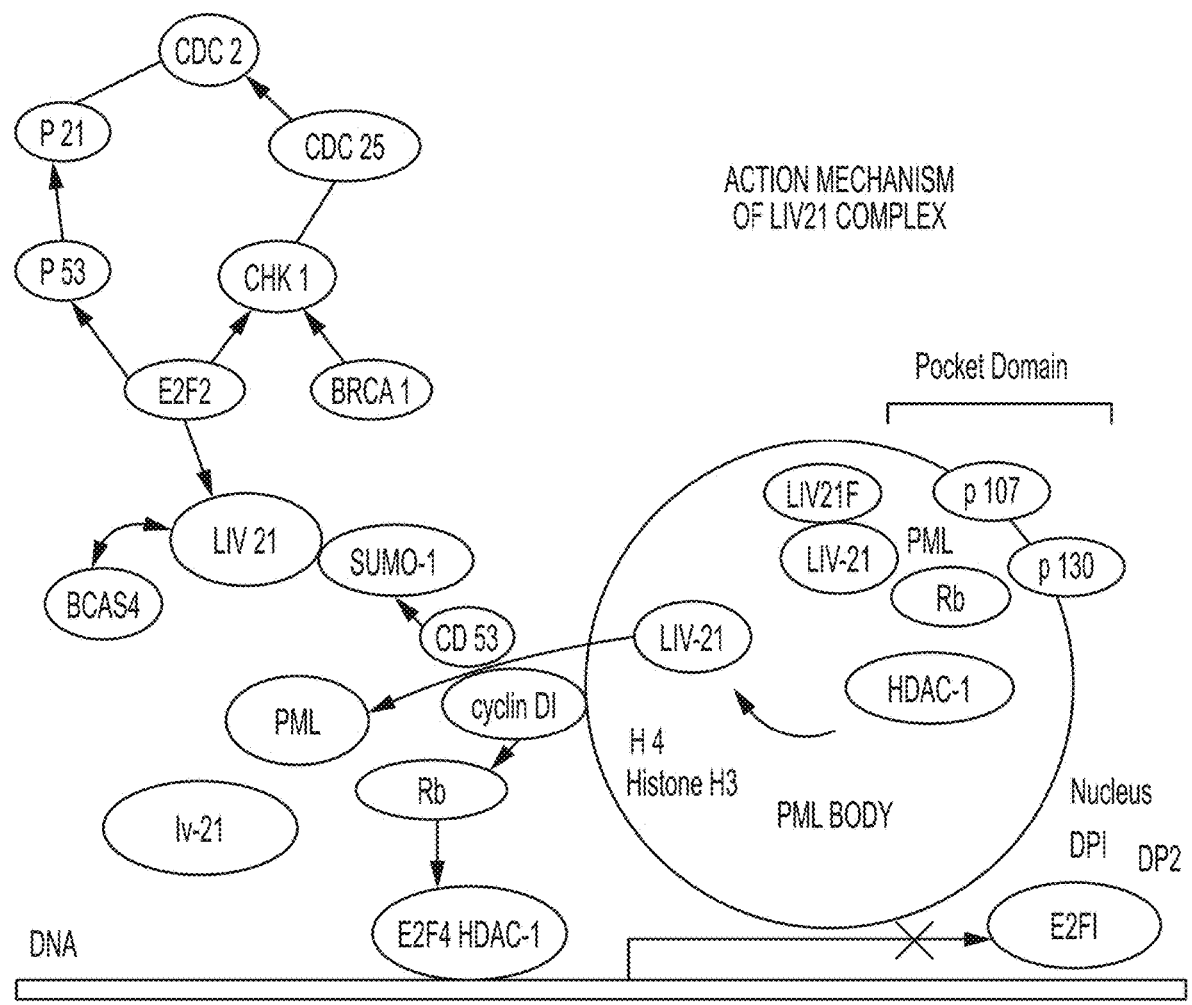
Figure 3B:
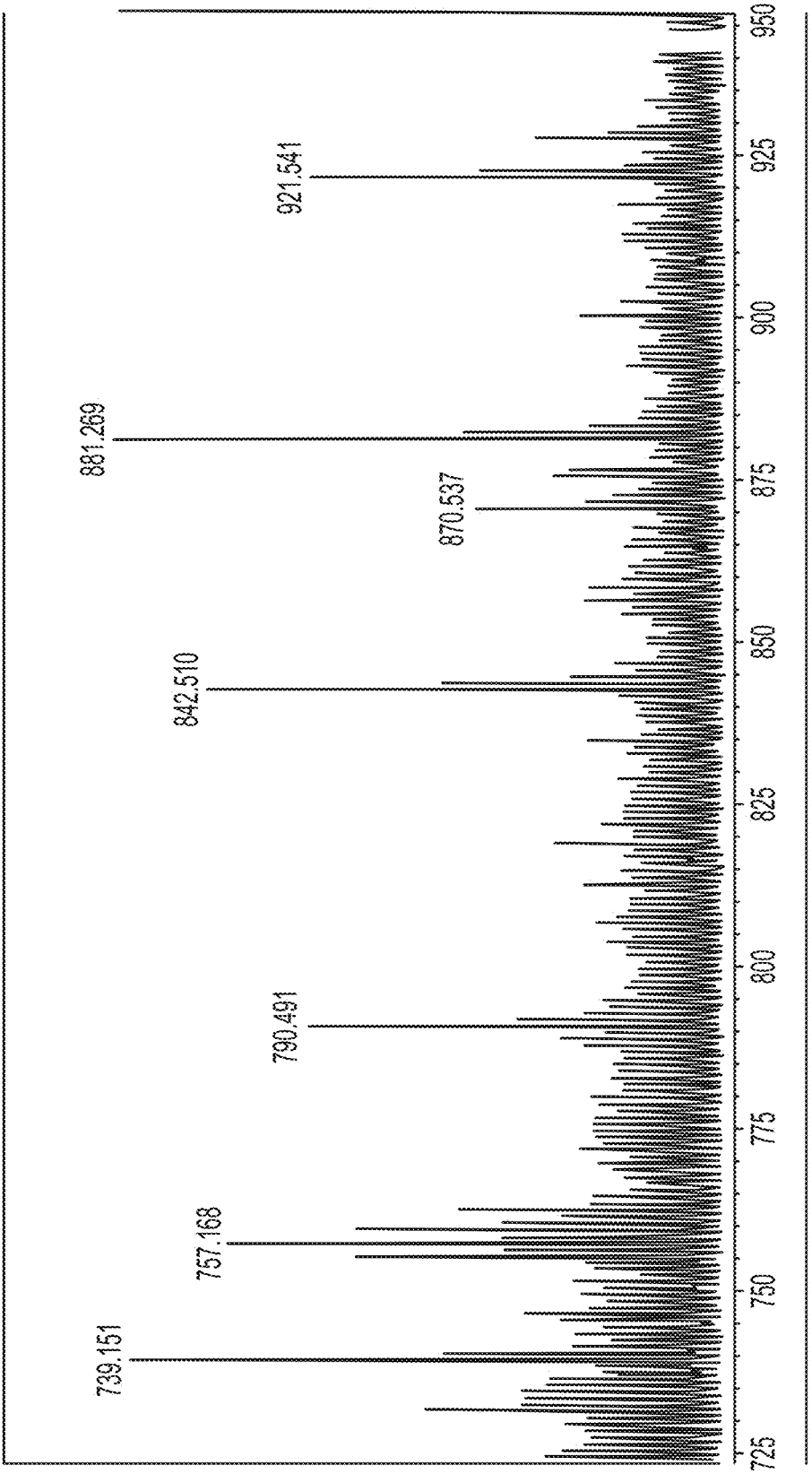
Figure 4A:
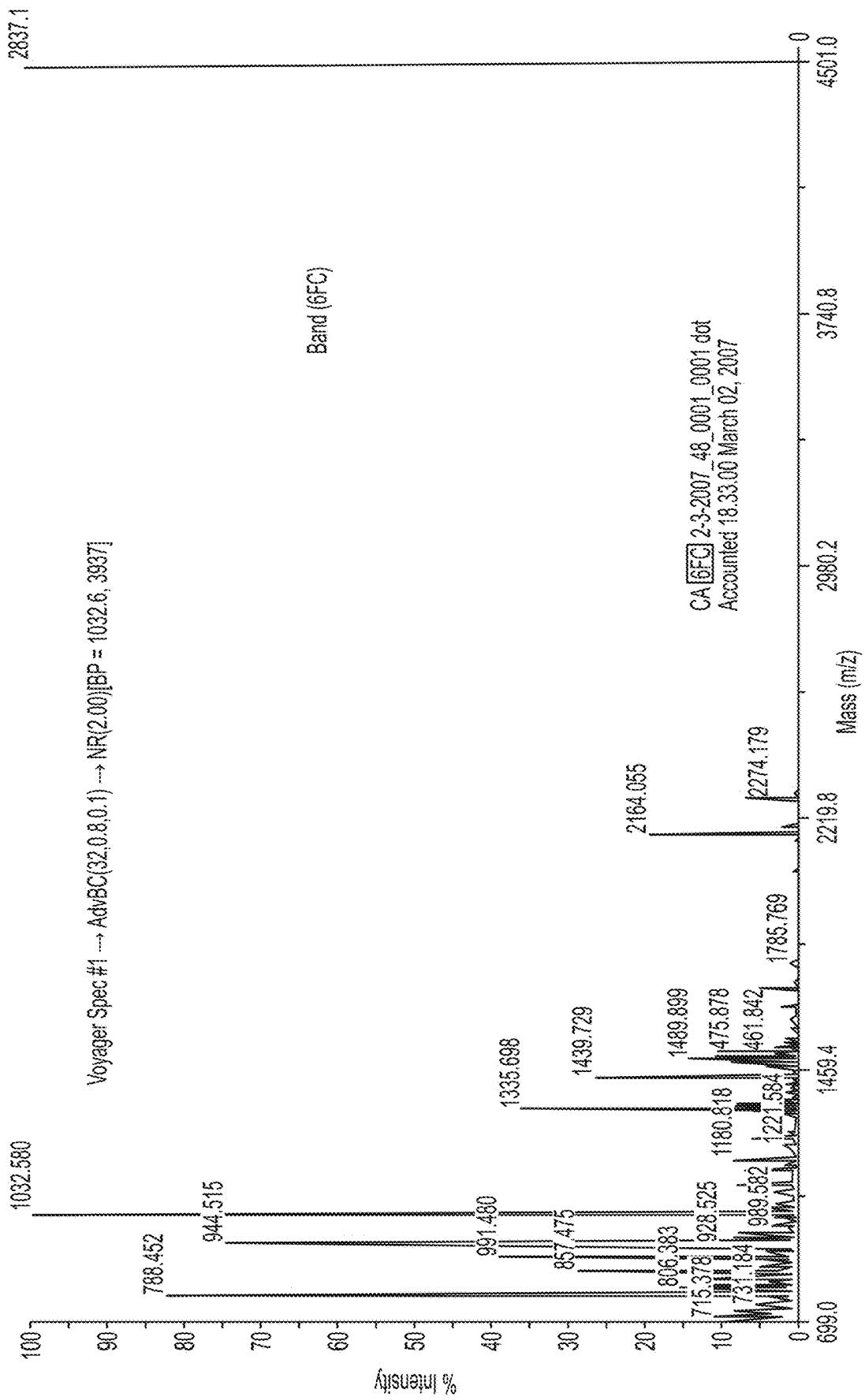
Figure 7A:
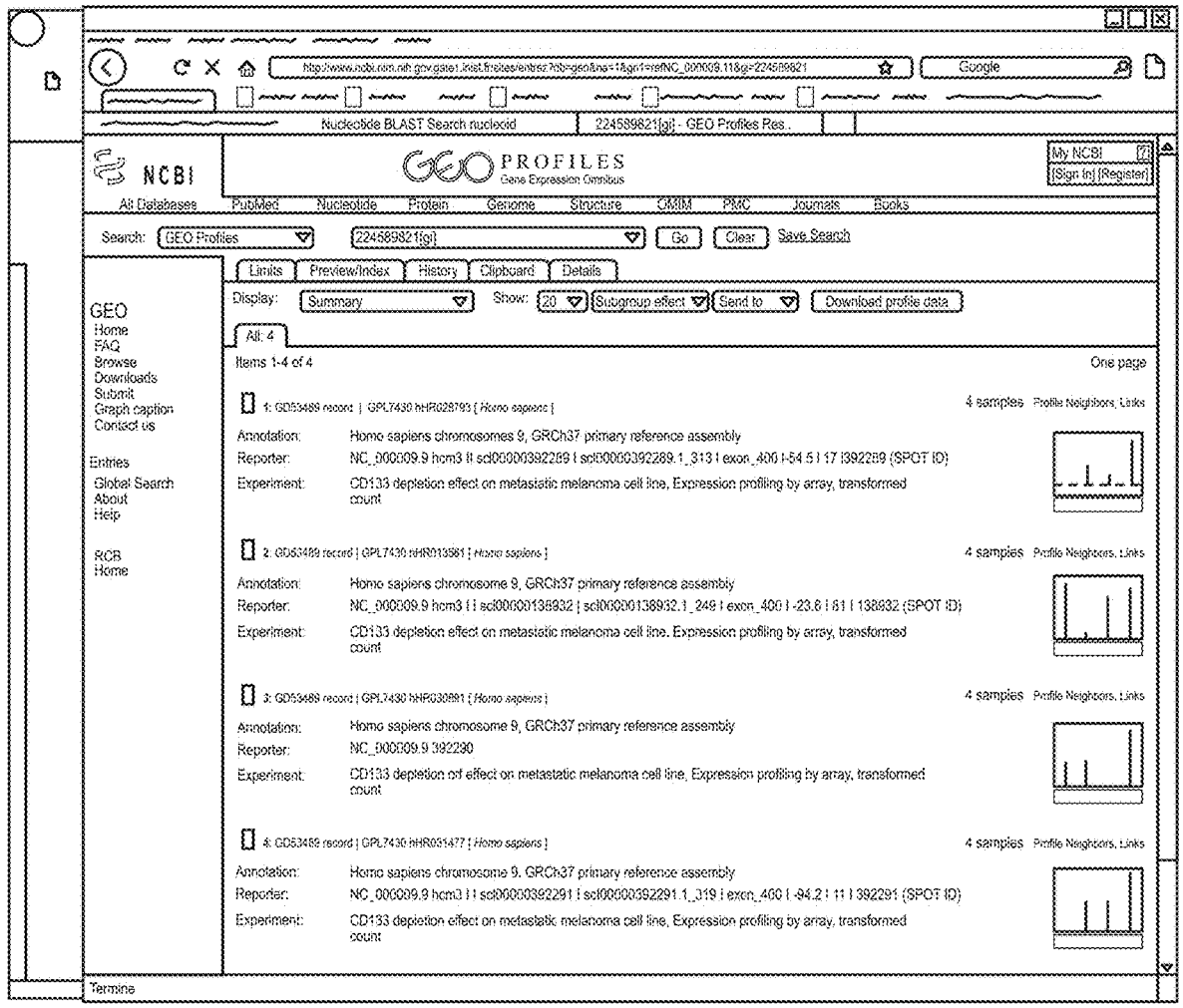
Figure 9:
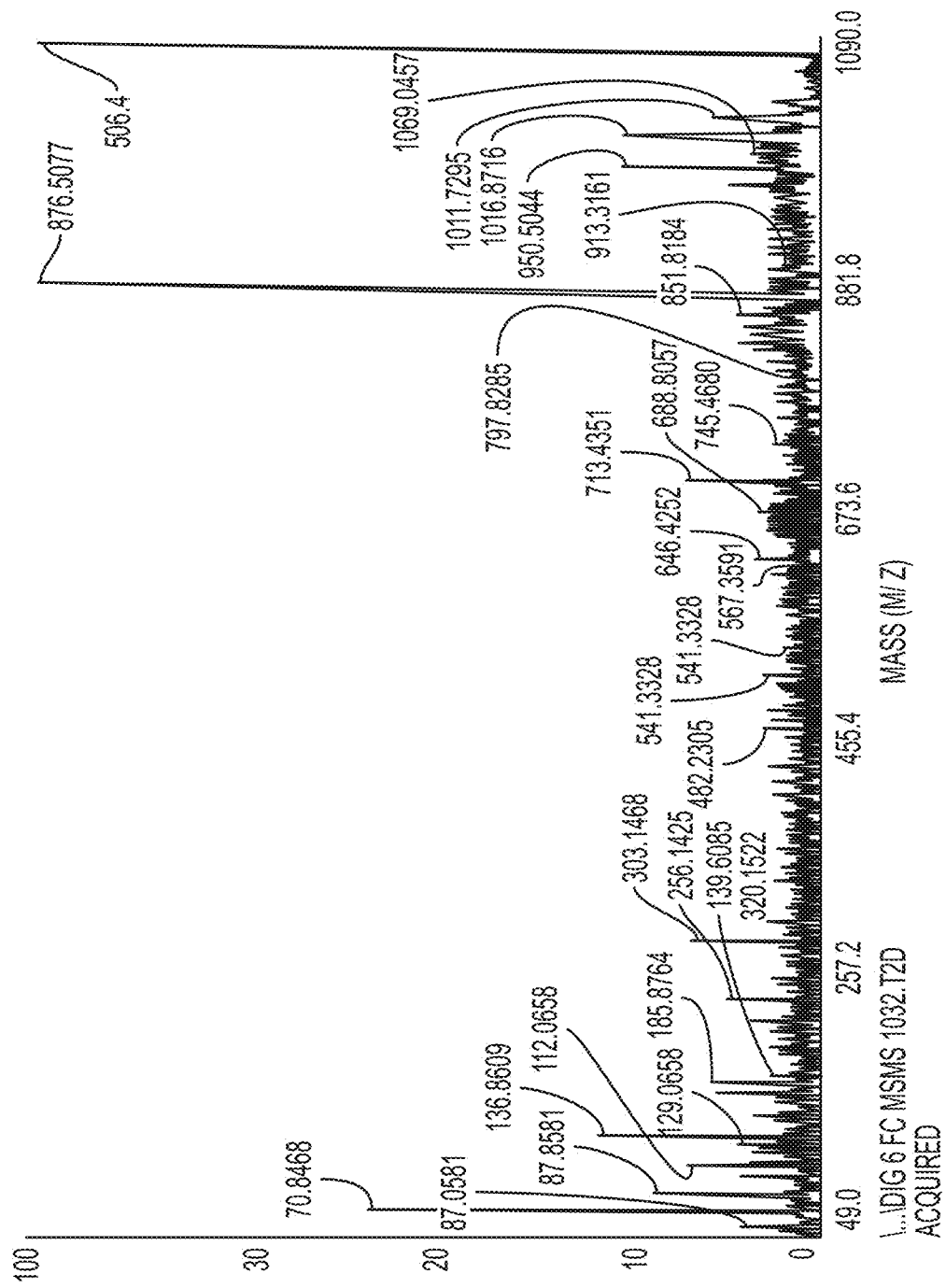
Figure 11B:
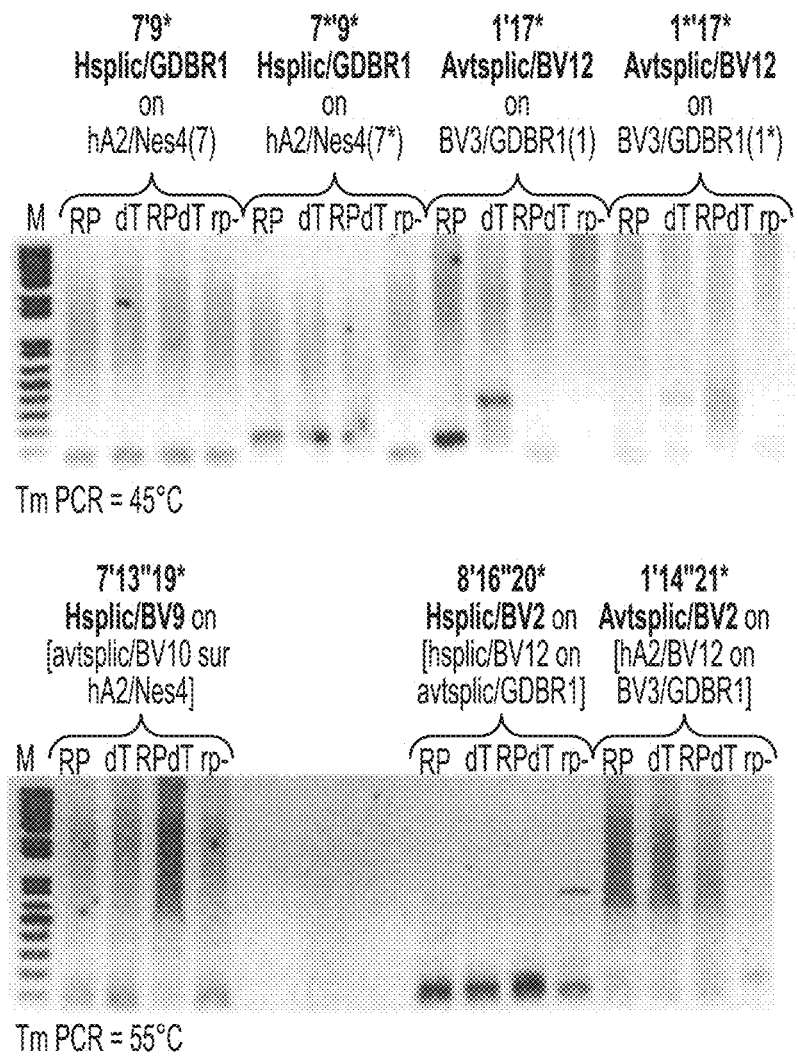
Figure 15:
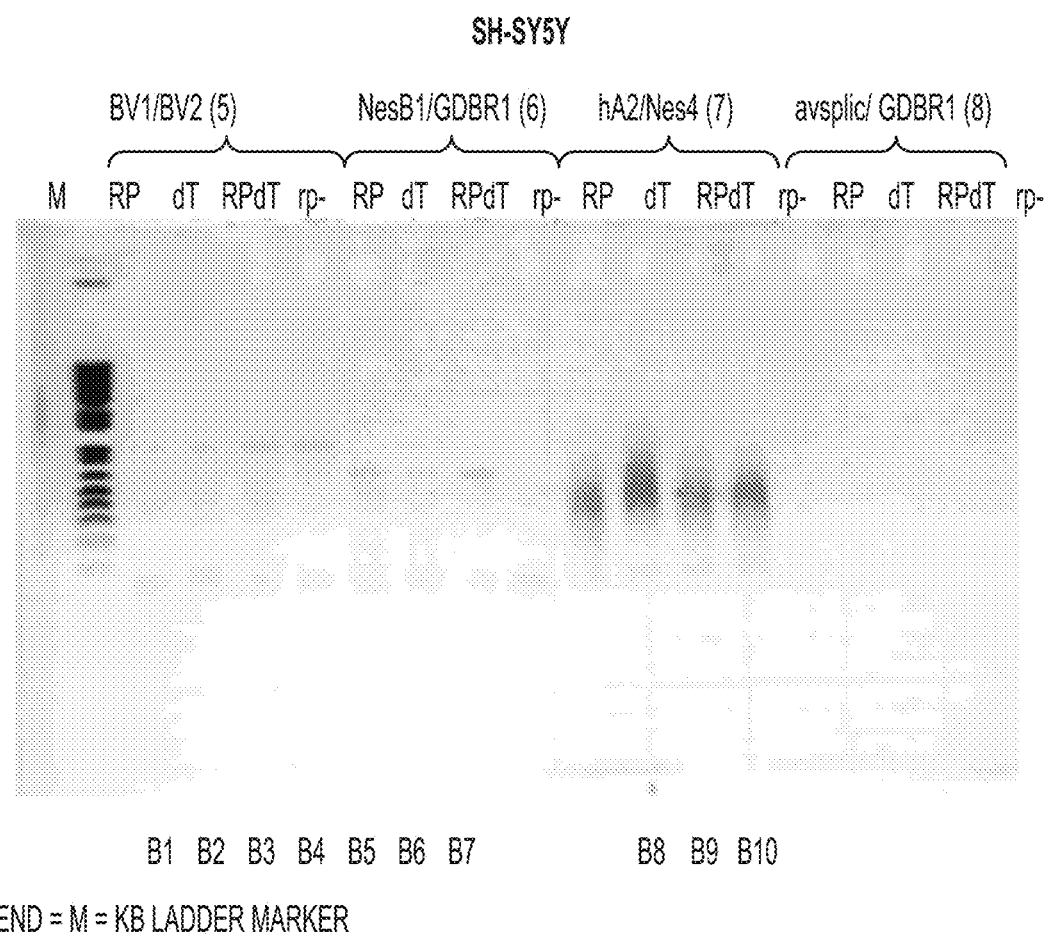
Figure 16:
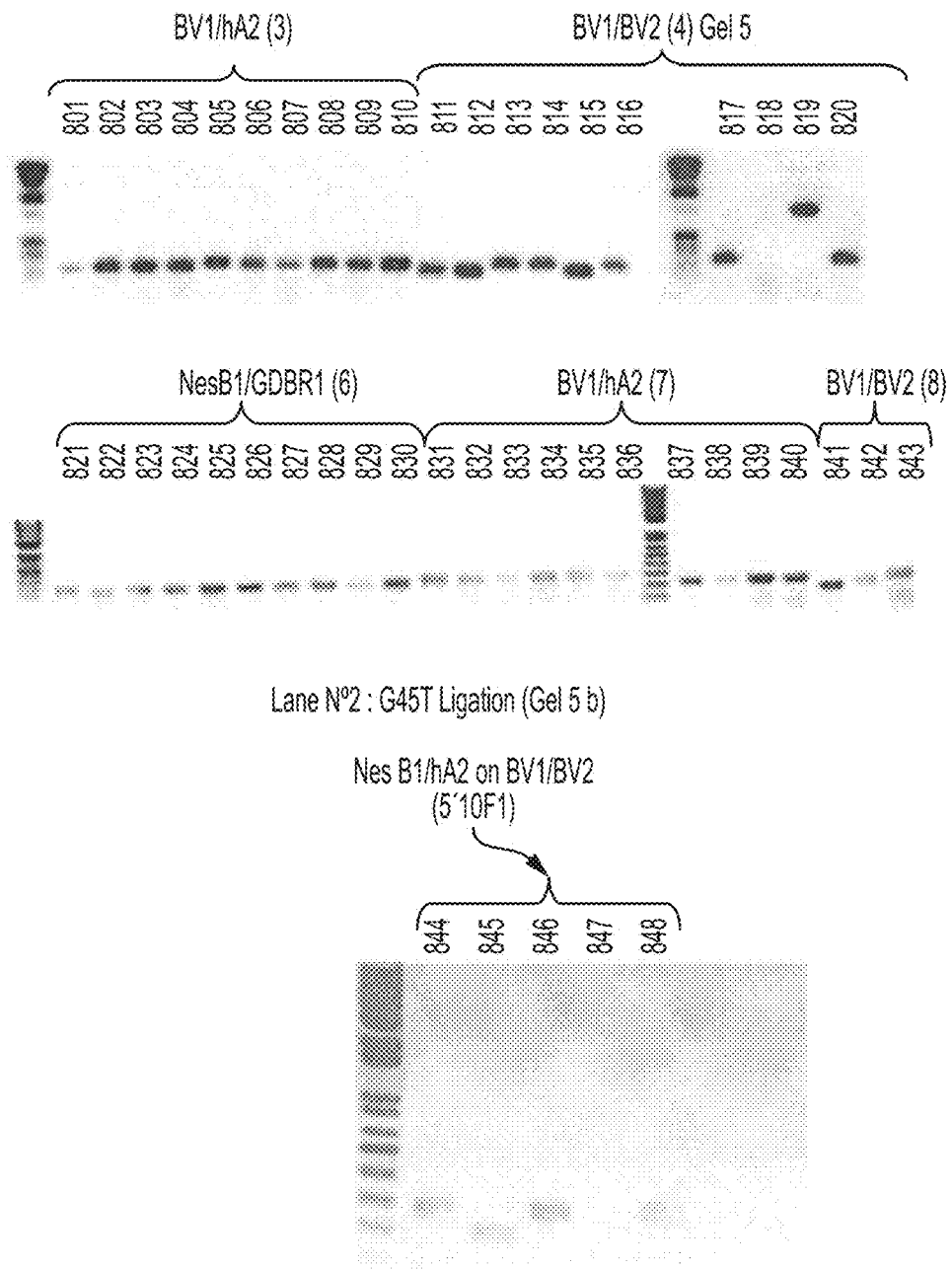
Figure 20B:
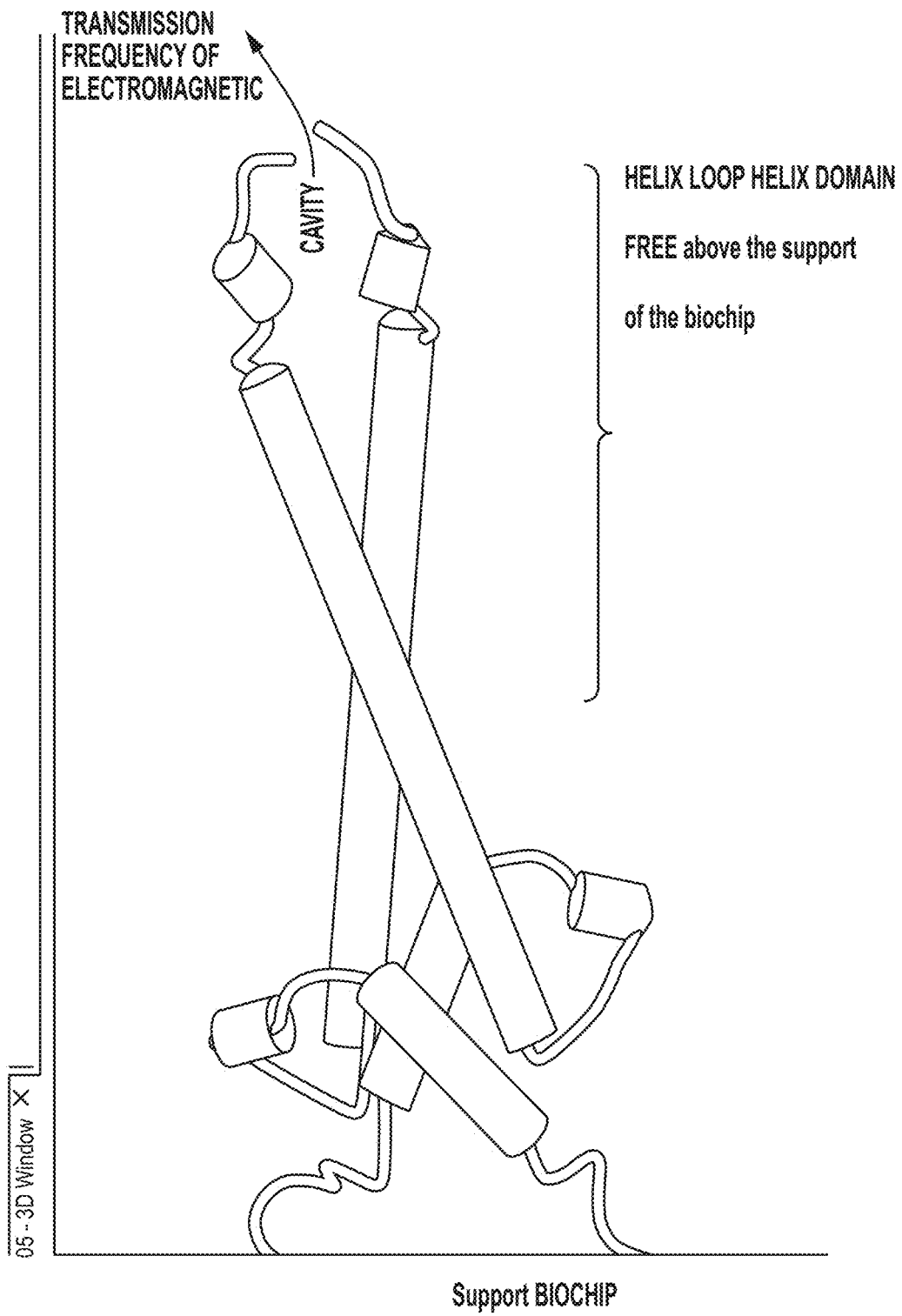
Figure 20C:
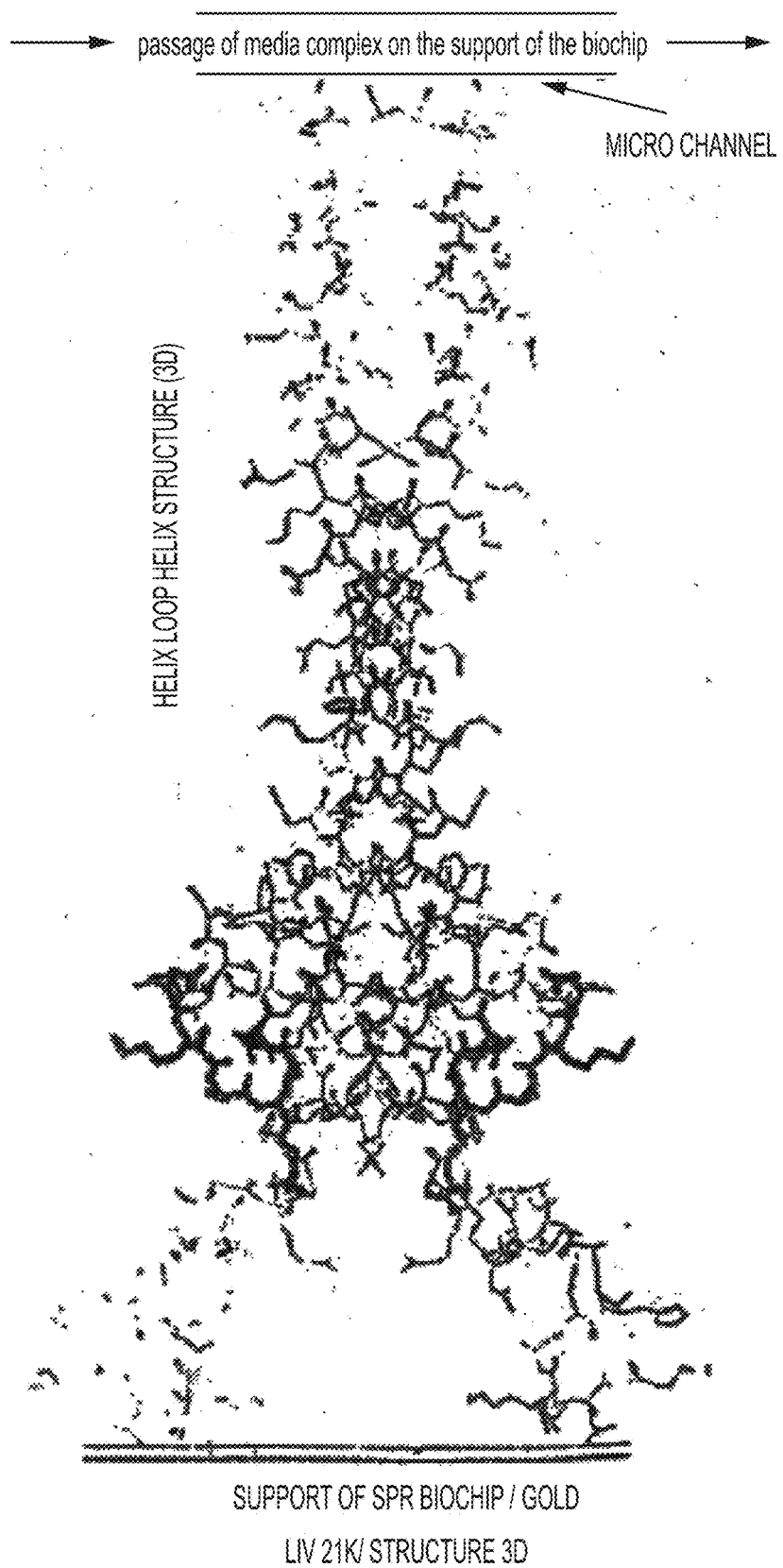
Figure 20D:
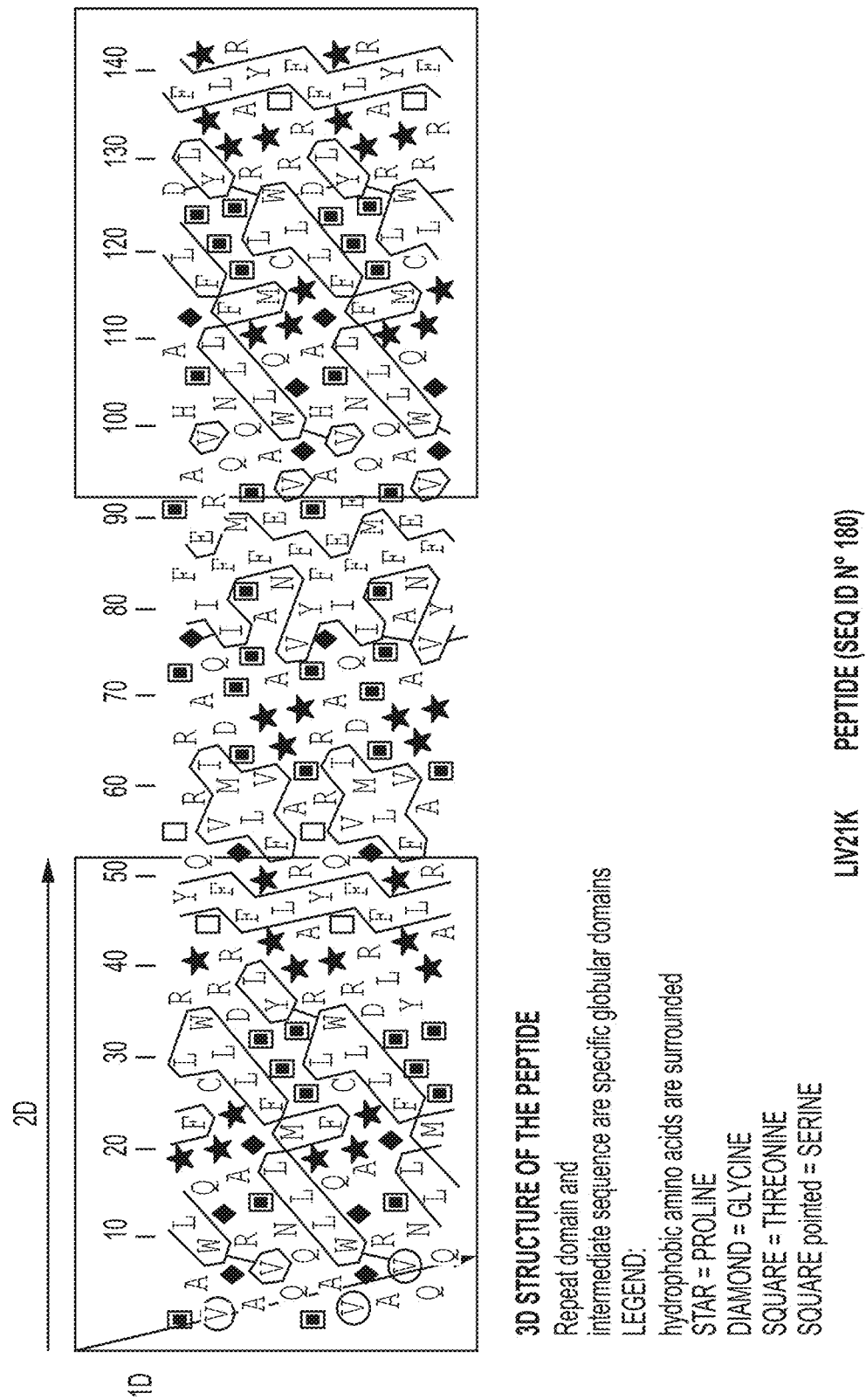
Figure 22:
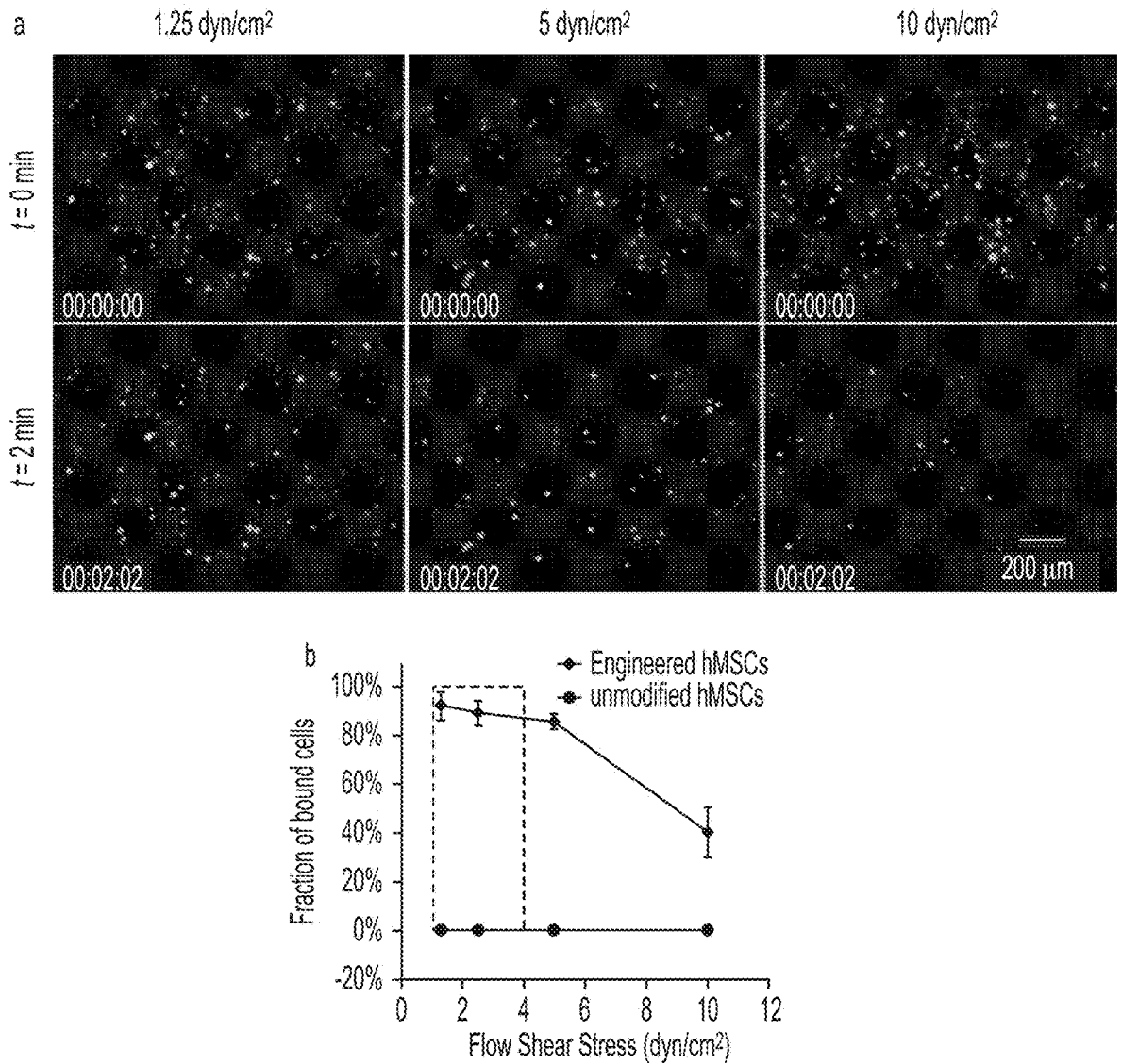

FIG. 1A: one-dimensional gel (acrylamide gradient 12%) revealing after three hours thirty of migration 11 tapes with certain triplets and doubled tapes and a two-dimensional gel SDS Page of total cellular extracts with spots between 15 and 20 KD and to 29-32 kD and 35 KD approximately with basic pH and of the spots with 190-180 and to 100 kD with acid pH;

FIG. 1B: diagram of the interactions of the bio-markers of complex Liv21 and the surrounding metabolic pathways;

FIG. 2: scheme of nuclear and cytoplasmic protein with domain DNA binding and effects on the study of therapeutic targeting the core and the cell cytoplasm;

FIG. 3A: The listing of monoisotopic peaks of the band 1 at 50 kD and the band 2 between 49 and 50 kD;

FIG. 3B: LIV21 protein profile by mass spectrometry (Maldi) M (H+) for the one-dimensional gel band corresponding to the band 2 migrating at 49-50 kD wherein the peptides derived from the digestion are solubilized in a solvent: acetonitrile/water (1/1) containing 0.1% of TFA (trifluoroacetic acid);

FIG. 4A is a profile of the spectrogram of the band 6 named 6FC;

FIG. 4B: monoisotopic of certain peaks from FIG. 4A;

FIG. 5 is the third spectrogram corresponding to the one-dimensional 12% acrylamide gel band migrating at 52 kD and revealed with coomassie blue and the LIV21 antibody;

FIG. 6: analysis on the data banks the listings of monoisotopic peaks;

FIGS. 7A and 7B relate to SEQ ID NO 217;

FIG. 8: RNA pool;

FIG. 9: PCR with housekeeping genes and analysis of molecular masses;

FIG. 10: PCR with the primers showing a band of 1400 bp;

FIGS. 11A & 11B: Gel 2 with analysis of molecular masses;

FIG. 12: Gel 3 at 55° and analysis of molecular masses;

FIG. 13: Gel 4 at 45° and at 55° and analysis of molecular masses;

FIG. 14: screening ligation of 400 pb band, clones B1 to B10;

FIG. 15: screening ligation of 1400 pb band, clones C1 to C10;

FIG. 16: Gel 5: ligation screening on the five new clones;

FIG. 17: Gel 6: Screening of the S55T and S55M recombinant clones and analysis of molecular masses;

FIG. 18: examples of comparison of nucleotide sequences between the sequenced clones;

FIGS. 19A & 19B: Si RNA design;

FIGS. 20A-20D: Protein biochip (array) from Yeretssian but in addition with peptides named of the proteins of the interested complex studied in the invention;

FIG. 21: Two biochips standard microfluidic of four shafts×2 with a control and three biomarkers;

FIG. 22: Example of biochip of 20 spots with 16 biomarkers of interest (and four controls) fixed on the sensorchip allowing to see by SPR on-expression and the underexpression of certain genes of complex LIV21 and its partners of interactions for example;

FIGS. 23A & 23B: Biochip with RNA allowing to explore mini RNA of complex LIV21; and FIG. 24: Example of biochip with DNA resulting from above mentioned genes of interest targeting pathology.

DETAILED DESCRIPTION OF THE INVENTION

FIG. 1A: one-dimensional gel (acrylamide gradient 12%) revealing after three hours thirty of migration 11 tapes with certain triplets and doubled tapes and a two-dimensional gel SDS Page of total cellular extracts with spots between 15 and 20 KD and to 29-32 kD and 35 KD approximately with basic pH and of the spots with 190-180 and to 100 kD with acid pH. Spots between 49 and 51 KD and to 64 KD. Into monodimensional: Tapes with ISO kD approximately (TOFC), 100 KD, 64 kD, 51 à49 kD, 49 kD, 35 kD, 29 kD, 15 to 17 kD.

FIG. 1B: diagram of the interactions of the bio-markers of complex Liv21 and the surrounding metabolic pathways.

FIG. 2: scheme of nuclear and cytoplasmic protein with domain DNA binding and effects on the study of therapeutic targeting the core and the cell cytoplasm.

FIG. 3 A: The listing of monoisotopic peaks of the band 1 at 50 kD and the band 2 between 49 and 50 kD. FIG. 3B: LIV21 protein profile by mass spectrometry (Maldi) M (H$^+$) for the one-dimensional gel band corresponding to the band 2 migrating at 49-50 kD. The peptides derived from the digestion are solubilized in a solvent: acetonitrile/water (1/1) containing 0.1% of TFA (trifluoroacetic acid). A saturated solution of the alpha-cyano-4-hydroxycinnamic acid matrix is prepared in the same solvent. The same volume of the two solutions is taken and mixed together, and 1 microliter is deposited onto the Maldi plate for analysis.

FIG. 4 is a profile of the spectrogram of the band 6 named 6FC.

The de novo analysis (MS MS Maldi Tof Top makes it possible to propose the sequences: RYLVTPVNA (SEQ ID NO: 13), RYVPSSNLP (SEQ ID NO: 12), RYVLSPVK (SEQ ID NO: 14), RYVPSSNPL (SEQ ID NO: 11), RYLPSANPD (SEQ ID NO: 342).

FIG. 4 bis: monoisotopic of the peak 1032.58 MSMS analyzes: YRPGTVALR (SEQ ID NO: 206), RYVPSSNPL (SEQ ID NO: 12)

The peak monoisotopic 944.6 is a sequence: FAVAF-PVGR (SEQ ID NO: 323)

The peak monoisotopic 1603.7: KPSHPKPSTK (SEQ ID NO: 15)

The peak 1328.69: KAHNLFKT (SEQ ID NO: 17), TFKNLC (SEQ ID NO: 16)

The common peaks monoisotopic between the first 2004 (230304 imagenium 03_H11_a_001) and the peak 6FC from 2008 are:

Following peaks monoisotopic: 1135.563, 1151.545; 1167.604; 1206.589; 1324.634; 1336.658; 1507.735; 1604.710; 1800.940; 2087.034.

The variation of the protocol is due only to three different stages: the first is the purification of the antibody used, the second is the separation of the fractions cytoplasmic and nuclear, the third is the heating two minutes with 100° of the sample before migration on freezing of acrylamide.

FIG. 5 is the third spectrogram corresponding to the one-dimensional 12% acrylamide gel band migrating at 52 kD and revealed with coomassie blue and the LIV21 antibody.

FIG. 5 bis is a table of the monoisotopic peaks of the third spectrogram corresponding to the one-dimensional acrylamide gel band migrating at 51 kD 52 kD and revealed with coomassie blue and the LIV21 antibody.

The monoisotopic peaks with a value M H+. The masses are give with three numbers after the decimal point by the proteomic platforms since they estimate that this is the acquisition precision limit of MALDI TOF machines. The FIGS. 3-5 describe the MALDI analyses giving a set of polypeptides that can be assigned to the LIV21 protein and its complex and contaminants sometimes different according to the observers from the various platforms of proteomics under discussing.

FIG. 6: analysis on the data banks the listings of monoisotopic peaks. Example of the histatine 3. The Mascot search parameters are: trypsin enzyme, variable modifications: carbamethylation and oxidation of methionins, without molecular mass limit, without isoelectric point restriction.

FIG. 7 idem but the second example:

Type of mass: monoisotopic. Mass error (MS): according to the observer 50 ppm or 100 ppm. Non-cleavage with trypsin: 1 The masses captured are M (H$^+$)/real masses. For spectrogram 1, the cysteins are blocked with iodoacetamide. The possibility of digestion with Promega bovine trypsin may be incomplete with cleavage oversight.

Sequences common with *Gallus gallus* (gi 50732569), the 30 Mouse Syntaxin, the histatin variant HIS3-2 (P15516-00-01-00), the ZN575-Human, the G6P translocase, the HSP60 chaperonin, the deiminase, ferrodoxin NADP (+) reductase, *pseudomonas* polyribonucleotide nucleotidyl-transferase, the clathrin, the dehydrolipoamide dehydrogenase.

FIG. 8: RNA pool

FIG. 9: PCR with housekeeping genes and analysis of molecular masses.

FIG. 10: PCR with the primers showing a band of 1400 bp.

FIG. 11: Gel 2 with analysis of molecular masses FIG. 12: Gel 3 at 55° and analysis of molecular masses FIG. 13: Gel 4 at 45° and at 55° and analysis of molecular masses.

FIG. 14: screening ligation of 400 pb band, clones B1 to B10.

FIG. 15: screening ligation of 1400 pb band, clones C1 to C10.

FIG. 16: Gel 5: ligation screening on the five new clones.
FIG. 17: Gel 6: Screening of the S55T and 555M recombinant clones and analysis of molecular masses.

FIG. 18: examples of comparison of nucleotide sequences between the sequenced clones.

FIG. 19: Si RNA design.

FIG. 20: Protein biochip (array) from Yeretssian but in addition with peptides named of the proteins of the interested complex studied in the invention.

FIG. 21: Two biochips standard microfluidic of four shafts×2 with a control and three biomarkers.

An on-expression of DDX1, MYCN and CRABPII is observed whereas one observes by testing the second sensorchip an under-expression of HUD, TP53 INP1 and a major under-expression of p21.

FIG. 22: Example of biochip of 20 spots with 16 biomarkers of interest (and four controls) fixed on the sensorchip allowing to see by SPR on-expression and the underexpression of certain genes of complex LIV21 and its partners of interactions for example.

An under-expression of DKK1, SKP2, DKK3, ID2, p21, SKP2, TP53INP1, ID2, P73 is observed whereas an onexpression of MYC N, ALK, NLRR1 (the leucine rich neuronal repeat is transactivated), CRABPII, DDX1, LIV21K, AURORA kinase A is observed.

FIG. 23 Biochip with RNA allowing to explore mini RNA of complex LIV21 and more particularly those resulting from genes of the polypeptides LIV21F and LIV21K added in Mir RNA, microRNA known to be implied in pathology ((miR (=MIR) 34A. MIR9. MIR 125A.125B.MIR128 MIR184 MIR221)).

We study also regulator PTEN and factors TR AIL.

FIG. 24: Example of biochip with DNA resulting from above mentioned genes of interest targeting pathology.

Figure 8:
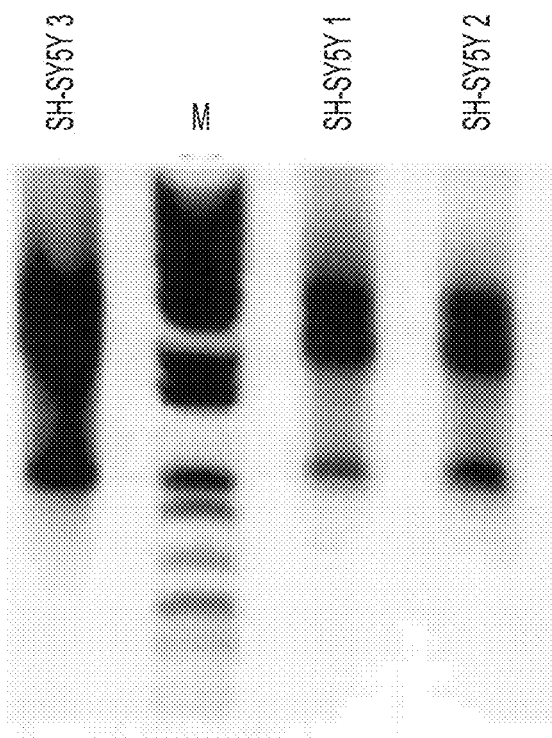

The invention relates to the identification of antigens in cell lysates by immunoprecipitation. The analysis of the physical interaction of various proteins associated in the LIV21 complex as E2F4 and E2F1 has been studied by coimmunoprecipitation of protein complexes. This analysis has made it possible to demonstrate novel 10 markers, which has a diagnostic and prognostic use for cancer (i.e. PCT/FR2006/000510). Begin by using the one dimensional and two dimensional gel electrophoresis analysis (FIGS. 1 and 2), the protein samples corresponding to the putative protein and to the elements of the complex were extracted from the gels and digested with trypsin (Promega) in order to be analysed by MALDI (FIGS. 3 to 5) and ESI MS/MS mass spectrometry. The results, when put up against proteomic databanks, made it possible to reveal several peptide sequences of interest, including some given as an example (FIGS. 6 and 7), some being found in humans with very significant scores (splicing of histatin, etc., FIGS. 8 and 9), these sequences were used as primers (once reverse-transcribed to cDNA) for screening a library formed from breast cancer-specific MCF7 cells (FIGS. 10 to 17).

The cloning made it possible to bring to the fore about twenty clones out of the 150 clones obtained, of which ten clones were sequenced and characterize the new LIV21 gene LIV21F and the gene LIV21K (FIG. 1B and FIG. 2). Based on these sequences, siRNAs were determined in order to allow regulation of silencing type within this metabolic complex of interest so as to develop therapeutic applications (FIG. 18).

In post-mitotic cells, apoptosis could correspond to an aborted attempt at mitosis. It is in this context that the application of LIV21 has been developed. The inventor has identified sequences of the LIV21 gene. Using the LIV21 antibody on affinity columns he has been able to extract peptides of the LIV21 protein; it has also used a second approach by means of a coimmunoprecipitation kit (Pierce) in order to have larger amounts of proteins (Example 1). Based on peptide sequences of the LIV21 protein, obtained by mass spectrometry (Example 2), primers which make it possible to amplify a cDNA fragment were designed (Example 3). After culturing and amplification of MCF7 line cells, extraction and purification of RNAs, RT PCRs and cloning in a shuttle vector were carried out, and then screening of the resistant colonies and sequencing made it possible to reveal sequences characterizing the genes LIV21F and LIV21K (Examples 4 and 5). More than twenty characteristic clones out of 150 clones were studied. The cDNA of these clones was used to screen a library prepared from the total mRNA of MCF7 cells.

The sequence of this new products are new transcription factors, the nuclear translocation of which change their role and their function, that being correlated for some of them with the establishment of the cellular quiescence such as for example LIV21F, E2F4. In addition it is linked to the DNA role and function. Furthermore, it forms heterodimers with other transcription factors and certain bind to DNA.

Using Northern blotting, the inventor then followed the expression of this new product during development, from the embryonic stage. It was observed that the amount of the LIV21 protein increases as development progresses, i.e. as a quiescent cell state becomes established. Through the same strategy, the inventor showed that the LIV21/E2F4 complex inhibited the expression of E2F1. This complex could correspond to a new checkpoint in the arrest of cell proliferation. LIV21 complex and associated metabolic complex:

The present invention relates to the LIV21 complex and its new nucleotide sequences SEQ ID No. 171 to SEQ ID NO 217 also used for some of them in the form of siRNA for diagnostic and therapeutic applications and also LIV21F and LIV21K polypeptides and derivatives and fragments and isoforms thereof (SEQ ID No 215).

LIV21 human complex, characterized in that it comprises: the nucleotide sequences SEQ ID NO 171 to 175, and siRNA sequence derived from one of the RNA sequences SEQ ID NO 120 and SEQ ID NO 121, and 171 to 175 a protein fraction comprising at least sequence SEQ ID NO 1 and 181 or a sequence having 90%, and preferably 80%, and more preferably 70% identity with said SEQ ID NO 1 and 181.

LIV21 human complex, characterized in that it comprises: The nucleotide sequences SEQ-ID NO 171, 172, and the protein fractions comprising at least sequence SEQ ID NO 1 or a sequence having 181 or 70, 10 80 or 90% identity with said SEQ ID NO 1 or 181 and SEQ ID NO 183 or a sequence having 70, 80 or 90% identity with said SEQ ID NO 183.

LIV21 complex human, characterized in that it also comprises:
nucleotide sequences SEQ ID NO 123, 124 and 127, and the protein fractions comprising at least sequence SEQ ID No. 1 or a sequence having 70, 80 or 90% identity with said SEQ ID NO 1 and the sequence from 181 to 185 or a sequence having 70, 80 or 90% identity with said SEQ ID NO 181 to 185.

LIV21 complex human characterized in that it further comprises:
Any of the nucleotide sequences or ribonucleic SEQ ID NO 119, 120, 121, 122, 123, 124, 125, 126 or 127 or a sequence having 90%, and preferably 80%, and more preferably 70% identity with said sequence SEQ ID NO 119 to 127, or

```
                                   (SEQ ID NO: 306)
    UUGGUAACGACCAUGCCAC,
or
                                   (SEQ ID NO: 307)
    UUCACUUAGAAUAAUGUCC,
or
                                   (SEQ ID NO: 308)
    UCUUUGUGAAUUUGACAAC,
or
                                   (SEQ ID NO: 309)
    UCAAGGUCCAGGCUACAAC,
``` or
Any of the siRNA following:

```
                                   (SEQ ID NO: 310)
    GUGGCAUGGUCGUUACCAA dTdT (SEQ ID NO: 311)
    dTdT CACCGUACCAGCAAUGGUU (SEQ ID NO: 312)
    GGACAUUAUUCUAAGUGAA dTdT (SEQ ID NO: 313)
    dTdT CCUGUAAUAAGAUUCACUU (SEQ ID NO: 290)
    GGAAGAAUCUCAUCUCAGAUUCAA )
    UUCCUUCUUAGAGUAGAGUCUAGAG- (SEQ ID NO: 112)
    GCAGAUCAUGAGGUCAAGAUUCAA )
    UUCGUCUAGUACUCCAGUUCUAGAG- (SEQ ID NO: 113)
    GAAGAAUCUCAUCUCAGAAUUCAA )
    UUCUUCUUAGAGUAGAGUCUUAGAG- (SEQ ID NO: 114)
    GUGUGAGACUCCAUCUGAAUUCAA )
    UUCACACUCUGAGGUAGACUDAGAG- (SEQ ID NO: 115)
    GAUCAUGAGGUCAAGAGAUUUCAA )
    UUCUAGUACUCCAGUUCUCUAAGAG- (SEQ ID NO: 291)
    GAGAGUCAUCUUACUCAGAUUCAA )
    UUCUCUCAGUAGAAUGAGUCUAGAG- (SEQ ID NO: 292)
    GCUGGGUGUGGUAGUGCAUUUCAA )
    UUCGACCCACACCAUCACGUAAGAG- (SEQ ID NO: 293)
    GUCAAGAGAUCGAGACCAUUUCAA )
    UUCAGUUCUCUAGCUCUGGUAAGAG- (SEQ ID NO: 294)
    GUCAUCUUACUCAGAGCAUUUCAA )
    UUCAGUAGAAUGAGUCUCGUAAGAG- (SEQ ID NO: 116)
    GGCUGAGGCAGGCAGAUCAUUCAA )
    UUCCGACUCCGUCCGUCUAGUAGAG- (SEQ ID NO: 295)
    GGAGUAUAGGAAUCUCCUAUUCAA )
    UUCCUCAUAUCCUUAGAGGAUAGAG- (SEQ ID NO: 117)
    GGUAGUGCAUGCCUGUAGUUUCAA )
    UUCCAUCACGUACGGACAUCAAGAG- (SEQ ID NO: 280)
    GAGAUGGCGCCACUGUACUUUCAA )
    UUCUCUACCGCGGUGACAUGAAGAG- (SEQ ID NO: 296)
    GCCUGGCGACAGUGUGAGAUDCAA )
    UUCGGACCGCUGUCACACUCUAGAG- (SEQ ID NO: 297)
    GCCUGUAGUCCCAGCUACUUUCAA )
    UUCGGACAUCAGGGUCGAUGAAGAG
```

LIV21 complex and associated metabolic complex:
The present invention relates to the LIV21 complex and its new nucleotide sequences SEQ ID No. 171 to SEQ ID NO 217 also used for some of them in the form of siRNA for diagnostic and therapeutic applications and also LB/21F and LIV21K polypeptides and derivatives and fragments and isoforms thereof (SEQ ID No 215).

LIV21 human complex, characterized in that it comprises:
the nucleotide sequences SEQ ID NO 171 to 175, and
siRNA sequence derived from one of the RNA sequences SEQ ID NO 120 and SEQ ID NO 121, and 171 to 175
a protein fraction comprising at least sequence SEQ ID NO 1 and 181 or a sequence having 90%, and preferably 80%, and more preferably 70% identity with said SEQ ID NO 1 and 181.

LIV21 human complex, characterized in that it comprises:
The nucleotide sequences SEQ-ID NO 171, 172, and the protein fractions comprising at least sequence SEQ ID NO 1 or a sequence having 181 or 70, 10 80 or 90% identity with said SEQ ID NO 1 or 181 and SEQ ID NO 183 or a sequence having 70, 80 or 90% identity with said SEQ ID NO 183.

LIV21 complex, human, characterized in that it also comprises:
nucleotide sequences SEQ ID NO 123, 124 and 127, and the protein fractions comprising at least sequence SEQ ID No. 1 or a sequence having 70, 80 or 90% identity with said SEQ ID NO 1 and the sequence from 181 to 185 or a sequence having 70, 80 or 90% identity with said SEQ ID NO 181 to 185.

LIV21 complex human characterized in that it further comprises:
Any of the nucleotide sequences or ribonucleic SEQ ID NO 119, 120, 121, 122, 123, 124, 125, 126 or 127 or a sequence having 90%, and preferably 80%, and more preferably 70% identity with said sequence SEQ ID NO 119 to 127, or

```
                                   (SEQ ID NO: 306)
    UUGGUAACGACCAUGCCAC,
or
                                   (SEQ ID NO: 307)
    UUCACUUAGAAUAAUGUCC,
or
```

-continued

UCUUUGUGAAUUUGACAAC, (SEQ ID NO: 308)

or

UCAAGGUCCAGGCUACAAC, (SEQ ID NO: 309)

or

Any of the siRNA following:

GUGGCAUGGUCGUUACCAA dTdT (SEQ ID NO: 310)

dTdT CACCGUACCAGCAAUGGUU (SEQ ID NO: 311)

GGACAUUAUUCUAAGUGAA dTdT (SEQ ID NO: 312)

dTdT CCUGUAAUAAGAUUCACUU (SEQ ID NO: 313)

LIV21 complex human (FIGS. 1 et 2) characterized in that it further comprises at least:
  Any one of the nucleotide sequences SEQ ID NO 123, SEQ ID NO 124 and SEQ ID NO 127 to 149, or SEQ ID NO 217
  any one of amino acid sequences SEQ ID NO 1 to 148 and SEQ ID NO 150 to 170 and SEQ ID NO 180 to 185, or a sequence having 90%, and preferably 80%, and more preferably 70% identity with said sequence SEQ ID NO 180 to 185 and SEQ ID 1, 2, 5 and SEQ ID NO 215

LIV21 Complex human characterized in that said protein fraction further comprises any of the following proteins: E2F1, E2F4, p130, p300, p107, Liv21F, HDAC-1, PML, SUMO et PKC epsilon, Aurora A, Survivin, BCAS4, BCAS3, RFSH.

LIV21 complex human characterized in that it interacts with at least one of its associated partners, at least one of its associated partners are selected from the group consisting of: any one of the following proteins: RBP2, TNFalpha, crb2, cycE/cdk2, cdkl, CREB1, p300, p107, NFkB, cdc2A, mdm2, p21, p53, p65, p73 MYC, NMYC, TGFbéta, Chlatrin, Aurora, AKT, BRCA1, FOX04 or cyclin A et D1, CHUK, HMGA2, IKBKB
  an antibody of anyone of the following proteins: RBP2, E2F4, E2F1, SUMO, HDAC-1, crb2, Int2, cmd2, cycE/cdk2, cdkl, CREB1 et p300, Rb, p 107, p 130 of the family of pocket proteins NFkB, cdc2A, mdm2, p21, p53, p65, p73, the cyclin A and D1, CHUK, MYC, NMYC, TGF Beta, Chlatrin (2), Aurora, AKT, BRCA1, FOX04, HMGA2, BCAS3, BCAS4, solute carrier.
  in that it comprises an extract of proteins and peptides obtained by latching to a polyclonal antibody of the LIV21, and
  in that its electrophoretic profile acrylamide gel comprises at least three bands: band of 50 kD, 51 kD band, and the band of 52 kD.

Complex human LIV21 is also characterized in that, after trypsin digestion, the profile of MALDI includes at least mono isotopic peaks following:
1135.563; 1151.545; 1167.604; 1206.589; 1324.634; 1336.658; 1507.735; 1604.710; 1800.940; 2087.034.

Method of detecting the complex human LIV21, characterized in that it comprises the implementation of at least one probe specific for at least one sequence of said complex LIV21 according to claim 1 or 2.

Method of detecting the complex human LIV21, characterized in that it further comprises the implementation of at least one probe specific for at least one sequence of the LIV21 said complex and its associated partners.

Method of detection of the complex and its partners LIV21 in that it is comprises at least the steps of:
  A step of extracting biological material from a biological sample taken from a patient,
  A step of contacting said biological material with at least said probe specific for any of the sequences of said human or complex LIV21 or LIV21 said complex and its content partners, and at least one control and
  A step of detecting the expression of the expression products of the genes of said complex of said human or LIV21 LIV21 complex and its content partners, said products being comprised of expression of messenger RNA, or peptides, or proteins.

Detection method is characterized in that it also aims to screen a candidate compound, said candidate compound is capable of modulating the activity of the complex human LIV21, and that it also includes:
  a step of contacting said biological material with said candidate compound, and a step of selecting said candidate compound.

Method is characterized in that said biological sample is taken from a cancer patient and in a healthy patient, and in that said biological material comprises cell nuclear extracts, and cytoplasmic cell extracts, cell membrane extracts, and in that it further comprises a step of determining of the under-expression and overexpression of the gene products of said complex of said human or LIV21 LIV21 human complex and its content partners said biological extracts.

Method is characterized in that it further comprises a step of determining the ratios of said sub-expression and over-expression of said gene products: cell nuclear extracts, and cytoplasmic cell extracts, cell extracts or membrane, and in that it further comprises a step of such analysis combined ratios of said biological material taken from a cancer patient and in a healthy patient.

Method is characterized in that said probe comprises a sequence specific siRNA labeled with rhodamine.

A method according to any one of the above approaches is, characterized in that it implements a biochip, on which is deposited at least one sequence-specific probes from said complex human LIV21.

Method is characterized in that, in addition, it implements at least one specific probe sequences LIV21 said complex human and associated partners Method is characterized in that said biochip is a protein biochip, or a biochip antibody, or a nucleotide acid microarray, or a RNAm biochip, or a siRNA biochip.

Method is characterized in that said detecting step implements any means of optical imaging, or any means of sonic or any means of spectroscopy.

FIG. 1 characterizing the protein complex, and its PI and its PM are dependent on the temperature and conditions of migration and its observation in total extracts or in extracts of cellular compartments.

FIGS. 1, 2, 3). It gives more than 54 peptides following digestion with Promega trypsin (FIG. 7). The characteristics of the LIV21F protein are also described in FIGS. 1, 2, 3, 4. Twenty specific peptides of LIV21 have been described: LIV21a (SEQ ID No 1) and LIV21b (SEQ ID No 2) at the sequence 180.

The gene of this protein is characterized by two main sequences (i.e. patent in listing) and sequences representing an alternate splicing.

LIV21K corresponds to a sequence of strong homology (of more than 60%) with AD7cNTP, the neural thread protein in N terminal (position 193 to 299) of (060448_Human). (SEQ ID NO: 180)

SVAQAGVQWRNLGSLQALPPGFMPFSCLSLLSSWDYRRLPPRPATFLYF

PRQGFTVLARMVSISPRDPPASASQSVGIAYISNFFFFEMESRSVAQAG

VQWHNLGSLQALPPGFMPFSCLSLLSSWDYRRLPPRPATFLYFPR

With variable ones within peptide in position (i.e. figure . . . ):
The structure of LIV21K is like that of the AD7C NTP, i.e. repeated regions that can be also analyzed under regions which correspond to functional fields.

(SEQ ID NO: 314)
SVXQAGVQWXNLGSLQXLPPGXXXFSCLSLXSSWDYXXLPPXPAXF

Or a variable one:

(SEQ ID NO: 315)
SVXQAGVQWXNLGSLQXLPPGFXXFSCXSLSSWDYRRXPPRXA

Between these two repeated reasons, there is a peptide of 40 amino-acids with a reason also preserved:

(SEQ ID NO: 316)
ISPXDXPASASQSXGIXXXSX

THE LIV21I:
(SEQ ID NO: 317)
FLYFPRQGFTVLARMVSISPRDPPASASQSVGIAYISN

With Alternatives in Position:
For example for LIV21I
In position 31, an A instead of the V and in position 34 a T instead of the amino-acid A.
Thus: the amendment of the end PASASQSAGIT (SEQ ID NO: 318) but also an alternative where the A becomes T in position 25: . . . DPPTSASQSVGI (SEQ ID NO: 319)
Item for LIV21F or K:
SEQ ID NO 320: FSCLSL L SSWDYRR L PPRPA T FLYF where the amino-acid in position 7 here becomes a proline (P instead of L) and/or in position 15 too (with the possibility of an alternative Alanine; sometimes the position 14 changes of a R in H and/or in position 21 where an amino-acid T becomes N.

SEQ ID NO 321:
FSCLSL P SSWDYRR P PPRPA N FLYF

Moreover, two other peptides of LIV21 are also described: the peptide LIV21c (SEQ ID No 3) and the peptide LIV21d (SEQ ID No 4). The peptide LIV21e (SEQ ID No 5), KFFVFALILALMLSMCGADSHAKR (SEQ ID NO: 322) with which the final section is homologous with a sequence with LIV21K.
Other specific peptides of LIV21 are described in the additional list.
A homology with a functional segment of the protein zinc finger 575 (ZN575-Human): score 13 to 48 and 91% of recovery
A homology of sequence 6 and 56 and with the field MF MR which is the bzip field of a transcription factors containing a signal of nuclear localization and a trans-regulating activity in TAF1.

For the purposes of the invention, a preferred protein comprises at least one sequence chosen from SEQ ID Nos 1-180 or a sequence having 70%, 80% or preferably 90% homology with said sequence (SEQ ID NO 215).
The LIV21 complex comprises proteins including 3D helices structures, which have a major functional role for their interactions with the rest of the Liv21 complex.
The present invention concerns a purified or recombinant, isolated human polypeptide having a sequence comprising the sequence SEQ ID No 1 and/or SEQ 5 ID No 2 and/or SEQ ID No 3 and/or SEQ ID No 4 and/or SEQ ID No 5. Preferably, the polypeptide LIV21F comprises the sequences SEQ ID Nos 1, 2 and 5. In a preferred embodiment, the complex is studied based on a sequence selected among the peptide sequences obtained by MALDI (FIGS. 3, 4 and 5). The invention also concerns the three peptides LIV21a (SEQ ID No 1), LIV21b (SEQ ID No 2) and LIV21e (SEQ ID No 5). It also concerns peptides comprising at least 10 consecutive amino acids of human LIV21, preferably at least 20, 30 or 50 consecutive amino acids of LIV21 peptides (i.e. sequences list 1-215 in annexes).
The present invention also relates a polynucleotide encoding for the human protein Liv21, Liv21a and/or Liv21b, generally a polynucleotide encoding for a polypeptide according to the present invention. The polynucleotide encoding for Liv21F and this one encoding for LIV21K may be an mRNA, a cDNA or a genomic DNA. The polynucleotides according to the present invention may be isolated from cells and more particularly from human cells or from human cDNA libraries. They can also be obtained by a polymerase chain reaction (PCR) carried out on the total DNA of the cells or else by RT-PCR carried out on the total cellular RNAs or by chemical synthesis. Probes and primers described in the present invention may be used to isolate and/or prepare a polynucleotype encoding for a protein of the Liv21F. It relates also a cloning or expression vector comprising such polynucleotide.
Such vector may include the elements required for the expression (expression vector) and eventually for the secretion of the protein in a host cell (signal peptide of secretion). Preferably the said vectors comprise: a promoter, signals of initiation and termination of translation, as well as adapted regions for transcription regulation. The vector can be a plasmid, a cosmid, a BAC, a phage, a virus, or other. The invention relates to a host cell or a non-human transgenic animal including a vector or a polynucleotide according to the present invention.
The invention also concerns derivatives of interest of LIV21F or LIV21K which are for example proteins of merger in which is amalgamated with proteins markers like the GFP. In addition, the LIV21F or LIV21K protein and all described peptides (i.e. patent in listing) can be marked by any known means of those skilled in the art. The siRNA too (SEQ ID NO 91 to 118).
The present invention also relates to an antibody which is linked specifically to a polypeptide according to the present invention, preferably human LIV21, a fragment or a derivative of this one. In a specific mode of realization, the antibody is linked specifically to a LIV21a or LIV21b peptide or LIV21F or LIV21K polypeptides.
The method can in particular comprise the detection of the product of expression of two of these genes or of the three genes. Moreover, at least one of the ratios LIV21/PKCS, LIV21/E2F4 and LIV21/E2F1 can be determined in the present method. This ratio can be determined in the cytoplasm and/or in the nucleus. Preferably, these ratios are determined in the nucleus. Preferably, these ratios are compared with those obtained in a normal cell.

In one embodiment, the expression product of the genes is detected at the mRNA level, it being possible for the mRNA to be detected by any means known to those skilled in the art.

Thus, the method according to the present invention also relates to the detection of a polynucleotide encoding the human LIV21 protein or a fragment thereof, for example LIV21a and/or LIV21b. The polynucleotide encoding LIV21 may be an mRNA, a cDNA or a genomic DNA. The polynucleotides may be isolated from cells of the biological sample. They may also be obtained by a polymerase chain reaction (PCR) carried out on the total DNA of the cells or else by RT PCR carried out on the total RNA of the cells or polyA RNAs.

The mRNA may be detected by an RT PCR analysis. For this, the method uses a pair of primers specific for the expression product to be detected, in particular LIV21, PKCε, E2F1 or E2F4. The term "specific pair of primers" is intended to mean that at least one of the primers is specific for the expression product to be detected, i.e. that this pair of primers makes it possible to specifically amplify a fragment of the desired mRNA. Preferably, the RT PCR analysis carried out on nuclear and/or cytoplasmic extracts of the cells contained in the sample from the patient. Optionally, the RT PCR analysis may be a quantitative analysis. A pair of primers specific for LIV21 can be prepared on the basis of the teachings of the present application. For example, the pair of primers may comprise the primers described in the sequences listing 5 SEQ ID Nos 3 and 4, and additional sequences of the list obvious thus numbered from 119 to 149 and 171 to 180 with optionally all the additional nucleotidic sequences of the additional list.

The pairs of primers specific for PKCε, E2F1 and E2F4 are well known by those skilled in the art (Caroll J S 2000; Mundle S D 2003; Stevaux 0 2002; Cheng T 2002; Opalka B 2002). The mRNA may also be detected by Northern blotting analysis. For this, the method uses a probe specific for the expression product to be detected, in particular LIV21, PKCε, E2F1 or E2F4. A probe specific for LIV21 can be prepared on the basis of the teachings of the present application. An example of a specific probe comprises the sequence SEQ ID No 5. Preferably, the Northern blotting analysis is carried out on nuclear and/or cytoplasmic extracts of the cells contained in the sample from the patient. The nucleic probe is labelled. The oligonucleotide labelling technique is well known to those skilled in the art. The labelling of the probes according to the invention can be carried out with radioactive elements or with non radioactive molecules. Among the radioactive isotopes used, mention may be made of $^{32}P$, $^{33}P$ or $^{3}H$. The non radioactive entities are selected from ligands such as biotin, avidin, streptavidin or digoxigenin, haptens, dyes and luminescent agents such as radioluminescent, chemoluminescent, bioluminescent, fluorescent or phosphorescent agents. The probes specific for PKCε, E2F1 and E2F4 are well known to those skilled in the art. In a preferred embodiment, the expression product of the genes is detected at the protein level. Preferably, the protein is detected using a specific antibody. Thus, the method comprises a step of bringing the cells of the biological sample into contact with an anti-human LIV21 antibody. The antibodies can be monoclonal or poly-clonal. The antibody can for example be a serum anti-LIV21. When the product of expression of one of the genes PKCε, E2F1 and E2F4 must be detected, the method can use antibodies specific for the PKCε, E2F1 and E2F4 proteins, respectively. Polyclonal and monoclonal antibodies directed against PKCε, E2F1 and E2F4 are commercially available. By way of example, mention may be made of, for PKCε, a rabbit polyclonal antibody (Santa Cruz Technology, sc-214), for E2F1, a rabbit polyclonal antibody (Santa Cruz Technology, sc-860), and for E2F4, a rabbit polyclonal antibody (Santa Cruz Technology, sc-866). Preferably, the antibodies are labelled, directly or by means of a secondary antibody. The antibody labelling techniques are well known to those skilled in the art. In a specific embodiment, the protein can be detected by Western blotting analysis. The Western blotting analysis can be carried out on nuclear and/or cytoplasmic extracts of the cells contained in the sample from the patient. Briefly, the proteins are migrated in a gel and then blotted onto a membrane. This membrane is then incubated in the presence of the antibodies and the binding of the antibodies is optionally revealed using labelled secondary antibodies. In another embodiment, the protein is detected by immunohistochemistry, immunocytochemistry or immuno-radiography. These techniques are well known to those skilled in the art. The immunocytochemical analysis can be carried out on whole cells originating from the sample or which are derived there from, for example by cell culture. It can also be carried out on isolated nuclei. The immunohistochemical analysis can be carried out on mammary, nerve tissue sections etc. . . . By way of illustration, an immunocytochemical analysis can include the following steps. However, it is understood that other preparatory methods can be carried out. Cells originating from the biological 5 sample are cultured, preferably on slides (Lab Tek, Nunc, Germany), and then washed with buffer and fixed with paraformaldehyde (for example, 4%). A saturation step is preferably carried out by incubating the cells with buffer S (PBS-0.1% Triton X100-10% FCS). The cells are then incubated with a primary antibody and are then washed and incubated with a fluorescent secondary antibody, if necessary. The nuclei can be labelled with propidium iodide (Sigma). The slides are mounted in moviol for observation by fluorescence microscopy. Moreover, isolated nuclei sampled during a nuclear extraction can be fixed with paraformaldehyde (for example, 4%). The suspensions of nuclei are deposited between a slide and cover slip and the observation is carried out by fluorescence microscopy and by confocal microscopy. The primary antibodies are, for example, rabbit antibodies and the secondary antibodies are labelled antibodies directed against rabbit IgGs. The biological samples originate from a patient potentially suffering from cancer or for whom it has been established that said patient is suffering from cancer. "Biological sample" is intended in particular to mean a sample of the biological fluid, living tissue, tissue fragment, mucosity, organ or organ fragment type, or any culture supernatant obtained by means of taking a sample. The method according to the present invention can comprise a step of taking a biological sample from the patient. The detection step can be carried out directly on a tissue section of the sample, or on a culture of cells originating from the sample, or on total cell extracts, nuclear extracts and/or cytoplasmic extracts. In a specific embodiment of the method comprising the detection of the product of expression of the PKCe gene, a significant increase in PKCε is indicative of the presence of cancer cells. More specifically, the amount of PKCε in normal cells is compared with the amount of PKCε in the cells of the sample, and the significant increase is determined by means of this comparison. The method according to the present invention can optionally comprise the measurement of the LIV21/PKCS content. This LIV21/PKCS ratio increases in the cytoplasmic fraction of cancer cells compared with normal cells. In another specific embodiment of the method comprising the detection of the product of expression of the E2F4 gene, the method comprises the detection of the association of LIV21 with the E2F4 protein, and a decrease in this association is indicative of the presence of cancer cells. The detection of the association of LIV21 with the E2F4 protein can be carried out by concurrent detection of LIV21 and of E2F4. The method according to the present invention can optionally comprise the measurement of the E2F4/LIV21 content. This E2F4/LIV21 ratio decreases in the nucleus of cancer cells compared with normal cells. In an additional embodiment of the method comprising the detection of the product of expression of the E2F1 gene, the presence of the E2F1 protein in the nucleus is indicative of the presence of cancer cells. The method according to the present invention can optionally comprise the measurement of the E2F1/LIV21F content. This E2F1/LIV21F ratio increases in the nuclear fraction of cancer cells compared with normal cells. The method according to the present invention allows in particular the detection of metastasized cancer, therapeutic monitoring and/or recurrences following treatment and makes it possible to determine the degree of invasiveness of a cancer or neurodegenerative disease or Alzheimer disease. The specificity of the detection can be related to the crossing over of information obtained through the existence and the topography of LIV21 by all imaging and spectroscopy means and obtained by combination with other known cancerological indicators via protein arrays or microarrays. Thus, the detection based on LIV21 can be combined with the detection of other cancer markers, in particular breast cancer markers, known to those skilled in the art and nerve cancers. In fact, the present invention concerns a method for the therapeutic monitoring of an anticancer treatment in a patient suffering from cancer, comprising the administration of the anticancer treatment to said patient and the detection of cancer cells in a biological sample from the patient, according to the method of the present invention. A decrease in cancer cells will be indicative of the effectiveness of the treatment. The detection of cancer cells in a biological sample from the patient, according to the method of the present invention, can be carried out once or several times over the course of the anticancer treatment or after the anticancer treatment. Preferably, the biological sample originates from the tissue affected by the cancer treated.

Moreover, the present invention also concerns a method for the detection of recurrences subsequent to an anticancer treatment of a cancer in a patient, comprising the detection of cancer cells in a biological sample from the patient, according to the method of the present invention. The detection of cancer cells in a biological sample from the patient, according to the method of the present invention, can be carried out once or several times after the anticancer treatment. The detection of cancer cells is indicative of recurrences. Preferably, the biological sample originates from the tissue affected by the cancer treated. The present invention also describes a kit for carrying out a method according to the invention. More particularly, the invention concerns a kit for the detection of cancer cells in a biological sample from a patient, comprising one or more elements selected from the group consisting of an antibody which binds specifically to human LIV21 according to the present invention and an anti-LIV21 serum according to the present invention, an oligonucleotide probe specific for the LIV21 mRNA and a pair of primers specific for the LIV21 mRNA. In a preferred embodiment, the kit comprises antibodies, which bind specifically to human LIV21. In another preferred embodiment, the kit comprises an oligonucleotide probe specific for the LIV21 mRNA. It may also comprise a probe specific for a "housekeeping" gene. The kit according to the present invention can comprise reagents for the detection of an LIV21-antibody complex produced during an immunoreaction. Optionally, the kit according to the present invention also comprises means for detecting the product of expression of at least one gene selected from the group consisting of the protein kinase C epsilon (PKCε) gene, the E2F1 gene and the E2F4 gene. This detection means can be antibodies specific for the protein, oligonucleotide probes specific for the mRNA concerned and/or a pair of primers specific for the mRNA. The present invention also relates to a diagnostic composition comprising one or more elements selected from the group consisting of an antibody according to the present invention and a serum according to the present invention, an oligonucleotide probe specific for the LIV21 mRNA and a pair of primers specific for the LIV21 mRNA.

Anticancer Therapy

In the context of an anticancer therapy, it is possible to envision increasing the amount of LIV21 present in the nucleus. For this, the nuclear localization in cancer cells of LIV21 expression could be promoted. Liv21 being able to translocate in the nucleus by itself, one could envisage the construction of an expression vector including a polynucleotide coding for human Liv21 in order to over express these protein in the cell nucleus for that we wish regulate the proliferation (SEQ ID NO 215). The expression vector encoding Human Liv21 can be administrate in vivo to the patient by any mean known by those skilled in the art, SEQ ID NO 215 for example and inhibitor peptide of Liv 21. For example, the expression vector can be administrated as naked DNA (for example EP 465529). The microinjection, electroporation, phosphate of calcium precipitation techniques and formulations using nanocapsules or liposomes are other techniques available (SEQ ID NO 217). The expression vector may also be in the form of a recombinant virus, including, a polynucleotide encoding human Liv21 inserted into its genome. The viral vector can be selected for example from an adenovirus, a retrovirus, in particular a lentivirus, and a virus adeno-associated (AAV), a herpes virus (HSV), a cytomegalovirus (CMV), a vaccine virus, etc. . . .

So advantageous, the recombinant virus is a defective virus.

Preferably, the expression vector permits a cellular targeting. So this vector could target cancer cells or a particular cell type that is affected by cancer. Targeting of particular cellular type can be realized by placing the polynucleotide coding Liv21 under the control of a promoter tissue-specific. In another alternative the expression vector may be targeted, for example, in association with a specific molecule of a particular tissue or cancer cells, for example a specific antibody to a molecule expressed specifically by the particular tissue or the cells of cancer. Also the choice of expression vector may also influence the cellular targeting. Indeed, if the vector is a virus, the virus tropism natural or amended may also allow a certain target.

The present invention concerns a pharmaceutical composition comprising a polynucleotide encoding for Liv21 (SEQ ID NO 215), more particularly an expression vector coding for Liv21. It also concerns the use of a pharmaceutical composition comprising a polynucleotide encoding for Liv21, in particular an expression vector encoding for Liv21 as medicament. Preferably, the present invention concerns the use of a pharmaceutical composition comprising a polynucleotide encoding for Liv21, in particular an expression vector encoding for Liv21, for the preparation of a medicament for use in treating cancer. Finally, it concerns a method for treating cancer in a patient, comprising the administration to the cancer cells of a polynucleotide encoding for Liv21, Liv21 expression making it possible to reduce or abolish the cancerous phenotype of the treated cells. Preferably, cancer is selected from breast cancer, bladder cancer, ovarian cancer, uterus cancer lung cancer, skin cancer, prostate cancer, colon cancer, a glioblastoma, without being limited thereto. Moreover, the nuclear localization of LIV21 could be promoted, for example by decreasing the activity of PKCs in the cancer cells and by using HDAC inhibitors.

In another specific embodiment of anticancer therapy, it is possible to envision decreasing the activity of PKCs in the cancer cells. This decrease in activity can be produced by decreasing the activity of the PKCs protein or by decreasing its expression. A decrease in the activity of the PKCs protein can be obtained by administering PKCs-protein inhibitors to the cancer cells. The PKCs-protein inhibitors are well known to those skilled in the art. A decrease in the expression of the PKCs protein can be obtained by using antisenses or siRNA specific for the PKCs gene. Kits are commercially available. Moreover, the techniques concerning inhibition by means of antisense or siRNA are well known to those skilled in the art (Arya R 2004, Lee W 2004, Sen A 2004, Platet N 1998, Hughes 1987) (SEQ ID NO 215 and SEQ ID NO 216).

The next siRNA can be also used:

```
                                  (SEQ ID NO: 108)
GCUGAGGCAGGCAGAUCAUUUCAA )
UUCGACUCCGUCCGUCUAGUAAGAG- (SEQ ID NO: 109)
GUACCAUUUCACAACAACUUUCAA )
UUCAUGGUAAAGUGUUGUUGAAGAG-
```

The present invention therefore concerns a pharmaceutical composition comprising a PKCs-protein inhibitor. It also concerns the use of a pharmaceutical composition comprising a PKCs-protein inhibitor as a medicament, in particular for the preparation of a medicament for use in treating cancer. Finally, it concerns a method for treating cancer in a patient, comprising the administration to the cancer cells of a PKCs-protein inhibitor, the pKCs-protein inhibitor making it possible to reduce or abolish the cancerous phenotype of the treated cells. In a first embodiment, the PKCs-protein inhibitor decreases the activity of the PKCs protein. In a second embodiment, the PKCs-protein inhibitor decreases the expression of the PKCs protein. Preferably, cancer is selected from breast cancer, bladder cancer, ovarian cancer, uterus cancer lung cancer, skin cancer, prostate cancer, colon cancer, liver cancer, a sarcoma, a leukaemia and glioblastoma, without being limited thereto. PKC epsilon inhibitors are published and commercially available for other applications.

In the context of a therapy for a neurodegenerative disease, it is possible to envision decreasing the amount of LIV21 present in the nucleus. For that, the Liv21 expression could be decreases or blocked in nuclear of the diseased cells of neurodegeneration. The cells affected by the neurodegenerative disease are generally neurons, motorneurons, etc.

In a preferred embodiment, the neurodegenerative disease is chosen from Alzheimer's disease, Huntington's disease, Parkinson's disease and amyotrophic lateral sclerosis (ALS). The inhibition or the blocking of LIV21 expression can be carried out by any means known to those skilled in the art. In particular, by way of illustration, mention may be made of the antisense strategy, siRNA and ribozymes. Thus, an antisense oligonucleotide or an expression vector encoding this antisense oligonucleotide could be prepared and used to block the translation of the mRNA encoding LIV21F in vivo. Moreover, a ribozyme can be prepared for cleaving and destroying, in vivo, the mRNA encoding LIV21. It is also possible to envisage a triple-helix strategy in which an oligonucleotide is designed so as to hybridize with the gene encoding LIV21 and to thus block the transcription of this gene.

Moreover, for this, the nuclear localization of LIV21 could also be hindered, for example by increasing the activity of PKCs in the cells affected by the neurodegenerative disease. In one particular therapeutic method against neurodegenerative diseases, it is possible to envision increasing PKC epsilon activity in the cells affected by the neurodegenerative disease. This increase in activity can be produced by increasing the activity of the PKCs protein or by increasing its expression. An increase in the activity of the PKCs protein can be obtained by administering PKCs-protein activators to the cells affected by the neurodegenerative disease. The PKCs-protein activators are well known to those skilled in the art (Toma 0(2004), Activation of PKCs by DAG, AGPI: oleic acid, linoleic acid, arachidonic acid, etc. . . .

Activation and proteolysis of PKCs in gonadotropic cells: Communication 2004 by Macciano H, Junoy B, Mas J L, Drouva S V, UMR6544 Marseille). An increase in the expression of the PKCs protein can be obtained by using expression vectors encoding the PKCs protein and which make it possible to overexpress it in the cells affected by the neurodegenerative disease.

Thus, the present invention concerns a pharmaceutical composition comprising a PKCs-protein activator or an expression vector encoding the PKCs protein. It also concerns the use of a PKCs-protein activator or of an expression vector encoding the PKCs protein, for the preparation of a medicament for use in the treatment of a neurodegenerative disease.

Screening Method

The invention concerns methods for the selection, identification, characterization or optimization of active compounds, which decrease cell proliferation, based on the measurement of the nuclear versus cytoplasmic localization of LIV21, or of the binding of the LIV21 protein to the E2F4 protein.

In a first embodiment, the selection, the identification, the characterization or the optimization of active compounds of therapeutic interest comprises bringing a candidate compound into contact with a cell and determining the nuclear versus cytoplasmic localization of the LIV21 expression product. An increase in the nuclear localization of LIV21 indicates that the candidate compound is active in terms of decreasing or abolishing cell proliferation. A decrease in the nuclear localization of LIV21 indicates that the candidate compound is active in terms of treating or preventing a neurodegenerative disease.

In a second embodiment, the selection, the identification, the characterization or the optimization of active compounds of therapeutic interest comprises bringing a candidate compound into contact with a cell and determining the level of expression of the gene encoding the PKCs protein. A decrease in the expression of PKCs indicates that the candidate compound is active in terms of decreasing or abolishing cell proliferation. An increase in the expression of PKCs indicates that the candidate compound is active in terms of treating or preventing a neurodegenerative disease.

In a third embodiment, the selection, the identification, the characterization or the optimization of active compounds of therapeutic interest comprises bringing a candidate compound into contact with a cell and determining the level of LIV21/E2F4 complex. An increase in the level of LIV21/E2F4 complex indicates that the candidate compound is active in terms of decreasing or abolishing cell proliferation. A decrease in the level of LIV21/E2F4 complex indicates that the candidate compound is active in terms of treating or preventing a neurodegenerative disease. In a fourth embodiment, the selection, the identification, the characterization or the optimization of active compounds of therapeutic interest comprises bringing a candidate compound into contact with a cell and determining the level of expression of the gene encoding the E2F1 protein. A decrease in the expression of E2F1 indicates that the candidate compound is active in terms of decreasing or abolishing cell proliferation. An increase in the expression of E2F1 indicates that the candidate compound is active in terms of treating or preventing a neurodegenerative disease.

The invention also relates to a method of screening for a compound capable of interacting in vitro, directly or indirectly, with LIV21, characterized in that: in a first step, the candidate compound and LIV21 are brought into contact and, in a second step, the complex formed between said candidate compound and LIV21 is detected by any appropriate means.

The present invention also relates to a method of screening for a compound capable of modulating (activating or inhibiting) the activity of the LIV21 protein, characterized in that: in a first step, cells of a biological sample expressing the LIV21 protein are brought into contact with a candidate compound, in a second step, the effect of said candidate compound on the activity of said LIV21 protein is measured by any appropriate means, and in a third step, candidate compounds capable of modulating said activity are selected. The activity of LIV21 can, for example, be estimated by means of evaluating the ability of the cell to divide, by measuring the expression of the E2F1 gene or by the cytoplasmic and/or nuclear localization of LIV21.

The candidate compound can be a protein, a peptide, a nucleic acid (DNA or RNA), a lipid, or an organic or inorganic compound. In particular, the candidate compound could be an antibody, an antisense, a ribozyme or an siRNA.

Other advantages and characteristics of the invention will appear in the examples and the figures which follow, and which are given in a non limiting manner.

EXAMPLES

Example 1

Extraction of Proteins of the Liv21 Complex.
The MCF-7 Cell Line

The MCF-7 line is a non clonal human line of breast denocarcinoma cells. During their differentiation induced by exogenous factors, these cells develop a hypertrophy, membrane protrusions and a tendency to dissociate from one another. They acquire a secretory phenotype which is characterized by the appearance of numerous granules and of secretory canaliculi. In vivo, these cells are relatively non metastatic and this low invasiveness is thought to be due to a low constitutive activity of the protein kinases C (PKCs) and to a relatively low level of expression of protein kinase C alpha.

This line is used in many studies on proliferation, differentiation and apoptosis. These studies use appropriate drugs, such as TNF for the induction of apoptosis, or TPA (12-0-tetradecanoyl phorbol-13-10 sumoate) for the induction of differentiation and therefore for the study of departure from the cell cycle.

Extraction of Proteins of the Liv21 Complex.

After culture cells MCF7 (ATCC passage 15) and cell extraction, 5 mg of protein are centrifuged after homogenization in 10 ml RIPA buffer, antiprotease added. These protein extracts went loop for seven hours at a peristaltic pump on a column of affinity (HITRAP NHS ACTIV HP 1×5 ml: Article and catalog 17071701) which was set Liv21 antibody. Wash 3 times, 10 ml in RIPA buffer and then a half-eluting fractions of 500 nl in a buffer glycine PH2/HCL, then control gel SDS Page 10% (deposit of 25 nl of the fraction) followed by a 25 western blot to verify. Revelation of a band on gel at 51 kD flanked by two other bands at 50 and 52 kD respectively and a lower trace of a band 80 kD and 100 kD in gel mono dimensional (FIG. 1A). Moreover revelation of 12 spots between 50 kD and 70 kD in bidimensional gel (FIGS. 1B and 2), idem cultures of SHSY5Y (i.e. FIG. 7).

```
Peptide LIV21a
                                         SEQ ID No 1
RVYGPLTNPKPQ Peptide LIV21a
                                         SEQ ID No 2
PLMIIHHLDDCPHSQALK Peptide LIV21c
                                         SEQ ID No 3
SYMSMFLLLMAISCVLAK peptide LIV21d
                                         SEQ ID No 4
CYRSILHTKV Peptide Liv21b
                                         SEQ ID No 5
KFFVFALILALMLSMCGADSHAKR
```

Example 2: Mass Spectrometry

A mass spectrometry (MALDI) was realized for the LIV21 protein and its complex. The LIV21 protein (polynucleotide Liv21F) was digested with trypsin. The peptides derived from the digestion are solubilized in a solvent: acetonitrile/water (l/l) containing 0.1% of TFA (trifluoroacetic acid). A saturated solution of the alpha-cyano-4-hydroxycinnamic matrix was prepared in the same solvent. The same volume of the two solutions was taken and mixed together and 1 µl was deposited onto the MALDI plate for analysis. The mass spectrometry showed that the LIV21 protein and its complex digested with trypsin reveals hundred peptides following the band of gel extracted between 49 and 54 kD (i.e. FIGS. 3-5). The LIV21 protein was characterized by a molecular weight of 50 kD revealed by Western blotting and by a two-dimensional SDS PAGE gel (FIG. 2). But we find a product of 100 kD at 130 kD which could be a Liv21 dimer. (I.e. description FIGS. 4,5 and 6)

When it changes cell compartment and when it is sumoylated, the LIV21 protein has a molecular weight of approximately 60 kD. When it is phosphorylated in the cytoplasm, it exhibits two forms which differ by a few kilobases. A doublet is then observed.

Example 3: Analysis of Sequences in the Proteomic Databases

Several peptides in the patent in listing of the patent characterize it:

```
Peptide LIV21b
                          SEQ ID No 51
FVFALILALMLSMCG

Peptide LIV21b
                          SEQ ID No 5
KFFVFALILALMLSMCGADSHAKR
```

For example, the inventor obtained a very significant score of 81, hoped: 0.0012 for the histatin 3-2 variant with 52% of overlapping of sequences between the tested sample and histatin, this sequence SEQ ID No 5 is commune to Liv21 and HIS3-HUMAN (FIGS. 6 and 7). Using different database and a ppm which differed to 20 to 50 ppm, we obtain the same sequence for the commune part: SEQ ID No 51.

Example 4

Reverse Transcriptions:

After MCF7 cells (ATCC passage 15) had been thawed and cultured up to 2 00 million, they were trypsinized and frozen at −80° C. The RNA was extracted from two pools of 50 million cells with the Nucleospin RNA L kit (Macherey Nagel) ref. 740.962.20, resulting in a pool 1 of 318 µg and a second of 182 µg.

The poly A+RNA was extracted from 313 µg of total RNA of pool 1 using the oligo Tex mRNA Midi kit (Qiagen) ref. 70042.

I Reverse Transcription:

The RNA was reverse transcribed with the Fermentas Revert Aid H minus M MuLV Reverse Transcriptase, ref. EP0451 batch 1124, with 3.64 µg of total RNA and 0.45 µg of mRNA, 0 according to the supplier's conditions, with an oligo dT primer. Reactions were carried out at 2 different temperatures at 45° C. and 55° C. so as to eliminate the RNA structures that may hinder reverse transcription.

II PCR

The PCRs were carried out with the reverse transcriptions as templates, initially with the primers A1+oligo dT. Nested PCRs were subsequently carried out on these first PCRs, with the primers A1+Splicing, A1+GDBR1, or ATG+Splicing, ATG+GDBR1.

PCR amplification was then carried out with the primers specific for the genes to be detected, using the cDNAs obtained after oligo dT RT.

Enzyme: Fermentas Taq DNA polymerase. Thermocycler: Bio Rad iCycler.

The quality of the cDNAs was tested by amplification of GAPDH, b actin and Histone H3.3 housekeeping genes.

TABLE 1

| | Primers | |
|---|---|---|
| Reference | 5'-3' sequence | Amplified fragment size |
| Histone N | 5'-gtg gta aag cac cca gga a-3'<br>(SEQ ID NO: 324) | 347 bp |
| Histone I (reverse) | 5'-gct agc tgg atg tct ttt gc-3'<br>(SEQ ID NO: 325) | |
| Hum GAPDH sense | 5'-TGA AGG TCG GAG TCA ACG G-3'<br>(SEQ ID NO: 326) | 983 bp |
| Hum GAPDH antisense | 5'-CAT GTG GGC CAT GAG GTC-3'<br>(SEQ ID NO: 327) | |
| Hum b-actin sense | 5'-GGA CTT CGA GCA AGA GATGG-3'<br>(SEQ ID NO: 328) | 234 bp |
| Hum b-actin antisense | 5*-AGC ACT GTG TTG GCG TAC AG-3'<br>(SEQ ID NO: 329) | |
| LIV21 (A1) | 5*-TCCTATGCTTTGACT ATTAG-3'<br>(SEQ ID NO: 330) | |
| LIV21 (A2) | 5'-CCTGACATCCCTACA TCACCGCA-3*<br>(SEQ ID NO: 331) | |
| odT | | |
| ATG galgal | 5*-ATGTATATTATATCT AA-3'<br>(SEQ ID NO: 332) | |
| Splicing sense histatin | 5'-TGTTGGGATTGCTTA TATTT-3'<br>(SEQ ID NO: 333) | |

TABLE 1-continued

Primers

| | | | | | | |
|---|---|---|---|---|---|---|
| Splicing reverse histatin | | 5'-AAATATAAGCAATCC C A AC A-3' (SEQ ID NO: 334) | | | | |
| GDBR1 reverse | | 5'-CTTTATTATTTTGTA AAAT-3* (SEQ ID NO: 335) | | | | |

| H₂O | 10X buffer | 25 M Mg (1.5 mM final concentration) | 10 mM dNTP (Ml) | Forward primer 10 uM (Ml) | Reverse primer 10 uM (Ml) | Taq (ul) 5U/ul | cDNA (MO |
|---|---|---|---|---|---|---|---|
| 18.3 | 2.5 | 1.5 | 0.5 | 0.5 | 0.5 | 0.2 | 1 |

Other oligonucleotides (I e patent in listing of Trail. PCR Cycles Denaturation: 94° C. 2 minutes Denaturation: 94° C. 3 0 seconds 5 Annealing: 52-55° C. 1 minute 35 cycles Elongation: 72° C. 1 minute 3 0 Final elongation: 72° C. 7 minutes Conservation: 4° C.
III Controls
The PCR Products were Subsequently Controlled on Agarose Gels and Analysed with the Biocapt 11.01 Software from Vilber Lourmat.
Gel 1 (i.e. FIG. 7): control of RNA on agarose gel 15 FIG. 8: RNA pool
FIG. 9: PCR with housekeeping genes and analysis of molecular masses.
FIG. 10: PCR with the primers showing a band of 1400 bp. 20 FIG. 11: Gel 2 with analysis of molecular masses
FIG. 12: Gel 3 at 55° and analysis of molecular masses
FIG. 13: Gel 4 at 45° and at 55° and analysis of molecular masses. 25 FIG. 14: screening ligation of 400 pb band, clones B1 to B10.
FIG. 15: screening ligation of 1400 pb band, clones C1 to C10.
FIG. 16: Gel 5: ligation screening on the five new clones.
FIG. 17: Gel 6: Screening of the S55T and S55M recombinant clones and analysis of molecular masses (i.e. patenting listing for oligonucleotidic sequences).
Gel2: PCRs carried out using templates from PCRs performed with the primers A1+oligo dT on the RTs carried out at 45° C. on the total RNA and the poly A+RNA (messenger RNA). The primers used for these PCRs are A1+GDBR1 or A1+Splicing reverse.
On the RTs carried out using the total RNA, a band of 1178 1253 bp is amplified with, the primers A1+GDBR1 and A1+Splicing reverse. The poly A RNA was used to carry out the RT and is weakly observed at the size (FIG. 10) of 1400 bp for amplification with the primers A1+G, and of 415 bp with the primers A1+Splicing reverse. In the A1+splicing PCR product, them are other bands, of 860 and 233 bp (FIG. 11).
Gel 3: PCRs carried out using templates from PCRs performed with the primers A1+oligo dT on the RTs carried out at 45° C. on the total RNA and the poly A+RNA (messenger RNA). The primers used for these PCRs are A1+GDBR1 or 25 A1+Splicing reverse (FIG. 12).
For the PCRs carried out on RTs performed at 55° C., the same overall pattern of bands as that obtained on the RTs performed at 45° C. is found.

No specific amplification is observed when the poly A RNA was used to carry out the RT. On the RTs carried out on the total RNA, a major band of 1554 1609 bp is found with the primers A1+GDBR1 and A1+Splicing reverse. A band at the theoretical size of 1455 bp is expected for an amplification with the primers A1+GDBR1 and a band with the theoretical size of 415 bp is expected with the primers A1+Splicing reverse. In the 2 profiles, very clear bands of 1900-2100 bp and of 1000-1300 bp are found, but with a weaker intensity than that of the band of 1500-1600 bp.
In the A1+splicing reverse PCR product, there is another major band, of 263 bp.
Gel4: Nested PCRs carried out using templates from PCRs 10 performed with the primers A1+GDBR1 or A1+Splicing reverse on the RTs carried out at 45° C. on the total RNA and the poly A+RNA (messenger RNA). The primers used for these PCRs are ATG+GDBR1 or ATG+Splicing reverse (FIG. 13).
The nested PCRs carried out with the primers ATG+GDBR1 give bands at 1213 bp (RT 45° C.) and 1559+1315 bp (RT at 55° C.); the expected theoretical size is 1455 bp. The PCRs carried out with the primers ATG+Splice reverse give more varied band profiles. These PCRs carried out on other PCRs performed with the primers A1+GDBR1 or A1+Splicing reverse. The presence of a band of 400 bp is noted in the profiles obtained from messenger RNA (the band obtained from the reverse transcription carried out at 55° C. is of greater intensity).
The profiles of the ATG+Splice reverse PCRs carried with total RNA at the start give a band of 424 437 bp of very strong intensity. Bands of 614 and 783 bp of very strong intensity are also found in the profile of the RT 45 and a greater number of bands, but of weaker intensity, is found in the profile of the RT 55, bands at 1118, 936 and 749 bp.
The products of these various PCRs were cloned and sequenced.

Example 5

The PCR products of lanes 2, 4, 6, 7 and 8 were ligated with the plasmid pGEMT Easy, Promega, and the recombinant clones were screened (FIG. 16).

| | |
|---|---|
| Lane 2: | G45T ligations |
| Lane 4: | S45T ligations |
| Lane 6: | G55T ligations |
| Lane 7: | S55M ligations |
| Lane 8: | S55T ligations |

The recombinant clones obtained were screened (after extraction of the plasmid DNA) by restriction with the Eco RI enzyme, the sites of which border the site of insertion of the PCR products into the pGEMT Easy vector.

Screening of the Recombinant Clones:

The first experiments had been carried out using the ten clones B and the ten clones C, FIGS. 14 and 15, and the results of the sequences of clones B2 and C8 are given in the following example, and exhibit, by sequence comparison between clones, great homology with the clones of the second series of experiments.

Gel 5: Screening of the S45T and G45T Recombinant Clones

Analysis of Molecular Masses

The screening of the clones with Eco RI shows that, out of the 9 S45T clones, 3 have inserts of 100 bp, 216 bp and 410 bp. On the G45T clones, out of the 6 clones tested, 3 have inserts of 57, 71 and 148 bp.

FIG. 17: screening of the S55T and S55M recombinant clones

Analysis of Molecular Masses

The screening with Eco RI shows that, out of the 13 clones screened, 7 have inserts of sizes between 239 and 637 bp. The clones G45T5 (148 bp), S45T9 (410 bp), S45T3 (100 bp), S55M1 (491 bp), S55T6 (251 bp) and S55T9 (637 bp) were extracted so as to be sequenced. Primers used for determining the sequences of the 15 various clones and are described in the patent listing:

```
ATG galgal
                              (SEQ ID NO: 119)
5' atgtatattatatatctaa 3'

INV COMP
                              (SEQ ID NO: 120)
ttagatatataatatacat

Splicing reverse
                              (SEQ ID NO: 336)
5' AAATATAAGCAATCCCAACA 3'

Splicing reverse
                              (SEQ ID NO: 337)
5' TGTTGGGATTGCTTATATTT 3' inv comp GDBR1 reverse
                              (SEQ ID NO: 338)
5' CTTTATTATTTTGTAAAAT 3'

GDBR1 reverse
                              (SEQ ID NO: 339)
5' ATTTACAAAATAATAAAG 3'
inverse complement
```

Cloned Fragments

The test of the bio-markers on extracts of neuroblastomas and cell cultures SHSY reveals by RT PCR the play of under expression and of on expression following in this example of analysis: Example of 16 biomarkers of interest analyzed by RT PCR which recuts the results obtained by biochip on sensor-chip making it possible to see by SPR the over expression and the under-expression of certain genes of the Liv21 complex and its partners of interaction for example. An under expression of DKK1, SKP2, DKK3, ID2, p21, SKP2, TP53INP1, ID2, P73 is observed whereas an over expression of MYCN, ALK, NLRR1 (the neuronal leucine rich repeat is transactivated), CRABPII, DDX1, LIV21K, AURORA kinase A is observed.

Example 6

From the cloning of the LIV21 gene described above, the new sequences are studied in order to design the most specific and effective siRNAs (i.e. listing of siRNAs and FIG. 19) for creating "silencing" of the gene, i.e., inhibiting its expression. In the knowledge that the effect of the inhibition at each injection of siRNA remains short, i.e. most commonly less than one hour, the inventor has developed diagnostic products and therapeutic products from this same tool, namely the siRNA.

Example 6.1

The inventor uses siRNAs labeled with rhodamine or fluorescein or any other label that can be revealed and followed by optical observation with a microscope in order to localize the site, in the cells, tissues or sample labeled, that the labeled siRNA will go to in order to attach to the specific sequence which characterizes it, and thus to indicate the site of the expression of the messenger RNA of the gene of interest. Thus, the specific siRNA can be used as a diagnostic marker as an antibody would be, and can make it possible to localize, in a specific case such as on extemporaneous samples or any other type of sample taken from a patient, for example a cancerous tissue sample, the fluorescence or any other labeling used on the siRNA and found in a cell compartment on the sample.

Thus, a labelled siRNA of LIV21 (FIG. 19) that is found, under a microscope, in the cell nuclei at the periphery of a surgical exeresis, would indicate a diagnosis of complete exeresis of the cancerous tissue; on the other hand, this same marker found in the cytoplasm or the membranes of this same sample would mean that the surgeon would have to perform an enlarged exeresis, immediately if this test can be carried out directly in the operating theatre, which would be the best situation for removing all the cancer cells visible only on this molecular and cellular scale by virtue is the siRNA marker. This could be a more rapid implementation alternative than the other application that the inventor has developed with the antibody or the LIV21 peptide, which can be used in the same manner.

Example 6.2

For the treatment products which rise directly from the observations made thanks to the results of expression of the biomarkers on the biochips, the interest is well illustrated for the example of the TGF Béta and p27:

The publication of Mr. Lecanda J and Gold Li of March 2009 is very well rich of teaching and famous all the interest of the pharmaco diagnostic biochips as described above, TGF Béta inhibits cell proliferation by increasing the level of p27 via the activation of the factors of transcription smad 2/3.

TGF Béta thus increases the total level of translocation of p27 in the core accumulates p27 in the cellular core through the activation of smad 2 and smad 3.

All these events are locked by an inhibitor of TGF Béta IH: serine kinase SD208: new centers therapeutic targeted for the carriers.

TGF Beta decreases the level of the components skp2 compared to protein but not the level of mRNA.

TGF Béta thus can mediate the degradation of p27 in the proteasome at the proteinic level because it maintains it in the core but on the other hand the inhibition of the transcription of p27 with a specific siRNA locks TGF beta.

TGF Beta prevents degradation proteasomale kinase cycles dependant inhibitor on p27. (Alvarez Rodriguez R Pon S J that sci 2009 Mar. 1-122).

The gene expression proneural coding for Mash 1 abolishes MYCN (mitotic activity). (2009 Liu W Wuz Guan M, Lu Y).

The inventor uses first labelled siRNAs of the Liv21 complex in order to evidence their expected presence in the cellular compartment and to visualize them. Then the inventor will use non-labelled Liv21 siRNAs solely for their therapeutic role. In a specific case, the injection of siRNA (FIG. 19) directly in a neurodegenerating tissue or any other mean of administration allowing to the siRNA to get to the neurodegenerating tissue (for example the ear, the eye, cephalorachidian liquid, etc.) and to act allowing proliferation until apoptosis and therefore the death of the neurodegenerating cell.

An experiment on human cell cultures then on animal models having a retinopathy generating a vitreo-retinal degeneration (direct injection of the siRNA in the eye) makes it possible to illustrate this method.

The siRNA are also transfected in the cells according to the Invitrogen protocol using the lipofectamine 2000.

The study of the specific role of the PKC epsilon on the nuclear translocation of Liv 21F can use a peptide which inhibits function PKC epsilon and the translocation like previously described but also according to the protocol of reference of Si RNA of PKC epsilon. The profile of expression observed corresponds to a doublet of tapes in the cytoplasm with approximately 51 KD (and with a tape of 64 kD according to the siRNA used) whereas it corresponds only to one simple tape with 50 kD in the nuclear fraction.

The molecules of siRNA resulting from the nucleotidic sequences of the Liv21 complex can be selected in the group made up of the molecules of siRNA understanding any of sequences SEQ ID NO 119 to 126 and 171 to 175, and SEQ ID NO—the use of a multitherapy based on the combination of several of these siRNA for the processing of cancerous or neurodegenerative pathology. These siRNA and the useful combination deduced from the results from on expression and from under expression of the biochips and RT PCR constitute an auxiliary processing of pathology and can be combined with small doses of chemical molecules having already proven reliable in the processing of pathology.

Example 6.3

The present invention, relates to methods and reagents useful in modulating gene expression associated with Alzheimer disease in a variety of applications, including use in validating therapeutic, diagnostic, target, and applications genomic discovery.

The invention concerns compounds, compositions and methods for the study, diagnosis and treatment of diseases that respond to the modulation of beta secretase (BACE) amyloid, expression and/or activity of protein gene the precursor APP, of pin 1 of presenillin 1 (PS-1) and/or of presenillin 2 (PS-2) in association with modulation of gene and protein complex Liv21. The invention concerns compounds, compositions and methods for the study, diagnosis and treatment of diseases that respond to the modulation of the expression and/or activity of genes involved in complex liv21 and in combination with the genes of the betasecretase (BACE), amyloid protein of precursor APP, pin-1, presenillin 1 (PS-1) and/or presenillin 2 (PS-2).

Specifically, the invention relates to small nucleic acid molecules, such as short nucleic acid interferent (siRNA), bicatener RNA (dsRNA), micro RNA (miRNA), short double spin RNA (shRNA) be able to interfere with RNA of mediation (RNAi) against beta secretase (BACE) mediation, gene expression of the protein precursor APP, of pin-1, of presenillin (PS-1) and/or presenillin 2 (PS-2).

Vectors to produce siRNAs are described.

Vectors are also commercially available. For example, the psilencer is available in Gene Therapy System, Inc. and the RNAi system of pSUPER is available in Oligoengine. They deliver compositions of siRNA with coding RNA part.

Xia et all 2002 Zeng et all 2002 Thijn et all 2002 Lee et all Biotechnology 19 Nature Mc Manus et all.

Sui et all PNAS 2002, Yu et all 2002 PNAS 99. Shi et all 2003.

The pharmaceutical compositions comprise a pharmaceutically acceptable carrier.

The compositions are also provided with a device for administering the composition in a cell or in a subject or a tumor. For example, a composition may be in a syringe or to a stent.

Example 7: Pharmaco-Diagnostic Test

Based on the observations that follow in annex at the end of the description of the example concerning the properties of the Liv21 complex, the inventor conceived a design for a pharmacodiagnostic test clinically applicable by known technologically means, which can differ according to users and correspond for each mean to a new product. The invention consists in the fabrication of diagnostic DNA, protein and antibody arrays, including the antibodies already known for the different proteins of the complex associated with Liv21 according to the phase of the cell cycle, that is the antibodies, peptides or nucleotide sequences of the following genes: RBP2, E2F4, E2F1, SUMO, INT2, CRB2, HDAC1, TGFbeta, integrin_alpha5 beta2, Myob, MyoD, cycE/cdk2, cdkl, chk1, chk2, TNFalpha, CREB1 and p300, Rb, p107, p130 from the pocket protein family. But also NFkB, cdc2A, mdm2, p21, p53, p65, p73 RAS, Ki67, CAF1. The protein arrays (FIG. 20) will allow the study of over or under expression of the gene products, the protein interactions and the post-translational modifications, more particularly phosphorylations and methylations of certain proteins, which indicate a specific state of the unhealthy cell that is different form the protein interactions and the metabolism of an healthy cell. The expression and silencing state of certain genes is different.

Example 7.1 pharmacodiagnostic biochip (FIG. 20) conceived based on nucleotide or peptide sequences fixed on classical supports and according to known techniques such as Agilent or Affymetrix or Caliper without restriction thereof and corresponding to known sequences of following genes and proteins listed in the patent, preferably using sequences that, by 3D analysis, show preferably a loop or helix-loop-helix or basic loop or zinc finger 3D structure or a 3D conformation similar to an helix corresponding in most cases to functional sites, or nucleotide sequences corresponding to a region of cystein methylation, methylation of the promoter region of the gene inducing a potential silencing (see general bibliography), as well as new sequences of Liv21F et Liv21K listed in the description and in annex, but also sequences common to certain genes and certain virus thought to be implicated in particular in breast cancer of Chinese population:
Mdm2 and HIV1:
GAVTSSNIAA; DLDQSV; EGF and HPV16; EWWRLD; KNSLD; MHIESLDS; BCAS3; BCAS4

These sequences may be tested by microfluidic techniques upon fixation on a gold coverslip in order to study the protein interactions with the cell extracts of the patient.

But which can also be studied by a MICAM technique implemented of the biochips which (cavities) bio-markers by piezo electric effect and not by physicochemical fixation.

Example 7.2 microfluidic test, for example type Biacore, using the SPR (plasmonic surface resonance) technique known by those skilled in the art based on a support fixed with a gold film, which allows, once the light beam has been sent to the interface, to obtain an adsorbed energy as a function of the presence and the size of protein complexes (in the case of protein or protein antibody interactions) or of protein DNA complexes (in the case of protein DNA interactions) or RNA, or protein or peptide and an evanescent wave perpendicular to the interface axis (use of a prism). The inventor fixes the selected peptide or DNA sequences on gold particles and calculates the rU number as a function of the size of molecules cited in this patent for each interaction complex studied. In microfluidic, the liquid flowing over these gold film arrays may be a cell extract (or a selective one, meaning that it is only made of cell nuclei, or solely cell cytoplasms or solely cytoskeletal proteins etc.) according to extraction, separation and fractionation techniques such as Calbiochem: subcellular proteome extraction or tissue or cell extracts without any other preparation than anti-proteases or cephalorachidian liquid or serum issued from a patient sample in order to study the circling marker (i.e. described nucleotide or peptide sequence list and/or known sequences of genes involved in the proliferation cycle listed).

Example 8 biochip of sequences SEQ ID NO 119 to 127 and 180 with compounds with the sequences of microRNA of interest in studied cancer: mir 21, mir 34a, etc. . . . without the biochip being limited to these. The technique of fixing of RNUMS on the supports defers according to the form of mediums, of revelation and biochip used. For example one uses the sequences RNUMS quoted in solution biothynilées then fixed on sensor-chips at the streptavidine, if one tests their interactions with the cellular or plasmatic extracts or of the rachidian fluid cephalo passing in the channels (fluidic microcomputer) of a A100 or T100. It can also be used as described in the US patent 2008 045418 A1 RNAs locked in end 3' and added a ligase T4 RNA and a "labeled nucleic acid adapter" having a residue 5' phosphates.

Example 9

Study of the Expression of LIV21 in Breast Cancer and Colon Cancer Biopsies

In order to determine whether the observations obtained above are applicable to human tissues, a large number of cancer biopsies obtained from patients were studied by immunohistochemical reaction with LIV21 specific antibodies. The immunohistochemical determination of LIV21 protein expression was carried out on several biopsies from patients. Moreover, some paraffin slides from patients suffering from bladder cancer and from breast cancer were also studied. The improvement of the invention is due to the fact of standardizing the biopsies or the punctures by a technique of taking away standardized and gauged in order to then allow reliable comparisons between cellular extracts of patients and witnesses or between cytoplasmic and nuclear and membrane fractions. This same standardization implemented to the taking away making it possible to compare the results of overexpression or of under expressions of the bio-markers by RTPCR is essential to obtain reliable and comparable results.

Immunocytochemical Analysis Protocol:
1) Deparaffinize the slides, Rehydrate the tissues.
2) Saturate the nonspecific sites and permeabilize the membranes.
3) Add the antibody in a humid chamber, Reveal the antibody.

Deparaffinize the slides under a hood.

Two successive baths of toluene (rectapur Prolabo) 2×30' min or 2×20 min; then dehydrate the tissues with rectapur alcohol at 100% for 15 min; then rectapur ethanol at 95% for 10 min; then rectapur 70% for a further 10 min.

Thaw the antibody at the same time. Rehydrate the tissues gently in PBS supplemented with 10% fetal calf serum and 0.1% Triton.

Saturate the nonspecific sites (for example, with ovalbumin) and permeabilize the membranes, Rehydrate for one hour.

Deposit one ml of this "PBS" per section in order to cover the slide without it drying out at any moment (when it is a slide with cells and not tissues, half an hour is sufficient).

Place the pane and the stainless steel cover and water below so as to create a humid chamber.

Add the antibody in the humid chamber.

Dilute the rabbit serum to 1/200 in 4 ml of PBS triton, so as to continue to permeabilize the membranes and FCS.

Place 1 ml on each slide and keep away from the light and avoid evaporation. Leave overnight or for a minimum of three hours.

Then rinse with 1× normal PBS pH 7, carry out two washes of 5 to 10 min so that no trace of the first antibody remains.

While preparing the Alexa 488 green probe (in the cold at 4° and in the dark) diluted to 1/250, therefore 10 μliter in 2.5 ml of PBS, still with 10% FCS and 0.1% Triton, Rest the slides on the plate. Cover the section again with 2.5 ml in order to maintain a humid chamber for one hour, and then wash with 1×PBS pH 7.

Wash with propidium iodide at 0.5 microgram per microliter to be diluted to 20 microgram per ml and then again to 1/50, but this time, diluted in 1×PBS alone (50 microliters per 2.5 ml of PBS). Drain while taking them out of the PBS and then dispense 2.5 ml of propidium iodide over the four slides for one minute, followed by two rinses with simple PBS. Mount the slides in Moviol before reading.

For an immunolabelling with peroxidase it is mandatory to mask the antigenic sites by a 20 minutes water bath step in order to obtain meaningful results when one is working with paraffined coverslips.

All these results show that the cytoplasmic localization of LIV21 is an indicator of the aggressiveness and of the metastatic potential of the cancer. The detection of LIV21 expression indicates the presence of invasive, aggressive and metastatic cancer cells. These results also show that the nuclear localization of LIV21 is an indicator of normal quiescent cells, that is of well-differentiated tissues.

Annex: Study of the nuclear translocation of LIV21 in MCF-7 and SHSY5Y cells

The study of the subcellular distribution of LIV21 in different tumor lines of various origins showed an plasmonic surface resonance exclusively cytoplasmic localization of this protein.

The presence of putative phosphorylation sites by protein kinases C (PKCs) in the Liv21 sequence directed the study toward an involvement of these proteins with respect to its nuclear translocation. The MCF-7 line treated with TPA modulates PKCs and is used in the present study.

The Effect of TPA on the MCF-7 Line

TPA is a known activator of PKCs. It activates the growth of normal breast cells, does not modify the proliferation of the cells of benign tumors from this same tissue, but drastically inhibits the proliferation of the cells of human mammary tumor lines such as the MCF-7 line. It reduces the cell growth of this line by positively controlling the c-erb-2 receptor and negatively controlling the retinoic acid receptor a, which are both expressed in particularly large amount in these cells. The TPA greatly and rapidly inhibits the expression and the function of estrogen receptors (ERs) and it induces the time- and dose-dependent translocation of protein kinases C (PKCs) from the cytosol to the membranes. Furthermore, TPA increases the migratory capacity of MCF-7 cells in vitro and a short period of treatment of these cells with TPA induces cellular expansion and microtubule organization characteristic of their differentiation.

Expression of LIV21 in MCF-7 Cells and in the SHSY5Y Cells

Firstly, the inventor verified the expression of LIV21 in these cells at the transcriptional level and at the protein level.

The expression of the LIV21 mRNA was demonstrated by RT-PCR sense primer: (CCTGACATCCCTACATCAC-CCAT SEQ ID NO: 340) (SEQ ID No 3, SEQ ID No 217 and SEQ ID No 127 to 171) and antisense primer: (TCCTAT-GCTTGACTATTGC SEQ ID NO: 341) (SEQ ID No 4) in these cells compared with the cells from breast tissues (FIG. 2A). An mRNA of the same size as the mRNA detected in the breast tissues and specific for LIV21 was detected. However, the level of expression of LIV21 in the MCF 7 cells is lower than in the breast tissues. This first result shows that the MCF 7 line expresses the LIV21 mRNA.

The inventor tackled the study of the expression of the LIV21 protein through the Western blotting technique, with an anti-LIV21 antibody, in MCF-7 cells compared with mammary tissues. The anti-LIV21 antibodies were obtained by the method described below. In this line, LIV21 is expressed, both in the mammary tissues and in the MCF-7 cells, in the form of a doublet which migrates at an apparent molecular weight of 51 kDa.

Production of Purified Anti-LIV21 Serum

The specific peptide sequences are the sequences No. 1 and No. 2 and No. 180.

These peptides were injected into rabbits (NZ W ESD 75 female, 2.3 kg at day 0), in agreement with standard immunization procedures, The effect of the inhibitors on the cells of neuroblastomas
Study of the Influence of PKCs on the Nuclear Translocation of LIV21

Effect of TPA on PKCε Expression

Western blotting study: Given that the protein sequence of LIV21 has putative PKCε phosphorylation sites, including two specific for PKCε, the inventor tested the variation in the expression of this PKC as a function of the duration of TPA treatment. It was observed that TPA acts very rapidly on PKCε expression, which decreases from 30 min. The expression of PKCzeta (PKCζ) is used as an internal control since it is not sensitive to TPA.

P65L26 Immunocyto . . . P66L4 Nucleaire de LIV21

Study of the specific role of PKCε on the nuclear translocation of LIV21 using an inhibiting peptide of the function and translocation of PKCε.

To determine the specific action of PKCε on the translocation of LIV21, the crops were discussed with a peptide, selective antagonist of the function and translocation of this PKC (EAVSLKPT (SEQ ID No 6), and the results were compared with those obtained by processing with TPA. This peptide is recognized by the enzyme and links themselves as a substrate amended to the level of its catalytic site. Not phosphorylable, he acts as a specific inhibitor of the activity of PKCε.

The effect of the selective inhibition of the activity of PKCε on the nuclear translocation of LIV21 was studied by immunocytochemistry. These experiments were carried out on nontreated cultures or cultures treated for 12 h with TPA at 25 nM or with the peptide at two different concentrations, 1 and 2 μM (the peptide used at the concentration of 2 μM has an effect identical to that of TPA on the nuclear translocation of LIV21).

These results were supported by cell fractionation experiments on cultures treated with the PKC inhibiting peptide at 2 μM, compared with TPA-treated cultures. The same LIV21 expression profile was observed in the form of a doublet in the cytoplasm and of a single band in the nuclear fraction.

The specific inhibition of PKCε induces a nuclear translocation of LIV21, which suggests that LIV21 could be the target of PKCε, which would maintain it in the cytoplasm in a phosphorylated form.

Example: Western Blotting Analysis

This example describes the conditions used for a Western blotting analysis of cancerous brain cells.

The protein extracts are heated at 80° C. for 5 minutes in a Laemmli buffer (pH 7.4, 0.06 M Tris, 3% SDS, 10% 3 5 glycerol, 1 mM PMSF, β-mercaptoethanol). The migration is carried out by SDS-PAGE (sodium dodecyl sulfate-polyacrylamide gel electrophoresis). 10 to 20 μg of proteins migrate in a 12% polyacrylamide gel for 1 h under denaturing conditions (migration buffer: 25 mM Tris base, 192 mM glycine, 1% SDS, pH 8.3). The proteins are then transferred onto a nitrocellulose membrane (Schleicher & Schnell) for one hour by liquid 5 transfer, in a transfer membrane (25 mM Tris, 192 mM glycine, 20% methanol, pH 8.3). The membranes, saturated in PBS-0.1% Tween-0.1% Triton X100-5% skimmed milk for one hour, are brought into contact with the primary antibody diluted in PBS-0.1% Tween-0.1% Triton X100-1% milk at ambient temperature with gentle agitation for one hour to two hours. After washing, the peroxidase-coupled secondary antibody is incubated with the membranes for 1 h. Revelation is carried out by means of a chemiluminescence reaction using the ECL kit according to the supplier's protocol (Amersham).

The Primary Antibodies Used are:

The anti-LIV21 serum which was produced using two synthetic peptides based on the sequence of LIV21F: peptide LIV21a (SEQ ID No 1) and peptide LIV21b (SEQ ID No 2) and/or peptide Liv21e (SEQ ID No 51). The peptides were coupled to hemocyanin before being injected into rabbits for the immunization. The polyclonal antibody was obtained from these two peptides by having immunized two rabbits and having bled one rabbit so as to have a preimmune serum (in order to be sure that this antibody did not already exist in this rabbit).

The rabbit anti-CDK2 polyclonal antibody (Santa-Cruz technology sc-163) diluted to 1/200.

The mouse anti-p21 monoclonal antibody (Dako, M72 02) diluted to 1/150.

The mouse anti-p27 monoclonal antibody (Santa-Cruz technology sc-1641) diluted to 1/100. It was shown before that protein LIV21 is associated with bodies PML and that, at the time of the sumoylation, LIV21 passes from a molecular weight of 50 kd to 60 kd. By immunoprecipitation, the inventor showed a Co-localization of LIV21 with SUMO in complex PML—SUMO/LIV21. (FIG. 12)

Antitumor role of PML bodies: At the proliferation stage, there are visualized modifications in the PML bodies since these PML bodies dissociate and degrade: (speckles), proteins then become available in the nucleus for ensuring transcription, proliferation, immune reactions and everything that is required for gene transcription. It has been shown that PML associates with SUMO and with HDAC-1 (histone deacetylase 1) and that its complex acts on the expression of E2F1 and PML thus acts on the arrest of proliferation by blocking E2F1. Thus, the PML/HDAC-1 complex down-regulates E2F1 expression. PML associated with Rb (p130) binds to the deacetylated histones and blocks E2F1 by binding to the chromatin.

In acute promyelocytic leukemias, PML is truncated and becomes a fusion protein with the retinoic acid receptor. This fusion protein (PMLRARalpha) is due to a 15/17 chromosomal translocation. A new treatment for this disease by combining arsenic and retinoic acid in order to induce cancer cells into apoptosis has been reported in the literature. The PML protein is thought to regulate proliferation in cancers and lymphomas. The inventor has shown, by immunoprecipitation, the association SUMO-PML in which LIV21 is located.

In the above patents, it was shown that LIV21 is phosphorylated by PKC. The TPA-treated MCF-7 lines show an inhibition of cancerous proliferation and a cell differentiation, and LIV21 is translocated into the nucleus. If a PKC-specific inhibitory peptide was used, it was the activity and not the expression of PKC which was inhibited.

During this TPA treatment (25 nM), when E2F4, p130 and LIV21 were studied (green fluorescence) in the nuclei labelled (DNA) with propidium iodide (red fluorescence), the following were observed:

After 12 h, intranuclear green fluorescence signals with the same pattern for E2F4, p130 and LIV21;

After 48 h, when the proliferation begins, E2F4 has a comparable localization; but at 72 h, it disappears from the nucleus (to the benefit of E2F1).

By observing, by double labeling, the co-localization of PML and of LIV21 at 24 h of PKC treatment (i.e. merge: yellow fluorescence), it was observed that they are co-localized in the nuclei. At 48 h, the co-localization between LIV21 and SUMO (i.e.). The hypothesis is that SUMO, which binds to LIV21, in fact targets LIV21 into the PML bodies and that LIV21 is involved in the PML/SUMO/Rb/HDAC-1 complexes. LIV21 is physically associated with PML and SUMO in the nuclear bodies, by immunoprecipitation and by colocalization by immuno cytochemistry (Rb, p130 and p107 are pocket proteins which have the same binding site). The Rb proteins repress cell growth (Fabbro, Regazzi R, Bioch Biophys Res Comm 1986 Feb. 2; 135 (1): 65-73).

Physical Interaction of LIV21 with the Proteins of the E2F Family

Coimmunoprecipitation experiments carried out using anti-LIV21, anti-E2F1 and anti-E2F4 antibodies made it possible to demonstrate that LIV21 associates with E2F4.

It was shown that BRCA1 also re-entered in interaction with family members E2F and thus complex LIV21. Indeed, E2F1 interacts with BRCA1 and Brca1 interacts with MYC, ESR1, CHEK1 and MAP3K3.

The members of the E2F family are transcription factors whose role has been widely described in the literature as being key molecules in the positive or negative control of the cell cycle (Slansky J E and Farnham P J 1996; Helin K 1998 and Yamasaki L, 1998), by virtue of their association with the pRb protein (WuCL, Zukerberg L R) or pocket proteins. E2F1 positively controls the cell cycle by transactivating 3 5 the promoter of the genes responsible for cell proliferation (DNA polymerase alpha, thymidine kinase, DHFR, etc.), whereas E2F4 is described as one of the members of the EF family which negatively controls the cycle. Furthermore, a high expression of E2F1 in embryonic mammary tissues has been shown (Espanel X, Gillet G 1998), whereas it is no longer expressed in post-mitotic mammary tissues, to the benefit of a large increase in E2F4 expression (Kastner A Brun G 1998).

The identification of antigens has been carried out in cell lysates by immunoprecipitation. The analysis of the physical interaction of various proteins associated with E2F4 and E2F1 was demonstrated by coimmuno-precipitation of protein complexes. The complex was studied using U. MACS PROTEIN with MICROBEADS (MILTENYIBIOTEC). When lysates of *S aureus* are added, the proteins A interact with the Fc portion of the specific antibodies and the immunocomplexes become insoluble and are therefore recovered by centrifugation. After breaking of the bonds (heating) between AG/AC and protein A-rich membranes, Western blotting was carried out. These results suggest that the LIV21/E2F4 complex appears to play an important Role in establishing cell quiescence. A study of co immunoprecipitation is following also with the profound mammalian kit Pierce.

Functional Interaction of LIV21 with the Proteins of the E2F Family

It was demonstrated that blocking the expression of the LIV21 protein was correlated with a decrease in the expression of E2F4 and with an increase in the expression of E2F1. In parallel, the functional aspect of the increase in E2F1 was verified by studying the transcription of two of its target genes, DHFR and DNA polymerase a.

In conclusion, these results suggest that the LIV21/E2F4 complex acts as a complex which inhibits the expression of the E2F1 gene. This complex could 3 5 correspond to a new point of control in the arrest of cell proliferation.

REFERENCES

Arya R, Kedar V, Hwang J R, McDonough H, Li H H, Taylor J, Patterson C. Muscle ring finger protein-1 inhibits PKC{epsilon} activation and prevents cardiomyocyte hypertrophy. J Cell Biol. 2004 Dec. 20; 167(6): 1147-59. Epub 2004 December Aurelian Radu, Nicolae Ghinea (2010)

Expression of FSH receptor in tumor blood vessels N England J Med (363:1621-16802010)

Stevaux O, Dyson N J. A revised picture of the E2F transcriptional network and RB function. (2002) *Curr Opin Cell Biol*, 14 (6): 684-91.

Yamasaki L, Growth regulation by the E2F and DP transcription factor families. (1998) *Results Probl Cell Differ*, 22:199-227.

The invention claimed is:

1. A method of killing neural glioblastoma or neuroblastoma tissue comprising the steps of:

(a) detecting the presence of LIV21 in a neural glioblastoma or neuroblastoma tissue, (b) administering one or more siRNAs selected from the group consisting of siRNA SEQ ID NO: 91-118 to the neural glioblastoma or neuroblastoma tissue wherein after administration the neural glioblastoma or neuroblastoma tissue undergoes apoptosis.

2. The method of claim 1 wherein the neural glioblastoma or neuroblastoma tissue comprises a cancer tumor.

* * * * *

SEQUENCE LISTING

<160> NUMBER OF SEQ ID NOS: 377

<210> SEQ ID NO 1
<211> LENGTH: 13
<212> TYPE: PRT
<213> ORGANISM: Homo Sapiens

<400> SEQUENCE: 1

Pro Ala Ser Ala Gly Ile Thr Gly Val Ser Cys Ala Arg
1               5                   10

<210> SEQ ID NO 2
<211> LENGTH: 28
<212> TYPE: PRT
<213> ORGANISM: Homo Sapiens

<400> SEQUENCE: 2

Gly Phe Thr Val Leu Ala Arg Met Val Ser Ile Ser Pro Arg Asp Pro
1               5                   10                  15

Pro Ala Ser Ala Ser Gln Ser Val Gly Ile Ala Tyr
            20                  25

<210> SEQ ID NO 3
<211> LENGTH: 13
<212> TYPE: PRT
<213> ORGANISM: Homo Sapiens

<400> SEQUENCE: 3

Phe Tyr Cys Arg Ser Leu Gln Ser Ser Trp Asp Tyr Arg
1               5                   10

<210> SEQ ID NO 4
<211> LENGTH: 24
<212> TYPE: PRT
<213> ORGANISM: Homo Sapiens

<400> SEQUENCE: 4

Ser Val Thr Gln Ala Gly Val Gln Trp Arg Asn Leu Gly Ser Arg Leu
1               5                   10                  15

Gln Pro Leu Pro Pro Gly Phe Lys
            20

<210> SEQ ID NO 5
<211> LENGTH: 36
<212> TYPE: PRT
<213> ORGANISM: Homo Sapiens

<400> SEQUENCE: 5

Ser Val Thr Gln Ala Gly Val Gln Trp Arg Asn Leu Gly Ser Leu Gln
1               5                   10                  15

Pro Leu Pro Pro Gly Phe Lys Phe Ser Cys Arg Ser Leu Gln Ser Ser
            20                  25                  30

Trp Asp Tyr Arg
        35

<210> SEQ ID NO 6
<211> LENGTH: 19
<212> TYPE: PRT
<213> ORGANISM: Homo Sapiens

<400> SEQUENCE: 6

Ser Ile Ser Pro His Asp Leu Pro Ala Ser Ala Ser Gln Ser Ala Gly
1               5                   10                  15

Ile Thr Gly

<210> SEQ ID NO 7
<211> LENGTH: 46
<212> TYPE: PRT
<213> ORGANISM: Artificial Sequence
<220> FEATURE:
<223> OTHER INFORMATION: Traduction of clone C8T7 come from
      microorganism ref: CNCM I-3940
<220> FEATURE:
<221> NAME/KEY: misc_feature
<223> OTHER INFORMATION: Synthetic

<400> SEQUENCE: 7

Asp Phe Leu Cys Leu Thr Ile Ser Ser Phe Ser Leu Pro Ile Ile Ile
1               5                   10                  15

Ile Tyr Phe Ser Asp Gly Val Ser His Cys Arg Gln Ala Gly Val Gly
            20                  25                  30

Gln Trp Arg Asn Leu Gly Ser Pro Pro Thr Gly Phe Lys
        35                  40                  45

<210> SEQ ID NO 8
<211> LENGTH: 46
<212> TYPE: PRT
<213> ORGANISM: Artificial Sequence
<220> FEATURE:
<223> OTHER INFORMATION: Traduction of clone S45T9 come from
      microorganism ref: CNCM I-3941
<220> FEATURE:
<221> NAME/KEY: misc_feature
<223> OTHER INFORMATION: Synthetic

<400> SEQUENCE: 8

Met Glu Ser Arg Ser Val Ala Gln Ala Gly Val Gln Trp His Asn Leu
1               5                   10                  15

Gly Ser Ala Leu Pro Pro Gly Phe Met Pro Phe Ser Cys Leu Ser Leu
            20                  25                  30

Gln Ser Ser Trp Asp Tyr Arg His Ala Pro Pro Arg Pro Ala
        35                  40                  45

<210> SEQ ID NO 9
<211> LENGTH: 15
<212> TYPE: PRT
<213> ORGANISM: Homo sapiens

<400> SEQUENCE: 9

Pro Pro Arg Pro Ala Thr Phe Leu Tyr Phe Pro Arg Gln Gly Phe
1               5                   10                  15

<210> SEQ ID NO 10
<211> LENGTH: 15
<212> TYPE: PRT
<213> ORGANISM: Homo sapiens

<400> SEQUENCE: 10

Arg Arg Phe Leu Tyr Ser Ser Asn Leu Phe Pro Ser Asn Gly Thr
1               5                   10                  15

<210> SEQ ID NO 11
<211> LENGTH: 9
<212> TYPE: PRT
<213> ORGANISM: Homo sapiens

<400> SEQUENCE: 11

Arg Tyr Val Pro Ser Ser Asn Pro Leu
1               5

<210> SEQ ID NO 12
<211> LENGTH: 9
<212> TYPE: PRT
<213> ORGANISM: Homo sapiens

<400> SEQUENCE: 12

Arg Tyr Val Pro Ser Ser Asn Leu Pro
1               5

<210> SEQ ID NO 13
<211> LENGTH: 9
<212> TYPE: PRT
<213> ORGANISM: Homo sapiens

<400> SEQUENCE: 13

Arg Tyr Leu Val Thr Pro Val Asn Ala
1               5

<210> SEQ ID NO 14
<211> LENGTH: 8
<212> TYPE: PRT
<213> ORGANISM: Homo sapiens

<400> SEQUENCE: 14

Arg Tyr Val Leu Ser Pro Val Lys
1               5

<210> SEQ ID NO 15
<211> LENGTH: 9
<212> TYPE: PRT
<213> ORGANISM: Homo sapiens

<400> SEQUENCE: 15

Lys Pro Ser His Pro Lys Pro Ser Lys
1               5

<210> SEQ ID NO 16
<211> LENGTH: 6
<212> TYPE: PRT
<213> ORGANISM: Homo sapiens

<400> SEQUENCE: 16

Thr Phe Lys Asn Leu Cys
1               5

<210> SEQ ID NO 17
<211> LENGTH: 8
<212> TYPE: PRT
<213> ORGANISM: Homo sapiens

<400> SEQUENCE: 17

Lys Ala His Asn Leu Phe Lys Thr
1               5

<210> SEQ ID NO 18
<211> LENGTH: 9
<212> TYPE: PRT
<213> ORGANISM: Homo sapiens

<400> SEQUENCE: 18

Arg Tyr Leu Pro Ala Asn Pro Arg Tyr
1               5

<210> SEQ ID NO 19
<211> LENGTH: 13
<212> TYPE: PRT
<213> ORGANISM: Homo sapiens

<400> SEQUENCE: 19

Phe Tyr Cys Arg Ser Leu Gln Ser Ser Trp Asp Tyr Arg
1               5                   10

<210> SEQ ID NO 20
<211> LENGTH: 13
<212> TYPE: PRT
<213> ORGANISM: Homo sapiens

<400> SEQUENCE: 20

Lys Thr Leu Pro Ser Ser Ser Cys Leu Val Ala Tyr Lys
1               5                   10

<210> SEQ ID NO 21
<211> LENGTH: 14
<212> TYPE: PRT
<213> ORGANISM: Homo sapiens

<400> SEQUENCE: 21

Lys Val Ile Ile Val Ala Val Asp Trp Asp Leu Ser Lys Glu
1               5                   10

<210> SEQ ID NO 22
<211> LENGTH: 16
<212> TYPE: PRT
<213> ORGANISM: Homo sapiens

<400> SEQUENCE: 22

Lys Ile Phe Ser Pro Ala Thr Val Phe Phe Thr Ser Ile Glu Lys His
1               5                   10                  15

<210> SEQ ID NO 23
<211> LENGTH: 18
<212> TYPE: PRT
<213> ORGANISM: Homo sapiens

<400> SEQUENCE: 23

Lys Asn Val Trp Ile Leu Thr Gly Phe Gln Gln Gly Gln Glu Phe Pro
1               5                   10                  15

Lys Phe

<210> SEQ ID NO 24
<211> LENGTH: 12
<212> TYPE: PRT
<213> ORGANISM: Homo sapiens

<400> SEQUENCE: 24

Arg Phe Asn Leu Phe Ala Gly Gly Ser Asn Lys Ala
1               5                   10

<210> SEQ ID NO 25
<211> LENGTH: 12
<212> TYPE: PRT
<213> ORGANISM: Homo sapiens

<400> SEQUENCE: 25

Arg Ala Tyr Ser Leu Leu Gly Thr Ser Glu Arg Thr
1               5                   10

```
<210> SEQ ID NO 26
<211> LENGTH: 12
<212> TYPE: PRT
<213> ORGANISM: Homo sapiens

<400> SEQUENCE: 26

Ala Met Ala Ala Asn Asp Thr Gly Gly Phe Val Lys
1               5                   10

<210> SEQ ID NO 27
<211> LENGTH: 11
<212> TYPE: PRT
<213> ORGANISM: Homo sapiens

<400> SEQUENCE: 27

Ala Ser Glu Glu Gly Ile Met Val Val Glu Arg
1               5                   10

<210> SEQ ID NO 28
<211> LENGTH: 18
<212> TYPE: PRT
<213> ORGANISM: Homo sapiens

<400> SEQUENCE: 28

Phe Asp Val Val Val Ile Gly Ala Gly Pro Gly Gly Tyr Val Ala Ala
1               5                   10                  15

Ile Lys

<210> SEQ ID NO 29
<211> LENGTH: 19
<212> TYPE: PRT
<213> ORGANISM: Homo sapiens

<400> SEQUENCE: 29

Arg Pro Val Thr Thr Asp Leu Leu Ala Ser Asp Ser Gly Val Thr Ile
1               5                   10                  15

Asp Glu Arg

<210> SEQ ID NO 30
<211> LENGTH: 7
<212> TYPE: PRT
<213> ORGANISM: Homo sapiens

<400> SEQUENCE: 30

Phe Tyr Cys Gly Trp Asp Arg
1               5

<210> SEQ ID NO 31
<211> LENGTH: 8
<212> TYPE: PRT
<213> ORGANISM: Homo sapiens

<400> SEQUENCE: 31

Asp Val Ala Gln Glu Glu Gly Lys
1               5

<210> SEQ ID NO 32
<211> LENGTH: 8
<212> TYPE: PRT
<213> ORGANISM: Homo sapiens

<400> SEQUENCE: 32
```

Ser Gly Ile Pro Ser Glu Leu Arg
1               5

<210> SEQ ID NO 33
<211> LENGTH: 7
<212> TYPE: PRT
<213> ORGANISM: Homo sapiens

<400> SEQUENCE: 33

Glu Ala His Ile Gln Met Lys
1               5

<210> SEQ ID NO 34
<211> LENGTH: 7
<212> TYPE: PRT
<213> ORGANISM: Homo sapiens

<400> SEQUENCE: 34

Glu Gly Ile Trp Ile Pro Lys
1               5

<210> SEQ ID NO 35
<211> LENGTH: 6
<212> TYPE: PRT
<213> ORGANISM: Homo sapiens

<400> SEQUENCE: 35

Tyr Thr Phe Asp Ser Arg
1               5

<210> SEQ ID NO 36
<211> LENGTH: 6
<212> TYPE: PRT
<213> ORGANISM: Homo sapiens

<400> SEQUENCE: 36

Leu Thr His Glu Ile Arg
1               5

<210> SEQ ID NO 37
<211> LENGTH: 5
<212> TYPE: PRT
<213> ORGANISM: Homo sapiens

<400> SEQUENCE: 37

Leu Tyr Leu Asp Lys
1               5

<210> SEQ ID NO 38
<211> LENGTH: 5
<212> TYPE: PRT
<213> ORGANISM: Homo sapiens

<400> SEQUENCE: 38

Tyr Gly Leu Gln Arg
1               5

<210> SEQ ID NO 39
<211> LENGTH: 5
<212> TYPE: PRT
<213> ORGANISM: Homo sapiens

<400> SEQUENCE: 39

Asp Ser Ile Ile Arg
1               5

<210> SEQ ID NO 40
<211> LENGTH: 16
<212> TYPE: PRT
<213> ORGANISM: Homo sapiens

<400> SEQUENCE: 40

Leu Glu Ala Ile Cys Ala Ala Met Ile Glu Ser Trp Gly Tyr Asp Lys
1               5                   10                  15

<210> SEQ ID NO 41
<211> LENGTH: 12
<212> TYPE: PRT
<213> ORGANISM: Homo sapiens

<400> SEQUENCE: 41

Gly Asp Leu Trp Phe Met Ser His Gln Gly His Lys
1               5                   10

<210> SEQ ID NO 42
<211> LENGTH: 11
<212> TYPE: PRT
<213> ORGANISM: Homo sapiens

<400> SEQUENCE: 42

Tyr Ala Phe Asp Phe Tyr Glu Met Thr Ser Arg
1               5                   10

<210> SEQ ID NO 43
<211> LENGTH: 14
<212> TYPE: PRT
<213> ORGANISM: Homo sapiens

<400> SEQUENCE: 43

Glu Val Asn Ala Gly Thr Ser Gly Thr Phe Ser Val Pro Arg
1               5                   10

<210> SEQ ID NO 44
<211> LENGTH: 9
<212> TYPE: PRT
<213> ORGANISM: Homo sapiens

<400> SEQUENCE: 44

Asn Gln Asp Arg Pro Tyr Met Pro Arg
1               5

<210> SEQ ID NO 45
<211> LENGTH: 9
<212> TYPE: PRT
<213> ORGANISM: Homo sapiens

<400> SEQUENCE: 45

Ile Val Ser Ile Leu Glu Trp Asp Arg
1               5

<210> SEQ ID NO 46
<211> LENGTH: 10
<212> TYPE: PRT
<213> ORGANISM: Homo sapiens

<400> SEQUENCE: 46

Ala Pro Tyr Ile Ala Glu Thr Ala Leu Arg
1               5                   10

```
<210> SEQ ID NO 47
<211> LENGTH: 9
<212> TYPE: PRT
<213> ORGANISM: Homo sapiens

<400> SEQUENCE: 47

Asn Met His Asn Leu Leu Gly Val Lys
1               5

<210> SEQ ID NO 48
<211> LENGTH: 9
<212> TYPE: PRT
<213> ORGANISM: Homo sapiens

<400> SEQUENCE: 48

Asn Leu Thr Asp Met Ser Leu Ala Arg
1               5

<210> SEQ ID NO 49
<211> LENGTH: 8
<212> TYPE: PRT
<213> ORGANISM: Homo sapiens

<400> SEQUENCE: 49

His Thr Thr Glu Asp Val Asn Arg
1               5

<210> SEQ ID NO 50
<211> LENGTH: 7
<212> TYPE: PRT
<213> ORGANISM: Homo sapiens

<400> SEQUENCE: 50

Lys Phe Phe Val Phe Ala Leu
1               5

<210> SEQ ID NO 51
<211> LENGTH: 15
<212> TYPE: PRT
<213> ORGANISM: Homo sapiens

<400> SEQUENCE: 51

Phe Val Phe Ala Leu Ile Leu Ala Leu Met Leu Ser Met Cys Gly
1               5                   10                  15

<210> SEQ ID NO 52
<211> LENGTH: 12
<212> TYPE: PRT
<213> ORGANISM: Homo sapiens

<400> SEQUENCE: 52

Thr Leu Gln Ile Phe Asn Ile Glu Met Lys Ser Lys
1               5                   10

<210> SEQ ID NO 53
<211> LENGTH: 17
<212> TYPE: PRT
<213> ORGANISM: Homo sapiens

<400> SEQUENCE: 53

Lys Asp Pro Glu Leu Trp Ala His Val Leu Glu Glu Thr Asn Thr Ser
1               5                   10                  15
Arg
```

```
<210> SEQ ID NO 54
<211> LENGTH: 12
<212> TYPE: PRT
<213> ORGANISM: Homo sapiens

<400> SEQUENCE: 54

Lys Ser Trp Glu Val Tyr Gln Gly Val Cys Gln Lys
1               5                   10

<210> SEQ ID NO 55
<211> LENGTH: 13
<212> TYPE: PRT
<213> ORGANISM: Homo sapiens

<400> SEQUENCE: 55

His Thr Ser Leu Val Gly Cys Gln Val Ile His Tyr Arg
1               5                   10

<210> SEQ ID NO 56
<211> LENGTH: 11
<212> TYPE: PRT
<213> ORGANISM: Homo sapiens

<400> SEQUENCE: 56

Gln Ala Gly Val Gln Trp Arg Asn Leu Gly Ser
1               5                   10

<210> SEQ ID NO 57
<211> LENGTH: 15
<212> TYPE: PRT
<213> ORGANISM: Homo sapiens

<400> SEQUENCE: 57

Ser Leu Gln Ser Ser Trp Asp Tyr Arg Arg His Pro Pro Pro Thr
1               5                   10                  15

<210> SEQ ID NO 58
<211> LENGTH: 21
<212> TYPE: PRT
<213> ORGANISM: Homo sapiens

<400> SEQUENCE: 58

Phe Leu Tyr Phe Leu Arg Trp Glu Phe Thr Gly Pro Thr Ala Ser Ala
1               5                   10                  15

Gly Ser Pro Pro Arg
            20

<210> SEQ ID NO 59
<211> LENGTH: 14
<212> TYPE: PRT
<213> ORGANISM: Homo sapiens

<400> SEQUENCE: 59

Gly Phe Thr Met Met Ala Arg Met Val Ser Ile Ser Pro His
1               5                   10

<210> SEQ ID NO 60
<211> LENGTH: 49
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
```

-continued

```
<400> SEQUENCE: 60
ggaggccauu cauauuuauu ucaauuccuc cgguaaguau aaauaagag        49

<210> SEQ ID NO 61
<211> LENGTH: 49
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic

<400> SEQUENCE: 61
gagaggauug guccaauaau ucaauucucu ccuaaccagg uuauuagag        49

<210> SEQ ID NO 62
<211> LENGTH: 49
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic

<400> SEQUENCE: 62
gcaggcggcc gcgaauucau ucauucguc cgccggcgcu uaaguagag         49

<210> SEQ ID NO 63
<211> LENGTH: 49
<212> TYPE: RNA
<213> ORGANISM: Artificial Sequence
<220> FEATURE:
<223> OTHER INFORMATION: siRNA seq 173

<400> SEQUENCE: 63
gguggcacac gcccguaauu ucaauuccac cgugugcggg cauuaagag        49

<210> SEQ ID NO 64
<211> LENGTH: 49
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic

<400> SEQUENCE: 64
gaauggaggc cauucauauu ucaauucuua ccuccgguaa guauaagag        49

<210> SEQ ID NO 65
<211> LENGTH: 49
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic

<400> SEQUENCE: 65
ggccauucau auuuauguau ucaauuccgg uaaguauaaa uacauagag        49

<210> SEQ ID NO 66
<211> LENGTH: 49
```

```
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic

<400> SEQUENCE: 66
ggcaagacuc ugucucaaau ucaauuccgu ucugagacag aguuuagag          49

<210> SEQ ID NO 67
<211> LENGTH: 49
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic

<400> SEQUENCE: 67
guuaagcuga gaucugaauu ucaauucaau ucgacucuag acuuaagag          49

<210> SEQ ID NO 68
<211> LENGTH: 20
<212> TYPE: RNA
<213> ORGANISM: Artificial Sequence
<220> FEATURE:
<223> OTHER INFORMATION: oligonucleotide first strain 5'-3'of siRNA
      sequence of SEQ ID NO 173
<220> FEATURE:
<221> NAME/KEY: misc_feature
<223> OTHER INFORMATION: Synthetic

<400> SEQUENCE: 68
gggaguagcc caagaaucau                                          20

<210> SEQ ID NO 69
<211> LENGTH: 25
<212> TYPE: RNA
<213> ORGANISM: Artificial Sequence
<220> FEATURE:
<223> OTHER INFORMATION: second strand antisens of double helix of siRNA
      stop by AA
<220> FEATURE:
<221> NAME/KEY: misc_feature
<223> OTHER INFORMATION: Synthetic

<400> SEQUENCE: 69
gagaugauuc uugggcuacu cccuu                                    25

<210> SEQ ID NO 70
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 70
gagaauaugg gagagcuccc aacuu                                    25

<210> SEQ ID NO 71
```

```
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 71
gagauugaga cagagucuug cccuu                                       25

<210> SEQ ID NO 72
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 72
gagauucaga ucucagcuua accuu                                       25

<210> SEQ ID NO 73
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 73
gagaagugau ucuugggcua cucuu                                       25

<210> SEQ ID NO 74
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 74
gagaugaugu ggucuuggcu cacuu                                       25

<210> SEQ ID NO 75
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
```

```
<223> OTHER INFORMATION: Synthetic
<220> FEATURE:
<221> NAME/KEY: misc_feature
<223> OTHER INFORMATION: antisense strand of siRNA

<400> SEQUENCE: 75
gagaagaucu cagcuuaacc aucuu                                              25

<210> SEQ ID NO 76
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 76
gagaaucuca gcuuaaccau cacuu                                              25

<210> SEQ ID NO 77
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 77
gagauaguga auucgcggcc gccuu                                              25

<210> SEQ ID NO 78
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: antisense strand of siRNA
<220> FEATURE:
<221> NAME/KEY: misc_feature
<223> OTHER INFORMATION: Synthetic

<400> SEQUENCE: 78
gagaucacua gugaauucgc ggcuu                                              25

<210> SEQ ID NO 79
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 79
```
gagaaccaua ugggagagcu cccuu                                        25

<210> SEQ ID NO 80
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 80
gagauuugcc auguuggcca ggcuu                                        25

<210> SEQ ID NO 81
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 81
gagaagaguc uugcccuguu accuu                                        25

<210> SEQ ID NO 82
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 82
gagaaguagc ugggauuacg ggcuu                                        25

<210> SEQ ID NO 83
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 83
gagauggucu ugaacuccug gccuu                                        25

<210> SEQ ID NO 84
<211> LENGTH: 25
<212> TYPE: RNA
<213> ORGANISM: Artificial Sequence

```
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 84
gagaucagcu uaaccaucac uucuu                                          25

<210> SEQ ID NO 85
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 85
gagaugggau uacgggcgug ugcuu                                          25

<210> SEQ ID NO 86
<211> LENGTH: 25
<212> TYPE: RNA
<213> ORGANISM: Artificial Sequence
<220> FEATURE:
<223> OTHER INFORMATION: siRNA seq 173
<220> FEATURE:
<221> NAME/KEY: misc_feature
<223> OTHER INFORMATION: Synthetic
<220> FEATURE:
<221> NAME/KEY: misc_feature
<223> OTHER INFORMATION: antisense strand of siRNA

<400> SEQUENCE: 86
gagaaugcca aagguaaggu agcuu                                          25

<210> SEQ ID NO 87
<211> LENGTH: 53
<212> TYPE: DNA
<213> ORGANISM: Artificial Sequence
<220> FEATURE:
<223> OTHER INFORMATION: primers siRNA 1 sequence of seq 173
<220> FEATURE:
<221> NAME/KEY: misc_feature
<223> OTHER INFORMATION: Synthetic

<400> SEQUENCE: 87
tctcggaggc cattcatatt tatttcaaga gaataaatat gaatggcctc cct           53

<210> SEQ ID NO 88
<211> LENGTH: 53
<212> TYPE: DNA
<213> ORGANISM: Artificial Sequence
<220> FEATURE:
<223> OTHER INFORMATION: primers antisens 3' to 5' of siRNA1 of seq 173
<220> FEATURE:
<221> NAME/KEY: misc_feature
<223> OTHER INFORMATION: Synthetic

<400> SEQUENCE: 88
cctccggtaa gtataaataa agttctctta tttatactta ccggagggac gtc           53
```

<210> SEQ ID NO 89
<211> LENGTH: 788
<212> TYPE: DNA
<213> ORGANISM: Artificial Sequence
<220> FEATURE:
<223> OTHER INFORMATION: reverse complement of C8 clone
<220> FEATURE:
<221> NAME/KEY: misc_feature
<223> OTHER INFORMATION: Synthetic
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 89

```
agagtcatct ntactncaga gncatttant tcaatattaa gaattaatac atcatcatan      60
tcaagacaaa cccatgtacc atttcacaac aactaataaa aattataqga agaatctcat     120
ctcagaataa ttgatttcta tttttcattc attaacgaga taagactctc agctttaggt    180
gtatttcatt gaattaactt tgtggaaata catactgcct gataaaaagc aaagatattt     240
aaatggaaaa agattacttt attaggagta taggaatctc ctacattgcc taataaagga    300
cattagaccc ataagtaggg tctggaattg aattaatgga gtcataggca aatataatcc     360
tgctgattaa tcttgtatcc tccacaggca tttcagcgtt ccattggatg aattcttgtt    420
attggatgaa ttcttgttat ttttaaaata ggtaggccta gcacagtggc tcatgcccgt    480
aatcccagca ctttgggagg ctgaggcagg cagatcatga ggtcaagaga tcgagaccat    540
cctggccatc atggtgaaac cccatctcaa ctaaaaatac aaaaaattag ctgggtgtgg    600
tagtgcatgc ctgtagtccc agctactctg gagactgcgg cagtagaatc acttgaaccc    660
ggtaggtgga gggttcagtg agccgagatg gcgccactgt actccagcct ggcgacagtg    720
tgagactcca tctgaaaaat aaataataat aataggtaaa gaaaaggagc taatagtcaa    780
gcatagga                                                              788
```

<210> SEQ ID NO 90
<211> LENGTH: 299
<212> TYPE: DNA
<213> ORGANISM: Artificial Sequence
<220> FEATURE:
<223> OTHER INFORMATION: oligonucleotidic probe which correspond to SEQ
      ID NO 194
<220> FEATURE:
<221> NAME/KEY: misc_feature
<223> OTHER INFORMATION: Synthetic
<220> FEATURE:
<221> NAME/KEY: misc_feature
<222> LOCATION: (63)..(63)
<223> OTHER INFORMATION: n is a, c, g, or t

<400> SEQUENCE: 90

```
cccccacccc acccagccgt gtactgcctg ggctcccctc aaagggaaat ttttacggaa    60
acntcttggc agcaagtgga aaaagatcta tggcccatga accaactgaa aactccaaga   120
accctctgtc tgcctctgcc agcagcgagt cctaagcgca gaatccagag ctcgtagctg   180
tcctcagctg taactactgt ttcagaatgt tgctgctgca tacatttgtc atgtcagccg   240
ccagctccgt gggtgagagt gtgcgtgtgc gcgtgtctgt gtgtgtgtgc gtgtctgtg    299
```

<210> SEQ ID NO 91
<211> LENGTH: 299
<212> TYPE: RNA
<213> ORGANISM: Artificial Sequence
<220> FEATURE:
<223> OTHER INFORMATION: ribonucleotidic probe which correspond to SEQ
      ID NO 194
<220> FEATURE:
<221> NAME/KEY: misc_feature
<223> OTHER INFORMATION: Synthetic
<220> FEATURE:
<221> NAME/KEY: misc_feature
<222> LOCATION: (63)..(63)
<223> OTHER INFORMATION: n is a, c, g, or u

<400> SEQUENCE: 91

```
cccccacccc acccagccgu guacugccug ggcuccccuc aaagggaaau uuuuacggaa    60
acnucuuggc agcaagugga aaaagaucua uggcccauga accaacugaa aacuccaaga   120
acccucuguc ugccucugcc agcagcgagu ccuaagcgca gaauccagag cucguagcug   180
uccucagcug uaacuacugu uucagaaugu ugcugcugca uacauuuguc augucagccg   240
ccagcuccgu gggugagagu gugcgugugc gcgucucugu gugugugugc gugucugug    299
```

<210> SEQ ID NO 92
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 92

```
gggucuggaa uugaauuaau ucaauuccca gaccuuaacu uaauuagag               49
```

<210> SEQ ID NO 93
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 93

```
ggucuggaau ugaauuaauu caauuccag accuuaacuu aauuaagag                49
```

<210> SEQ ID NO 94
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

```
<400> SEQUENCE: 94
ggagucauag gcaaauauau ucaauuccuc aguauccguu uauauagag         49

<210> SEQ ID NO 95
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 95
gagucauagg caaauauaau caauucuca guauccguuu auauuagag          49

<210> SEQ ID NO 96
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 96
gaaucucauc ucagaauaau ucaauucuua gaguagaguc uuauuagag         49

<210> SEQ ID NO 97
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 97
guuccauugg augaauucuu ucaauucaag guaaccuacu uaagaagag         49

<210> SEQ ID NO 98
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 98
guagggucug gaauugaauu ucaauucauc ccagaccuua acuuaagag         49

<210> SEQ ID NO 99
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 99
ggacauuaga cccauaaguu ucaauuccug uaaucugggu auucaagag         49
```

-continued

```
<210> SEQ ID NO 100
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 100
gacaaagaga gucaucuuau ucaauucugu uucucucagu agaauagag          49

<210> SEQ ID NO 101
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 101
gagacugcgg caguagaauu ucaauucucu gacgccguca ucuuaagag          49

<210> SEQ ID NO 102
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 102
gacauuagac ccauaaguau ucaauucugu aaucugggua uucauagag          49

<210> SEQ ID NO 103
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 103
ggcaguagaa ucacuugaau ucaauuccgu caucuuagug aacuuagag          49

<210> SEQ ID NO 104
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 104
gauaagacuc ucagcuuuau ucaauucuau ucugagaguc gaaauagag          49

<210> SEQ ID NO 105
<211> LENGTH: 49
<212> TYPE: RNA
```

```
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 105
gacugcggca guagaaucau ucaauucuga cgccgucauc uuaguagag                49

<210> SEQ ID NO 106
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 106
guauaggaau cuccuacauu ucaauucaua uccuuagagg auguaagag                49

<210> SEQ ID NO 107
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 107
ggagacugcg gcaguagaau ucaauuccuc ugacgccguc aucuuagag                49

<210> SEQ ID NO 108
<211> LENGTH: 49
<212> TYPE: RNA
<213> ORGANISM: Artificial Sequence
<220> FEATURE:
<223> OTHER INFORMATION: primers of siRNA 1 sequence of SEQ ID NO 150
<220> FEATURE:
<221> NAME/KEY: misc_feature
<223> OTHER INFORMATION: Synthetic

<400> SEQUENCE: 108
gcugaggcag gcagaucauu ucaauucgac uccguccguc uaguaagag                49

<210> SEQ ID NO 109
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 109
guaccauuuc acaacaacuu ucaauucaug guaaaguguu guugaagag                49

<210> SEQ ID NO 110
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
```

<221> NAME/KEY: misc_feature
<223> OTHER INFORMATION: Synthetic

<400> SEQUENCE: 110
ggagcuaaua gucaagcauu ucaauccuc gauuaucagu ucguaagag       49

<210> SEQ ID NO 111
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 111
gguaggugga ggguucaguu ucaauuccau ccaccuccca agucaagag       49

<210> SEQ ID NO 112
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 112
gcagaucaug aggucaagau ucaaucguc uaguacucca guucuagag       49

<210> SEQ ID NO 113
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 113
gaagaaucuc aucucagaau ucaauucuuc uuagaguaga gucuuagag       49

<210> SEQ ID NO 114
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 114
gugugagacu ccaucugaau ucaaucaca cucugaggua gacuuagag       49

<210> SEQ ID NO 115
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 115
gaucaugagg ucaagagauu ucaauucuag uacuccaguu cucuaagag        49

<210> SEQ ID NO 116
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 116
ggcugaggca ggcagaucau ucaauuccga cuccguccgu cuaguagag        49

<210> SEQ ID NO 117
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 117
gguagugcau gccuguaguu ucaauuccau cacguacgga caucaagag        49

<210> SEQ ID NO 118
<211> LENGTH: 49
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 118
gagauggcgc cacuguacuu ucaauucucu accgcgguga caugaagag        49

<210> SEQ ID NO 119
<211> LENGTH: 30
<212> TYPE: DNA
<213> ORGANISM: Artificial Sequence
<220> FEATURE:
<223> OTHER INFORMATION: oligonucleotidic probe
<220> FEATURE:
<221> NAME/KEY: misc_feature
<223> OTHER INFORMATION: Synthetic

<400> SEQUENCE: 119
atgtatatta tatatctaaa gttatactaa        30

<210> SEQ ID NO 120
<211> LENGTH: 36
<212> TYPE: DNA
<213> ORGANISM: Artificial Sequence
<220> FEATURE:
<223> OTHER INFORMATION: oligonucleotidic probe
<220> FEATURE:
<221> NAME/KEY: misc_feature
<223> OTHER INFORMATION: Synthetic

<400> SEQUENCE: 120
tttcctgcta agcttatgtt gggattgctt atattt        36

```
<210> SEQ ID NO 121
<211> LENGTH: 36
<212> TYPE: DNA
<213> ORGANISM: Artificial Sequence
<220> FEATURE:
<223> OTHER INFORMATION: antisens oligonucleotide (histatine)
<220> FEATURE:
<221> NAME/KEY: misc_feature
<223> OTHER INFORMATION: Synthetic

<400> SEQUENCE: 121
aaatataagc aatcccaaca taagcttagc aggaaa                                36

<210> SEQ ID NO 122
<211> LENGTH: 19
<212> TYPE: RNA
<213> ORGANISM: Artificial Sequence
<220> FEATURE:
<223> OTHER INFORMATION: insert of siRNA (PKC epsilon)
<220> FEATURE:
<221> NAME/KEY: misc_feature
<223> OTHER INFORMATION: Synthetic

<400> SEQUENCE: 122
guuguagccu ggaccuuga                                                   19

<210> SEQ ID NO 123
<211> LENGTH: 420
<212> TYPE: DNA
<213> ORGANISM: Homo Sapiens
<220> FEATURE:
<221> NAME/KEY: misc_feature
<222> LOCATION: (1)..(420)
<223> OTHER INFORMATION: insert S45T9T7 come from clone extract to cells
      in culture MCF7

<400> SEQUENCE: 123
taaatataag caatcccaac actttgggag gccgaggcgg gcggatcacg aggtcaggag       60
atggagacca tcctggctaa cacagtgaaa ccctgtctct actgaaaata caaaaaagta     120
gccgggcgtg gcggcaggcg cctgtagccc cagctactca ggaggctgag gcaggagaat     180
ggcatgaacc caggaggcag agcttgcagt gagccgagat tgtgccactg cactccagcc     240
tgggcaacag agcgagactc catctcaaaa aaaaaaaaaa aatcacccca aagcaataag     300
gagaactaga acaggacata cactccaaca ctggtgaaac taggaaaaca tatgtaaccc     360
caaaccacaa tatatacaca caaaactata cgagatgttg ggattgctta tatttaatcn     420

<210> SEQ ID NO 124
<211> LENGTH: 456
<212> TYPE: DNA
<213> ORGANISM: Homo Sapiens
<220> FEATURE:
<221> NAME/KEY: misc_feature
<223> OTHER INFORMATION: S55M1 450 pb M13 come from clone extract to
      cells in MCF7 culture
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 124
nnnnnngntc cggccgccat ggcggccgcg ggattcgatt aaatataagc aatcccaaca       60
ctttgggagg ccgaggcggg cggatcacga ggtcaggaga tggagaccat cctggctaac     120
```

```
acagtgaaac cctgtctcta cggaaaatac aaaaaagtag ccgggcgtgg cggcaggcgc      180
ctgtagtccc agctactcag gaggctgagg caggagaatg gcatgaaccc aggaggcaga      240
gcttgcagtg agccgagatt gtgccactgc actccagcct gggcaacaga gcgagactcc      300
atctcaaaaa aaaaaaaaaa tcaccccaaa gcaataagga gaactagaac aggacataca      360
ctccaacact ggtgaaacta ggaaaacata tgtaaccccca aaccacaata tatacacaca     420
aaactatacg agatgttggg attgcttata tttaat                                456
```

<210> SEQ ID NO 125
<211> LENGTH: 587
<212> TYPE: DNA
<213> ORGANISM: Homo Sapiens
<220> FEATURE:
<221> NAME/KEY: misc_feature
<223> OTHER INFORMATION: S55T9 M13 reverse 700 pb come from clone
      extract to cells in culture MCF7
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 125

```
nnnnnnnnng nnnnngnncc ntggcggccg cgggattcga ttaaatataa gcaatcccaa       60
cactttgggg gggtgaggcg gacagatcac ttgaggtcag gggtttgaga ccagcatggc      120
caacgtggtg aaaactcaac tactcaaaat agaaaaatta gctggacatg gtggcacaca      180
cctgtgaagc cagctactca ggaggctgaa gcatgagaat tgcttgaacc ctggagatgg      240
aggttacagt gagcccacgt cgcgtccctg cacgcaagcc taggcaagaa agcaagaccc      300
tgtctcaaaa aaagaaaaga gatgctgata catgctacaa catagatgaa ccttgaggac      360
attattctaa gtgaaatgag cttgtcacaa agaacaaat attgcatgat tccagttata       420
tgaggtgccc atagttgtca aattcacaaa gacaaaaagt ggcatggtcg ttaccaaggg      480
ctgggagaaa agaggaatgg tgagttagtg tttaattggt acagagtttc agttttgcaa      540
gatgaaaaga gttctggaga tgaatgttgg gattgcttat atttaat                   587
```

<210> SEQ ID NO 126
<211> LENGTH: 514
<212> TYPE: DNA
<213> ORGANISM: Homo Sapiens
<220> FEATURE:
<221> NAME/KEY: misc_feature
<223> OTHER INFORMATION: insert of clone extract from MCF7 cells
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature

```
<222> LOCATION: (13)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(80)
<223> OTHER INFORMATION: n is a, c, g, or t

<400> SEQUENCE: 126
nnnnnnnngn ncnnnnanng nannncnact cactnnaggg cgaattgggc ccgacgtcgc        60
atgctcccgg ccgnnannnn ggccgcggga attcgattaa atataagcaa tcccaacact       120
ttgggaggcc gaggcgggcg gatcacgagg tcaggagatg gagaccatcc tggctaacac       180
agtgaaaccc tgtctctact gaaaatacaa aaaagtagcc gggcgtggcg gcaggcgcct       240
gtagtcccag ctactcagga ggctgaggca ggagaatggc atgaacccag gaggcagagc       300
ttgcagtgag ccgagattgt gccactgcac tccagcctgg gcaacagagc gagactccat       360
ctcaaaaaaa aaaaaaaatc accccaaagc aataaggaga actagaacag gacatacact       420
ccaacactgg tgaaactagg aaaacatatg taaccccaaa ccacaatata tacacacaaa       480
actatacgag atgttgggat tgcttatatt taat                                  514

<210> SEQ ID NO 127
<211> LENGTH: 770
<212> TYPE: DNA
<213> ORGANISM: Homo Sapiens
<220> FEATURE:
<221> NAME/KEY: misc_feature
<223> OTHER INFORMATION: insert C8 PGEMT M13 rev1605 come from clone
      extract of cells in MCF7 culture
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (760)..(760)
```

<223> OTHER INFORMATION: n is a, c, g, or t

<400> SEQUENCE: 127

```
tcctatgctt gactattagc tccttttctt tacctattat tattatttat ttttcagatg    60
gagtctcaca ctgtcgccag gctggagtac agtggcgcca tctcggctca ctgaaccctc   120
cacctaccgg gttcaagtga ttctactgcc gcagtctcca gagtagctgg gactacaggc   180
atgcactacc acacccagct aattttttgt attttagtt gagatggggt ttcaccatga   240
tggccaggat ggtctcgatc tcttgacctc atgatctgcc tgcctcagcc tcccaaagtg   300
ctgggattac gggcatgagc cactgtgcta ggcctaccta ttttaaaaat aacaagaatt   360
catccaatgg aacgctgaaa tgcctgtgga ggatacaaga ttaatcagca ggattatatt   420
tgcctatgac tccattaatt caattccaga ccctacttat gggtctaatg tcctttatta   480
ggcaatgtag gagattccta tactcctaat aaagtaatct ttttccattt aaatatcttt   540
gcttttatc aggcagtatg tatttccaca aagttaattc aatgaaatac acctaaagct   600
gagagtctta tctcgttaat gaatgaaaaa tagaaatcaa ttattctgag atgagattct   660
tcctataatt tttattagtt gttgtgaaat ggtacatggg tttgtcttga ntatgatgat   720
gtattaattc ttaatattga antaaatgnc tctgnagtan agatgactct             770
```

<210> SEQ ID NO 128
<211> LENGTH: 18
<212> TYPE: DNA
<213> ORGANISM: Artificial Sequence
<220> FEATURE:
<223> OTHER INFORMATION: oligonucleotide BV1 S for PCR
<220> FEATURE:
<221> NAME/KEY: misc_feature
<223> OTHER INFORMATION: Synthetic

<400> SEQUENCE: 128

```
atgtgcacca acgcccgc                                                  18
```

<210> SEQ ID NO 129
<211> LENGTH: 19
<212> TYPE: DNA
<213> ORGANISM: Artificial Sequence
<220> FEATURE:
<223> OTHER INFORMATION: oligonucleotide BV2 AS for PCR
<220> FEATURE:
<221> NAME/KEY: misc_feature
<223> OTHER INFORMATION: Synthetic

<400> SEQUENCE: 129

```
gttttcagtt ggttcatgg                                                 19
```

<210> SEQ ID NO 130
<211> LENGTH: 20
<212> TYPE: DNA
<213> ORGANISM: Artificial Sequence
<220> FEATURE:
<223> OTHER INFORMATION: oligonucleotide BV3-A1S
<220> FEATURE:
<221> NAME/KEY: misc_feature
<223> OTHER INFORMATION: Synthetic

<400> SEQUENCE: 130

```
gatgtctgca cctttatccc                                                20
```

<210> SEQ ID NO 131
<211> LENGTH: 20
<212> TYPE: DNA

```
<213> ORGANISM: Artificial Sequence
<220> FEATURE:
<223> OTHER INFORMATION: oligonucleotide BV4 AS
<220> FEATURE:
<221> NAME/KEY: misc_feature
<223> OTHER INFORMATION: Synthetic

<400> SEQUENCE: 131
catggccatg aagcagagac                                              20

<210> SEQ ID NO 132
<211> LENGTH: 19
<212> TYPE: DNA
<213> ORGANISM: Artificial Sequence
<220> FEATURE:
<223> OTHER INFORMATION: oligonucleotide A2 S
<220> FEATURE:
<221> NAME/KEY: misc_feature
<223> OTHER INFORMATION: Synthetic

<400> SEQUENCE: 132
cctgacatcc catcatccc                                               19

<210> SEQ ID NO 133
<211> LENGTH: 19
<212> TYPE: DNA
<213> ORGANISM: Artificial Sequence
<220> FEATURE:
<223> OTHER INFORMATION: oligonucleotide A2 AS
<220> FEATURE:
<221> NAME/KEY: misc_feature
<223> OTHER INFORMATION: Synthetic

<400> SEQUENCE: 133
gggatgatgg gatgtcagg                                               19

<210> SEQ ID NO 134
<211> LENGTH: 22
<212> TYPE: DNA
<213> ORGANISM: Artificial Sequence
<220> FEATURE:
<223> OTHER INFORMATION: oligonucleotide GDBR1 S
<220> FEATURE:
<221> NAME/KEY: misc_feature
<223> OTHER INFORMATION: Synthetic

<400> SEQUENCE: 134
gcgctttgta aaattcacat tt                                           22

<210> SEQ ID NO 135
<211> LENGTH: 23
<212> TYPE: DNA
<213> ORGANISM: Artificial Sequence
<220> FEATURE:
<223> OTHER INFORMATION: oligonucleotide NES 4 AS
<220> FEATURE:
<221> NAME/KEY: misc_feature
<223> OTHER INFORMATION: Synthetic

<400> SEQUENCE: 135
tcagacgctt tgtagtgctt cag                                          23

<210> SEQ ID NO 136
<211> LENGTH: 19
<212> TYPE: DNA
<213> ORGANISM: Artificial Sequence
<220> FEATURE:
<223> OTHER INFORMATION: oligonucleotide NESB1 S
<220> FEATURE:
```

<221> NAME/KEY: misc_feature
<223> OTHER INFORMATION: Synthetic

<400> SEQUENCE: 136
gcgttcgcaa gcgctggct                                                     19

<210> SEQ ID NO 137
<211> LENGTH: 22
<212> TYPE: DNA
<213> ORGANISM: Artificial Sequence
<220> FEATURE:
<223> OTHER INFORMATION: oligonucleotide SPLIC AS
<220> FEATURE:
<221> NAME/KEY: misc_feature
<223> OTHER INFORMATION: Synthetic

<400> SEQUENCE: 137
gtaaatataa gcaatcccaa ca                                                 22

<210> SEQ ID NO 138
<211> LENGTH: 22
<212> TYPE: DNA
<213> ORGANISM: Artificial Sequence
<220> FEATURE:
<223> OTHER INFORMATION: oligonucleotide AVT SPLIC S
<220> FEATURE:
<221> NAME/KEY: misc_feature
<223> OTHER INFORMATION: Synthetic

<400> SEQUENCE: 138
tcctcattcg acagctgaaa ct                                                 22

<210> SEQ ID NO 139
<211> LENGTH: 25
<212> TYPE: DNA
<213> ORGANISM: Artificial Sequence
<220> FEATURE:
<223> OTHER INFORMATION: oligonucleotide HUM SPLIC S
<220> FEATURE:
<221> NAME/KEY: misc_feature
<223> OTHER INFORMATION: Synthetic

<400> SEQUENCE: 139
atttttacgg aaacatcttg gcagc                                              25

<210> SEQ ID NO 140
<211> LENGTH: 25
<212> TYPE: DNA
<213> ORGANISM: Artificial Sequence
<220> FEATURE:
<223> OTHER INFORMATION: oligonucleotide HUM SPLIC AS
<220> FEATURE:
<221> NAME/KEY: misc_feature
<223> OTHER INFORMATION: Synthetic

<400> SEQUENCE: 140
gctgccaaga tgtttccgta aaaat                                              25

<210> SEQ ID NO 141
<211> LENGTH: 19
<212> TYPE: DNA
<213> ORGANISM: Artificial Sequence
<220> FEATURE:
<223> OTHER INFORMATION: oligonucleotide  humA2S
<220> FEATURE:
<221> NAME/KEY: misc_feature
<223> OTHER INFORMATION: Synthetic

<400> SEQUENCE: 141

```
cagatactgt gagcccggc                                                 19

<210> SEQ ID NO 142
<211> LENGTH: 19
<212> TYPE: DNA
<213> ORGANISM: Artificial Sequence
<220> FEATURE:
<223> OTHER INFORMATION: oligonucleotide humA2AS
<220> FEATURE:
<221> NAME/KEY: misc_feature
<223> OTHER INFORMATION: Synthetic

<400> SEQUENCE: 142
gccgggctca cagtatctg                                                 19

<210> SEQ ID NO 143
<211> LENGTH: 24
<212> TYPE: DNA
<213> ORGANISM: Artificial Sequence
<220> FEATURE:
<223> OTHER INFORMATION: oligonucleotide POZ S
<220> FEATURE:
<221> NAME/KEY: misc_feature
<223> OTHER INFORMATION: Synthetic

<400> SEQUENCE: 143
acctactgaa ctgctactgt tgcc                                           24

<210> SEQ ID NO 144
<211> LENGTH: 24
<212> TYPE: DNA
<213> ORGANISM: Artificial Sequence
<220> FEATURE:
<223> OTHER INFORMATION: oligonucleotide POZ AS
<220> FEATURE:
<221> NAME/KEY: misc_feature
<223> OTHER INFORMATION: Synthetic

<400> SEQUENCE: 144
ggcaacagta gcagttcagt aggt                                           24

<210> SEQ ID NO 145
<211> LENGTH: 806
<212> TYPE: DNA
<213> ORGANISM: Artificial Sequence
<220> FEATURE:
<223> OTHER INFORMATION: T7 antisens come from cells in MCF7 culture
<220> FEATURE:
<221> NAME/KEY: misc_feature
<223> OTHER INFORMATION: Synthetic
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t

<400> SEQUENCE: 145
cttatctcgt taatgaatga aaaatagaaa tcaanttatt ctgagatgag attcttccct    60 ataatttta ttagttgttg tgaaatggta catgggtttg tcttgaagat atgatgatgt    120
attaattctt aatattgaat taaatgcctc tgaagtagag atgactctct tgtcatgga    180 gttacagttg tttgattaaa ttgcattgaa ttttgaatgt taatgttata tattaactta   240
aatgagattt tccaatataa atactctgtg aacctccagc cttgtgtttc tttctttttt   300
```

-continued

| | | |
|---|---|---|
| tttttttttt tttttttttt ttgatacaga gtctcaatct gtcgcccagg ctggagtgca | 360 | |
| gtggcacgat ctcggctcac tgcaacctct gcctcccagg ttcaagcaat tctcctgcct | 420 | |
| cagcctccca agcagagtag ctggaactac aagtgcgcac caccatgcct ggctattttt | 480 | |
| tttattttttg gtagagacgg ggtttcacca tgttggccag gctagtctca aactcctgac | 540 | |
| atcggtgatc tgcctgcctt ggcctcccaa aatgctggaa ttacaagcat cagccactgc | 600 | |
| acccggcctc agatacccctt ttaagaattg taggccatac atctcatgga aattgaatgg | 660 | |
| taatacctgc ctgcattcat actcttgtag agctaagacc agcatgactt tttctgtcct | 720 | |
| cttacttctt tggagaggaa accgncatct cagctaatag tcaagcatag gaaatcgaat | 780 | |
| tcccgcggcc gccatggcgg ccggag | 806 | |

<210> SEQ ID NO 146
<211> LENGTH: 720
<212> TYPE: DNA
<213> ORGANISM: Homo Sapiens
<220> FEATURE:
<221> NAME/KEY: misc_feature
<223> OTHER INFORMATION: 2006M13rev2005 come from clone from cells in
      MCF7 culture
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (645)..(646)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (707)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t

<400> SEQUENCE: 146

| | | |
|---|---|---|
| tcaagctatg catccaacgc gttgggagct ctcccatatg gtcgacctgc aggcggccgc | 60 | |
| gaattcacta gtgatttcct atgcttgact attagctcct tttctttacc tattattatt | 120 | |
| atttattttt cagatggagt ctcacactgt cgccaggctg gagtacagtg gcgccatctc | 180 | |
| ggctcactga accctccacc taccgggttc aagtgattct actgccgcag tctccagagt | 240 | |
| agctgggact acaggcatgc actaccacac ccagctaatt ttttgtattt ttagttgaga | 300 | |
| tggggtttca ccatgatggc caggatggtc tcgatctctt gacctcatga tctgcctgcc | 360 | |
| tcagcctccc aaagtgctgg gattacgggc atgagccact gtgctaggcc tacctatttt | 420 | |
| aaaaataaca agaattcatc caatggaacg ctgaaatgcc tgtggaggat acaagattaa | 480 | |
| tcagcaggat tatatttgcc tatgactcca ttaattcaat tccagaccct acttatgggt | 540 | |

```
ctaatgtcct ttattaggca atgtaggaga ttcctatact cctantaaag taatcttttt        600
ccatttaaan atctttgctt tttatcaggc agtatgtatt ttccnnaaag ttaattcaat        660
gaantacacc ctaaagctga nagtcttatc ctcgttaatg gaatggnnaa nanaaattca        720
```

<210> SEQ ID NO 147
<211> LENGTH: 783
<212> TYPE: DNA
<213> ORGANISM: Homo Sapiens
<220> FEATURE:
<221> NAME/KEY: misc_feature
<223> OTHER INFORMATION: C8sens1605 come from clone from cells in MCF7
      culture
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 147

```
catgacaaag agagtcatct ntactncaga gncatttant tcaatattaa gaattaatac         60
atcatcatan tcaagacaaa cccatgtacc atttcacaac aactaataaa aattatagga        120
agaatctcat ctcagaataa ttgatttcta tttttcattc attaacgaga taagactctc        180
agctttaggt gtatttcatt gaattaactt tgtggaaata catactgcct gataaaaagc        240
aaagatattt aaatggaaaa agattacttt attaggagta taggaatctc ctacattgcc        300
taataaagga cattagaccc ataagtaggg tctggaattg aattaatgga gtcataggca        360
aatataatcc tgctgattaa tcttgtatcc tccacaggca tttcagcgtt ccattggatg        420
aattcttgtt attttttaaaa taggtaggcc tagcacagtg gctcatgccc gtaatcccag        480
cactttggga ggctgaggca ggcagatcat gaggtcaaga gatcgagacc atcctggcca        540
tcatggtgaa acccccatctc aactaaaaat acaaaaaatt agctgggtgt ggtagtgcat        600
gcctgtagtc ccagctactc tggagactgc ggcagtagaa tcacttgaac ccggtaggtg        660
gagggttcag tgagccgaga tggcgccact gtactccagc ctggcgacag tgtgagactc        720
catctgaaaa ataaataata ataataggat aagaaaagga gctaatagtc aagcatagga        780
aat                                                                     783
```

<210> SEQ ID NO 148
<211> LENGTH: 29
<212> TYPE: PRT
<213> ORGANISM: Homo Sapiens
<220> FEATURE:
<221> NAME/KEY: MISC_FEATURE
<223> OTHER INFORMATION: Domain zn finger example: ZN 99
<220> FEATURE:
<221> NAME/KEY: misc_feature
<223> OTHER INFORMATION: Domain zn finger example: ZN 99
<220> FEATURE:

```
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid

<400> SEQUENCE: 148

Phe Leu Val Glu Thr Gly Phe His His Xaa Gln Ala Xaa Leu Leu Thr
1               5                   10                  15

Ser Xaa Xaa Pro Pro Xaa Xaa Ala Ser Gln Ser Ala Pro
            20                  25

<210> SEQ ID NO 149
<211> LENGTH: 23
<212> TYPE: PRT
<213> ORGANISM: Homo Sapiens
<220> FEATURE:
<221> NAME/KEY: misc_feature
<223> OTHER INFORMATION: domain kinase and zinc finger
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 149

Phe Phe Phe Phe Xaa Xaa Xaa Val Xaa Trp Xaa Leu Pro Pro Ala Leu
1               5                   10                  15

Ala Ser Gln Xaa Ser Ala Pro
            20

<210> SEQ ID NO 150
<211> LENGTH: 780
<212> TYPE: DNA
<213> ORGANISM: Homo Sapiens
<220> FEATURE:
<221> NAME/KEY: misc_feature
<223> OTHER INFORMATION: C8 sens come from clone from cells in MCF7
      culture
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
```

<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 150

```
catgacaaag agagtcatct ntactncaga gncatttant tcaatattaa gaattaatac    60
atcatcatan tcaagacaaa cccatgtacc atttcacaac aactaataaa aattatagga   120
agaatctcat ctcagaataa ttgatttcta tttttcattc attaacgaga taagactctc   180
agctttaggt gtatttcatt gaattaactt tgtggaaata catactgcct gataaaaagc   240
aaagatattt aaatggaaaa agattacttt attaggagta taggaatctc ctacattgcc   300
taataaagga cattagaccc ataagtaggg tctggaattg aattaatgga gtcataggca   360
aatataatcc tgctgattaa tcttgtatcc tccacaggca tttcagcgtt ccattggatg   420
aattcttgtt attttaaaa taggtaggcc tagcacagtg gctcatgccc gtaatcccag   480
cactttggga ggctgaggca ggcagatcat gaggtcaaga gatcgagacc atcctggcca   540
tcatggtgaa accccatctc aactaaaaat acaaaaaatt agctgggtgt ggtagtgcat   600
gcctgtagtc ccagctactc tggagactgc ggcagtagaa tcacttgaac ccggtaggtg   660
gagggttcag tgagccgaga tggcgccact gtactccagc ctggcgacag tgtgagactc   720
catctgaaaa ataataata ataataggat aagaaaagga gctaatagtc aagcatagga   780
```

<210> SEQ ID NO 151
<211> LENGTH: 19
<212> TYPE: DNA
<213> ORGANISM: Artificial Sequence
<220> FEATURE:
<223> OTHER INFORMATION: oligonucleotide BV12 S for PCR
<220> FEATURE:
<221> NAME/KEY: misc_feature
<223> OTHER INFORMATION: Synthetic

<400> SEQUENCE: 151

```
gaggccgagg cggcgaatc                                                19
```

<210> SEQ ID NO 152
<211> LENGTH: 20
<212> TYPE: DNA
<213> ORGANISM: Artificial Sequence
<220> FEATURE:
<223> OTHER INFORMATION: oligonuclotide BV12 AS for PCR
<220> FEATURE:
<221> NAME/KEY: misc_feature
<223> OTHER INFORMATION: Synthetic

<400> SEQUENCE: 152

```
gattcgcccg cctcggcctc                                               20
```

<210> SEQ ID NO 153
<211> LENGTH: 20
<212> TYPE: DNA
<213> ORGANISM: Artificial Sequence
<220> FEATURE:
<223> OTHER INFORMATION: oligonucleotide BV10 S for PCR
<220> FEATURE:
<221> NAME/KEY: misc_feature
<223> OTHER INFORMATION: Synthetic

<400> SEQUENCE: 153

```
ggctgccctc tgctggctcc                                                    20
```

<210> SEQ ID NO 154
<211> LENGTH: 22
<212> TYPE: DNA
<213> ORGANISM: Artificial Sequence
<220> FEATURE:
<223> OTHER INFORMATION: oligonucleotide GDBR1 AS
<220> FEATURE:
<221> NAME/KEY: misc_feature
<223> OTHER INFORMATION: Synthetic

<400> SEQUENCE: 154

```
aaatgtgaat tttacaaagc gc                                                 22
```

<210> SEQ ID NO 155
<211> LENGTH: 21
<212> TYPE: DNA
<213> ORGANISM: Artificial Sequence
<220> FEATURE:
<223> OTHER INFORMATION: oligonucleotide AVT BV1 S
<220> FEATURE:
<221> NAME/KEY: misc_feature
<223> OTHER INFORMATION: Synthetic

<400> SEQUENCE: 155

```
ttgcagcccc atcacccggt c                                                  21
```

<210> SEQ ID NO 156
<211> LENGTH: 24
<212> TYPE: PRT
<213> ORGANISM: Homo sapiens

<400> SEQUENCE: 156

```
Ala Glu Ala Gly Gly Ser Arg Gly Gln Glu Met Glu Thr Ile Leu Ala
1               5                   10                  15

Asn Thr Val Lys Pro Cys Leu Tyr
            20
```

<210> SEQ ID NO 157
<211> LENGTH: 35
<212> TYPE: PRT
<213> ORGANISM: Homo sapiens

<400> SEQUENCE: 157

```
Leu Gly Leu Gln Ala Pro Ala Ala Thr Pro Gly Tyr Phe Phe Val Phe
1               5                   10                  15

Ser Val Glu Thr Gly Phe His Cys Val Ser Gln Asp Gly Leu His Leu
            20                  25                  30

Leu Thr Ser
        35
```

<210> SEQ ID NO 158
<211> LENGTH: 26
<212> TYPE: PRT
<213> ORGANISM: Homo sapiens

<400> SEQUENCE: 158

```
Val Ala Gly Ala Thr Gly Ala Cys Arg His Ala Arg Leu Leu Phe Cys
1               5                   10                  15

Ile Phe Ser Arg Asp Arg Val Ser Leu Cys
            20                  25
```

<210> SEQ ID NO 159

```
<211> LENGTH: 49
<212> TYPE: PRT
<213> ORGANISM: Homo sapiens

<400> SEQUENCE: 159

Thr Gln Glu Ala Glu Leu Ala Val Ser Arg Asp Cys Ala Thr Ala Leu
1               5                   10                  15

Gln Pro Gly Gln Gln Ser Glu Thr Pro Ser Gln Lys Lys Lys Lys Asn
            20                  25                  30

His Pro Lys Ala Ile Arg Arg Thr Arg Thr Gly His Thr Leu Gln His
        35                  40                  45

Trp

<210> SEQ ID NO 160
<211> LENGTH: 28
<212> TYPE: PRT
<213> ORGANISM: Homo sapiens

<400> SEQUENCE: 160

Ala Glu Ile Val Pro Leu His Ser Ser Leu Gly Asn Arg Ala Arg Leu
1               5                   10                  15

His Leu Lys Lys Lys Lys Lys Ile Thr Pro Lys Gln
            20                  25

<210> SEQ ID NO 161
<211> LENGTH: 50
<212> TYPE: PRT
<213> ORGANISM: Homo sapiens

<400> SEQUENCE: 161

Gly Glu Leu Glu Gln Asp Ile His Ser Asn Thr Gly Glu Thr Arg Lys
1               5                   10                  15

Thr Tyr Val Thr Pro Asn His Asn Ile Tyr Thr Gln Asn Tyr Thr Arg
            20                  25                  30

Cys Trp Asp Cys Leu Ile Thr Ser Glu Phe Ala Ala Cys Arg Ser
        35                  40                  45

Thr Ile
    50

<210> SEQ ID NO 162
<211> LENGTH: 33
<212> TYPE: PRT
<213> ORGANISM: Homo sapiens

<400> SEQUENCE: 162

Ala Ile Pro Thr Ser Arg Ile Val Leu Cys Val Tyr Ile Val Val Trp
1               5                   10                  15

Gly Tyr Ile Cys Phe Pro Ser Phe Thr Ser Val Gly Val Tyr Val Leu
            20                  25                  30

Phe

<210> SEQ ID NO 163
<211> LENGTH: 24
<212> TYPE: PRT
<213> ORGANISM: Homo sapiens

<400> SEQUENCE: 163

Glu Asn Ile Cys Asn Pro Lys Pro Gln Tyr Ile His Thr Lys Leu Tyr
1               5                   10                  15

Glu Met Leu Gly Leu Leu Asn His
```

20

<210> SEQ ID NO 164
<211> LENGTH: 34
<212> TYPE: PRT
<213> ORGANISM: Homo sapiens

<400> SEQUENCE: 164

Asn Thr Gln Ala Met His Pro Thr Arg Trp Glu Leu Ser His Met Val
1               5                   10                  15

Asp Leu Gln Ala Ala Ala Asn Ser Leu Val Ile Lys Gln Ser Gln His
            20                  25                  30

Leu Val

<210> SEQ ID NO 165
<211> LENGTH: 22
<212> TYPE: PRT
<213> ORGANISM: Homo sapiens

<400> SEQUENCE: 165

Ser Leu Val Asn Ser Arg Pro Pro Ala Gly Arg Pro Tyr Gly Arg Ala
1               5                   10                  15

Pro Asn Ala Leu Asp Ala
            20

<210> SEQ ID NO 166
<211> LENGTH: 27
<212> TYPE: PRT
<213> ORGANISM: Homo sapiens

<400> SEQUENCE: 166

His Tyr Arg Ile Leu Lys Leu Cys Ile Gln Arg Val Gly Ser Ser Pro
1               5                   10                  15

Ile Trp Ser Thr Cys Arg Arg Pro Arg Ile His
            20                  25

<210> SEQ ID NO 167
<211> LENGTH: 24
<212> TYPE: PRT
<213> ORGANISM: Homo sapiens

<400> SEQUENCE: 167

Ile Arg Gly Arg Leu Gln Val Asp His Met Gly Glu Leu Pro Thr Arg
1               5                   10                  15

Trp Met His Ser Leu Ser Ile Leu
            20

<210> SEQ ID NO 168
<211> LENGTH: 29
<212> TYPE: PRT
<213> ORGANISM: Homo sapiens

<400> SEQUENCE: 168

Ile Ala Trp Arg Asn His Gly His Ser Cys Phe Leu Cys Glu Ile Val
1               5                   10                  15

Ile Arg Ser Gln Phe His Thr Thr Tyr Glu Pro Glu Ala
            20                  25

<210> SEQ ID NO 169
<211> LENGTH: 30
<212> TYPE: PRT
<213> ORGANISM: Homo sapiens

<400> SEQUENCE: 169

| Leu | Gly | Val | Ile | Met | Val | Ile | Ala | Val | Ser | Cys | Val | Lys | Leu | Leu | Ser |
|---|---|---|---|---|---|---|---|---|---|---|---|---|---|---|---|
| 1 | | | | 5 | | | | | 10 | | | | | 15 | |

| Ala | His | Asn | Ser | Thr | Gln | His | Thr | Ser | Arg | Lys | His | Lys | Val |
|---|---|---|---|---|---|---|---|---|---|---|---|---|---|
| | | | 20 | | | | | 25 | | | | | 30 |

<210> SEQ ID NO 170
<211> LENGTH: 1125
<212> TYPE: PRT
<213> ORGANISM: Homo Sapiens

<400> SEQUENCE: 170

| Met | Ser | Lys | Thr | Leu | Lys | Lys | Lys | His | Trp | Leu | Ser | Lys | Val | Gln |
|---|---|---|---|---|---|---|---|---|---|---|---|---|---|---|
| 1 | | | | 5 | | | | | 10 | | | | | 15 |

| Glu | Cys | Ala | Val | Ser | Trp | Ala | Gly | Pro | Gly | Asp | Phe | Gly | Ala | Glu |
|---|---|---|---|---|---|---|---|---|---|---|---|---|---|---|
| | | | 20 | | | | | 25 | | | | | 30 | |

| Ile | Arg | Gly | Gly | Ala | Glu | Arg | Gly | Glu | Phe | Pro | Tyr | Leu | Gly | Arg | Leu |
|---|---|---|---|---|---|---|---|---|---|---|---|---|---|---|---|
| | | 35 | | | | | 40 | | | | | 45 | | | |

| Arg | Glu | Glu | Pro | Gly | Gly | Gly | Thr | Cys | Cys | Val | Val | Ser | Gly | Lys | Ala |
|---|---|---|---|---|---|---|---|---|---|---|---|---|---|---|---|
| | 50 | | | | | 55 | | | | | 60 | | | | |

| Pro | Ser | Pro | Gly | Asp | Val | Leu | Leu | Glu | Val | Asn | Gly | Thr | Pro | Val | Ser |
|---|---|---|---|---|---|---|---|---|---|---|---|---|---|---|---|
| 65 | | | | | 70 | | | | | 75 | | | | | 80 |

| Gly | Leu | Thr | Asn | Arg | Asp | Thr | Leu | Ala | Val | Ile | Arg | His | Phe | Arg | Glu |
|---|---|---|---|---|---|---|---|---|---|---|---|---|---|---|---|
| | | | | 85 | | | | | 90 | | | | | 95 | |

| Pro | Ile | Arg | Leu | Lys | Thr | Val | Lys | Pro | Gly | Lys | Val | Ile | Asn | Lys | Asp |
|---|---|---|---|---|---|---|---|---|---|---|---|---|---|---|---|
| | | | 100 | | | | | 105 | | | | | 110 | | |

| Leu | Arg | His | Tyr | Leu | Ser | Leu | Gln | Phe | Gln | Lys | Gly | Ser | Ile | Asp | His |
|---|---|---|---|---|---|---|---|---|---|---|---|---|---|---|---|
| | | 115 | | | | | 120 | | | | | 125 | | | |

| Lys | Leu | Gln | Gln | Val | Ile | Arg | Asp | Asn | Leu | Tyr | Leu | Arg | Thr | Ile | Pro |
|---|---|---|---|---|---|---|---|---|---|---|---|---|---|---|---|
| | 130 | | | | | 135 | | | | | 140 | | | | |

| Cys | Thr | Thr | Arg | Ala | Pro | Arg | Asp | Gly | Glu | Val | Pro | Gly | Val | Asp | Tyr |
|---|---|---|---|---|---|---|---|---|---|---|---|---|---|---|---|
| 145 | | | | | 150 | | | | | 155 | | | | | 160 |

| Asn | Phe | Ile | Ser | Val | Glu | Gln | Phe | Lys | Ala | Leu | Glu | Glu | Ser | Gly | Ala |
|---|---|---|---|---|---|---|---|---|---|---|---|---|---|---|---|
| | | | | 165 | | | | | 170 | | | | | 175 | |

| Leu | Leu | Glu | Ser | Gly | Thr | Tyr | Asp | Gly | Asn | Phe | Tyr | Gly | Thr | Pro | Lys |
|---|---|---|---|---|---|---|---|---|---|---|---|---|---|---|---|
| | | | 180 | | | | | 185 | | | | | 190 | | |

| Pro | Pro | Ala | Glu | Pro | Ser | Pro | Phe | Gln | Pro | Asp | Pro | Val | Asp | Gln | Val |
|---|---|---|---|---|---|---|---|---|---|---|---|---|---|---|---|
| | | 195 | | | | | 200 | | | | | 205 | | | |

| Leu | Phe | Asp | Asn | Glu | Phe | Asp | Ala | Glu | Ser | Gln | Arg | Lys | Arg | Thr | Thr |
|---|---|---|---|---|---|---|---|---|---|---|---|---|---|---|---|
| | 210 | | | | | 215 | | | | | 220 | | | | |

| Ser | Val | Ser | Lys | Met | Glu | Arg | Met | Asp | Ser | Ser | Leu | Pro | Glu | Glu | Glu |
|---|---|---|---|---|---|---|---|---|---|---|---|---|---|---|---|
| 225 | | | | | 230 | | | | | 235 | | | | | 240 |

| Glu | Asp | Glu | Asp | Lys | Glu | Ala | Ile | Asn | Gly | Ser | Gly | Asn | Ala | Glu | Asn |
|---|---|---|---|---|---|---|---|---|---|---|---|---|---|---|---|
| | | | | 245 | | | | | 250 | | | | | 255 | |

| Arg | Glu | Arg | His | Ser | Glu | Ser | Ser | Asp | Trp | Met | Lys | Thr | Val | Pro | Ser |
|---|---|---|---|---|---|---|---|---|---|---|---|---|---|---|---|
| | | | 260 | | | | | 265 | | | | | 270 | | |

| Tyr | Asn | Gln | Thr | Asn | Ser | Ser | Met | Asp | Phe | Arg | Asn | Tyr | Met | Met | Arg |
|---|---|---|---|---|---|---|---|---|---|---|---|---|---|---|---|
| | | 275 | | | | | 280 | | | | | 285 | | | |

| Asp | Glu | Thr | Leu | Glu | Pro | Leu | Pro | Lys | Asn | Trp | Glu | Met | Ala | Tyr | Thr |
|---|---|---|---|---|---|---|---|---|---|---|---|---|---|---|---|
| | 290 | | | | | 295 | | | | | 300 | | | | |

| Asp | Thr | Gly | Met | Ile | Tyr | Phe | Ile | Asp | His | Asn | Thr | Lys | Thr | Thr | Thr |
|---|---|---|---|---|---|---|---|---|---|---|---|---|---|---|---|
| 305 | | | | | 310 | | | | | 315 | | | | | 320 |

| Trp | Leu | Asp | Pro | Arg | Leu | Cys | Lys | Lys | Ala | Lys | Ala | Pro | Glu | Asp | Cys |
|---|---|---|---|---|---|---|---|---|---|---|---|---|---|---|---|
| | | | | 325 | | | | | 330 | | | | | 335 | |

-continued

Glu Asp Gly Glu Leu Pro Tyr Gly Trp Glu Lys Ile Glu Asp Pro Gln
                340                 345                 350

Tyr Gly Thr Tyr Tyr Val Asp His Leu Asn Gln Lys Thr Gln Phe Glu
            355                 360                 365

Asn Pro Val Glu Glu Ala Lys Arg Lys Gln Leu Gly Gln Val Glu
        370                 375                 380

Ile Gly Ser Ser Lys Pro Asp Met Glu Lys Ser His Phe Thr Arg Asp
385                 390                 395                 400

Pro Ser Gln Leu Lys Gly Val Leu Val Arg Ala Ser Leu Lys Lys Ser
                405                 410                 415

Thr Met Gly Phe Gly Phe Thr Ile Ile Gly Gly Asp Arg Pro Asp Glu
                420                 425                 430

Phe Leu Gln Val Lys Asn Val Leu Lys Asp Gly Pro Ala Ala Gln Asp
            435                 440                 445

Gly Lys Ile Ala Pro Gly Asp Val Ile Val Asp Ile Asn Gly Asn Cys
        450                 455                 460

Val Leu Gly His Thr His Ala Asp Val Val Gln Met Phe Gln Leu Val
465                 470                 475                 480

Pro Val Asn Gln Tyr Val Asn Leu Thr Leu Cys Arg Gly Tyr Pro Leu
                485                 490                 495

Pro Asp Asp Ser Glu Asp Pro Val Val Asp Ile Val Ala Ala Thr Pro
            500                 505                 510

Val Ile Asn Gly Gln Ser Leu Thr Lys Gly Glu Thr Cys Met Asn Pro
        515                 520                 525

Gln Asp Phe Lys Pro Gly Ala Met Val Leu Glu Gln Asn Gly Lys Ser
    530                 535                 540

Gly His Thr Leu Thr Gly Asp Gly Leu Asn Gly Pro Ser Asp Ala Ser
545                 550                 555                 560

Glu Gln Arg Val Ser Met Ala Ser Ser Gly Ser Ser Gln Pro Glu Leu
                565                 570                 575

Val Thr Ile Pro Leu Ile Lys Gly Pro Lys Gly Phe Gly Phe Ala Ile
            580                 585                 590

Ala Asp Ser Pro Thr Gly Gln Lys Val Lys Met Ile Leu Asp Ser Gln
        595                 600                 605

Trp Cys Gln Gly Leu Gln Lys Gly Asp Ile Ile Lys Glu Ile Tyr His
    610                 615                 620

Gln Asn Val Gln Asn Leu Thr His Leu Gln Val Val Glu Val Leu Lys
625                 630                 635                 640

Gln Phe Pro Val Gly Ala Asp Val Pro Leu Leu Ile Leu Arg Gly Gly
                645                 650                 655

Pro Pro Ser Pro Thr Lys Thr Ala Lys Met Lys Thr Asp Lys Lys Glu
            660                 665                 670

Asn Ala Gly Ser Leu Glu Ala Ile Asn Glu Pro Ile Pro Gln Pro Met
        675                 680                 685

Pro Phe Pro Pro Ser Ile Ile Arg Ser Gly Ser Pro Lys Leu Asp Pro
    690                 695                 700

Ser Glu Val Tyr Leu Lys Ser Lys Thr Leu Tyr Glu Asp Lys Pro Pro
705                 710                 715                 720

Asn Thr Lys Asp Leu Asp Val Phe Leu Arg Lys Gln Glu Ser Gly Phe
                725                 730                 735

Gly Phe Arg Val Leu Gly Gly Asp Gly Pro Asp Gln Ser Ile Tyr Ile
            740                 745                 750

Gly Ala Ile Ile Pro Leu Gly Ala Glu Lys Asp Gly Arg Leu Arg
            755                 760                 765

Ala Ala Asp Glu Leu Met Cys Ile Asp Gly Ile Pro Val Lys Gly Lys
770                 775                 780

Ser His Lys Gln Val Leu Asp Leu Met Thr Thr Ala Ala Arg Asn Gly
785                 790                 795                 800

His Val Leu Leu Thr Val Arg Arg Lys Ile Phe Tyr Gly Glu Lys Gln
                805                 810                 815

Pro Glu Asp Asp Ser Ser Gln Ala Phe Ile Ser Thr Gln Asn Gly Ser
            820                 825                 830

Pro Arg Leu Asn Arg Ala Glu Val Pro Ala Arg Pro Ala Pro Gln Glu
        835                 840                 845

Pro Tyr Asp Val Val Leu Gln Arg Lys Glu Asn Glu Gly Phe Gly Phe
    850                 855                 860

Val Ile Leu Thr Ser Lys Asn Lys Pro Pro Pro Gly Val Ile Pro His
865                 870                 875                 880

Lys Ile Gly Arg Val Ile Glu Gly Ser Pro Ala Asp Arg Cys Gly Lys
                885                 890                 895

Leu Lys Val Gly Asp His Ile Ser Ala Val Asn Gly Gln Ser Ile Val
            900                 905                 910

Glu Leu Ser His Asp Asn Ile Val Gln Leu Ile Lys Asp Ala Gly Val
        915                 920                 925

Thr Val Thr Leu Thr Val Ile Ala Glu Glu His His Gly Pro Pro
    930                 935                 940

Ser Gly Thr Asn Ser Ala Arg Gln Ser Pro Ala Leu Gln His Arg Pro
945                 950                 955                 960

Met Gly Gln Ser Gln Ala Asn His Ile Pro Gly Asp Arg Ser Ala Leu
                965                 970                 975

Glu Gly Glu Ile Gly Lys Asp Val Ser Thr Ser Tyr Arg His Ser Trp
            980                 985                 990

Ser Asp His Lys His Leu Ala Gln Pro Asp Thr Ala Val Ile Ser Val
        995                 1000                1005

Val Gly Ser Arg His Asn Gln Asn Leu Gly Cys Tyr Pro Val Glu
    1010                1015                1020

Leu Glu Arg Gly Pro Arg Gly Phe Gly Phe Ser Leu Arg Gly Gly
    1025                1030                1035

Lys Glu Tyr Asn Met Gly Leu Phe Ile Leu Arg Leu Ala Glu Asp
    1040                1045                1050

Gly Pro Ala Ile Lys Asp Gly Arg Ile His Val Gly Asp Gln Ile
    1055                1060                1065

Val Glu Ile Asn Gly Glu Pro Thr Gln Gly Ile Thr His Thr Arg
    1070                1075                1080

Ala Ile Glu Leu Ile Gln Ala Gly Gly Asn Lys Val Leu Leu Leu
    1085                1090                1095

Leu Arg Pro Gly Thr Gly Leu Ile Pro Asp His Gly Leu Ala Pro
    1100                1105                1110

Ser Gly Leu Cys Ser Tyr Val Lys Pro Glu Gln His
    1115                1120                1125

<210> SEQ ID NO 171
<211> LENGTH: 1202
<212> TYPE: DNA
<213> ORGANISM: Homo sapiens
<220> FEATURE:
<221> NAME/KEY: misc_feature
<223> OTHER INFORMATION: Sequence of Liv21 complex
<220> FEATURE:
<221> NAME/KEY: misc_feature
<222> LOCATION: (1070)..(1070)
<223> OTHER INFORMATION: n is a, c, g, or t

<400> SEQUENCE: 171

| | | | | |
|---|---|---|---|---|
| ggagaagggt | ccccactgct | cctgtcaagc | cttgttgtgt | cgggacttga | actttattct | 60 |
| aagcaggtga | atgcggtgca | tgcaagagag | acagagagaa | tgtggcagga | ccaaggagga | 120 |
| ggctatgcca | cttatgtcac | tcctggcaaa | ataaggggg | catggagtag | gctgtttgtg | 180 |
| gtgcagatgg | tgagagcagt | caggtccagc | acagatttta | aaggttggac | ccagagaatt | 240 |
| tgctgcagaa | tcagatgtgg | ggtgtaaggc | agagaggagt | caagggcaac | ttcaggattt | 300 |
| ggggccggaa | ctgccattag | acagacagag | ggacactggg | ggagaagcag | gttaggtggg | 360 |
| attaaaatca | agagttcaag | ttaagtttga | gcagcctgtt | agacctccaa | cgagggccag | 420 |
| atagaagaat | ctggtttcca | gggagaggtc | aggatgagag | atacacacgt | gggaatgatt | 480 |
| ggcattgggc | ggactttata | ttctctgggc | cagtgagaca | gctgggaagt | gaccacggat | 540 |
| agagaagaga | caaagtcaca | gaaaccaaga | gaggtaatgt | tgcaaggacg | aacactcaa | 600 |
| ctctcaaatg | ctgctgagac | gtgggctgag | ggctgagaat | ggaattggga | agaaccgagg | 660 |
| tcactggtga | tcctgagggt | ttcagtggca | agggcaggtg | gactgcagtg | gggcccggtg | 720 |
| gggatcggtg | gagcatgggc | ccctctcccg | gagagttgca | ctgtaaacga | gggcagacat | 780 |
| atgggagtgc | agctagaggg | agggaacgta | ggctcaaggg | agagtttatt | ctgaatgaga | 840 |
| gagatcacag | cttgttttta | ggctgacggg | catgatccat | agagggaaa | gtaattaaga | 900 |
| tgcagaagag | aggccggggg | tggtggctca | cgcctgtaat | ctcagcactt | gggaggctc | 960 |
| gaggtgggtg | gatcatttga | ggacaggagt | tcgagaccat | cctggccagc | atggtgaaac | 1020 |
| ctcgcctcta | ctaaaaataa | aaataaaaaa | aaattagctg | ggtgcggtgn | acggcacct | 1080 |
| gtagtaccag | ctacttggga | ggctgaggta | acagaatcgc | ttgaaccctg | gaggcagggg | 1140 |
| ttgcagtgag | ctgagattgt | gccactgcac | tctagcctgg | gcaacaaatt | gagactccac | 1200 |
| tc | | | | | 1202 |

<210> SEQ ID NO 172
<211> LENGTH: 1199
<212> TYPE: DNA
<213> ORGANISM: Homo sapiens
<220> FEATURE:
<221> NAME/KEY: misc_feature
<223> OTHER INFORMATION: Sequence of LIV21 complex

<400> SEQUENCE: 172

| | | | | |
|---|---|---|---|---|
| ggagaagggt | ccccactgct | cctgtcaagc | cttgttgtgt | cgggacttga | actttattct | 60 |
| aagcaggtga | atgcggtgca | tgcaagagag | acagagagaa | tgtggcacga | ccaaggagga | 120 |
| ggctatgcca | cttatgtcac | tcctggcaaa | ataaggggg | catggagtag | gctgtttgtg | 180 |
| gtgcagatgg | tgagagcagt | caggtccagc | acagatttta | aaggttggac | ccagagaatt | 240 |
| tgctgcagaa | tcagatgtgg | ggtgtaaggc | agagaggagt | caagggcaac | ttcaggattt | 300 |
| ggggccggaa | ctgccattag | acagacaggg | acactggggg | agaagcaggt | taggtgggat | 360 |
| taaaatcaag | agttcaagtt | aagtttgagc | agcctgttag | acctccaacg | agggccagat | 420 |
| agaagaatct | ggtttccagg | gagaggtcag | gatgagagat | acacacgtgg | gaatgattgg | 480 |
| cattgggcgg | actttatatt | ctctgggcca | gtgagacagc | tgggaagtga | ccacggatag | 540 |

```
agaagagaca aagtcacaga aaccaagaga ggtaatgttg caaggacgga acactcaact      600
ctcaaatgct gctgagacgt gggctgaggg ctgagaatgg aattgggaag aaccgaggtc      660
actggtgatc ctgagggttt cagtggcaag ggcaggtgga ctgcagtggg gcccggtggg      720
gatgggtgga gcatgggccc ctctcccgga gagttgcact gtaaacgagg gcagacatat      780
gggagtgcag ctagagggag ggaacgtagg gtcaagggag agtttattct gaatgagaga      840
gatcacagct tgtttttagg ctgacgggca tgatccatag aggggaaagt aattaagatg      900
cagaagagag gccggggggtg gtggctcacg cctgtaatct cagcactttg ggaggctgag     960
gtgggtggat catttgagga caggagttcg agaccatcct ggccagcatg gtgaaacctc     1020
gcctctacta aaataaaaa taaaaaaaaa ttagctgggt gcggtgacgg gcacctgtag     1080
taccagctac ttgggaggct gaggtaacag aatcgcttga accctggagg cagggggttgc     1140 agtgagctga gattgtgcca ctgcactcta gcctgggcaa caaattgaga ctccatctc     1199
```

<210> SEQ ID NO 173
<211> LENGTH: 20
<212> TYPE: DNA
<213> ORGANISM: Artificial Sequence
<220> FEATURE:
<223> OTHER INFORMATION: oligonucleotide for PCR
<220> FEATURE:
<221> NAME/KEY: misc_feature
<223> OTHER INFORMATION: Synthetic

<400> SEQUENCE: 173
tttccgtcac gccgacctgc      20

<210> SEQ ID NO 174
<211> LENGTH: 20
<212> TYPE: DNA
<213> ORGANISM: Artificial Sequence
<220> FEATURE:
<223> OTHER INFORMATION: oligonucleotide reverse for PCR
<220> FEATURE:
<221> NAME/KEY: misc_feature
<223> OTHER INFORMATION: Synthetic

<400> SEQUENCE: 174
gcaggtcggc gtgacggaaa      20

<210> SEQ ID NO 175
<211> LENGTH: 20
<212> TYPE: DNA
<213> ORGANISM: Artificial Sequence
<220> FEATURE:
<223> OTHER INFORMATION: oligonucleotide for PCR
<220> FEATURE:
<221> NAME/KEY: misc_feature
<223> OTHER INFORMATION: Synthetic

<400> SEQUENCE: 175
cgccacgaac tccagcagca      20

<210> SEQ ID NO 176
<211> LENGTH: 20
<212> TYPE: DNA
<213> ORGANISM: Artificial Sequence
<220> FEATURE:
<223> OTHER INFORMATION: oligonucleotide for PCR
<220> FEATURE:
<221> NAME/KEY: misc_feature
<223> OTHER INFORMATION: Synthetic

<400> SEQUENCE: 176

```
ggcctgcgct cgcctgtaaa                                                    20
```

<210> SEQ ID NO 177
<211> LENGTH: 20
<212> TYPE: DNA
<213> ORGANISM: Artificial Sequence
<220> FEATURE:
<223> OTHER INFORMATION: oligonucleotide for PCR
<220> FEATURE:
<221> NAME/KEY: misc_feature
<223> OTHER INFORMATION: Synthetic

<400> SEQUENCE: 177

```
cagtggagaa gcggcggcaa                                                    20
```

<210> SEQ ID NO 178
<211> LENGTH: 19
<212> TYPE: PRT
<213> ORGANISM: Artificial Sequence
<220> FEATURE:
<223> OTHER INFORMATION: sequence of Liv21 complex
<220> FEATURE:
<221> NAME/KEY: misc_feature
<223> OTHER INFORMATION: Synthetic

<400> SEQUENCE: 178

Pro Pro Arg Ala Ser Gln Ser Ala Glu Ile Thr Gly Val Ser His His
1               5                   10                  15

Pro Arg Pro

<210> SEQ ID NO 179
<211> LENGTH: 19
<212> TYPE: PRT
<213> ORGANISM: Artificial Sequence
<220> FEATURE:
<223> OTHER INFORMATION: isoforme of sequence of complexe Liv21
<220> FEATURE:
<221> NAME/KEY: misc_feature
<223> OTHER INFORMATION: Synthetic

<400> SEQUENCE: 179

Pro Thr Leu Ala Ser Gln Ser Ala Gly Ile Thr Gly Val Ser His Arg
1               5                   10                  15

Ala Trp Pro

<210> SEQ ID NO 180
<211> LENGTH: 144
<212> TYPE: PRT
<213> ORGANISM: Artificial Sequence
<220> FEATURE:
<223> OTHER INFORMATION: Liv 21K
<220> FEATURE:
<221> NAME/KEY: misc_feature
<223> OTHER INFORMATION: Synthetic
<220> FEATURE:
<221> NAME/KEY: misc_feature
<222> LOCATION: (83)..(83)
<223> OTHER INFORMATION: Xaa is any amino acid

<400> SEQUENCE: 180

Ser Val Ala Gln Ala Gly Val Gln Trp Arg Asn Leu Gly Ser Leu Gln
1               5                   10                  15

Ala Leu Pro Pro Gly Phe Met Pro Phe Ser Cys Leu Ser Leu Leu Ser
            20                  25                  30

Ser Trp Asp Tyr Arg Arg Leu Pro Pro Arg Pro Ala Asn Phe Leu Tyr
        35                  40                  45

-continued

```
Phe Pro Arg Gln Gly Phe Thr Val Leu Ala Arg Met Val Ser Ile Ser
    50                  55                  60

Pro Arg Asp Pro Pro Ala Ser Ala Ser Gln Ser Ala Gly Ile Thr Tyr
 65                  70                  75                  80

Ile Ser Xaa Phe Phe Phe Phe Glu Met Glu Ser Arg Ser Ser Val Ala
                 85                  90                  95

Gln Ala Gly Val Gln Trp Arg Asn Leu Gly Ser Leu Gln Ala Leu Pro
            100                 105                 110

Pro Gly Phe Met Pro Phe Ser Cys Leu Ser Leu Leu Ser Ser Trp Asp
            115                 120                 125

Tyr Arg Arg Leu Pro Pro Arg Pro Ala Thr Phe Leu Tyr Phe Pro Arg
130                 135                 140
```

<210> SEQ ID NO 181
<211> LENGTH: 95
<212> TYPE: PRT
<213> ORGANISM: Artificial Sequence
<220> FEATURE:
<223> OTHER INFORMATION: Liv 21F
<220> FEATURE:
<221> NAME/KEY: misc_feature
<223> OTHER INFORMATION: Synthetic
<220> FEATURE:
<221> NAME/KEY: misc_feature
<222> LOCATION: (83)..(83)
<223> OTHER INFORMATION: Xaa is any amino acid

<400> SEQUENCE: 181

```
Ser Val Ala Gln Ala Gly Val Gln Trp Arg Asn Leu Gly Ser Leu Gln
1               5                   10                  15

Ala Leu Pro Pro Gly Phe Met Pro Phe Ser Cys Leu Ser Leu Leu Ser
                20                  25                  30

Ser Trp Asp Tyr Arg Arg Leu Pro Pro Arg Pro Ala Thr Phe Leu Tyr
            35                  40                  45

Phe Pro Arg Gln Gly Phe Thr Val Leu Ala Arg Met Val Ser Ile Ser
    50                  55                  60

Pro Arg Asp Pro Pro Ala Ser Ala Ser Gln Ser Val Gly Ile Ala Tyr
 65                  70                  75                  80

Ile Ser Xaa Phe Phe Phe Phe Glu Met Glu Ser Arg Ser Val Ala
                 85                  90                  95
```

<210> SEQ ID NO 182
<211> LENGTH: 129
<212> TYPE: PRT
<213> ORGANISM: Artificial Sequence
<220> FEATURE:
<223> OTHER INFORMATION: traduction of clone C18
<220> FEATURE:
<221> NAME/KEY: misc_feature
<223> OTHER INFORMATION: Synthetic
<220> FEATURE:
<221> NAME/KEY: misc_feature
<222> LOCATION: (83)..(83)
<223> OTHER INFORMATION: Xaa is any amino acid

<400> SEQUENCE: 182

```
Ser Val Ala Gln Ala Gly Val Gln Trp Arg Asn Leu Gly Ser Leu Gln
1               5                   10                  15

Ala Leu Pro Pro Gly Phe Met Pro Phe Ser Cys Leu Ser Leu Leu Ser
                20                  25                  30

Ser Trp Asp Tyr Arg Arg Leu Pro Pro Arg Pro Ala Asn Phe Leu Tyr
            35                  40                  45
```

```
Phe Pro Arg Gln Gly Phe Thr Val Leu Ala Arg Met Val Ser Ile Ser
    50                  55                  60

Pro Arg Asp Pro Pro Ala Ser Ala Ser Gln Ser Ala Gly Ile Thr Tyr
65                  70                  75                  80

Ile Ser Xaa Phe Phe Phe Phe Glu Met Glu Ser Arg Ser Val Ala Phe
                85                  90                  95

Leu Tyr Phe Pro Arg Gln Gly Phe Thr Val Leu Ala Arg Met Val Ser
                100                 105                 110

Ile Ser Pro Arg Asp Pro Pro Ala Ser Ala Ser Gln Ser Ala Gly Ile
            115                 120                 125

Thr
```

```
<210> SEQ ID NO 183
<211> LENGTH: 78
<212> TYPE: PRT
<213> ORGANISM: Artificial Sequence
<220> FEATURE:
<223> OTHER INFORMATION: isoforme of sequence NO 180
<220> FEATURE:
<221> NAME/KEY: misc_feature
<223> OTHER INFORMATION: Synthetic
<220> FEATURE:
<221> NAME/KEY: misc_feature
<222> LOCATION: (42)..(43)
<223> OTHER INFORMATION: Xaa is any amino acid
<220> FEATURE:
<221> NAME/KEY: misc_feature
<222> LOCATION: (48)..(48)
<223> OTHER INFORMATION: Xaa is any amino acid

<400> SEQUENCE: 183

Ser Leu Ala Leu Leu Pro Lys Leu Glu Cys Arg Gly Thr Ile Ser Ala
1               5                   10                  15

His Cys Asn Leu His Leu Pro Gly Ser Ser Asp Phe Pro Ala Ser Ala
                20                  25                  30

Ser Gln Val Ala Gly Thr Thr Gly Ala Xaa Xaa Cys His His Ala Xaa
            35                  40                  45

Trp Leu Ile Phe Val Phe Leu Val Glu Ala Arg Phe His His Val Gly
    50                  55                  60

Gln Asp Gly Leu Glu Leu Leu Thr Ser Asn Asp Pro Pro Thr
65                  70                  75
```

```
<210> SEQ ID NO 184
<211> LENGTH: 78
<212> TYPE: PRT
<213> ORGANISM: Artificial Sequence
<220> FEATURE:
<223> OTHER INFORMATION: isoforme of sequence NO 183
<220> FEATURE:
<221> NAME/KEY: misc_feature
<223> OTHER INFORMATION: Synthetic
<220> FEATURE:
<221> NAME/KEY: misc_feature
<222> LOCATION: (43)..(43)
<223> OTHER INFORMATION: Xaa is any amino acid

<400> SEQUENCE: 184

Ser Leu Asn Leu Leu Pro Arg Leu Glu Cys Ser Gly Thr Ile Ser Ala
1               5                   10                  15

His Cys Asn Pro Cys Leu Gln Gly Ser Ser Asp Ser Val Thr Ser Ala
                20                  25                  30

Ser Gln Val Ala Gly Thr Thr Gly Ala Arg Xaa Pro His Pro Ala Asn
            35                  40                  45
```

```
Phe Phe Leu Phe Leu Phe Leu Val Glu Ala Arg Phe His His Ala Gly
    50                  55                  60

Gln Asp Gly Leu Glu Leu Leu Ser Ser Asn Asp Pro Pro Thr
 65                  70                  75
```

<210> SEQ ID NO 185
<211> LENGTH: 76
<212> TYPE: PRT
<213> ORGANISM: Artificial Sequence
<220> FEATURE:
<223> OTHER INFORMATION: isoforme of sequence NO 183
<220> FEATURE:
<221> NAME/KEY: misc_feature
<223> OTHER INFORMATION: Synthetic

<400> SEQUENCE: 185

```
Ser Leu Ala Leu Ser Pro Arg Leu Glu Cys Ser Gly Thr Ile Leu Ala
  1               5                  10                  15

His Cys Asn Leu Cys Leu Leu Gly Ser Ser Asp Ser Pro Ala Ser Ala
             20                  25                  30

Ser Arg Val Ala Gly Thr Thr Gly Thr Cys His His Ala Gln Leu Ile
         35                  40                  45

Phe Val Phe Leu Val Glu Thr Arg Phe His His Ile Gly Gln Asp Gly
    50                  55                  60

Leu Asp Leu Leu Thr Tyr Asp Pro Pro Ala Ser Ala
 65                  70                  75
```

<210> SEQ ID NO 186
<211> LENGTH: 184
<212> TYPE: PRT
<213> ORGANISM: Homo sapiens
<220> FEATURE:
<221> NAME/KEY: misc_feature
<223> OTHER INFORMATION: AD7c NTP: 060448 - HUMAN
<220> FEATURE:
<221> NAME/KEY: misc_feature
<223> OTHER INFORMATION: Synthetic

<400> SEQUENCE: 186

```
Leu Ile Phe Ile Phe Ile Phe Asn Phe Leu Arg Gln Ser Leu Asn Ser
  1               5                  10                  15

Val Thr Gln Ala Gly Val Gln Trp Arg Asn Leu Gly Ser Leu Gln Pro
             20                  25                  30

Leu Pro Pro Gly Phe Lys Leu Phe Ser Cys Pro Ser Leu Leu Ser
         35                  40                  45

Ser Trp Asp Tyr Arg Arg Pro Arg Leu Ala Asn Phe Phe Val Phe
    50                  55                  60

Leu Val Glu Met Gly Phe Thr Met Phe Ala Arg Leu Ile Leu Ile Ser
 65                  70                  75                  80

Gly Pro Cys Asp Leu Pro Ala Ser Ala Ser Gln Ser Ala Gly Ile Thr
                 85                  90                  95

Gly Val Ser His His Ala Arg Leu Ile Phe Asn Phe Cys Leu Phe Glu
                100                 105                 110

Met Glu Ser His Ser Val Thr Gln Ala Gly Val Gln Trp Pro Asn Leu
            115                 120                 125

Gly Ser Leu Asp Pro Leu Pro Pro Gly Leu Lys Arg Phe Ser Cys Leu
        130                 135                 140

Ser Leu Pro Ser Ser Trp Asp Tyr Gly His Leu Pro Pro His Pro Ala
145                 150                 155                 160
```

```
Asn Phe Cys Ile Phe Ile Arg Gly Gly Val Ser Pro Tyr Leu Ser Gly
                165                 170                 175

Trp Ser Gln Thr Pro Asp Leu Arg
            180

<210> SEQ ID NO 187
<211> LENGTH: 60
<212> TYPE: PRT
<213> ORGANISM: Artificial Sequence
<220> FEATURE:
<223> OTHER INFORMATION: part of EAW88192.1 Figure 20
<220> FEATURE:
<221> NAME/KEY: misc_feature
<223> OTHER INFORMATION: Synthetic

<400> SEQUENCE: 187

Met Cys Val Ser Val Arg Val Cys Val Cys Val Cys Ala Ser Val Cys
1               5                   10                  15

Ala Cys Val Cys Ala Ser Val Cys Met Cys Ala Arg Ala Ser Val Cys
                20                  25                  30

Thr Cys Val Ser Leu His Ala Cys Leu Cys Met Cys Ala Arg Val Cys
            35                  40                  45

Leu Cys Val Cys Thr Arg Val His Val Thr Thr Gly
        50                  55                  60

<210> SEQ ID NO 188
<211> LENGTH: 95
<212> TYPE: PRT
<213> ORGANISM: Artificial Sequence
<220> FEATURE:
<223> OTHER INFORMATION: isoforme of sequence 183 (1202 _ 915)
<220> FEATURE:
<221> NAME/KEY: misc_feature
<223> OTHER INFORMATION: Synthetic
<220> FEATURE:
<221> NAME/KEY: misc_feature
<222> LOCATION: (44)..(44)
<223> OTHER INFORMATION: Xaa is any amino acid
<220> FEATURE:
<221> NAME/KEY: misc_feature
<222> LOCATION: (86)..(86)
<223> OTHER INFORMATION: Xaa is any amino acid

<400> SEQUENCE: 188

Glu Trp Ser Leu Asn Leu Leu Pro Arg Leu Glu Cys Ser Gly Thr Ile
1               5                   10                  15

Ser Ala His Cys Asn Pro Cys Leu Gln Gly Ser Ser Asp Val Thr Ser
                20                  25                  30

Ala Ser Gln Val Ala Gly Thr Thr Gly Ala Arg Xaa Pro His Pro Ala
            35                  40                  45

Asn Phe Phe Leu Phe Leu Phe Leu Val Glu Ala Arg Phe His His Ala
        50                  55                  60

Gly Gln Asp Gly Leu Glu Leu Leu Ser Ser Asn Asp Pro Pro Thr Ser
65                  70                  75                  80

Ser Leu Pro Lys Cys Xaa Asp Tyr Arg Arg Glu Pro Pro Pro Pro
                85                  90                  95

<210> SEQ ID NO 189
<211> LENGTH: 80
<212> TYPE: PRT
<213> ORGANISM: Artificial Sequence
<220> FEATURE:
<223> OTHER INFORMATION: isoforme of sequence NO 183
<220> FEATURE:
<221> NAME/KEY: misc_feature
```

<223> OTHER INFORMATION: Synthetic
<220> FEATURE:
<221> NAME/KEY: misc_feature
<222> LOCATION: (43)..(43)
<223> OTHER INFORMATION: Xaa is any amino acid

<400> SEQUENCE: 189

Ser Leu Asn Leu Leu Pro Arg Leu Glu Cys Ser Gly Thr Ile Ser Ala
1               5                   10                  15

His Cys Asn Pro Cys Leu Gln Gly Ser Ser Asp Ser Val Thr Ser Ala
            20                  25                  30

Ser Gln Val Ala Gly Thr Thr Gly Ala Arg Xaa Pro His Pro Ala Asn
        35                  40                  45

Phe Phe Leu Phe Leu Phe Leu Val Glu Ala Arg Phe His Ala Gly
    50                  55                  60

Gln Asp Gly Leu Glu Leu Leu Ser Ser Asn Asp Pro Pro Thr Ser Ser
65                  70                  75                  80

<210> SEQ ID NO 190
<211> LENGTH: 96
<212> TYPE: PRT
<213> ORGANISM: Artificial Sequence
<220> FEATURE:
<223> OTHER INFORMATION: zinc finger (sbjt 97 - 192)
<220> FEATURE:
<221> NAME/KEY: misc_feature
<223> OTHER INFORMATION: Synthetic

<400> SEQUENCE: 190

Lys Trp Ser Leu Thr Leu Ser Pro Lys Leu Glu Cys Asn Gly Ala Ile
1               5                   10                  15

Ser Val His Cys Asn Leu Arg Leu Leu Gly Ser Ser Asp Ser Leu Ala
            20                  25                  30

Ser Thr Ser Gln Ala Ala Gly Ile Ala Gly Ala Cys His His Ala Gln
        35                  40                  45

Leu Ile Phe Val Phe Leu Val Glu Thr Gly Phe His His Phe Asp Gln
    50                  55                  60

Ala Gly Phe Glu Leu Leu Thr Ser Ser Asp Pro Pro Ala Leu Ala Ser
65                  70                  75                  80

Gln Ser Ala Pro Lys Cys Trp Asp Tyr Lys His Glu Pro Leu Ser Pro
                85                  90                  95

<210> SEQ ID NO 191
<211> LENGTH: 20
<212> TYPE: PRT
<213> ORGANISM: Artificial Sequence
<220> FEATURE:
<223> OTHER INFORMATION: variant Leucine reach repeat
<220> FEATURE:
<221> NAME/KEY: misc_feature
<223> OTHER INFORMATION: Synthetic

<400> SEQUENCE: 191

Ile Ser Pro Arg Asp Pro Pro Ala Ser Ala Ser Gln Ser Val Glu Ile
1               5                   10                  15

Ala Tyr Ile Ser
            20

<210> SEQ ID NO 192
<211> LENGTH: 20
<212> TYPE: PRT
<213> ORGANISM: Artificial Sequence
<220> FEATURE:

<223> OTHER INFORMATION: Leucine reach repeat
<220> FEATURE:
<221> NAME/KEY: misc_feature
<223> OTHER INFORMATION: Synthetic

<400> SEQUENCE: 192

Leu Ser Ser Glu Asp Pro Pro Ala Ser Ala Ser Gln Ser Val Gly Ile
1               5                   10                  15

Ile Gly Val Ser
            20

<210> SEQ ID NO 193
<211> LENGTH: 43
<212> TYPE: PRT
<213> ORGANISM: Artificial Sequence
<220> FEATURE:
<223> OTHER INFORMATION: variant of sequence NO 186 (sbjct 19) unamed
      protein
<220> FEATURE:
<221> NAME/KEY: misc_feature
<223> OTHER INFORMATION: Synthetic

<400> SEQUENCE: 193

Ser Val Ala Gln Ala Gly Val Gln Trp Arg Asp Leu Gly Ser Leu Gln
1               5                   10                  15

Ala Pro Pro Pro Gly Phe Thr Pro Phe Ser Cys Leu Ser Leu Pro Ser
                20                  25                  30

Ser Trp Asp Tyr Arg Arg Pro Pro Leu Arg Pro
            35                  40

<210> SEQ ID NO 194
<211> LENGTH: 43
<212> TYPE: PRT
<213> ORGANISM: Homo sapiens
<220> FEATURE:
<221> NAME/KEY: misc_feature
<223> OTHER INFORMATION: part of sequence NO 182 homologue at "unamed
      protein"
<220> FEATURE:
<221> NAME/KEY: misc_feature
<223> OTHER INFORMATION: Synthetic

<400> SEQUENCE: 194

Ser Val Ala Gln Ala Gly Val Gln Trp Arg Asn Leu Gly Ser Leu Gln
1               5                   10                  15

Ala Leu Pro Pro Gly Phe Met Pro Phe Ser Cys Leu Ser Leu Leu Ser
                20                  25                  30

Ser Trp Asp Tyr Arg Arg Leu Pro Pro Arg Pro
            35                  40

<210> SEQ ID NO 195
<211> LENGTH: 41
<212> TYPE: PRT
<213> ORGANISM: Artificial Sequence
<220> FEATURE:
<223> OTHER INFORMATION: variant of sequence NO 186 (sbjct 15) unamed
      protein
<220> FEATURE:
<221> NAME/KEY: misc_feature
<223> OTHER INFORMATION: Synthetic

<400> SEQUENCE: 195

Ala Gln Ala Gly Val Gln Trp Arg Tyr Leu Gly Ser Leu Gln Pro Pro
1               5                   10                  15

Pro Pro Gly Phe Thr Arg Phe Ser Cys Leu Ser Leu Leu Ser Ser Trp
                20                  25                  30

```
Asp Tyr Arg Arg Pro Pro Pro Arg Pro
        35                  40

<210> SEQ ID NO 196
<211> LENGTH: 43
<212> TYPE: PRT
<213> ORGANISM: Artificial Sequence
<220> FEATURE:
<223> OTHER INFORMATION: variant de la sequence NO 186 (sbjct 5) E2F2
<220> FEATURE:
<221> NAME/KEY: misc_feature
<223> OTHER INFORMATION: Synthetic

<400> SEQUENCE: 196

Ser Val Ala Gln Ala Gly Val Gln Trp Pro Asp Leu Gly Ser Leu Gln
1               5                   10                  15

Pro Leu Pro Pro Arg Phe Lys Arg Phe Cys Leu Ser Leu Gln Ser
            20                  25                  30

Ser Trp Asp Tyr Arg His Ala Pro Pro Arg Pro
        35                  40

<210> SEQ ID NO 197
<211> LENGTH: 43
<212> TYPE: PRT
<213> ORGANISM: Artificial Sequence
<220> FEATURE:
<223> OTHER INFORMATION: transcription factor (sbjct 265) TFIID
<220> FEATURE:
<221> NAME/KEY: misc_feature
<223> OTHER INFORMATION: Synthetic

<400> SEQUENCE: 197

Ser Val Thr Gln Ala Gly Val Gln Trp Gln Asp Leu Gly Ser Leu Gln
1               5                   10                  15

Pro Pro Pro Pro Gly Phe Lys Arg Phe Ser Ser Leu Ser Leu Leu Ser
            20                  25                  30

Ser Trp Asn Tyr Arg Arg Ile Leu Glu Pro Arg
        35                  40

<210> SEQ ID NO 198
<211> LENGTH: 41
<212> TYPE: PRT
<213> ORGANISM: Artificial Sequence
<220> FEATURE:
<223> OTHER INFORMATION: variant (sbjct 565) vmyb
<220> FEATURE:
<221> NAME/KEY: misc_feature
<223> OTHER INFORMATION: Synthetic

<400> SEQUENCE: 198

Ala Pro Thr Gly Val Gln Trp His Asp Phe Gly Ser Leu Gln Pro Leu
1               5                   10                  15

Pro Pro Gly Phe Lys Arg Phe Ser Cys Leu Ser Leu Pro Arg Ser Trp
            20                  25                  30

Asp Tyr Arg His Pro Pro Pro Arg Pro
        35                  40

<210> SEQ ID NO 199
<211> LENGTH: 41
<212> TYPE: PRT
<213> ORGANISM: Artificial Sequence
<220> FEATURE:
<223> OTHER INFORMATION: variant (sbjct 20) macaque
<220> FEATURE:
<221> NAME/KEY: misc_feature
```

<223> OTHER INFORMATION: Synthetic

<400> SEQUENCE: 199

Ser Val Ile Gln Ser Gly Val Gln Trp His Asn Leu Gly Ser Leu Gln
1               5                   10                  15

Pro Pro Pro Pro Glu Phe Asn Arg Phe Ser Cys Leu Ser Leu Pro Asn
            20                  25                  30

Ser Trp Asp Tyr Arg Cys Met Pro Pro
        35                  40

<210> SEQ ID NO 200
<211> LENGTH: 38
<212> TYPE: PRT
<213> ORGANISM: Artificial Sequence
<220> FEATURE:
<223> OTHER INFORMATION: initiation of translation factor (sbjct 159)
<220> FEATURE:
<221> NAME/KEY: misc_feature
<223> OTHER INFORMATION: Synthetic

<400> SEQUENCE: 200

Gln Ala Gly Val Gln Trp His His Leu Gly Ser Leu Gln Ser Pro Pro
1               5                   10                  15

Pro Gly Phe Lys His Phe Thr Cys Leu Ser Leu Pro Ser Ser Trp Asp
            20                  25                  30

Tyr Met His Met Pro Pro
        35

<210> SEQ ID NO 201
<211> LENGTH: 41
<212> TYPE: PRT
<213> ORGANISM: Artificial Sequence
<220> FEATURE:
<223> OTHER INFORMATION: DNA polymerase transactivated (sbjct 9)
<220> FEATURE:
<221> NAME/KEY: misc_feature
<223> OTHER INFORMATION: Synthetic

<400> SEQUENCE: 201

Ser Val Pro His Ala Gly Val Gln Trp His Asn Leu Ser Ser Leu Gln
1               5                   10                  15

Pro Pro Pro Ser Gly Phe Lys Pro Phe Ser Tyr Leu Ser Leu Leu Ser
            20                  25                  30

Ser Arg Asp Gln Arg Arg Pro Leu Pro
        35                  40

<210> SEQ ID NO 202
<211> LENGTH: 32
<212> TYPE: PRT
<213> ORGANISM: Artificial Sequence
<220> FEATURE:
<223> OTHER INFORMATION: unamed protein (sbjct 15)
<220> FEATURE:
<221> NAME/KEY: misc_feature
<223> OTHER INFORMATION: Synthetic

<400> SEQUENCE: 202

Ala Gly Val Gln Trp Arg Asn Leu Gly Ser Leu Gln Ala Leu Pro Pro
1               5                   10                  15

Gly Phe Met Pro Phe Ser Cys Leu Ser Leu Leu Ser Ser Trp Asp Tyr
            20                  25                  30

<210> SEQ ID NO 203
<211> LENGTH: 35

```
<212> TYPE: PRT
<213> ORGANISM: Artificial Sequence
<220> FEATURE:
<223> OTHER INFORMATION: RNA binding motif (sbjct 2)
<220> FEATURE:
<221> NAME/KEY: misc_feature
<223> OTHER INFORMATION: Synthetic

<400> SEQUENCE: 203

Ala Lys Ala Gly Val Gln Trp Arg Asp Leu Asp Ser Leu Gln Pro Leu
1               5                   10                  15

Pro Pro Arg Phe Lys Arg Phe Ser His Leu Cys Leu Leu Ser Ser Trp
                20                  25                  30

Asp Tyr Arg
        35

<210> SEQ ID NO 204
<211> LENGTH: 32
<212> TYPE: PRT
<213> ORGANISM: Artificial Sequence
<220> FEATURE:
<223> OTHER INFORMATION: isoforme 3 mitogene activating protein kinase
<220> FEATURE:
<221> NAME/KEY: misc_feature
<223> OTHER INFORMATION: Synthetic

<400> SEQUENCE: 204

Ala Gly Val Gln Trp His Asp Leu Gly Ser Leu Gln Pro Leu Pro Pro
1               5                   10                  15

Arg Phe Lys Arg Phe Ser Cys Leu Ser Leu Gln Ser Ser Trp Asp Tyr
                20                  25                  30

<210> SEQ ID NO 205
<211> LENGTH: 39
<212> TYPE: PRT
<213> ORGANISM: Artificial Sequence
<220> FEATURE:
<223> OTHER INFORMATION: PP2121 ((Sbjct:90)  76% of homology with SEQ NO
      203)
<220> FEATURE:
<221> NAME/KEY: misc_feature
<223> OTHER INFORMATION: Synthetic

<400> SEQUENCE: 205

Ala Gly Val Gln Leu Ser Gly Leu Gly Ser Leu Gln Pro Leu Pro Pro
1               5                   10                  15

Gly Phe Gln Arg Phe Ser Cys Leu Ser Leu Leu Ser Ser Trp Asp Tyr
                20                  25                  30

Arg Cys Met Leu Pro Arg Pro
        35

<210> SEQ ID NO 206
<211> LENGTH: 9
<212> TYPE: PRT
<213> ORGANISM: Artificial Sequence
<220> FEATURE:
<223> OTHER INFORMATION: Sequence of Figure 4B (Obtain by spectrometry
      ESI MS MS)
<220> FEATURE:
<221> NAME/KEY: misc_feature
<223> OTHER INFORMATION: Synthetic

<400> SEQUENCE: 206

Tyr Arg Pro Gly Thr Val Ala Leu Arg
1               5
```

<210> SEQ ID NO 207
<211> LENGTH: 9
<212> TYPE: PRT
<213> ORGANISM: Artificial Sequence
<220> FEATURE:
<223> OTHER INFORMATION: Sequence obtain by spectrometry ESI MS MS analysis
<220> FEATURE:
<221> NAME/KEY: misc_feature
<223> OTHER INFORMATION: Synthetic

<400> SEQUENCE: 207

Lys Ala Val Ala Phe Pro Val Gly Arg
1               5

<210> SEQ ID NO 208
<211> LENGTH: 939
<212> TYPE: DNA
<213> ORGANISM: Artificial Sequence
<220> FEATURE:
<223> OTHER INFORMATION: Sequence of gene
<220> FEATURE:
<221> NAME/KEY: misc_feature
<223> OTHER INFORMATION: Synthetic

<400> SEQUENCE: 208

| | | | | | |
|---|---|---|---|---|---|
| ggcagctggg | ttgcatggag | aggtccagga | gggaccggag | gtgtgacaga | tactgtgagc | 60 |
| ggcagctggg | ttgcatggag | aggtccagga | gggaccggag | gtgtgacaga | tactgtgagc | 120 |
| ccggcgggcc | gcgcctggct | gggtgcctcg | gtacttgaat | tctgtcttgt | tttccgcatt | 180 |
| gtgtctgtcc | acccgagttc | tctgtcgtca | cttaactttg | cattggattt | ggttgttgta | 240 |
| cttttgcccct | gaatgtggac | aaagctgtgg | gcaagaggtc | agcaggaccc | gcctggggt | 300 |
| gccggcgttg | gtgactgcgg | gtcggggctc | ctagaacata | ggagccggct | gcctggcctc | 360 |
| ctttctcctc | caggaagagt | cattctttgg | catttgtgtt | tagagccagg | aggaaggcgg | 420 |
| aaggtaggga | gggagggctg | gtcccccctct | gaggggggctc | tagtgcctga | ccctgacctg | 480 |
| tcctcattcg | acagctgaaa | ctgttaagcg | ctggcccagt | cccccccaccc | cacccagccg | 540 |
| tgtactgcct | gggctcccct | caaagggaaa | tttttacgga | acatcttgg | cagcaagtgg | 600 |
| aaaaagatct | atggcccatg | aaccaactga | aaactccaag | aaccctctgt | ctgcctctgc | 660 |
| cagcagcgag | tcctaagcgc | agaatccaga | gctcgtagct | gtcctcagct | gtaactactg | 720 |
| tttcagaatg | ttgctgctgc | atacatttgt | catgtcagcc | agccagctcc | gtgggtgaaa | 780 |
| gtgtgcgtgt | gcgcgtgtct | gtgtgtgtgt | gcgtgtctgt | gtgtgtgcac | gtctgtgcgt | 840 |
| gcgcgtccgt | gcatgtgtgt | gtctgtgcgt | gtgtgcgtcc | gtgtgtgtgc | gtctgtgtgc | 900 |
| gcgtgtgtgt | cccccttctg | tatgtgtgca | cgccgcgtc | | | 939 |

<210> SEQ ID NO 209
<211> LENGTH: 20
<212> TYPE: DNA
<213> ORGANISM: Artificial Sequence
<220> FEATURE:
<223> OTHER INFORMATION: oligonucleotide BV9 S for PCR
<220> FEATURE:
<221> NAME/KEY: misc_feature
<223> OTHER INFORMATION: Synthetic

<400> SEQUENCE: 209
tgggaggttg cctgcgggtc                                          20

<210> SEQ ID NO 210
<211> LENGTH: 21

```
<212> TYPE: DNA
<213> ORGANISM: Artificial Sequence
<220> FEATURE:
<223> OTHER INFORMATION: oligonucleotide BV8 S for PCR
<220> FEATURE:
<221> NAME/KEY: misc_feature
<223> OTHER INFORMATION: Synthetic

<400> SEQUENCE: 210
gcattcctag ggccgcaggt g                                              21

<210> SEQ ID NO 211
<211> LENGTH: 22
<212> TYPE: DNA
<213> ORGANISM: Articial Sequence
<220> FEATURE:
<221> NAME/KEY: misc_feature
<223> OTHER INFORMATION: oligonucleotide BV7 S for PCR
<220> FEATURE:
<221> NAME/KEY: misc_feature
<223> OTHER INFORMATION: Synthetic

<400> SEQUENCE: 211
ggaggcctgt gtccttgtcc ag                                             22

<210> SEQ ID NO 212
<211> LENGTH: 21
<212> TYPE: DNA
<213> ORGANISM: Artificial Sequence
<220> FEATURE:
<223> OTHER INFORMATION: oligonucleotide BV6 S for PCR
<220> FEATURE:
<221> NAME/KEY: misc_feature
<223> OTHER INFORMATION: Synthetic

<400> SEQUENCE: 212
agggacagtg gaggaagggc c                                              21

<210> SEQ ID NO 213
<211> LENGTH: 21
<212> TYPE: DNA
<213> ORGANISM: Artificial Sequence
<220> FEATURE:
<223> OTHER INFORMATION: oligonucleotide BV5 S for PCR
<220> FEATURE:
<221> NAME/KEY: misc_feature
<223> OTHER INFORMATION: Synthetic

<400> SEQUENCE: 213 gaggggctg agctgtgcgt c                                               21

<210> SEQ ID NO 214
<211> LENGTH: 75
<212> TYPE: RNA
<213> ORGANISM: Artificial Sequence
<220> FEATURE:
<223> OTHER INFORMATION: Stem loop domain NO 100492041_1 / 19_10049183
<220> FEATURE:
<221> NAME/KEY: misc_feature
<223> OTHER INFORMATION: Synthetic
<220> FEATURE:
<221> NAME/KEY: misc_feature
<222> LOCATION: (42)..(42)
<223> OTHER INFORMATION: n is a, c, g, or u
<220> FEATURE:
<221> NAME/KEY: misc_feature
<222> LOCATION: (47)..(47)
<223> OTHER INFORMATION: n is a, c, g, or u
<220> FEATURE:
<221> NAME/KEY: misc_feature
<222> LOCATION: (59)..(59)
```

<223> OTHER INFORMATION: n is a, c, g, or u

<400> SEQUENCE: 214
ugucggguag cuuaucagac ugauguugac uguugaaucu cnauggncaa caccagucng    60
augggcuguc ugaca    75

<210> SEQ ID NO 215
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic
<220> FEATURE:
<221> NAME/KEY: MISC_FEATURE
<223> OTHER INFORMATION: Breast cancer suppressor Liv21

<400> SEQUENCE: 215

Gly Trp Trp Leu Thr Pro Val Ile Ser Ala Leu Trp Glu Ala Glu Val
1               5                   10                  15

Gly Gly Ser Phe Glu Asp Arg Ser Ser
            20                  25

<210> SEQ ID NO 216
<211> LENGTH: 86
<212> TYPE: PRT
<213> ORGANISM: Homo sapiens
<220> FEATURE:
<221> NAME/KEY: misc_feature
<223> OTHER INFORMATION: VMYB v-myb myeloblastosis viral oncogene
      homolog (avian) Homo sapiens
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 216

Gly Val Gln Trp Arg His Leu Gly Ser Leu Asn Pro Pro Pro Thr Gly
1               5                   10                  15

Phe Leu Xaa Phe Tyr Cys Arg Ser Leu Gln Ser Ser Trp Asp Tyr Arg
            20                  25                  30

His Ala Leu Pro His Pro Ala Asn Phe Leu Tyr Phe Leu Arg Trp Gly
        35                  40                  45

Phe Thr Met Met Ala Arg Met Xaa Val Ser Ile Ser Pro His Asp Leu
50                  55                  60

Pro Ala Ser Ala Ser Gln Ser Ala Gly Ile Thr Gly Met Ser His Cys
65                  70                  75                  80

Ala Arg Pro Thr Tyr Phe
            85

<210> SEQ ID NO 217
<211> LENGTH: 906
<212> TYPE: DNA
<213> ORGANISM: Homo sapiens
<220> FEATURE:
<221> NAME/KEY: misc_feature
<223> OTHER INFORMATION: A1S1 M13 Rev Clone from MCF7 cells
<220> FEATURE:
<221> NAME/KEY: misc_feature
<222> LOCATION: (2)..(2)

<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (828)..(832)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (881)..(881)
<223> OTHER INFORMATION: n is a, c, g, or t
<220> FEATURE:
<221> NAME/KEY: misc_feature
<222> LOCATION: (887)..(888)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (898)..(898)
<223> OTHER INFORMATION: n is a, c, g, or t
<220> FEATURE:
<221> NAME/KEY: misc_feature
<222> LOCATION: (900)..(901)
<223> OTHER INFORMATION: n is a, c, g, or t
<220> FEATURE:
<221> NAME/KEY: misc_feature
<222> LOCATION: (904)..(904)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t

<400> SEQUENCE: 217

```
tntangngan nataganact caagctatgc atccaacgcg ttgggagctc tcccatatgg      60
tcgacctgca ggcggccgcg aattcactag tgatttccta tgcttgacta ttagcctttc    120
tgtgagagca gttgctcaga gttgaggaca ctcggaacaa ccatcaactg tcaattagaa    180
atatggcaaa ttatttcagt ggttttccct ggctcttgct gagtttatta ccacaatgct    240
```

-continued

```
tagttgttgt ttacttaggg aatcaatgcc aagtttgaag tgactgaaga accagcctgt    300
ttgaacagtc catgtggaag agctacgtgt gagagtattt cagagaagct gagaaaacgc    360
taaatgagta cagcctaaac tggaatatgc taggcagtgt tacaactgtg gtggtaaaaa    420
tgcgcggaac agaaagggg tcaaacatcc aaaacctgtg taagggttac tcactgcatt    480
attactcatg agcatgtacc ttgtgggaaa cacatgaatc tattgtgctc atgaacgagt    540
aatgtcagtg atgaatttaa cacgctcctg tgaacctgac catcagcagg tcatgagttt    600
ctgtcagaaa caaaaagtga aaattctgac acagttcgat gtcttagcag cgctaaagtt    660
ttactgactt ttttctgagc acagggatgg aactgatttc ttttcctgaa caagaactac    720
ccttaaccac tattgttgaa cgctgaatgg nttcggaaat tagccttngg gcagacttga    780
tttgatttct gaatgaattc aacctaaaat tacaaggcaa acgnactnnn nnaaacttac    840
actctggnaa agtcatttcg acagctagca tantttttaa ncaaaannat gtcnaacngn    900 nttnan                                                                906
```

<210> SEQ ID NO 218
<211> LENGTH: 45
<212> TYPE: PRT
<213> ORGANISM: Homo sapiens
<220> FEATURE:
<221> NAME/KEY: misc_feature
<223> OTHER INFORMATION: VMYB DNA binding domain tandem repeats GC rich
      motifs

<400> SEQUENCE: 218

Arg Trp Thr Arg Glu Glu Asp Glu Lys Leu Lys Lys Leu Val Glu Gln
1               5                   10                  15

Asn Gly Thr Asp Asp Trp Lys Val Ile Ala Asn Tyr Leu Pro Asn Arg
            20                  25                  30

Thr Asp Val Gln Cys Gln His Arg Trp Gln Lys Val Leu
        35                  40                  45

<210> SEQ ID NO 219
<211> LENGTH: 211
<212> TYPE: PRT
<213> ORGANISM: Homo sapiens
<220> FEATURE:
<221> NAME/KEY: misc_feature
<223> OTHER INFORMATION: bcas4: sequence 1 starting following

<400> SEQUENCE: 219

Met Gln Arg Thr Gly Gly Gly Ala Pro Arg Pro Gly Arg Asn His Gly
1               5                   10                  15

Leu Pro Gly Ser Leu Arg Gln Pro Asp Pro Val Ala Leu Leu Met Leu
            20                  25                  30

Leu Val Asp Ala Asp Gln Pro Glu Pro Met Arg Ser Gly Ala Arg Glu
        35                  40                  45

Leu Ala Leu Phe Leu Thr Pro Glu Pro Gly Ala Glu Ala Lys Glu Val
    50                  55                  60

Glu Glu Thr Ile Glu Gly Met Leu Leu Arg Leu Glu Glu Phe Cys Ser
65                  70                  75                  80

Leu Ala Asp Leu Ile Arg Ser Asp Thr Ser Gln Ile Leu Glu Glu Asn
                85                  90                  95

Ile Pro Val Leu Lys Ala Lys Leu Thr Glu Met Arg Gly Ile Tyr Ala
            100                 105                 110

Lys Val Asp Arg Leu Glu Ala Phe Val Lys Met Val Gly His His Val

```
            115                 120                 125
Ala Phe Leu Glu Ala Asp Val Leu Gln Ala Glu Arg Asp His Gly Ala
    130                 135                 140

Phe Pro Gln Ala Leu Arg Arg Trp Leu Gly Ser Ala Gly Leu Pro Ser
145                 150                 155                 160

Phe Arg Asn Val Glu Cys Ser Gly Thr Ile Pro Ala Arg Cys Asn Leu
                165                 170                 175

Arg Leu Pro Gly Ser Ser Asp Ser Pro Ala Ser Ala Ser Gln Val Ala
            180                 185                 190

Gly Ile Thr Glu Val Thr Cys Thr Gly Ala Arg Asp Val Arg Ala Ala
            195                 200                 205

His Thr Val
    210

<210> SEQ ID NO 220
<211> LENGTH: 23
<212> TYPE: PRT
<213> ORGANISM: Homo sapiens

<400> SEQUENCE: 220

Thr Asp Thr Ala Leu Asp Val Ala Val Lys Thr Phe Pro Pro Glu Arg
1               5                   10                  15

His Val Ala Val Lys Cys Phe
            20

<210> SEQ ID NO 221
<211> LENGTH: 10
<212> TYPE: PRT
<213> ORGANISM: Homo sapiens

<400> SEQUENCE: 221

Glu Leu Gln Arg Glu Gly Ser Ile Glu Thr
1               5                   10

<210> SEQ ID NO 222
<211> LENGTH: 10
<212> TYPE: PRT
<213> ORGANISM: Homo sapiens

<400> SEQUENCE: 222

Pro Leu Ser Leu Phe Pro Thr Gly Phe Pro
1               5                   10

<210> SEQ ID NO 223
<211> LENGTH: 10
<212> TYPE: PRT
<213> ORGANISM: Homo sapiens

<400> SEQUENCE: 223

Asp Thr Ala Leu Asp Val Ala Val Lys Thr
1               5                   10

<210> SEQ ID NO 224
<211> LENGTH: 10
<212> TYPE: PRT
<213> ORGANISM: Homo sapiens

<400> SEQUENCE: 224

Ser Ala Arg Gly Lys His Arg Asp Ser Glu
1               5                   10
```

```
<210> SEQ ID NO 225
<211> LENGTH: 46
<212> TYPE: PRT
<213> ORGANISM: Homo sapiens
<220> FEATURE:
<221> NAME/KEY: misc_feature
<223> OTHER INFORMATION: sp|Q9H6U6|69-114   3 WD repeat

<400> SEQUENCE: 225

Asp Leu Asn Asp Thr Ser Arg Asn Leu Glu Phe His Glu Ile His Ser
1               5                   10                  15

Thr Gly Asn Glu Pro Pro Leu Leu Ile Met Ile Gly Tyr Ser Asp Gly
                20                  25                  30

Met Gln Val Trp Ser Ile Pro Ile Ser Gly Glu Ala Gln Glu
            35                  40                  45

<210> SEQ ID NO 226
<211> LENGTH: 41
<212> TYPE: PRT
<213> ORGANISM: Homo sapiens
<220> FEATURE:
<221> NAME/KEY: misc_feature
<223> OTHER INFORMATION: sp|Q9H6U6|349-389

<400> SEQUENCE: 226

Ala His Glu Lys Pro Val Cys Cys Met Ala Phe Asn Thr Ser Gly Met
1               5                   10                  15

Leu Leu Val Thr Thr Asp Thr Leu Gly His Asp Phe His Val Phe Gln
                20                  25                  30

Ile Leu Thr His Pro Trp Ser Ser Ser
            35                  40

<210> SEQ ID NO 227
<211> LENGTH: 45
<212> TYPE: PRT
<213> ORGANISM: Homo sapiens
<220> FEATURE:
<221> NAME/KEY: misc_feature
<223> OTHER INFORMATION: sp|Q9H6U6|403-447

<400> SEQUENCE: 227

Glu Thr Glu Ala Lys Val Gln Asp Ile Cys Phe Ser His Asp Cys Arg
1               5                   10                  15

Trp Val Val Val Ser Thr Leu Arg Gly Thr Ser His Val Phe Pro Ile
                20                  25                  30

Asn Pro Tyr Gly Gly Gln Pro Cys Val Arg Thr His Met
            35                  40                  45

<210> SEQ ID NO 228
<211> LENGTH: 20
<212> TYPE: PRT
<213> ORGANISM: Homo sapiens

<400> SEQUENCE: 228

Cys Phe Gly Lys Lys Gly Lys Lys Gln Cys Gln Gln Pro Ser
1               5                   10                  15

Val Arg Glu Gln
            20

<210> SEQ ID NO 229
<211> LENGTH: 24
<212> TYPE: PRT
<213> ORGANISM: Homo sapiens
<220> FEATURE:
```

```
<221> NAME/KEY: misc_feature
<223> OTHER INFORMATION: sp|Q9H6U6|403-447 sequence in isoform 5

<400> SEQUENCE: 229

Pro Asn Ser Asn Lys Ala Cys Val Arg Asp Gly Gly Arg Thr Ser Ala
1               5                   10                  15

Arg Gly Lys His Arg Asp Ser Glu
            20

<210> SEQ ID NO 230
<211> LENGTH: 87
<212> TYPE: PRT
<213> ORGANISM: Homo sapiens

<400> SEQUENCE: 230

Gln Val Gln Trp His Asp Phe Gly Ser Leu Gln Pro Leu Pro Pro Gly
1               5                   10                  15

Phe Lys Arg Phe Ser Cys Leu Ser Leu Pro Arg Ser Trp Asp Tyr Arg
            20                  25                  30

His Pro Pro Pro Arg Pro Ala Asn Phe Glu Phe Leu Val Glu Thr Gly
        35                  40                  45

Phe Leu His Val Gly Gln Ala Gly Leu Gln Leu Thr Ser Gly Asp
    50                  55                  60

Leu Pro Ala Ser Ala Ser Gln Ser Ala Arg Ile Thr Gly Val Ser His
65                  70                  75                  80

Arg Ala Arg Pro Gly Ile Phe
                85

<210> SEQ ID NO 231
<211> LENGTH: 28
<212> TYPE: PRT
<213> ORGANISM: Homo sapiens

<400> SEQUENCE: 231

Ala Asp Asn Asn Phe Thr Gln Glu Thr Ala Met Thr Met Ile Thr Pro
1               5                   10                  15

Ser Tyr Leu Gly Asp Thr Ile Glu Tyr Ser Ser Tyr
            20                  25

<210> SEQ ID NO 232
<211> LENGTH: 22
<212> TYPE: PRT
<213> ORGANISM: Homo sapiens

<400> SEQUENCE: 232

Ala Ser Asn Ala Leu Gly Ala Leu Pro Tyr Gly Arg Pro Ala Gly Gly
1               5                   10                  15

Arg Glu Phe Thr Ser Asp
            20

<210> SEQ ID NO 233
<211> LENGTH: 151
<212> TYPE: PRT
<213> ORGANISM: Homo sapiens
<220> FEATURE:
<221> NAME/KEY: misc_feature
<223> OTHER INFORMATION: sp|Q6AI08|HEAT6_HUMAN HEAT repeat-containing
      protein 6 OS=Homo sapiens GN=HEATR6 PE=1 SV=1 Sequence 2

<400> SEQUENCE: 233

Met Ala Ala Val Gln Val Val Gly Ser Trp Pro Ser Val Gln Pro Arg
1               5                   10                  15
```

```
Glu Ala Pro Arg Glu Ala Ile Pro Glu Arg Gly Asn Gly Phe Arg Leu
            20                  25                  30

Leu Ser Ala Arg Leu Cys Ala Leu Arg Pro Asp Asp Ser Ser Ser Ala
        35                  40                  45

Arg Thr Glu Ile Pro Gln Gln Ser Glu Ser Ser Ala Ser Arg Pro Thr
    50                  55                  60

Leu Asn Lys Lys Lys Ser Lys Val Lys Pro Lys Lys Ile Gln Gln
65                  70                  75                  80

Gly Glu Glu Glu Lys Glu Ser Ser Gly Glu Ile Glu Ala Ala Pro
                85                  90                  95

Val Thr Leu Ser Ala Ile Leu Glu Gly Ser Lys Gln Phe Leu Ser Val
            100                 105                 110

Ala Glu Asp Thr Ser Asp His Arg Arg Ala Phe Thr Pro Phe Ser Val
            115                 120                 125

Met Ile Ala Cys Ser Ile Arg Glu Leu His Arg Cys Leu Leu Leu Ala
130                 135                 140

Leu Val Ala Glu Ser Ser Ser
145                 150

<210> SEQ ID NO 234
<211> LENGTH: 5
<212> TYPE: PRT
<213> ORGANISM: Homo sapiens
<220> FEATURE:
<221> NAME/KEY: misc_feature
<223> OTHER INFORMATION: Natural variations Alternative sequence 1 162
      162 MEIPN

<400> SEQUENCE: 234

Met Glu Ile Pro Asn
1               5

<210> SEQ ID NO 235
<211> LENGTH: 5
<212> TYPE: PRT
<213> ORGANISM: Homo sapiens
<220> FEATURE:
<221> NAME/KEY: misc_feature
<223> OTHER INFORMATION: Natural variations Alternative sequence 1 162
      VHGEE

<400> SEQUENCE: 235

Val His Gly Glu Glu
1               5

<210> SEQ ID NO 236
<211> LENGTH: 23
<212> TYPE: PRT
<213> ORGANISM: Homo sapiens
<220> FEATURE:
<221> NAME/KEY: misc_feature
<223> OTHER INFORMATION: Natural variations in isoform 5 VSP_036384

<400> SEQUENCE: 236

Met Glu Glu Ala Ser Cys Pro Thr Cys Ser Val Asn Glu Ala Cys Glu
1               5                   10                  15

Trp Thr Pro Phe Ser Gln Lys
            20

<210> SEQ ID NO 237
<211> LENGTH: 7
<212> TYPE: PRT
```

```
<213> ORGANISM: Homo sapiens
<220> FEATURE:
<221> NAME/KEY: misc_feature
<223> OTHER INFORMATION: Alternative sequence 1 ? 70 70 Missing in
      isoform 4. VSP_036385 MEDYSKM in isoform 2 conflict   535 4
      DSTC / EAL in BAA25019. Ref.2

<400> SEQUENCE: 237

Met Glu Asp Tyr Ser Lys Met
1               5

<210> SEQ ID NO 238
<211> LENGTH: 5
<212> TYPE: PRT
<213> ORGANISM: Homo sapiens
<220> FEATURE:
<221> NAME/KEY: misc_feature
<223> OTHER INFORMATION: Sequence conflict 591 / 602 ASEHW

<400> SEQUENCE: 238

Ala Ser Glu His Trp
1               5

<210> SEQ ID NO 239
<211> LENGTH: 5
<212> TYPE: PRT
<213> ORGANISM: Homo sapiens
<220> FEATURE:
<221> NAME/KEY: misc_feature
<223> OTHER INFORMATION: Sequence conflict 591 / 602 12 KVVSC

<400> SEQUENCE: 239

Lys Val Val Ser Cys
1               5

<210> SEQ ID NO 240
<211> LENGTH: 12
<212> TYPE: PRT
<213> ORGANISM: Homo sapiens
<220> FEATURE:
<221> NAME/KEY: misc_feature
<223> OTHER INFORMATION: PQSTGTARWFPV in BAA25019

<400> SEQUENCE: 240

Pro Gln Ser Thr Gly Thr Ala Arg Trp Phe Pro Val
1               5                   10

<210> SEQ ID NO 241
<211> LENGTH: 53
<212> TYPE: PRT
<213> ORGANISM: Homo sapiens
<220> FEATURE:
<221> NAME/KEY: misc_feature
<223> OTHER INFORMATION: HELICASE: Probable ATP-dependent RNA helicase
      DHX40 779 aas

<400> SEQUENCE: 241

Gln Gln Arg Arg Ile Phe Leu Pro Pro Pro Gly Ile Arg Lys Cys
1               5                   10                  15

Val Ile Ser Thr Asn Ile Ser Ala Thr Ser Leu Thr Ile Asp Gly Ile
            20                  25                  30

Arg Tyr Val Val Asp Gly Gly Phe Val Lys Gln Leu Asn His Asn Pro
        35                  40                  45

Arg Leu Gly Leu Glu
    50
```

```
<210> SEQ ID NO 242
<211> LENGTH: 7
<212> TYPE: PRT
<213> ORGANISM: Homo sapiens
<220> FEATURE:
<221> NAME/KEY: misc_feature
<223> OTHER INFORMATION: Isoform 3 (identifier: Q8IX18-3) 716-722:
      REDARRR The sequence of this isoform differs from the canonical
      sequence as follows:

<400> SEQUENCE: 242

Arg Glu Asp Ala Arg Arg Arg
1               5

<210> SEQ ID NO 243
<211> LENGTH: 7
<212> TYPE: PRT
<213> ORGANISM: Homo sapiens
<220> FEATURE:
<221> NAME/KEY: misc_feature
<223> OTHER INFORMATION: Isoform 3 (identifier: Q8IX18-3) The sequence
      of this isoform differs from the canonical sequence as follows:

<400> SEQUENCE: 243

Met Lys Ile Tyr Tyr Phe Gln
1               5

<210> SEQ ID NO 244
<211> LENGTH: 25
<212> TYPE: PRT
<213> ORGANISM: Homo sapiens
<220> FEATURE:
<221> NAME/KEY: misc_feature
<223> OTHER INFORMATION: globular part of protein
<220> FEATURE:
<221> NAME/KEY: misc_feature
<222> LOCATION: (2)..(2)
<223> OTHER INFORMATION: Xaa is any naturally occurring amino acid
<220> FEATURE:
<221> NAME/KEY: misc_feature
<222> LOCATION: (9)..(10)
<223> OTHER INFORMATION: Xaa is any naturally occurring amino acid
<220> FEATURE:
<221> NAME/KEY: misc_feature
<222> LOCATION: (15)..(16)
<223> OTHER INFORMATION: Xaa is any naturally occurring amino acid
<220> FEATURE:
<221> NAME/KEY: misc_feature
<222> LOCATION: (20)..(20)
<223> OTHER INFORMATION: Xaa is any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 244

Gly Xaa Trp Leu Thr Pro Val Ile Xaa Xaa Leu Trp Glu Ala Xaa Xaa
1               5                   10                  15

Gly Gly Ser Xaa Glu Xaa Arg Ser Ser
            20                  25

<210> SEQ ID NO 245
<211> LENGTH: 12
<212> TYPE: PRT
<213> ORGANISM: Homo sapiens
<220> FEATURE:
<221> NAME/KEY: misc_feature
<223> OTHER INFORMATION: second important domain

<400> SEQUENCE: 245

Leu Arg Gly Arg Gly Trp Trp Leu Trp Pro Val Ile
```

<210> SEQ ID NO 246
<211> LENGTH: 19
<212> TYPE: PRT
<213> ORGANISM: Homo sapiens
<220> FEATURE:
<221> NAME/KEY: misc_feature
<223> OTHER INFORMATION: domain variant
<220> FEATURE:
<221> NAME/KEY: misc_feature
<222> LOCATION: (2)..(2)
<223> OTHER INFORMATION: Xaa is any naturally occurring amino acid
<220> FEATURE:
<221> NAME/KEY: misc_feature
<222> LOCATION: (13)..(13)
<223> OTHER INFORMATION: Xaa is any naturally occurring amino acid

<400> SEQUENCE: 246

Leu Xaa Gly Arg Ala Arg Trp Leu Trp Pro Val Ile Xaa Ala Leu Thr
1               5                   10                  15

Glu Ala Glu

<210> SEQ ID NO 247
<211> LENGTH: 904
<212> TYPE: DNA
<213> ORGANISM: Homo Sapiens
<220> FEATURE:
<221> NAME/KEY: misc_feature
<223> OTHER INFORMATION: A1S6 clone extracted from MCF7 cells
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (828)..(832)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:

<220> FEATURE:
<221> NAME/KEY: misc_feature
<222> LOCATION: (881)..(881)
<223> OTHER INFORMATION: n is a, c, g, or t
<220> FEATURE:
<221> NAME/KEY: misc_feature
<222> LOCATION: (887)..(888)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (898)..(898)
<223> OTHER INFORMATION: n is a, c, g, or t
<220> FEATURE:
<221> NAME/KEY: misc_feature
<222> LOCATION: (900)..(901)
<223> OTHER INFORMATION: n is a, c, g, or t

<400> SEQUENCE: 247

```
tntangngan nataganact caagctatgc atccaacgcg ttgggagctc tcccatatgg    60
tcgacctgca ggcggccgcg aattcactag tgatttccta tgcttgacta ttagcctttc   120
agtgagagca gttgctcaga gttgaggaca ctcggaacaa ccatcaactg tcaattaaga   180
aacatggcaa attatttcag tggttttccc tggctcttgc tgagtttatt accacaatgc   240
tcagttgttg tttacttagg gaatcaatgc caagtttgaa gtgactgaag aaccagcctg   300
tatgaacagt ccatgtggaa gagctacgtg tgagagtatt tcagagaag ctgagaaaac   360
gctaaatgag tacagcctaa actggaatat gctaggcagt gttacaactg atggtggtaa   420
aaatgcgcgg aacagaaagg gggtcaaaca tgcaaaacct gtgtaagggt tactcactgc   480
attactcatg agcatgtacc ttgtgggaaa cacatgaatc tattgtgctc atgaacgagt   540
aatgtcagtg atgaattta cacgctcctg tgaacctgac catcagcagg tcatgagttt   600
ctgtcagaaa caaaaagtga aaattctgac acagttcgat gtcttagcag cgctaaagtt   660
ttactgactt ttttctgagc acagggatgg aactgatttc ttttcctgaa caagaactac   720
ccttaaccac tattgttgaa cgctgaatgg nttcggaaat tagccttngg gcagacttga   780
tttgatttct gaatgaattc aacctaaaat tacaaggcaa acgnactnnn nnaaacttac   840
actctggnaa agtcatttcg acagctagca tanttttaa ncaaaannat gtcnaacngn   900
nttt                                                                904
```

<210> SEQ ID NO 248
<211> LENGTH: 20
<212> TYPE: RNA
<213> ORGANISM: Artificial Sequence
<220> FEATURE:
<223> OTHER INFORMATION: oligonucleotide siRNA sequence of seq NO 150
<220> FEATURE:
<221> NAME/KEY: misc_feature
<223> OTHER INFORMATION: Synthetic

<400> SEQUENCE: 248

```
gagcuaauag ucaagcauau                                                20
```

<210> SEQ ID NO 249
<211> LENGTH: 46
<212> TYPE: PRT
<213> ORGANISM: Homo sapiens

<400> SEQUENCE: 249

Met Lys Phe Phe Val Phe Ala Leu Ile Leu Ala Leu Met Leu Ser Met
1               5                   10                  15

```
Thr Gly Ala Asp Ser His Ala Lys Arg His His Gly Tyr Lys Arg Lys
            20                  25                  30

Phe His Glu Lys His His Ser His Gln Gly Tyr Arg Ser Asn
            35                  40                  45
```

<210> SEQ ID NO 250
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 250
gagcuaauag ucaagcauau                                              20

<210> SEQ ID NO 251
<211> LENGTH: 20
<212> TYPE: RNA
<213> ORGANISM: Artificial Sequence
<220> FEATURE:
<223> OTHER INFORMATION: siRNA reverse complement of sequence 250 of seq
      NO 150
<220> FEATURE:
<221> NAME/KEY: misc_feature
<223> OTHER INFORMATION: Synthetic

<400> SEQUENCE: 251
auaugcuuga cuauuagcuc                                              20

<210> SEQ ID NO 252
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 252
ggaagaaucu caucucagau                                              20

<210> SEQ ID NO 253
<211> LENGTH: 20
<212> TYPE: RNA
<213> ORGANISM: Artificial Sequence
<220> FEATURE:
<223> OTHER INFORMATION: siRNA reverse complement of sequence 252 of seq
      NO 150
<220> FEATURE:
<221> NAME/KEY: misc_feature
<223> OTHER INFORMATION: Synthetic

<400> SEQUENCE: 253
aucugagaug agauucuucc                                              20

<210> SEQ ID NO 254
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

```
<400> SEQUENCE: 254
gagagucauc uuacucagau                                              20

<210> SEQ ID NO 255
<211> LENGTH: 20
<212> TYPE: RNA
<213> ORGANISM: Artificial Sequence
<220> FEATURE:
<223> OTHER INFORMATION: siRNA reverse complement of sequence 254 of seq
      NO 150

<400> SEQUENCE: 255
aucugaguaa gaugacucuc                                              20

<210> SEQ ID NO 256
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 256
gcugggugug guagugcauu                                              20

<210> SEQ ID NO 257
<211> LENGTH: 20
<212> TYPE: RNA
<213> ORGANISM: Artificial Sequence
<220> FEATURE:
<223> OTHER INFORMATION: siRNA reverse complement of sequence 256 of seq
      NO 150
<220> FEATURE:
<221> NAME/KEY: misc_feature
<223> OTHER INFORMATION: Synthetic

<400> SEQUENCE: 257
aaugcacuac cacacccagc                                              20

<210> SEQ ID NO 258
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 258
gucaagagau cgagaccauu                                              20

<210> SEQ ID NO 259
<211> LENGTH: 20
<212> TYPE: RNA
<213> ORGANISM: Artificial Sequence
<220> FEATURE:
<223> OTHER INFORMATION: siRNA reverse complement of sequence 258 of seq
      NO 150
<220> FEATURE:
<221> NAME/KEY: misc_feature
<223> OTHER INFORMATION: Synthetic

<400> SEQUENCE: 259
aauggucucg aucucuugac                                              20
```

```
<210> SEQ ID NO 260
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 260
gucaucuuac ucagagcauu                                              20

<210> SEQ ID NO 261
<211> LENGTH: 20
<212> TYPE: RNA
<213> ORGANISM: Artificial Sequence
<220> FEATURE:
<223> OTHER INFORMATION: siRNA reverse complement of sequence 260 of seq
      NO 150
<220> FEATURE:
<221> NAME/KEY: misc_feature
<223> OTHER INFORMATION: Synthetic

<400> SEQUENCE: 261
aaugcucuga guaagauguc                                              20

<210> SEQ ID NO 262
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 262
ggaguauagg aaucuccuau                                              20

<210> SEQ ID NO 263
<211> LENGTH: 20
<212> TYPE: RNA
<213> ORGANISM: Artificial Sequence
<220> FEATURE:
<223> OTHER INFORMATION: siRNA reverse complement of sequence 262 of seq
      NO 150
<220> FEATURE:
<221> NAME/KEY: misc_feature
<223> OTHER INFORMATION: Synthetic

<400> SEQUENCE: 263
auaggagauu ccuauacucc                                              20

<210> SEQ ID NO 264
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 264
gccuggcgac agugugagau                                              20
```

```
<210> SEQ ID NO 265
<211> LENGTH: 22
<212> TYPE: RNA
<213> ORGANISM: Artificial Sequence
<220> FEATURE:
<223> OTHER INFORMATION: siRNA reverse complement of sequence 264 of seq
      NO 150
<220> FEATURE:
<221> NAME/KEY: misc_feature
<223> OTHER INFORMATION: Synthetic

<400> SEQUENCE: 265
aucucacaca cugucgccag gc                                              22

<210> SEQ ID NO 266
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 266
gccuguaguc ccagcuacuu                                                 20

<210> SEQ ID NO 267
<211> LENGTH: 20
<212> TYPE: RNA
<213> ORGANISM: Artificial Sequence
<220> FEATURE:
<223> OTHER INFORMATION: siRNA reverse complement of sequence 266 of seq
      NO 150
<220> FEATURE:
<221> NAME/KEY: misc_feature
<223> OTHER INFORMATION: Synthetic

<400> SEQUENCE: 267
aaguagcugg gacuacaggc                                                 20

<210> SEQ ID NO 268
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 268
ggaaucuccu acauugccuu                                                 20

<210> SEQ ID NO 269
<211> LENGTH: 20
<212> TYPE: RNA
<213> ORGANISM: Artificial Sequence
<220> FEATURE:
<223> OTHER INFORMATION: siRNA reverse complement of sequence 268 of seq
      NO 150
<220> FEATURE:
<221> NAME/KEY: misc_feature
<223> OTHER INFORMATION: Synthetic

<400> SEQUENCE: 269
aaggcaaugu aggagauucc                                                 20

<210> SEQ ID NO 270
```

-continued

```
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 270
gacucucagc uuuagguguu                                                   20

<210> SEQ ID NO 271
<211> LENGTH: 20
<212> TYPE: RNA
<213> ORGANISM: Artificial Sequence
<220> FEATURE:
<223> OTHER INFORMATION: siRNA reverse complement of sequence 270 of seq
      NO 150
<220> FEATURE:
<221> NAME/KEY: misc_feature
<223> OTHER INFORMATION: Synthetic

<400> SEQUENCE: 271
aacaccuaaa gcugagaguc                                                   20

<210> SEQ ID NO 272
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 272
gcucaugccc guaaucccau                                                   20

<210> SEQ ID NO 273
<211> LENGTH: 20
<212> TYPE: RNA
<213> ORGANISM: Artificial Sequence
<220> FEATURE:
<223> OTHER INFORMATION: siRNA reverse complement of sequence 272 of seq
      NO 150
<220> FEATURE:
<221> NAME/KEY: misc_feature
<223> OTHER INFORMATION: Synthetic

<400> SEQUENCE: 273
augggauuac gggcaugagc                                                   20

<210> SEQ ID NO 274
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 274
ggaauugaau uaauggaguu                                                   20

<210> SEQ ID NO 275
<211> LENGTH: 20
<212> TYPE: RNA
```

```
<213> ORGANISM: Artificial Sequence
<220> FEATURE:
<223> OTHER INFORMATION: siRNA reverse complement of sequence 274 of seq
      NO 150
<220> FEATURE:
<221> NAME/KEY: misc_feature
<223> OTHER INFORMATION: Synthetic

<400> SEQUENCE: 275
aacuccauua auucaauucc                                                    20

<210> SEQ ID NO 276
<211> LENGTH: 20
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 276
ggcaggcaga ucaugagguu                                                    20

<210> SEQ ID NO 277
<211> LENGTH: 20
<212> TYPE: RNA
<213> ORGANISM: Artificial Sequence
<220> FEATURE:
<223> OTHER INFORMATION: siRNA reverse complement of sequence 276 of seq
      NO 150
<220> FEATURE:
<221> NAME/KEY: misc_feature
<223> OTHER INFORMATION: Synthetic

<400> SEQUENCE: 277
aaccacauga ucugccugcc                                                    20

<210> SEQ ID NO 278
<211> LENGTH: 20
<212> TYPE: RNA
<213> ORGANISM: Artificial Sequence
<220> FEATURE:
<223> OTHER INFORMATION: siRNA sequence of seq NO 150 (ex118)
<220> FEATURE:
<221> NAME/KEY: misc_feature
<223> OTHER INFORMATION: Synthetic

<400> SEQUENCE: 278
gaaucuccua cauugccuau                                                    20

<210> SEQ ID NO 279
<211> LENGTH: 20
<212> TYPE: RNA
<213> ORGANISM: Artificial Sequence
<220> FEATURE:
<223> OTHER INFORMATION: siRNA reverse complement of sequence 278 of seq
       NO 150
<220> FEATURE:
<221> NAME/KEY: misc_feature
<223> OTHER INFORMATION: Synthetic

<400> SEQUENCE: 279
auaggcaaug uaggagauuc                                                    20

<210> SEQ ID NO 280
<211> LENGTH: 49
<212> TYPE: RNA
<213> ORGANISM: Artificial Sequence
```

-continued

```
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 280
gagauggcgc cacuguacuu ucaauucucu accgcgguga caugaagag        49

<210> SEQ ID NO 281
<211> LENGTH: 23
<212> TYPE: RNA
<213> ORGANISM: Artificial Sequence
<220> FEATURE:
<223> OTHER INFORMATION: MicroRNA mIR-21 MIMAT 0001787
<220> FEATURE:
<221> NAME/KEY: misc_feature
<223> OTHER INFORMATION: Synthetic

<400> SEQUENCE: 281
uagcuuauca gacugguguu ggc                                    23

<210> SEQ ID NO 282
<211> LENGTH: 73
<212> TYPE: RNA
<213> ORGANISM: Artificial Sequence
<220> FEATURE:
<223> OTHER INFORMATION: MicroRNA mIR-21 MIMAT 0003325
<220> FEATURE:
<221> NAME/KEY: misc_feature
<223> OTHER INFORMATION: Synthetic

<400> SEQUENCE: 282
ugucaaauag cuuaucagac ugguguuggc uguuaagauu gcaaggcgac aacagucugu   60
aggcugucug aca                                               73

<210> SEQ ID NO 283
<211> LENGTH: 119
<212> TYPE: RNA
<213> ORGANISM: Artificial Sequence
<220> FEATURE:
<223> OTHER INFORMATION: MicroRNA mIR-21 MIMAT 0004994
<220> FEATURE:
<221> NAME/KEY: misc_feature
<223> OTHER INFORMATION: Synthetic

<400> SEQUENCE: 283
cugacauuuu gguaucucuc auguaccauc cugucggaua gcuuaucaga cugauuuga    60 cguuggauc ucauggcaac aacagucggu aggcugucug acauuuuugg uaucucuca   119

<210> SEQ ID NO 284
<211> LENGTH: 22
<212> TYPE: RNA
<213> ORGANISM: Artificial Sequence
<220> FEATURE:
<223> OTHER INFORMATION: MicroRNA mIR-21 MIMAT 0003774
<220> FEATURE:
<221> NAME/KEY: misc_feature
<223> OTHER INFORMATION: Synthetic

<400> SEQUENCE: 284
uagcuuauca gacugauguu ga                                     22

<210> SEQ ID NO 285
<211> LENGTH: 74
<212> TYPE: RNA
<213> ORGANISM: Artificial Sequence
```

```
<220> FEATURE:
<223> OTHER INFORMATION: MicroRNA mIR-21 MIMAT 0005275
<220> FEATURE:
<221> NAME/KEY: misc_feature
<223> OTHER INFORMATION: Synthetic

<400> SEQUENCE: 285
ugucgggusg cuuaucagac ugauguugac uguuggaucu cauggcaaca gcagucgaug      60
agcugucuga cauu                                                       74

<210> SEQ ID NO 286
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic
<220> FEATURE:
<221> NAME/KEY: misc_feature
<223> OTHER INFORMATION: MicroRNA mIR-21 MIMAT 0002320

<400> SEQUENCE: 286
uagcuuauca gacugauguu ga                                              22

<210> SEQ ID NO 287
<211> LENGTH: 92
<212> TYPE: RNA
<213> ORGANISM: Artificial Sequence
<220> FEATURE:
<223> OTHER INFORMATION: MicroRNA mIR-21 MIMAT 0000569
<220> FEATURE:
<221> NAME/KEY: misc_feature
<223> OTHER INFORMATION: Synthetic

<400> SEQUENCE: 287
uguaccaccu ugucggauag cuuaucagac ugauguugac uguugaaucu cauggcaaca      60
gcagucgaug ggcugucuga cauuuuggua uc                                   92

<210> SEQ ID NO 288
<211> LENGTH: 22
<212> TYPE: RNA
<213> ORGANISM: Artificial Sequence
<220> FEATURE:
<223> OTHER INFORMATION: MicroRNA mIR-21 MIMAT 0004628
<220> FEATURE:
<221> NAME/KEY: misc_feature
<223> OTHER INFORMATION: Synthetic

<400> SEQUENCE: 288
caacagcagu cgaugggcug uc                                              22

<210> SEQ ID NO 289
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 289
gagcuaauag ucaagcauau ucaauucucg auuaucaguu cguauagag                 49

<210> SEQ ID NO 290
```

```
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 290
ggaagaaucu caucucagau ucaauuccuu cuuagaguag agucuagag                    49

<210> SEQ ID NO 291
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 291
gagagucauc uuacucagau ucaauucucu caguagaaug agucuagag                    49

<210> SEQ ID NO 292
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 292
gcugggugug guagugcauu ucaauucgac ccacaccauc acguaagag                    49

<210> SEQ ID NO 293
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 293
gucaagagau cgagaccauu ucaauucagu ucucuagcuc ugguaagag                    49

<210> SEQ ID NO 294
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 294
gucaucuuac ucagagcauu ucaauucagu agaaugaguc ucguaagag                    49

<210> SEQ ID NO 295
<211> LENGTH: 49
<212> TYPE: RNA
<213> ORGANISM: Artificial Sequence
<220> FEATURE:
```

<223> OTHER INFORMATION: siRNA sequence of seq NO 150
<220> FEATURE:
<221> NAME/KEY: misc_feature
<223> OTHER INFORMATION: Synthetic

<400> SEQUENCE: 295
ggaguauagg aaucuccuau ucaauuccuc auauccuuag aggauagag                49

<210> SEQ ID NO 296
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 296
gccuggcgac agugugagau ucaauucgga ccgcugucac acucuagag                49

<210> SEQ ID NO 297
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 297
gccuguaguc ccagcuacuu ucaauucgga caucaggguc gaugaagag                49

<210> SEQ ID NO 298
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 298
ggaaucuccu acauugccuu ucaauuccuu agaggaugua acggaagag                49

<210> SEQ ID NO 299
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 299
gacucucagc uuuaggguguu ucaauucuga gagucgaaau ccacaagag                49

<210> SEQ ID NO 300
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 300
gcucaugccc guaaucccau ucaauucgag uacgggcauu agggguagag         49

<210> SEQ ID NO 301
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 301
ggaauugaau uaauggaguu ucaauuccuu aacuuaauua ccucaagag          49

<210> SEQ ID NO 302
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 302
ggcaggcaga ucaugagguu ucaauuccgu ccgucuagua cuccaagag          49

<210> SEQ ID NO 303
<211> LENGTH: 49
<212> TYPE: RNA
<213> ORGANISM: Artificial Sequence
<220> FEATURE:
<223> OTHER INFORMATION: siRNA sequence of seq NO 150
<220> FEATURE:
<221> NAME/KEY: misc_feature
<223> OTHER INFORMATION: Synthetic

<400> SEQUENCE: 303
gaaucuccua cauugccuau ucaauucuua gaggauguaa cggauagag          49

<210> SEQ ID NO 304
<211> LENGTH: 23
<212> TYPE: PRT
<213> ORGANISM: Homo sapiens

<400> SEQUENCE: 304

Leu Ser Asn Pro Asn Ile Ser Tyr Ser Phe Val Cys Ile Tyr Cys Gly
1               5                   10                  15

Leu Gly Leu His Met Phe Ser
            20

<210> SEQ ID NO 305
<211> LENGTH: 121
<212> TYPE: PRT
<213> ORGANISM: Homo sapiens
<220> FEATURE:
<221> NAME/KEY: MISC_FEATURE
<223> OTHER INFORMATION: Domain 612 / 732 SET Motif of Histone-lysine
      N-methyltransferase EZH1

<400> SEQUENCE: 305

Lys Lys His Leu Leu Leu Ala Pro Ser Asp Val Ala Gly Trp Gly Thr
1               5                   10                  15

```
Phe Ile Lys Glu Ser Val Gln Lys Asn Glu Phe Ile Ser Glu Tyr Cys
                20                  25                  30
Gly Glu Leu Ile Ser Gln Asp Glu Ala Asp Arg Arg Gly Lys Val Tyr
            35                  40                  45
Asp Lys Tyr Met Ser Ser Phe Leu Phe Asn Leu Asn Asn Asp Phe Val
 50                  55                  60
Val Asp Ala Thr Arg Lys Gly Asn Lys Ile Arg Phe Ala Asn His Ser
 65                  70                  75                  80
Val Asn Pro Asn Cys Tyr Ala Lys Val Val Met Val Asn Gly Asp His
                85                  90                  95
Arg Ile Gly Ile Phe Ala Lys Arg Ala Ile Gln Ala Gly Glu Glu Leu
                100                 105                 110
Phe Phe Asp Tyr Arg Tyr Ser Gln Ala
            115                 120

<210> SEQ ID NO 306
<211> LENGTH: 19
<212> TYPE: RNA
<213> ORGANISM: Artificial Sequence
<220> FEATURE:
<223> OTHER INFORMATION: oligonucleotidic probe
<220> FEATURE:
<221> NAME/KEY: misc_feature
<223> OTHER INFORMATION: Synthetic

<400> SEQUENCE: 306
uugguaacga ccaugccac                                              19

<210> SEQ ID NO 307
<211> LENGTH: 19
<212> TYPE: RNA
<213> ORGANISM: Artificial Sequence
<220> FEATURE:
<223> OTHER INFORMATION: oligonucleotide probe
<220> FEATURE:
<221> NAME/KEY: misc_feature
<223> OTHER INFORMATION: Synthetic

<400> SEQUENCE: 307
uucacuuaga auaaugucc                                              19

<210> SEQ ID NO 308
<211> LENGTH: 19
<212> TYPE: RNA
<213> ORGANISM: Artificial Sequence
<220> FEATURE:
<223> OTHER INFORMATION: oligonucleotide probe
<220> FEATURE:
<221> NAME/KEY: misc_feature
<223> OTHER INFORMATION: Synthetic

<400> SEQUENCE: 308
ucuuugugaa uuugacaac                                              19

<210> SEQ ID NO 309
<211> LENGTH: 19
<212> TYPE: RNA
<213> ORGANISM: Artificial Sequence
<220> FEATURE:
<223> OTHER INFORMATION: oligonucleotide probe
<220> FEATURE:
<221> NAME/KEY: misc_feature
<223> OTHER INFORMATION: Synthetic

<400> SEQUENCE: 309
```
ucaaggucca ggcuacaac                                         19

<210> SEQ ID NO 310
<211> LENGTH: 19
<212> TYPE: RNA
<213> ORGANISM: Artificial Sequence
<220> FEATURE:
<223> OTHER INFORMATION: siRNA sequence of SEQ ID NO 150
<220> FEATURE:
<221> NAME/KEY: misc_feature
<223> OTHER INFORMATION: Synthetic

<400> SEQUENCE: 310
guggcauggu cguuaccaa                                         19

<210> SEQ ID NO 311
<211> LENGTH: 19
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 311
caccguacca gcaaugguu                                         19

<210> SEQ ID NO 312
<211> LENGTH: 19
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 312
ggacauuauu cuaagugaa                                         19

<210> SEQ ID NO 313
<211> LENGTH: 19
<212> TYPE: RNA
<213> ORGANISM: Artificial Sequence
<220> FEATURE:
<223> OTHER INFORMATION: siRNA 1 sequence of SEQ ID NO 150
<220> FEATURE:
<221> NAME/KEY: misc_feature
<223> OTHER INFORMATION: Synthetic

<400> SEQUENCE: 313
ccuguaauaa gauucacuu                                         19

<210> SEQ ID NO 314
<211> LENGTH: 46
<212> TYPE: PRT
<213> ORGANISM: Artificial Sequence
<220> FEATURE:
<223> OTHER INFORMATION: Subsection of Liv21K of SEQ ID NO 180
<220> FEATURE:
<221> NAME/KEY: misc_feature
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(10)

```
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 314

Ser Val Xaa Gln Ala Gly Val Gln Trp Xaa Asn Leu Gly Ser Leu Gln
1               5                   10                  15

Xaa Leu Pro Pro Gly Xaa Xaa Xaa Phe Ser Cys Leu Ser Leu Xaa Ser
            20                  25                  30

Ser Trp Asp Tyr Xaa Xaa Leu Pro Pro Xaa Pro Ala Xaa Phe
        35                  40                  45

<210> SEQ ID NO 315
<211> LENGTH: 43
<212> TYPE: PRT
<213> ORGANISM: Artificial Sequence
<220> FEATURE:
<223> OTHER INFORMATION: Subsection of Liv21K SEQ ID NO: 180
<220> FEATURE:
<221> NAME/KEY: misc_feature
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid

<400> SEQUENCE: 315

Ser Val Xaa Gln Ala Gly Val Gln Trp Xaa Asn Leu Gly Ser Leu Gln
```

```
1               5                  10                 15
Xaa Leu Pro Pro Gly Phe Xaa Xaa Phe Ser Cys Xaa Ser Leu Ser Ser
            20                 25                 30

Trp Asp Tyr Arg Arg Xaa Pro Pro Arg Xaa Ala
            35                 40

<210> SEQ ID NO 316
<211> LENGTH: 21
<212> TYPE: PRT
<213> ORGANISM: Artificial Sequence
<220> FEATURE:
<223> OTHER INFORMATION: Preserved Region between SEQ ID NO: 314 and 315
      of Liv21K
<220> FEATURE:
<221> NAME/KEY: misc_feature
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 316

Ile Ser Pro Xaa Asp Xaa Pro Ala Ser Ala Ser Gln Ser Xaa Gly Ile
1               5                  10                 15

Xaa Xaa Xaa Ser Xaa
            20

<210> SEQ ID NO 317
<211> LENGTH: 38
<212> TYPE: PRT
<213> ORGANISM: Artificial Sequence
<220> FEATURE:
<223> OTHER INFORMATION: Sequence of Liv21I Complex
<220> FEATURE:
<221> NAME/KEY: misc_feature
<223> OTHER INFORMATION: Synthetic

<400> SEQUENCE: 317

Phe Leu Tyr Phe Pro Arg Gln Gly Phe Thr Val Leu Ala Arg Met Val
1               5                  10                 15

Ser Ile Ser Pro Arg Asp Pro Pro Ala Ser Ala Ser Gln Ser Val Gly
            20                 25                 30

Ile Ala Tyr Ile Ser Asn
            35

<210> SEQ ID NO 318
<211> LENGTH: 11
<212> TYPE: PRT
<213> ORGANISM: Artificial Sequence
<220> FEATURE:
<223> OTHER INFORMATION: Variation of end region of Liv21I of SEQ ID 317
<220> FEATURE:
<221> NAME/KEY: misc_feature
```

```
<223> OTHER INFORMATION: Synthetic

<400> SEQUENCE: 318

Pro Ala Ser Ala Ser Gln Ser Ala Gly Ile Thr
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Variation of end region of Liv 21I of SEQ ID
      317
<220> FEATURE:
<221> NAME/KEY: misc_feature
<223> OTHER INFORMATION: Synthetic

<400> SEQUENCE: 319

Asp Pro Pro Thr Ser Ala Ser Gln Ser Val Gly Ile
1               5                   10

<210> SEQ ID NO 320
<211> LENGTH: 25
<212> TYPE: PRT
<213> ORGANISM: Artificial Sequence
<220> FEATURE:
<223> OTHER INFORMATION: Variation for Liv21F or Liv21K
<220> FEATURE:
<221> NAME/KEY: misc_feature
<223> OTHER INFORMATION: Synthetic

<400> SEQUENCE: 320

Phe Ser Cys Leu Ser Leu Leu Ser Ser Trp Asp Tyr Arg Arg Leu Pro
1               5                   10                  15

Pro Arg Pro Ala Thr Phe Leu Tyr Phe
            20                  25

<210> SEQ ID NO 321
<211> LENGTH: 25
<212> TYPE: PRT
<213> ORGANISM: Artificial Sequence
<220> FEATURE:
<223> OTHER INFORMATION: Variation of Liv21F and Liv21K
<220> FEATURE:
<221> NAME/KEY: misc_feature
<223> OTHER INFORMATION: Synthetic

<400> SEQUENCE: 321

Phe Ser Cys Leu Ser Leu Pro Ser Ser Trp Asp Tyr Arg Arg Pro Pro
1               5                   10                  15

Pro Arg Pro Ala Asn Phe Leu Tyr Phe
            20                  25

<210> SEQ ID NO 322
<211> LENGTH: 24
<212> TYPE: PRT
<213> ORGANISM: Artificial Sequence
<220> FEATURE:
<223> OTHER INFORMATION: Homologous region between Liv21e and Liv21K
<220> FEATURE:
<221> NAME/KEY: misc_feature
<223> OTHER INFORMATION: Synthetic

<400> SEQUENCE: 322

Lys Phe Phe Val Phe Ala Leu Ile Leu Ala Leu Met Leu Ser Met Cys
1               5                   10                  15

Gly Ala Asp Ser His Ala Lys Arg
```

```
<210> SEQ ID NO 323
<211> LENGTH: 9
<212> TYPE: PRT
<213> ORGANISM: Homo Sapiens

<400> SEQUENCE: 323

Phe Ala Val Ala Phe Pro Val Gly Arg
1               5

<210> SEQ ID NO 324
<211> LENGTH: 19
<212> TYPE: DNA
<213> ORGANISM: Homo sapiens
<220> FEATURE:
<221> NAME/KEY: misc_feature
<223> OTHER INFORMATION: Olilgonucleotide Primer

<400> SEQUENCE: 324
gtggtaaagc acccaggaa                                                    19

<210> SEQ ID NO 325
<211> LENGTH: 20
<212> TYPE: DNA
<213> ORGANISM: Homo sapiens
<220> FEATURE:
<221> NAME/KEY: misc_feature
<223> OTHER INFORMATION: Oligonucleotide Primer

<400> SEQUENCE: 325
gctagctgga tgtcttttgc                                                   20

<210> SEQ ID NO 326
<211> LENGTH: 19
<212> TYPE: DNA
<213> ORGANISM: Homo sapiens
<220> FEATURE:
<221> NAME/KEY: misc_feature
<223> OTHER INFORMATION: Oligonucleotide Primer

<400> SEQUENCE: 326
tgaaggtcgg agtcaacgg                                                    19

<210> SEQ ID NO 327
<211> LENGTH: 18
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 327
catgtgggcc atgaggtc                                                     18

<210> SEQ ID NO 328
<211> LENGTH: 20
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 328
ggacttcgag caagagatgg                                                   20
```

```
<210> SEQ ID NO 329
<211> LENGTH: 20
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 329
agcactgtgt tggcgtacag                                          20

<210> SEQ ID NO 330
<211> LENGTH: 20
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 330
tcctatgctt tgactattag                                          20

<210> SEQ ID NO 331
<211> LENGTH: 23
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 331
cctgacatcc ctacatcacc gca                                      23

<210> SEQ ID NO 332
<211> LENGTH: 17
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 332
atgtatatta tatctaa                                             17

<210> SEQ ID NO 333
<211> LENGTH: 20
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 333
tgttgggatt gcttatattt                                          20

<210> SEQ ID NO 334
<211> LENGTH: 20
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 334
aaatataagc aatcccaaca                                          20

<210> SEQ ID NO 335
```

```
<211> LENGTH: 19
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 335
ctttattatt ttgtaaaat                                                    19

<210> SEQ ID NO 336
<211> LENGTH: 20
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 336
aaatataagc aatcccaaca                                                   20

<210> SEQ ID NO 337
<211> LENGTH: 20
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 337
tgttgggatt gcttatattt                                                   20

<210> SEQ ID NO 338
<211> LENGTH: 19
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 338
ctttattatt ttgtaaaat                                                    19

<210> SEQ ID NO 339
<211> LENGTH: 18
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 339
atttacaaaa taataaag                                                     18

<210> SEQ ID NO 340
<211> LENGTH: 23
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 340
cctgacatcc ctacatcacc cat                                               23

<210> SEQ ID NO 341
<211> LENGTH: 19
```

```
<212> TYPE: DNA
<213> ORGANISM: Homo sapiens
<220> FEATURE:
<221> NAME/KEY: misc_feature
<223> OTHER INFORMATION: oligonucleotide primer

<400> SEQUENCE: 341
tcctatgctt gactattgc                                              19

<210> SEQ ID NO 342
<211> LENGTH: 9
<212> TYPE: PRT
<213> ORGANISM: Homo Sapiens

<400> SEQUENCE: 342

Arg Tyr Leu Pro Ser Ala Asn Pro Asp
1               5

<210> SEQ ID NO 343
<211> LENGTH: 7
<212> TYPE: PRT
<213> ORGANISM: Homo sapiens

<400> SEQUENCE: 343

Leu Ala His Tyr Asn Lys Arg
1               5

<210> SEQ ID NO 344
<211> LENGTH: 10
<212> TYPE: PRT
<213> ORGANISM: Homo sapiens

<400> SEQUENCE: 344

Tyr Tyr Gly Arg Ile Leu His Tyr Leu Lys
1               5                   10

<210> SEQ ID NO 345
<211> LENGTH: 9
<212> TYPE: PRT
<213> ORGANISM: Homo sapiens

<400> SEQUENCE: 345

Met Glu Glu Ala Leu Gly Arg Val Lys
1               5

<210> SEQ ID NO 346
<211> LENGTH: 8
<212> TYPE: PRT
<213> ORGANISM: Homo sapiens

<400> SEQUENCE: 346

Glu Glu Ala Leu Gly Arg Val Lys
1               5

<210> SEQ ID NO 347
<211> LENGTH: 8
<212> TYPE: PRT
<213> ORGANISM: Homo sapiens

<400> SEQUENCE: 347

Glu Thr Pro Ala Ser Asp Lys Lys
1               5

<210> SEQ ID NO 348
<211> LENGTH: 24
```

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 348
gggaguagcc caagaaucau ucaa                                            24

<210> SEQ ID NO 349
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 349
guugggagcu cucccauauu ucaa                                            24

<210> SEQ ID NO 350
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 350
gggcaagacu cugucucaau ucaa                                            24

<210> SEQ ID NO 351
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 351
gguuaagcug agaucugaau ucaa                                            24

<210> SEQ ID NO 352
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 352
gaguagccca agaaucacuu ucaa                                            24

<210> SEQ ID NO 353
<211> LENGTH: 24
<212> TYPE: RNA
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: sense strand of siRNA

<400> SEQUENCE: 353
gugagccaag accacaucau ucaa                                          24

<210> SEQ ID NO 354
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 354
gaugguuaag cugagaucuu ucaa                                          24

<210> SEQ ID NO 355
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 355
gugaugguua agcugagauu ucaa                                          24

<210> SEQ ID NO 356
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 356
ggcggccgcg aauucacuau ucaa                                          24

<210> SEQ ID NO 357
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 357
gccgcgaauu cacuagugau ucaa                                          24

<210> SEQ ID NO 358
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA
```

```
<400> SEQUENCE: 358
gggagcucuc ccauaugguu ucaa                                              24

<210> SEQ ID NO 359
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 359
gccuggccaa cauggcaaau ucaa                                              24

<210> SEQ ID NO 360
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 360
gguaacaggg caagacucuu ucaa                                              24

<210> SEQ ID NO 361
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 361
gcccguaauc ccagcuacuu ucaa                                              24

<210> SEQ ID NO 362
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 362
ggccaggagu ucaagaccau ucaa                                              24

<210> SEQ ID NO 363
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 363
gaagugaugg uuaagcugau ucaa                                              24
```

```
<210> SEQ ID NO 364
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 364
gcacacgccc guaucccau ucaa                                           24

<210> SEQ ID NO 365
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: sense strand of siRNA

<400> SEQUENCE: 365
gcuaccuuac cuuuggcauu ucaa                                          24

<210> SEQ ID NO 366
<211> LENGTH: 24
<212> TYPE: DNA
<213> ORGANISM: Artificial Sequence
<220> FEATURE:
<223> OTHER INFORMATION: Synthetic

<400> SEQUENCE: 366
ggaaucuccu acauugccuu ucaa                                          24

<210> SEQ ID NO 367
<211> LENGTH: 25
<212> TYPE: DNA
<213> ORGANISM: Artificial Sequence
<220> FEATURE:
<223> OTHER INFORMATION: Synthetic

<400> SEQUENCE: 367
gagaaggcaa uguaggagau uccuu                                         25

<210> SEQ ID NO 368
<211> LENGTH: 24
<212> TYPE: DNA
<213> ORGANISM: Artificial Sequence
<220> FEATURE:
<223> OTHER INFORMATION: Synthetic

<400> SEQUENCE: 368
gacucucagc uuuaggucuu ucaa                                          24

<210> SEQ ID NO 369
<211> LENGTH: 25
<212> TYPE: DNA
<213> ORGANISM: Artificial Sequence
<220> FEATURE:
<223> OTHER INFORMATION: Synthetic

<400> SEQUENCE: 369
gagaacaccu aaagcugaga gucuu                                         25
```

```
<210> SEQ ID NO 370
<211> LENGTH: 24
<212> TYPE: DNA
<213> ORGANISM: Artificial Sequence
<220> FEATURE:
<223> OTHER INFORMATION: Synthetic

<400> SEQUENCE: 370
gcucaugccc guaaucccau ucaa                                             24

<210> SEQ ID NO 371
<211> LENGTH: 25
<212> TYPE: DNA
<213> ORGANISM: Artificial Sequence
<220> FEATURE:
<223> OTHER INFORMATION: Synthetic

<400> SEQUENCE: 371
gagaugggau uacgggcaug agcuu                                            25

<210> SEQ ID NO 372
<211> LENGTH: 24
<212> TYPE: DNA
<213> ORGANISM: Artificial Sequence
<220> FEATURE:
<223> OTHER INFORMATION: Synthetic

<400> SEQUENCE: 372
ggaauugaau uaauggaguu ucaa                                             24

<210> SEQ ID NO 373
<211> LENGTH: 25
<212> TYPE: DNA
<213> ORGANISM: Artificial Sequence
<220> FEATURE:
<223> OTHER INFORMATION: Synthetic

<400> SEQUENCE: 373
gagaacucca uuaauucaau uccuu                                            25

<210> SEQ ID NO 374
<211> LENGTH: 24
<212> TYPE: DNA
<213> ORGANISM: Artificial Sequence
<220> FEATURE:
<223> OTHER INFORMATION: Synthetic

<400> SEQUENCE: 374
ggcaggcaga ucaugagguu ucaa                                             24

<210> SEQ ID NO 375
<211> LENGTH: 25
<212> TYPE: DNA
<213> ORGANISM: Artificial Sequence
<220> FEATURE:
<223> OTHER INFORMATION: Synthetic

<400> SEQUENCE: 375
gagaaccuca ugaucugccu gccuu                                            25

<210> SEQ ID NO 376
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 376
gaaucuccua cauugccuau ucaa                                          24

<210> SEQ ID NO 377
<211> LENGTH: 25
<212> TYPE: DNA
<213> ORGANISM: Artificial Sequence
<220> FEATURE:
<223> OTHER INFORMATION: Synthetic

<400> SEQUENCE: 377
gagauaggca auguaggaga uucuu                                         25
```